(12) United States Patent
Renslo et al.

(10) Patent No.: US 11,072,594 B2
(45) Date of Patent: Jul. 27, 2021

(54) TRIOXOLANE AGENTS

(71) Applicant: THE REGENTS OF THE UNIVERSITY OF CALIFORNIA, Oakland, CA (US)

(72) Inventors: Adam Robert Renslo, Oakland, CA (US); Brian Richard Blank, Daly City, CA (US); Ryan Keith Muir, Colma, CA (US); Michael John Evans, South San Francisco, CA (US); Poulami Talukder, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/625,237

(22) PCT Filed: Jun. 27, 2018

(86) PCT No.: PCT/US2018/039768
§ 371 (c)(1),
(2) Date: Dec. 20, 2019

(87) PCT Pub. No.: WO2019/005977
PCT Pub. Date: Jan. 3, 2019

(65) Prior Publication Data
US 2020/0140406 A1    May 7, 2020

Related U.S. Application Data

(60) Provisional application No. 62/525,517, filed on Jun. 27, 2017.

(51) Int. Cl.
| | | |
|---|---|---|
| *A61K 31/357* | (2006.01) | |
| *C07D 323/02* | (2006.01) | |
| *C07D 405/12* | (2006.01) | |
| *C07D 407/12* | (2006.01) | |
| *A61P 33/06* | (2006.01) | |
| *C07D 413/12* | (2006.01) | |

(52) U.S. Cl.
CPC ........... *C07D 323/02* (2013.01); *A61P 33/06* (2018.01); *C07D 405/12* (2013.01); *C07D 407/12* (2013.01); *C07D 413/12* (2013.01)

(58) Field of Classification Search
CPC .. A61K 31/357; C07D 323/02; C07D 405/12; C07D 407/12
See application file for complete search history.

(56) References Cited

U.S. PATENT DOCUMENTS

| | | |
|---|---|---|
| 5,578,637 A | 11/1996 | Lai et al. |
| 6,486,199 B1 | 11/2002 | Vennerstrom et al. |
| 2004/0039008 A1 | 2/2004 | Vennerstrom et al. |
| 2016/0362439 A1 | 12/2016 | Renslo et al. |

FOREIGN PATENT DOCUMENTS

| | | | |
|---|---|---|---|
| WO | WO-2007/138435 A2 | 12/2007 | |
| WO | WO-2007/138435 A3 | 12/2007 | |
| WO | WO-2009/058859 A2 | 5/2009 | |
| WO | WO-2009/058859 A3 | 5/2009 | |
| WO | WO 2009/091433 | * | 7/2009 |

OTHER PUBLICATIONS

CAPLUS printout of RN 1036382-92-2 (Year: 2008).*
Dong et al., Structure-Activity Relationship of the Antimalarial Ozonide Artefenomel (OZ439), Journal of Medicinal Chemistry, vol. 60, No. 7, pp. 2654-2665 (Year: 2017).*
Moehrle et al., First-in-man Safety and Pharmacokinetics of Synthetic Ozonide OZ439 Demonstrates an Improved Exposure Profile Relative to Other Peroxide Antimalarials, Bristish Journal of Clinical Pharmacology, vol. 75, No. 2, pp. 524-537 (Year: 2013).*
Charman, S. A. et al. "Synthetic Ozonide Drug Candidate OZ439 Offers New Hope for a Single-Dose Cure of Uncomplicated Malaria," Proc. Natl. Acad. Sci. U. S. A. 2011, 108:4400-4405.
Coulter, D.W. et al. (Nov. 8, 2016). "Treatment of a chemoresistant neuroblastoma cell line with the antimalarial ozonide OZ513," BMC Cancer 16(1):867.
Creek, D. et al. Iron-Mediated Degradation Kinetics of Substituted Dispiro-1,2,4-Trioxolane Antimalarials. J. Pharm. Sci. 2007, 96, 2945-2956.
Dong Y. et al. (Apr. 13, 2017, e-published Jan. 18, 2017). "Structure-Activity Relationship of the Antimalarial Ozonide Artefenomel (OZ439)" J Med Chem. 60(7):2654-2668.
Fontaine, S. D. et al. "Efficient and Stereocontrolled Synthesis of 1,2,4-Trioxolanes Useful for Ferrous Iron-Dependent Drug Delivery," Org. Lett. 2014, 16, 5776-5779.
International Search Report dated Oct. 18, 2018, for PCT Application No. PCT/US2018/039768, filed Jun. 27, 2018, 5 pages.
Ismail, H. M. et al. "A Click Chemistry-Based Proteomic Approach Reveals That 1,2,4-Trioxolane and Artemisinin Antimalarials Share a Common Protein Alkylation Profile," Angew. Chem., Int. Ed. 2016, 128, 6511-6515.
Jourdan J. et al. "Monoclonal Antibodies That Recognize the Alkylation Signature of Antimalarial Ozonides OZ277 (Arterolane) and OZ439 (Artefenomel)" ACS Infect Dis. Jan. 8, 2016;2(1):54-61. Epub Sep. 28, 2015.
Jourdan J. et al. (Dec. 13, 2019). "Stochastic Protein Alkylation by Antimalarial Peroxides," ACS Infect Dis. 5(12):2067-2075.
Moehrle, J. J. et al. "First-in-Man Safety and Pharmacokinetics of Synthetic Ozonide OZ439 Demonstrates an Improved Exposure Profile Relative to Other Peroxide Antimalarials," Br. J. Clin. Pharmacol. 2013, 75, 524-537.
Phyo, A.P. et al. "Antimalarial Activity of Artefenomel (OZ439), a Novel Synthetic Antimalarial Endoperoxide, in Patients with Plasmodium Falciparum and Plasmodium Vivax Malaria: An Open-Label Phase 2 Trial," Lancet Infect. Dis. 2016, 16, 61-69.
Tiwari M.K..et al. (2019). "Recent Developments in Natural Product Inspired Synthetic 1,2,4-Trioxolanes (Ozonides): An Unusual Entry into Antimalarial Chemotherapy," Curr Top Med Chem. 19(10):831-846.

(Continued)

*Primary Examiner* — Brenda L Coleman
(74) *Attorney, Agent, or Firm* — Mintz Levin Cohn Ferris Glovsky and Popeo, P.C.; Kenneth E. Jenkins; Joohee Lee

(57) ABSTRACT

Disclosed herein, inter alia, are trioxolane compounds and methods of using the same for treatment and detection of diseases.

23 Claims, 8 Drawing Sheets

(56) References Cited

OTHER PUBLICATIONS

Vennerstrom, J. L. et al. "Identification of an Antimalarial Synthetic Trioxolane Drug Development Candidate," Nature 2004, 430, 900-904.

Walz A. et al. (Dec. 18, 2019). "Anti-malarial ozonides OZ439 and OZ609 tested at clinically relevant compound exposure parameters in a novel ring-stage survival assay," Malar J. 18(1):427.

Wang X. et al. "Comparative antimalarial activities and ADME profiles of ozonides (1,2,4-trioxolanes) OZ277, OZ439, and their 1,2-dioxolane, 1,2,4-trioxane, and 1,2,4,5-tetraoxane isosteres," J Med Chem. Mar. 28, 2013;56(6):2547-55. Epub Mar. 15, 2013.

Wang Y. et al. (Dec. 21, 2018). "Inhibition of Cytomegalovirus Replication with Extended-Half-Life Synthetic Ozonides," Antimicrob Agents Chemother.63(1) :e01735-18.

Written Opinion dated Oct. 18, 2018, for PCT Application No. PCT/US2018/039768, filed Jun. 27, 2018, 5 pages.

Wu J. et al. (Apr. 9, 2020). "Structure-Activity Relationship of Antischistosomal Ozonide Carboxylic Acid," J Med Chem. 63(7):3723-3736.

Xue J. et al. "Effect of ozonide OZ418 against Schistosoma japonicum harbored in mice," Parasitol Res. Sep. 2014;113(9):3259-66. Epub Jun. 20, 2014.

Yang, T. et al. "Comparison of the Exposure Time Dependence of the Activities of Synthetic Ozonide Antimalarials and Dihydroartemisinin against K13 Wild-Type and Mutant Plasmodium Falciparum Strains," Antimicrob. Agents Chemother. 2016, 60, 4501-4510.

Zhao, Q. et al. "Structure-Activity Relationship of an Ozonide Carboxylic Acid (OZ78) Against Fasciola Hepatica," J. Med. Chem. 2010, 53, 4223-4233.

\* cited by examiner artemisinin/qinghaosu (1Z)

arterolane/OZ277 (2a)

artefenomel/OZ439 (3Z)

TRIOXOLANE AGENTS

CROSS-REFERENCES TO RELATED APPLICATIONS

This application is the national stage filing under USC 371 of international application PCT/US2018/039768, filed Jun. 27, 2018, which claims the benefit of U.S. Provisional Application No. 62/525,517, filed on Jun. 27, 2017, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. R01 AI105106, awarded by the National Institutes of Health. The government has certain rights in the invention.

BACKGROUND OF THE INVENTION

In normal cells and tissues, iron remains sequestered in forms that are non-toxic to the cell, bound to the iron carrying protein transferrin for example, or bound as heme within hemoglobin. Diseased tissues and cells, on the other hand, can contain higher than normal concentrations of iron. Many neoplastic cells for example over-express the transferrin receptor to increase their uptake of iron. Increased iron uptake has been proposed to explain the increased toxicity that iron-dependent endoperoxides like artemisinin exhibit towards cancer cell lines as compared to normal cells (Efferth, T. *Drug Resistance Updates*, 2005, 8:85-97). In one study, the expression level of the transferrin receptor was shown to correlate with the cytotoxicity of an artemisinin derivative towards HeLa cells (see for example Disbrow, G. L., et al *Cancer Research*, 2005, 65, 10854-10861). Artemisinin and its derivatives are believed to exert their cytotoxic effect via reaction with $Fe^{II}$ and the resulting generation of reactive oxygen and carbon centered radical species. The cytotoxicity of artemisinin derivatives towards leukemia, astrocytoma, and breast cancer cell lines can be potentiated by the addition of exogenous $Fe^{II}$ salts or transferrin (Efferth, T. et al *Free Radical Biology & Medicine*, 2004, 37, 998-1009; Singh, N. P. et al *Life Sciences*, 2001, 70, 49-56). U.S. Pat. No. 5,578,637 describes the use of an endoperoxide moiety (i.e., an artemisinin) to kill cancer cells under conditions that enhance intracellular iron concentrations.

The blood-scavenging parasites responsible for diseases such as malaria and schistosomiasis also possess biological compartments rich in ferrous iron. In malaria parasites, unbound heme is generated in the parasite digestive vacuole where hemoglobin is degraded by a number of proteases (See Rosenthal, P. J. in *Protease and hemoglobin degradation. Molecular Approaches to Malaria*, 2005: p. 311-326). Hence, while the concentration of unbound, ferrous iron is vanishingly small in human plasma (~$10^{-16}$M), significant quantities of ferrous iron are present within malaria parasites (see Robert, A. et al *Coordination Chemistry Reviews*, 2005, 249, p. 1927-1936). The antimalarial drug artemisinin and its related synthetic derivatives are thought to confer their antiparasitic effect via reaction with ferrous iron and the resulting generation of reactive oxygen and carbon centered radical species. An excess of iron, and ferrous iron in particular, is therefore a distinguishing characteristic of many neoplastic cells and pathogenic parasites. Disclosed herein, inter alia, are solutions to these and other problems in the art.

BRIEF SUMMARY OF THE INVENTION

In an aspect is provided a compound having the formula:

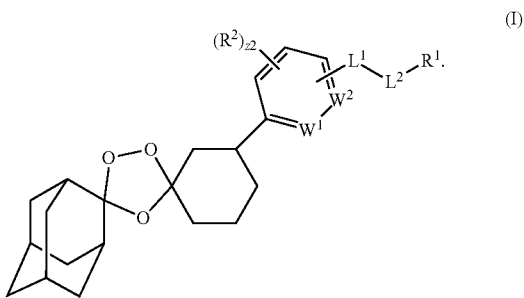

(I)

$W^1$ and $W^2$ are independently =N—, =C($R^2$)—, or =CH—. $L^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, or —S—. $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. z2 is an integer from 0 to 4. Each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl. Each X, $X^1$, and $X^2$ is independently —F, —Cl, —Br, or —I. n1 is independently an integer from 0 to 4. m1 and v1 are independently 1 or 2.

In an aspect is provided a compound having the formula:

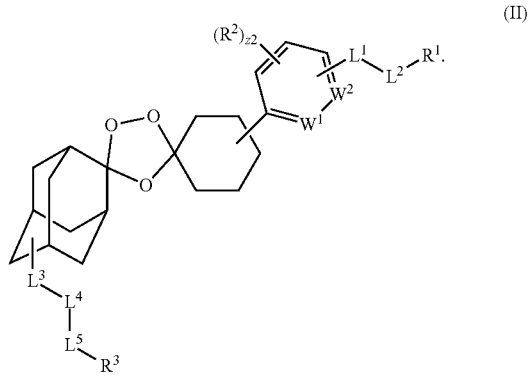

$W^1$, $W^2$, $L^1$, $L^2$, $R^1$, $R^2$, z2, $R^{1A}$, $R^{1B}$, $R^{1C}$, $R^{1D}$, X, $X^1$, $X^2$, n1, m1, and v1 are as described herein, including in embodiments. $L^3$, $L^4$, and $L^5$ are independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^3$ is a detectable moiety.

In an aspect is provided a pharmaceutical composition including a pharmaceutically acceptable excipient and a compound described herein (including in an aspect, embodiment, table, example, or claim), or a pharmaceutically acceptable salt thereof.

In an aspect is provided a method of treating a disease in a patient in need of such treatment, said method including administering a therapeutically effective amount of a compound described herein (including in an aspect, embodiment, table, example, or claim), or a pharmaceutically acceptable salt thereof, to the patient.

In an aspect is provided a method of detecting a disease associated with a cell or organism having an increased $Fe^{II}$ level compared to a standard control, in a subject, the method including administering an effective amount of a compound described herein (including in an aspect, embodiment, table, example, or claim), or a pharmaceutically acceptable salt thereof, to the subject and measuring the level of the compound in the subject.

In an aspect is provided a method of identifying a patient having a disease associated with a cell or organism having an increased $Fe^{II}$ level compared to a standard control, the method including administering an effective amount of a compound described herein (including in an aspect, embodiment, table, example, or claim), or a pharmaceutically acceptable salt thereof, to the patient.

DETAILED DESCRIPTION OF THE INVENTION

A. Definitions

Figure 1:
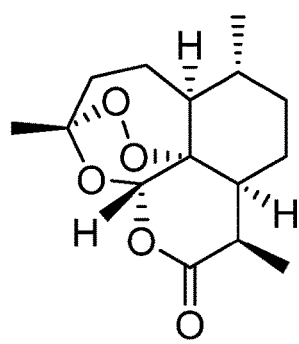
FIG. 1. Structures of antimalarial endoperoxides.
Figure 1:
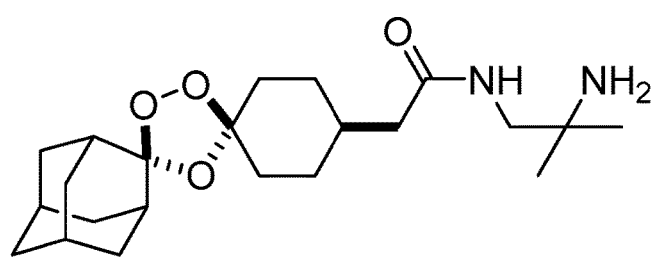
Figure 1:
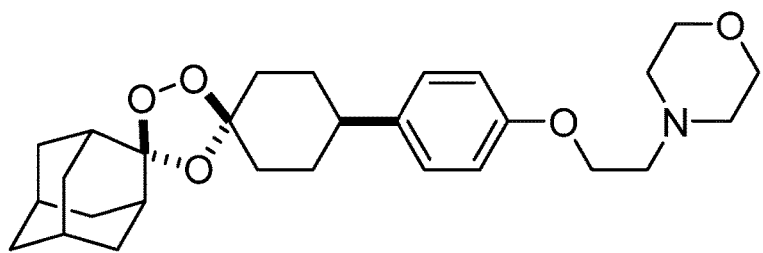

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S, and wherein the nitrogen and sulfur atoms may optionally be oxidized, and the nitrogen heteroatom may optionally be quaternized). The heteroatom(s) (e.g., O, N, P, S, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R—C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbomenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

The term "oxo," as used herein, means an oxygen that is double bonded to a carbon atom.

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) and aryl and heteroaryl groups can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the group. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CCl$_3$, —CBr$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl, (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(b) alkyl, heteroalkyl, cycloalkyl, heterocycloalkyl, aryl, heteroaryl, substituted with at least one substituent selected from: oxo, halogen, CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl, (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, e.g., Berge et al., "Pharmaceutical Salts", *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Compound provided herein may be agents (e.g. compounds, proteins, drugs, detectable agents, therapeutic agents) in a prodrug form. Prodrugs of the compounds described herein are those compounds that readily undergo chemical changes under select physiological conditions (e.g. increased $Fe^{II}$ concentration relative to normal physiological levels, increased reductant levels relative to normal physiological levels) to provide the final agents (e.g. compounds, proteins, drugs, detectable agents, therapeutic agents). Additionally, prodrugs can be converted to agents (e.g. compounds, proteins, drugs, detectable agents, therapeutic agents) by chemical or biochemical methods in an ex vivo environment. Prodrugs described herein include compounds that readily undergo chemical changes under select physiological conditions (e.g. increased $Fe^{II}$ concentration relative to normal physiological levels, increased reductant levels relative to normal physiological levels) to provide agents (e.g. compounds, proteins, drugs, detectable agents, therapeutic agents) to a biological system (e.g. in a subject, in an infected cell, in a cancer cell, in the extracellular space near an infected cell, in the extracellular space near a cancer cell from the moieties (e.g. moiety of a protein, drug, detectable agent) attached to the prodrug moiety and included in the prodrug (e.g. compound of formula I, including embodiments, compound described herein, examples)).

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those, which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

The symbol "⁓" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "label", "detectable agent", or "detectable moiety" is a substance (e.g., compound, atom, composition) detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99}mTc$, 99Mo, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$ fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), fluorodeoxyglucose nucleotide or nucleoside (e.g. fluorine-18 labeled A, C, G, or T), gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable agents also include any of the above compositions encapsulated in nanoparticles, particles, aggregates, coated with additional compositions, derivatized for binding to a targeting agent (e.g. antibody or antigen binding fragment). A detectable moiety is a radical of a detectable agent. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr $^{143}$Pr $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

The terms "fluorophore" or "fluorescent agent" are used interchangeably and refer to a composition (e.g. compound) that can absorb light at one or more wavelengths and re-emit light at one or more longer wavelengths, relative to the one or more wavelengths of absorbed light. Examples of fluorophores that may be included in the compositions described herein include fluorescent proteins, xanthene derivatives (e.g. fluorescein, rhodamine, Oregon green, eosin, or Texas red), cyanine and derivatives (e.g. cyanine, indocarbocyanine, oxacarbocyanine, thiacarbocyanine or merocyanine), napththalene derivatives (e.g. dansyl or prodan derivatives), coumarin and derivatives, oxadiazole derivatives (e.g. pyridyloxazole, nitrobenzoxadiazole or benzoxadiazole), anthracene derivatives (e.g. anthraquinones, DRAQ5, DRAQ7, or CyTRAK Orange), pyrene derivatives (e.g. cascade blue and derivatives), oxazine derivatives (e.g. Nile red, Nile blue, cresyl violet, oxazine 170), acridine derivatives (e.g. proflavin, acridine orange, acridine yellow), arylmethine derivatives (e.g. auramine, crystal violet, malachite green), tetrapyrrole derivatives (e.g. porphin, phthalocyanine, bilirubin), CF Dye™, DRAQ™, CyTRAK™, BODIPY™, Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™, RPE™, and/or BPE™. A fluorescent moiety is a radical of a fluorescent agent.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "solution" is used in accor and refers to a liquid mixture in which the minor component (e.g., a solute or compound) is uniformly distributed within the major component (e.g., a solvent).

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease. For example, certain methods herein treat infectious diseases (e.g., malaria, bacterial diseases, viral diseases, parasitic diseases). For example certain methods herein treat infectious diseases (e.g., malaria, bacterial diseases, viral diseases, parasitic diseases) by decreasing a symptom of the infectious disease (e.g., malaria, bacterial diseases, viral diseases, parasitic diseases). For example certain methods herein treat infectious diseases (e.g., malaria, bacterial diseases, viral diseases, parasitic diseases) by decreasing the level or viability or amount of the infectious agent (e.g., bacterium, virus, or parasite).

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease (e.g. cancer) is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with an infectious organism may be treated with an agent (e.g. compound as described herein) effective for decreasing the amount of the infectious organism.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition may include, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "modulator" refers to a composition that increases or decreases the level of a target molecule or the function of a target molecule or the physical state of the target of the molecule relative to the absence of the modulator. In embodiments, a modulator is an anti-cancer agent. In embodiments, a modulator is an anti-infective agent. In embodiments, a modulator is an anti-malarial agent.

"Anti-cancer agent" or "anti-cancer drug" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (-)-Phenylahistin (i.e. NSCL-96F037), D-68838 (Asta *Medica*), D-68836 (Asta *Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term "inflammatory disease" refers to a disease or condition characterized by aberrant inflammation (e.g. an increased level of inflammation compared to a control such as a healthy person not suffering from a disease). Examples of inflammatory diseases include auto-immune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

A "bioconjugate linker" is a covalent linker moiety that results from bioconjugate chemistry as generally known in the art. See for example, *Bioconiugate Techniques*, Second Edition, Greg T. Hermanson.

Conjugates described herein may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982, all of which are incorporated by reference in their entirety for all purposes. In embodiments, the bioconjugation reaction is a click chemistry reaction (Angewandte Chemie International Edition 40 (11): 2004-2021). In embodiments, the bioconjugation reaction is a Huisgen cyclization of azides. In embodiments, the bioconjugation reaction is a copper catalyzed Huisgen cyclization of azides. In embodiments, the bioconjugation reaction is a click chemistry reaction that does not require copper.

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed or non-copper catalyzed cycloaddition click chemistry; and (o) biotin conjugate can react with avidin or strepavidin to form a avidin-biotin complex or streptavidin-biotin complex.

The terms "anti-malarial agent" or "anti-malarial drug" or "anti-malarial" are interchangeable and are used in accordance with their plain ordinary meaning and refer to a composition (e.g. compound, drug, antagonist, inhibitor, modulator) having anti-malarial properties or the ability to inhibit the growth or proliferation of *Plasmodium* that infect humans (e.g. *P. vivax, P. ovale, P. malariae P. falciparum, P. knowlesi, P. brasilianum, P. cynomolgi, P. cynomolgi bastianellii, P. inui, P. rhodiani, P. schweitzi, P. semiovale,* or *P. simium*). In embodiments, an anti-malarial agent treats infection with *P. vivax, P. ovale, P. malariae,* and/or *P. falciparum*. In embodiments, an anti-malarial agent treats infection with *P. falciparum*. In some embodiments, an anti-malarial agent is an agent approved by the FDA or similar regulatory agency of a country other than the USA, for treating malaria. An anti-malarial moiety is a radical of an anti-malarial.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of an increased amount of $Fe^{II}$ relative to normal $Fe^{II}$ amounts in a subject (e.g. human). In some embodiments, the disease is a disease having the symptom of an increased amount of a reductant (e.g. biological reductant, $Fe^{II}$) relative to normal reductant (e.g. biological reductant, $Fe^{II}$) amounts in a subject (e.g. human). In embodiments, the disease is an infectious disease. In embodiments, the disease is a bacterial disease. In embodiments, the disease is a parasitic disease. In embodiments, the disease is a viral disease. In embodiments, the disease is malaria. In embodiments, the disease is drug-resistant malaria. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "infectious disease" refers to a disease or condition related to the presence of an organism (the agent or infectious agent) within or contacting the subject or patient. Examples include a parasite, bacterium, fungus, virus, or other microorganism.

"Infectious agent" refers to an organism that is associated with (in or contacting) patients with an infectious disease but not in patients without the infectious disease and wherein contacting a patient without the infectious disease with the organism results in the patient having the infectious disease. In some embodiments, the infectious agent associated with a disease that may be treated by the compounds and/or methods described herein is a bacterium.

As used herein, the term "cancer" refers to all types of cancer, neoplasm or malignant tumors found in mammals (e.g. humans), including leukemia, lymphomas, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer, brain cancer, glioma, glioblastoma, neuroblastoma, prostate cancer, melanoma, cervical cancer, gastric cancer, ovarian cancer, lung cancer, cancer of the head, and lymphomas. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma or neuroblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compound of the disclosure can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent, protein). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. The compositions of the present disclosurecan also be delivered as nanoparticles.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%.

Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "Parasitic disease" refers to an infectious disease that is caused or transmitted by a parasite. In embodiment, a parasitic disease is also known as parasitosis. In embodiments, the parasitic disease is caused by the protozoan parasite *Plasmodium*. In embodiments, the parasitic disease is cause by *P. falciparum, P. malariae, P. ovale, P. vivax*, or *P. knowlesi*. In some embodiments, the parasitic disease may be treated by the compounds and/or methods described herein.

B. Compounds

In an aspect is provided a compound having the formula:

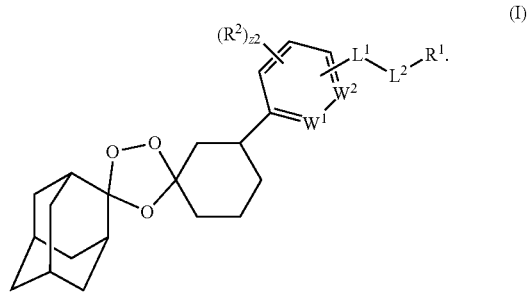

(I)

$W^1$ and $W^2$ are independently =N—, =C($R^2$)—, or =CH—.

$L^1$ is a bond, —O—, —NH—, —OC(O)—, —C(O)O—, —NHC(O)—, —C(O)NH—, —OC(O)O—, —OC(O) NH—, —NHC(O)O—, —NHC(O)NH—, or —S—.

$L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —C(O) $NR^{1A}R^{1B}$, —$OR^{1D}$, —$NR^{1A}SO_2R^{1D}$, —$NR^{1A}C(O)R^{1C}$, —NR$^{1A}$C(O)OR$^{1C}$, —NR$^{1A}$OR$^{1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^2$ is independently halogen, —CX$^2_3$, —CHX$^2_2$, —CH$_2$X$^2$, —OCX$^2_3$, —OCH$_2$X$^2$, —OCHX$^2_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

z2 is an integer from 0 to 4.

Each R$^{1A}$, R$^{1B}$, R$^{1C}$, and R$^{1D}$ is independently hydrogen, —CX$_3$, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl.

Each X, X$^1$, and X$^2$ is independently —F, —Cl, —Br, or —I.

n1 is independently an integer from 0 to 4.

m1 and v1 are independently 1 or 2.

In embodiments, the compound has the formula:

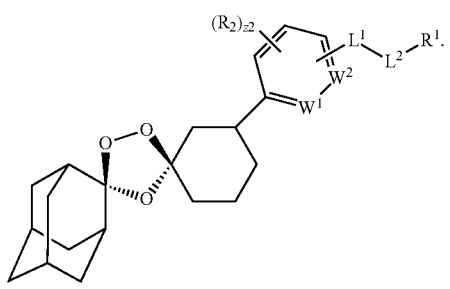

(Ia)

W$^1$, W$^2$, L$^1$, L$^2$, R$^1$, R$^2$, and z2 are as described herein, including in embodiments.

In embodiments, the compound has the formula:

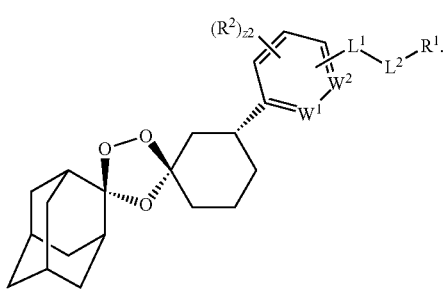

(Ib)

W$^1$, W$^2$, L$^1$, L$^2$, R$^1$, R$^2$, and z2 are as described herein, including in embodiments.

In embodiments, the compound has the formula:

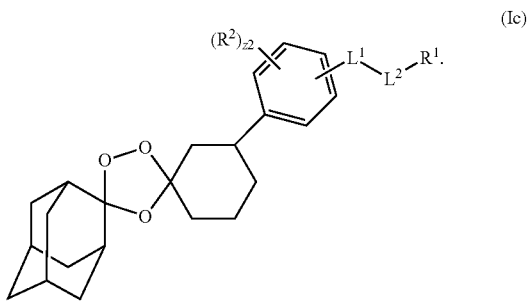

(Ic)

In embodiments, W$^1$ is =N—. In embodiments, W$^1$ is =CH—. In embodiments, W$^1$ is =C(R$^2$)—. In embodiments, W$^2$ is =N—. In embodiments, W$^2$ is =CH—. In embodiments, W$^2$ is =C(R$^2$)—.

In embodiments, R$^2$ is independently unsubstituted C$_1$-C$_3$ alkyl. In embodiments, R$^2$ is independently substituted C$_1$-C$_3$ alkyl. In embodiments, R$^2$ is independently unsubstituted methyl. In embodiments, R$^2$ is independently —OCF$_3$. In embodiments, R$^2$ is independently —OCH$_3$.

In embodiments, a substituted R$^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^2$ is substituted with a plurality of groups selected from substituent groups, size-limited substituent groups, and lower substituent groups; each substituent group, size-limited substituent group, and/or lower substituent group may optionally be different.

In embodiments, z2 is 0. In embodiments, z2 is 1. In embodiments, z2 is 2.

In embodiments, L$^1$ is a bond. In embodiments, L$^1$ is —O—. In embodiments, L$^1$ is —NH—. In embodiments, L$^1$ is —OC(O)—. In embodiments, L$^1$ is —C(O)O—. In embodiments, L$^1$ is —NHC(O)—. In embodiments, L$^1$ is —C(O)NH—. In embodiments, L$^1$ is —OC(O)O—. In embodiments, L$^1$ is —OC(O)NH—. In embodiments, L$^1$ is —NHC(O)O—. In embodiments, L$^1$ is —NHC(O)NH—. In embodiments, L$^1$ is —S—.

In embodiments, L$^2$ is a substituted or unsubstituted C$_1$-C$_4$ alkylene. In embodiments, L$^2$ is an unsubstituted C$_1$-C$_4$ alkylene. In embodiments, L$^2$ is an unsubstituted ethylene. In embodiments, L$^2$ is an unsubstituted n-propylene. In embodiments, L$^2$ is —CH$_2$C(CH$_3$)$_2$—. In embodiments, L$^2$ is an unsubstituted methylene. In embodiments, L$^2$ is a substituted or unsubstituted C$_4$-C$_6$ cycloalkylene. In embodiments, L$^2$ is an unsubstituted C$_4$-C$_6$ cycloalkylene. In embodiments, L$^2$ is a substituted or unsubstituted cyclohexylene. In embodiments, L$^2$ is a unsubstituted cyclohexylene. In embodiments, L$^2$ is a bond.

In embodiments, a substituted L$^2$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted L$^2$ is substituted with a plurality of groups selected from substituent groups, size-limited substituent groups, and lower substituent groups; each substituent group, size-limited substituent group, and/or lower substituent group may optionally be different.

In embodiments, $R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NH_2$, $-NHC(O)NR^{1A}R^{1B}$, $-N(O)_{m1}$, $-NH_2$, $-C(O)R^{1C}$, $-C(O)-OH$, $-C(O)NH_2$, $-OR^{1D}$, $-NHSO_2R^{1D}$, $-NHC(O)R^{1C}$, $-NHC(O)OR^{1C}$, $-NHOR^{1C}$, $-N_3$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl). In embodiments, $R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_2NH_2$, $-NHC(O)NH_2$, $-NO_2$, $-NH_2$, $-C(O)R^{1C}$, $-C(O)-OH$, $-C(O)NH_2$, $-OH$, $-NHSO_2R^{1D}$, $-NHC(O)H$, $-NHC(O)OH$, $-NHOH$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^1$ is $-NR^{1A}R^{1B}$, $-C(O)NR^{1A}R^{1B}$, $-NR^AC(O)R^{1C}$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. In embodiments, $R^1$ is $-NR^{1A}R^{1B}$, $-C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, or $R^{20}$-substituted or unsubstituted 5 to 7 membered heterocycloalkyl. In embodiments, $R^1$ is $-NR^{1A}R^{1B}$. In embodiments, $R^1$ is $-C(O)NR^{1A}R^{1B}$. In embodiments, $R^1$ is substituted or unsubstituted 6 to 7 membered heterocycloalkyl. In embodiments, $R^1$ is $R^{20}$-substituted or unsubstituted 6 to 7 membered heterocycloalkyl. In embodiments, $R^1$ is $R^{20}$-substituted 6 membered heterocycloalkyl. In embodiments, $R^1$ is $R^{20}$-substituted 7 membered heterocycloalkyl. In embodiments, $R^1$ is unsubstituted 6 membered heterocycloalkyl. In embodiments, $R^1$ is unsubstituted 7 membered heterocycloalkyl. In embodiments, $R^1$ is $-NR^{1A}C(O)R^{1C}$. In embodiments, $R^1$ is $-NHC(O)R^{1C}$. In embodiments, $R^1$ is $-NHC(O)R^{1C}$, wherein $R^{1C}$ is a substituted or unsubstitued phenyl. In embodiments, $R^1$ is $-NHC(O)R^{1C}$, wherein $R^{1C}$ is a fluoro-substituted or unsubstitued phenyl. In embodiments, $R^1$ is $-SO_2CH_3$.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different.

In embodiments, $R^1$ is substituted morpholinyl. In embodiments, $R^1$ is unsubstituted morpholinyl. In embodiments, $R^1$ is $R^{20}$-substituted morpholinyl. In embodiments, $R^1$ is $-NH_2$. In embodiments, $R^1$ is $-CH_2C(CH_3)_2NH_2$. In embodiments, $R^1$ is $-C(O)NH_2$. In embodiments, $R^1$ is $-CH_2CH_2NH_2$. In embodiments, $R^1$ is substituted piperidinyl. In embodiments, $R^1$ is unsubstituted piperidinyl. In embodiments, $R^1$ is $R^{20}$-substituted piperidinyl. In embodiments, $R^1$ is substituted oxazepanyl. In embodiments, $R^1$ is unsubstituted oxazepanyl. In embodiments, $R^1$ is $R^{20}$-substituted oxazepanyl. In embodiments, $R^1$ is substituted 1,4-oxazepanyl. In embodiments, $R^1$ is unsubstituted 1,4-oxazepanyl. In embodiments, $R^1$ is $R^{20}$-substituted 1,4-oxazepanyl. In embodiments, $R^1$ is substituted thiomorpholinyl. In embodiments, $R^1$ is unsubstituted thiomorpholinyl. In embodiments, $R^1$ is $R^{20}$-substituted thiomorpholinyl. In embodiments, $R^1$ is substituted thiomorpholinyl 1-oxide. In embodiments, $R^1$ is unsubstituted thiomorpholinyl 1-oxide. In embodiments, $R^1$ is $R^{20}$-substituted thiomorpholinyl 1-oxide. In embodiments, $R^1$ is substituted piperazinyl. In embodiments, $R^1$ is unsubstituted piperazinyl. In embodiments, $R^1$ is $R^{20}$-substituted piperazinyl.

In embodiments, $R^1$ is

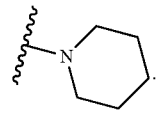 [SMILES: *N1CCCCC1]

In embodiments, $R^1$ is

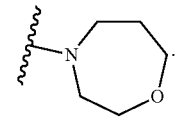

In embodiments, $R^1$ is

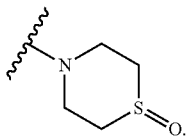 [SMILES: *N1CCS(=O)CC1]

In embodiments, $R^1$ is

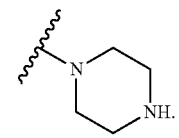

In embodiments, $R^1$ is

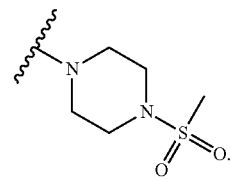 [SMILES: *N1CCN(S(C)(=O)=O)CC1]

In embodiments, $R^1$ is

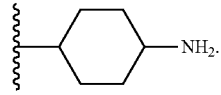

In embodiments, $R^1$ is

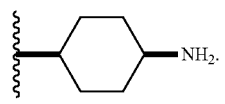

In embodiments, $R^1$ is

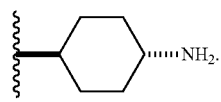

In embodiments, $R^1$ is

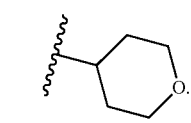

In embodiments, $R^1$ is

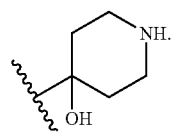 [SMILES: *C1(O)CCNCC1]

In embodiments, $R^1$ is

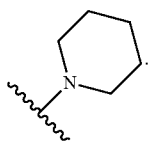 [SMILES: *N1CCCCC1]

In embodiments, $R^1$ is

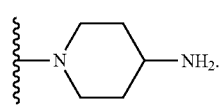 [SMILES: *N1CCC(N)CC1]

In embodiments, $R^1$ is

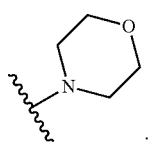 [SMILES: *N1CCOCC1]

In embodiments, $R^1$ is

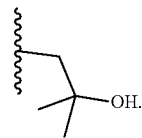 [SMILES: *CC(C)(C)O]

In embodiments, $R^1$ is hydrogen. In embodiments, $R^1$ is —$NH_2$. In embodiments, $R^1$ is —$NO_2$.

In embodiments, -$L^2$-$R^1$ is

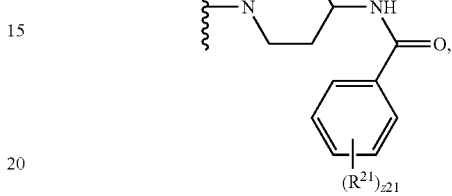

wherein z21 is an integer from 0 to 5. In embodiments, -$L^2$-$R^1$ is

In embodiments, -$L^2$-$R^1$ is

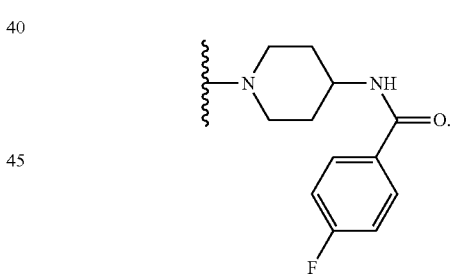

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{20}$ is independently oxo, halogen, —$CF_3$, —$CHF_2$, —$CH_2F$, —$OCF_3$, —$OCH_2F$, —$OCHF_2$, —$CCl_3$, —$CHCl_2$, —$CH_2Cl$, —$OCCl_3$, —$OCH_2Cl$, —$OCHCl_2$, —$CBr_3$, —$CHBr_2$, —$CH_2Br$, —$OCBr_3$, —$OCH_2Br$, —$OCHBr_2$, —$CI_3$, —$CHI_2$, —$CH_2I$, —$OCI_3$, —$OCH_2I$, —$OCHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl). Each $X^{20}$ is independently —F, —Cl, —Br, or —I.

In embodiments, $R^{20}$ is independently oxo. In embodiments, $R^{20}$ is independently halogen. In embodiments, $R^{20}$ is independently —$CF_3$. In embodiments, $R^{20}$ is independently —$CHF_2$. In embodiments, $R^{20}$ is independently —$CH_2F$. In embodiments, $R^{20}$ is independently —$OCF_3$. In embodiments, $R^{20}$ is independently —$OCH_2F$. In embodiments, $R^{20}$ is independently —$OCHF_2$. In embodiments, $R^{20}$ is independently —$CCl_3$. In embodiments, $R^{20}$ is independently —$CHCl_2$. In embodiments, $R^{20}$ is independently —$CH_2Cl$. In embodiments, $R^{20}$ is independently —$OCCl_3$. In embodiments, $R^{20}$ is independently —$OCH_2Cl$. In embodiments, $R^{20}$ is independently —$OCHCl_2$. In embodiments, $R^{20}$ is independently —$CBr_3$. In embodiments, $R^{20}$ is independently —$CHBr_2$. In embodiments, $R^{20}$ is independently —$CH_2Br$. In embodiments, $R^{20}$ is independently —$OCBr_3$. In embodiments, $R^{20}$ is independently —$OCH_2Br$. In embodiments, $R^{20}$ is independently —$OCHBr_2$. In embodiments, $R^{20}$ is independently —$CI_3$. In embodiments, $R^{20}$ is independently —$CHI_2$. In embodiments, $R^{20}$ is independently —$CH_2I$. In embodiments, $R^{20}$ is independently —$OCI_3$. In embodiments, $R^{20}$ is independently —$OCH_2I$. In embodiments, $R^{20}$ is independently —$OCHI_2$. In embodiments, $R^{20}$ is independently —CN. In embodiments, $R^{20}$ is independently —OH. In embodiments, $R^{20}$ is independently —$NH_2$. In embodiments, $R^{20}$ is independently —COOH. In embodiments, $R^{20}$ is independently —$CONH_2$. In embodiments, $R^{20}$ is independently —$NO_2$. In embodiments, $R^{20}$ is independently —SH. In embodiments, $R^{20}$ is independently —$SO_3H$. In embodiments, $R^{20}$ is independently —$SO_4H$. In embodiments, $R^{20}$ is independently —$SO_2NH_2$. In embodiments, $R^{20}$ is independently —$NHNH_2$. In embodiments, $R^{20}$ is independently —$ONH_2$. In embodiments, $R^{20}$ is independently —NHC=(O)$NHNH_2$. In embodiments, $R^{20}$ is independently —NHC=(O)$NH_2$. In embodiments, $R^{20}$ is independently —$NHSO_2H$. In embodiments, $R^{20}$ is independently —NHC=(O)H. In embodiments, $R^{20}$ is independently —NHC(O)—OH. In embodiments, $R^{20}$ is independently —NHOH. In embodiments, $R^{20}$ is independently —$N_3$. In embodiments, $R^{20}$ is independently —$SO_2CH_3$.

In embodiments, $R^{20}$ is $R^{21}$-substituted or unsubstituted alkyl (e.g., $C_1$-$C_8$ alkyl, $C_1$-$C_6$ alkyl, or $C_1$-$C_4$ alkyl). In embodiments, $R^{20}$ is $R^{21}$-substituted alkyl (e.g., $C_1$-$C_8$ alkyl, $C_1$-$C_6$ alkyl, or $C_1$-$C_4$ alkyl). In embodiments, $R^{20}$ is an unsubstituted alkyl (e.g., $C_1$-$C_8$ alkyl, $C_1$-$C_6$ alkyl, or $C_1$-$C_4$ alkyl).

In embodiments, $R^{20}$ is $R^{21}$-substituted or unsubstituted methyl. In embodiments, $R^{20}$ is $R^{21}$-substituted or unsubstituted $C_2$ alkyl. In embodiments, $R^{20}$ is $R^{21}$-substituted or unsubstituted $C_3$ alkyl. In embodiments, $R^{20}$ is $R^{21}$-substituted or unsubstituted $C_4$ alkyl. In embodiments, $R^{20}$ is $R^{21}$-substituted or unsubstituted $C_5$ alkyl. In embodiments, $R^{20}$ is $R^{21}$-substituted or unsubstituted $C_6$ alkyl. In embodiments, $R^{20}$ is $R^{21}$-substituted or unsubstituted $C_7$ alkyl. In embodiments, $R^{20}$ is $R^{21}$-substituted or unsubstituted $C_8$ alkyl. In embodiments, $R^{20}$ is $R^{21}$-substituted methyl. In embodiments, $R^{20}$ is $R^{21}$-substituted $C_2$ alkyl. In embodiments, $R^{20}$ is $R^{21}$-substituted $C_3$ alkyl. In embodiments, $R^{20}$ is $R^{21}$-substituted $C_4$ alkyl. In embodiments, $R^{20}$ is $R^{21}$-substituted $C_5$ alkyl. In embodiments, $R^{20}$ is $R^{21}$-substituted $C_6$ alkyl. In embodiments, $R^{20}$ is $R^{21}$-substituted $C_7$ alkyl. In embodiments, $R^{20}$ is $R^{21}$-substituted $C_8$ alkyl. In embodiments, $R^{20}$ is an unsubstituted methyl. In embodiments, $R^{20}$ is an unsubstituted $C_2$ alkyl. In embodiments, $R^{20}$ is an unsubstituted $C_3$ alkyl. In embodiments, $R^{20}$ is an unsubstituted $C_4$ alkyl. In embodiments, $R^{20}$ is an unsubstituted $C_5$ alkyl. In embodiments, $R^{20}$ is an unsubstituted $C_6$ alkyl. In embodiments, $R^{20}$ is an unsubstituted $C_7$ alkyl. In embodiments, $R^{20}$ is an unsubstituted $C_8$ alkyl.

In embodiments, $R^{20}$ is independently oxo, halogen, —$CF_3$, —$CHF_2$, —$CH_2F$, —$OCF_3$, —$OCH_2F$, —$OCHF_2$, —$CCl_3$, —$CHCl_2$, —$CH_2Cl$, —$OCCl_3$, —$OCH_2Cl$, —$OCHCl_2$, —$CBr_3$, —$CHBr_2$, —$CH_2Br$, —$OCBr_3$, —$OCH_2Br$, —$OCHBr_2$, —$CI_3$, —$CHI_2$, —$CH_2I$, —$OCI_3$, —$OCH_2I$, —$OCHI_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{20}$ is independently oxo, —OH, or —$S(O)_2CH_3$. In embodiments, $R^{20}$ is independently oxo. In embodiments, $R^{20}$ is independently —OH. In embodiments, $R^{20}$ is independently —$S(O)_2CH_3$. In embodiments, $R^{20}$ is —$CH_2C(CH_3)_2OH$.

In embodiments, $R^{20}$ is independently —SH. In embodiments, $R^{20}$ is independently —$S(O)_2CH_3$. In embodiments, $R^{20}$ is independently unsubstituted $C_1$-$C_6$ alkyl. In embodiments, $R^{20}$ is independently unsubstituted 2 to 6 membered heteroalkyl. In embodiments, $R^{20}$ is independently unsubstituted $C_3$-$C_6$ cycloalkyl. In embodiments, $R^{20}$ is independently unsubstituted 3 to 6 membered heterocycloalkyl. In embodiments, $R^{20}$ is independently unsubstituted phenyl. In embodiments, $R^{20}$ is independently or unsubstituted 5 to 6 membered heteroaryl.

In embodiments, a substituted $R^{20}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{20}$ is substituted with a plurality of groups selected from substituent groups, size-limited substituent groups, and lower substituent groups; each substituent group, size-limited substituent group, and/or lower substituent group may optionally be different.

In embodiments, $R^{20}$ is oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

$R^{21}$ is independently oxo, halogen, —CX$^{21}$$_3$, —CHX$^{21}$$_2$, —CH$_2$X$^{21}$, —OCX$^{21}$$_3$, —OCH$_2$X$^{21}$, —OCHX$^{21}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{21}$ is independently oxo, halogen, —CF$_3$, —CHF$_2$, —CH$_2$F, —OCF$_3$, —OCH$_2$F, —OCHF$_2$, —CCl$_3$, —CHCl$_2$, —CH$_2$Cl, —OCCl$_3$, —OCH$_2$Cl, —OCHCl$_2$, —CBr$_3$, —CHBr$_2$, —CH$_2$Br, —OCBr$_3$, —OCH$_2$Br, —OCHBr$_2$, —CI$_3$, —CHI$_2$, —CH$_2$I, —OCI$_3$, —OCH$_2$I, —OCHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{22}$-substituted or unsubstituted alkyl (e.g., C$_1$-C$_8$ alkyl, C$_1$-C$_6$ alkyl, or C$_1$-C$_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., C$_6$-C$_{10}$ aryl, C$_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). Each X$^{21}$ is independently —F, —Cl, —Br, or —I. In embodiments, $R^{21}$ is independently halogen. In embodiments, $R^{21}$ is independently —F.

In embodiments, $R^{21}$ is oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

$R^{22}$ is independently oxo, halogen, —CX$^{22}$$_3$, —CHX$^{22}$$_2$, —CH$_2$X$^{22}$, —OCX$^{22}$$_3$, —OCH$_2$X$^{22}$, —OCHX$^{22}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). Each X$^{22}$ is independently —F, —Cl, —Br, or —I.

In embodiments, each $R^{1A}$ is independently hydrogen, —CX$_3$, —COOH, —CONH$_2$, —CHX$_2$, —CH$_2$X, $R^{20}$-substituted or unsubstituted alkyl (e.g., C$_1$-C$_8$ alkyl, C$_1$-C$_6$ alkyl, or C$_1$-C$_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., C$_6$-C$_{10}$ aryl, C$_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, each $R^{1A}$ is independently hydrogen, —CX$_3$, —COOH, —CONH$_2$, —CHX$_2$, —CH$_2$X, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, each $R^{1A}$ is independently hydrogen, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl, or substituted or unsubstituted heteroaryl (e.g., 5 to 10 membered heteroaryl, 5 to 9 membered heteroaryl, or 5 to 6 membered heteroaryl). In embodiments, each $R^{1A}$ is independently hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, each $R^{1A}$ is independently hydrogen, OH-substituted C$_1$-C$_4$ alkyl, NH$_2$-substituted C$_1$-C$_4$ alkyl, or unsubstituted 5 to 6 membered heterocycloalkyl. In embodiments, each $R^{1A}$ is independently hydrogen. In embodiments, each $R^{1A}$ is independently OH-substituted C$_1$-C$_4$ alkyl. In embodiments, $R^{1A}$ is an OH-substituted ethyl. In embodiments, $R^{1A}$ is an OH-substituted n-propyl. In embodiments, $R^{1A}$ is —CH$_2$C(CH$_3$)$_2$OH. In embodiments, $R^{1A}$ is an OH-substituted methyl. In embodiments, each $R^{1A}$ is independently NH$_2$-substituted C$_1$-C$_4$ alkyl. In embodiments, $R^{1A}$ is an NH$_2$-substituted ethyl. In embodiments, $R^{1A}$ is an NH$_2$-substituted n-propyl. In embodiments, $R^{1A}$ is —CH$_2$C(CH$_3$)$_2$NH$_2$. In embodiments, $R^{1A}$ is —CH$_2$CH$_2$NH$_2$. In embodiments, $R^{1A}$ is an NH$_2$-substituted methyl. In embodiments, each $R^{1A}$ is independently unsubstituted 5 to 6 membered heterocycloalkyl. In embodiments, each $R^{1A}$ is independently unsubstituted tetrahydropyran.

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different.

In embodiments, each $R^{1B}$ is independently hydrogen, $-CX_3$, $-COOH$, $-CONH_2$, $-CHX_2$, $-CH_2X$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, each $R^{1B}$ is independently hydrogen, $-CX_3$, $-COOH$, $-CONH_2$, $-CHX_2$, $-CH_2X$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, each $R^{1B}$ is independently hydrogen, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl, or substituted or unsubstituted heteroaryl (e.g., 5 to 10 membered heteroaryl, 5 to 9 membered heteroaryl, or 5 to 6 membered heteroaryl). In embodiments, each $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, each $R^{1B}$ is independently hydrogen, OH-substituted $C_1$-$C_4$ alkyl, NH$_2$-substituted $C_1$-$C_4$ alkyl, or substituted 5 to 6 membered heterocycloalkyl. In embodiments, each $R^{1B}$ is independently hydrogen. In embodiments, each $R^{1B}$ is independently OH-substituted $C_1$-$C_4$ alkyl. In embodiments, $R^{1B}$ is an OH-substituted ethyl. In embodiments, $R^{1B}$ is an OH-substituted n-propyl. In embodiments, $R^{1B}$ is $-CH_2C(CH_3)_2OH$. In embodiments, $R^{1B}$ is an OH-substituted methyl. In embodiments, each $R^{1B}$ is independently NH2-substituted $C_1$-$C_4$ alkyl. In embodiments, $R^{1B}$ is an NH2-substituted ethyl. In embodiments, $R^{1B}$ is an NH2-substituted n-propyl. In embodiments, $R^{1B}$ is $-CH_2C(CH_3)_2NH_2$. In embodiments, $R^{1B}$ is $-CH_2CH_2NH_2$. In embodiments, $R^{1B}$ is an NH$_2$-substituted methyl. In embodiments, each $R^{1B}$ is independently unsubstituted 5 to 6 membered heterocycloalkyl. In embodiments, each $R^{1B}$ is independently unsubstituted tetrahydropyran.

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, a substituted $R^{1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, a substituted $R^{1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1D}$ is substituted with a plurality of groups selected from substituent groups, size-limited substituent groups, and lower substituent groups; each substituent group, size-limited substituent group, and/or lower substituent group may optionally be different.

In embodiments, $R^{1A}$ and $R^{1B}$ substituents bonded to the same nitrogen atom are joined to form a substituted or unsubstituted 5 to 6 membered heterocycloalkyl. In embodiments, $R^{1A}$ and $R^{1B}$ substituents bonded to the same nitrogen atom are joined to form a substituted morpholinyl. In embodiments, $R^{1A}$ and $R^{1B}$ substituents bonded to the same nitrogen atom are joined to form an unsubstituted morpholinyl. In embodiments, $R^{1A}$ and $R^{1B}$ substituents bonded to the same nitrogen atom are joined to form a substituted piperidinyl. In embodiments, $R^{1A}$ and $R^{1B}$ substituents bonded to the same nitrogen atom are joined to form an unsubstituted piperidinyl. In embodiments, $R^{1A}$ and $R^{1B}$ substituents bonded to the same nitrogen atom are joined to form a substituted oxazepanyl. In embodiments, $R^{1A}$ and $R^{1B}$ substituents bonded to the same nitrogen atom are joined to form an unsubstituted oxazepanyl. In embodiments, $R^{1A}$ and $R^{1B}$ substituents bonded to the same nitrogen atom are joined to form a substituted 1,4-oxazepanyl. In embodiments, $R^{1A}$ and $R^{1B}$ substituents bonded to the same nitrogen atom are joined to form an unsubstituted 1,4-oxazepanyl. In embodiments, $R^{1A}$ and $R^{1B}$ substituents bonded to the same nitrogen atom are joined to form a substituted thiomorpholinyl. In embodiments, $R^{1A}$ and $R^{1B}$ substituents bonded to the same nitrogen atom are joined to form an unsubstituted thiomorpholinyl. In embodiments, $R^{1A}$ and $R^{1B}$ substituents bonded to the same nitrogen atom are joined to form a substituted thiomorpholinyl 1-oxide. In embodiments, $R^{1A}$ and $R^{1B}$ substituents bonded to the same nitrogen atom are joined to form an unsubstituted thiomorpholinyl 1-oxide. In embodiments, $R^{1A}$ and $R^{1B}$ substituents bonded to the same nitrogen atom are joined to form a substituted piperazinyl. In embodiments, $R^{1A}$ and $R^{1B}$ substituents bonded to the same nitrogen atom are joined to form an unsubstituted piperazinyl.

In embodiments, $R^{1A}$ and $R^{1B}$ substituents bonded to the same nitrogen atom may optionally be joined to form an $R^{20}$-substituted or unsubstituted heterocycloalkyl or $R^{20}$-substituted or unsubstituted heteroaryl. In embodiments, $R^{1A}$ and $R^{1B}$ substituents bonded to the same nitrogen atom are joined to form an $R^{20}$-substituted or unsubstituted 5 to 6 membered heterocycloalkyl. In embodiments, $R^{1A}$ and $R^{1B}$ substituents bonded to the same nitrogen atom are joined to form an $R^{20}$-substituted morpholinyl. In embodiments, $R^{1A}$ and $R^{1B}$ substituents bonded to the same nitrogen atom are joined to form an unsubstituted morpholinyl. In embodiments, $R^{1A}$ and $R^{1B}$ substituents bonded to the same nitrogen atom are joined to form an $R^{20}$-substituted piperidinyl. In embodiments, $R^{1A}$ and $R^{1B}$ substituents bonded to the same nitrogen atom are joined to form an unsubstituted piperidinyl. In embodiments, $R^{1A}$ and $R^{1B}$ substituents bonded to the same nitrogen atom are joined to form an $R^{20}$-substituted oxazepanyl. In embodiments, $R^{1A}$ and $R^{1B}$ substituents bonded to the same nitrogen atom are joined to form an unsubstituted oxazepanyl. In embodiments, $R^{1A}$ and $R^{1B}$ substituents bonded to the same nitrogen atom are joined to form an $R^{20}$-substituted 1,4-oxazepanyl. In embodiments, $R^{1A}$ and $R^{1B}$ substituents bonded to the same nitrogen atom are joined to form an unsubstituted 1,4-oxazepanyl. In embodiments, $R^{1A}$ and $R^{1B}$ substituents bonded to the same nitrogen atom are joined to form an $R^{20}$-substituted thiomorpholinyl. In embodiments, $R^{1A}$ and $R^{1B}$ substituents bonded to the same nitrogen atom are joined to form an unsubstituted thiomorpholinyl. In embodiments, $R^{1A}$ and $R^{1B}$ substituents bonded to the same nitrogen atom are joined to form an $R^{20}$-substituted thiomorpholinyl 1-oxide. In embodiments, $R^{1A}$ and $R^{1B}$ substituents bonded to the same nitrogen atom are joined to form an unsubstituted thiomorpholinyl 1-oxide. In embodiments, $R^{1A}$ and $R^{1B}$ substituents bonded to the same nitrogen atom are joined to form an $R^{20}$-substituted piperazinyl. In embodiments, $R^{1A}$ and $R^{1B}$ substituents bonded to the same nitrogen atom are joined to form an unsubstituted piperazinyl.

In embodiments, a substituted heterocycloalkyl formed by the joining of $R^{1A}$ and $R^{1B}$ substituents bonded to the same nitrogen atom is substituted with at least one substituent group, size-limited substituent group, or lower substituent group; wherein if the substituted heterocycloalkyl is substituted with a plurality of groups selected from substituent groups, size-limited substituent groups, and lower substituent groups; each substituent group, size-limited substituent group, and/or lower substituent group may optionally be different.

In embodiments, each $R^{1C}$ is independently hydrogen, —$CX_3$, —COOH, —$CONH_2$, —$CHX_2$, —$CH_2X$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl). In embodiments, $R^{1C}$ is $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl). In embodiments, $R^{1C}$ is $R^{20}$-substituted or unsubstituted aryl (e.g., $C_6$-$C_{10}$ aryl, $C_{10}$ aryl, or phenyl). In embodiments, $R^{1C}$ is $R^{20}$-substituted or unsubstituted phenyl. In embodiments, $R^{1C}$ is an unsubstituted phenyl. In embodiments, $R^{1C}$ is $R^{20}$-substituted phenyl.

In embodiments, each $R^{1C}$ is independently hydrogen, —$CX_3$, —COOH, —$CONH_2$, —$CHX_2$, —$CH_2X$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, each $R^{1D}$ is independently hydrogen, —$CX_3$, —COOH, —$CONH_2$, —$CHX_2$, —$CH_2X$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, each $R^{1D}$ is independently hydrogen, —$CX_3$, —COOH, —$CONH_2$, —$CHX_2$, —$CH_2X$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)—OH, —NHOH, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl, or substituted or unsubstituted heteroaryl (e.g., 5 to 10 membered heteroaryl, 5 to 9 membered heteroaryl, or 5 to 6 membered heteroaryl). In embodiments, $R^2$ is independently —$CF_3$, —$CHF_2$, —$CH_2F$, —$OCF_3$, —$OCH_2F$, —$OCHF_2$, —$CCl_3$, —$CHCl_2$, —$CH_2Cl$, —$OCCl_3$, —$OCH_2Cl$, —$OCHCl_2$, —$CBr_3$, —$CHBr_2$, —$CH_2Br$, —$OCBr_3$, —$OCH_2Br$, —$OCHBr_2$, —$CI_3$, —$CHI_2$, —$CH_2I$, —$OCI_3$, —$OCH_2I$, —$OCHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl). In embodiments, $R^2$ is independently —$CF_3$, —$CHF_2$, —$CH_2F$, —$OCF_3$, —$OCH_2F$, —$OCHF_2$, —$CCl_3$, —$CHCl_2$, —$CH_2Cl$, —$OCCl_3$, —$OCH_2Cl$, —$OCHCl_2$, —$CBr_3$, —$CHBr_2$, —$CH_2Br$, —$OCBr_3$, —$OCH_2Br$, —$OCHBr_2$, —$CI_3$, —$CHI_2$, —$CH_2I$, —$OCI_3$, —$OCH_2I$, —$OCHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^2$ is $R^{23}$-substituted or unsubstituted alkyl (e.g., $C_1$-$C_8$ alkyl, $C_1$-$C_6$ alkyl, or $C_1$-$C_4$ alkyl). In embodiments, $R^2$ is $R^{23}$-substituted alkyl (e.g., $C_1$-$C_8$ alkyl, $C_1$-$C_6$ alkyl, or $C_1$-$C_4$ alkyl). In embodiments, $R^2$ is an unsubstituted alkyl (e.g., $C_1$-$C_8$ alkyl, $C_1$-$C_6$ alkyl, or $C_1$-$C_4$ alkyl).

In embodiments, $R^2$ is $R^{23}$-substituted or unsubstituted methyl. In embodiments, $R^2$ is $R^{23}$-substituted or unsubstituted $C_2$ alkyl. In embodiments, $R^2$ is $R^{23}$-substituted or unsubstituted $C_3$ alkyl. In embodiments, $R^2$ is $R^{23}$-substituted or unsubstituted $C_4$ alkyl. In embodiments, $R^2$ is $R^{23}$-substituted or unsubstituted $C_5$ alkyl. In embodiments, $R^2$ is $R^{23}$-substituted or unsubstituted $C_6$ alkyl. In embodiments, $R^2$ is $R^{23}$-substituted or unsubstituted $C_7$ alkyl. In embodiments, $R^2$ is $R^{23}$-substituted or unsubstituted $C_8$ alkyl. In embodiments, $R^2$ is $R^{23}$-substituted methyl. In embodiments, $R^2$ is $R^{23}$-substituted $C_2$ alkyl. In embodiments, $R^2$ is $R^{23}$-substituted $C_3$ alkyl. In embodiments, $R^2$ is $R^{23}$-substituted $C_4$ alkyl. In embodiments, $R^2$ is $R^{23}$-substituted $C_5$ alkyl. In embodiments, $R^2$ is $R^{23}$-substituted $C_6$ alkyl. In embodiments, $R^2$ is $R^{23}$-substituted $C_7$ alkyl. In embodiments, $R^2$ is $R^{23}$-substituted $C_8$ alkyl. In embodiments, $R^2$ is an unsubstituted methyl. In embodiments, $R^2$ is an unsubstituted $C_2$ alkyl. In embodiments, $R^2$ is an unsubstituted $C_3$ alkyl. In embodiments, $R^2$ is an unsubstituted $C_4$ alkyl. In embodiments, $R^2$ is an unsubstituted $C_5$ alkyl. In embodiments, $R^2$ is an unsubstituted $C_6$ alkyl. In embodiments, $R^2$ is an unsubstituted $C_7$ alkyl. In embodiments, $R^2$ is an unsubstituted $C_8$ alkyl.

$R^{23}$ is independently oxo, halogen, —$CX^{23}_3$, —$CHX^{23}_2$, —$CH_2X^{23}$, —$OCX^3_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each $X^{23}$ is independently —F, —Cl, —Br, or —I. In embodiments, $R^{23}$ is oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

In embodiments, $L^2$ is a bond, $R^{24}$-substituted or unsubstituted alkylene (e.g., $C_1$-$C_8$ alkylene, $C_1$-$C_6$ alkylene, or $C_1$-$C_4$ alkylene), $R^{24}$-substituted or unsubstituted heteroalkylene (e.g., 2 to 8 membered heteroalkylene, 2 to 6 membered heteroalkylene, or 2 to 4 membered heteroalkylene), $R^{24}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{24}$-substituted or unsubstituted heterocycloalkylene (e.g., 3 to 8 membered heterocycloalkylene, 3 to 6 membered heterocycloalkylene, or 5 to 6 membered heterocycloalkylene), $R^{24}$-substituted or unsubstituted arylene (e.g., $C_6$-$C_{10}$ arylene, $C_{10}$ arylene, or phenyl), or $R^{24}$-substituted or unsubstituted heteroarylene (e.g., 5 to 10 membered heteroarylene, 5 to 9 membered heteroarylene, or 5 to 6 membered heteroaryl). In embodiments, $L^2$ is a bond, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenyl), or unsubstituted heteroarylene (e.g., 5 to 10 membered heteroarylene, 5 to 9 membered heteroarylene, or 5 to 6 membered heteroaryl).

In embodiments, $L^2$ is $R^{24}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{24}$-substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene).

In embodiments, $L^2$ is $R^{24}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{24}$-substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene).

In embodiments, $L^2$ is $R^{24}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{24}$-substituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cyclohexenylene.

In embodiments, $L^2$ is $R^{24}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{24}$-substituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted piperidinylene. In embodiments, $L^2$ is an unsubstituted piperizinylene.

In embodiments, $L^2$ is $R^{24}$-substituted or unsubstituted arylene (e.g., $C_6$-$C_{10}$ arylene, $C_{10}$ arylene, or phenylene). In embodiments, $L^2$ is $R^{24}$-substituted arylene (e.g., $C_6$-$C_{10}$ arylene, $C_{10}$ arylene, or phenylene). In embodiments, $L^2$ is an unsubstituted arylene (e.g., $C_6$-$C_{10}$ arylene, $C_{10}$ arylene, or phenylene). In embodiments, $L^2$ is an unsubstituted phenylene.

In embodiments, $L^2$ is $R^{24}$-substituted or unsubstituted heteroarylene (e.g., 5 to 10 membered heteroarylene, 5 to 9 membered heteroarylene, or 5 to 6 membered heteroarylene). In embodiments, $L^2$ is $R^{24}$-substituted heteroarylene (e.g., 5 to 10 membered heteroarylene, 5 to 9 membered heteroarylene, or 5 to 6 membered heteroarylene). In embodiments, $L^2$ is an unsubstituted heteroarylene (e.g., 5 to 10 membered heteroarylene, 5 to 9 membered heteroarylene, or 5 to 6 membered heteroarylene).

In embodiments, $L^2$ is $R^{24}$-substituted or unsubstituted $C_1$-$C_6$ alkylene. In embodiments, $L^2$ is $R^{24}$-substituted $C_1$-$C_6$ alkylene. In embodiments, $L^2$ is unsubstituted $C_1$-$C_6$ alkylene. In embodiments, $L^2$ is $R^{24}$-substituted or unsubstituted $C_2$-$C_6$ alkylene. In embodiments, $L^2$ is $R^{24}$-substituted $C_2$-$C_6$ alkylene. In embodiments, $L^2$ is unsubstituted $C_2$-$C_6$ alkylene. In embodiments, $L^2$ is $R^{24}$-substituted or unsubstituted $C_1$ alkylene. In embodiments, $L^2$ is $R^{24}$-substituted $C_1$ alkylene. In embodiments, $L^2$ is unsubstituted $C_1$ alkylene. In embodiments, $L^2$ is $R^{24}$-substituted or unsubstituted $C_2$ alkylene. In embodiments, $L^2$ is $R^{24}$-substituted $C_2$ alkylene. In embodiments, $L^2$ is unsubstituted $C_2$ alkylene. In embodiments, $L^2$ is $R^{24}$-substituted or unsubstituted $C_3$ alkylene. In embodiments, $L^2$ is $R^{24}$-substituted $C_3$ alkylene. In embodiments, $L^2$ is unsubstituted $C_3$ alkylene. In embodiments, $L^2$ is $R^{24}$-substituted or unsubstituted $C_4$ alkylene. In embodiments, $L^2$ is $R^{24}$-substituted $C_4$ alkylene. In embodiments, $L^2$ is unsubstituted $C_4$ alkylene. In embodiments, $L^2$ is $R^{24}$-substituted or unsubstituted $C_5$ alkylene. In embodiments, $L^2$ is $R^{24}$-substituted $C_5$ alkylene. In embodiments, $L^2$ is unsubstituted $C_5$ alkylene. In embodiments, $L^2$ is $R^{24}$-substituted or unsubstituted $C_6$ alkylene. In embodiments, $L^2$ is $R^{24}$-substituted $C_6$ alkylene. In embodiments, $L^2$ is unsubstituted $C_6$ alkylene.

In embodiments, $L^2$ is $R^{24}$-substituted or unsubstituted 2 to 8 membered heteroalkylene. In embodiments, $L^2$ is $R^{24}$-substituted 2 to 8 membered heteroalkylene. In embodiments, $L^2$ is unsubstituted 2 to 8 membered heteroalkylene. In embodiments, $L^2$ is $R^{24}$-substituted or unsubstituted 2 membered heteroalkylene. In embodiments, $L^2$ is $R^{24}$-substituted 2 membered heteroalkylene. In embodiments, $L^2$ is unsubstituted 2 membered heteroalkylene. In embodiments, $L^2$ is $R^{24}$-substituted or unsubstituted 3 membered heteroalkylene. In embodiments, $L^2$ is $R^{24}$-substituted 3 membered heteroalkylene. In embodiments, $L^2$ is unsubstituted 3 membered heteroalkylene. In embodiments, $L^2$ is $R^{24}$-substituted or unsubstituted 4 membered heteroalkylene. In embodiments, $L^2$ is $R^{24}$-substituted 4 membered heteroalkylene. In embodiments, $L^2$ is unsubstituted 4 membered heteroalkylene. In embodiments, $L^2$ is $R^{24}$-substituted or unsubstituted 5 membered heteroalkylene. In embodiments, $L^2$ is $R^{24}$-substituted 5 membered heteroalkylene. In embodiments, $L^2$ is unsubstituted 5 membered heteroalkylene. In embodiments, $L^2$ is $R^{24}$-substituted or unsubstituted 6 membered heteroalkylene. In embodiments, $L^2$ is $R^{24}$-substituted 6 membered heteroalkylene. In embodiments, $L^2$ is unsubstituted 6 membered heteroalkylene. In embodiments, $L^2$ is $R^{24}$-substituted or unsubstituted$^2$ membered heteroalkylene. In embodiments, $L^2$ is $R^{24}$-substituted$^2$ membered heteroalkylene. In embodiments, $L^2$ is unsubstituted$^2$ membered heteroalkylene.

In embodiments, $L^2$ is $R^{24}$-substituted or unsubstituted $C_4$-$C_6$ cycloalkylene. In embodiments, $L^2$ is $R^{24}$-substituted $C_4$-$C_6$ cycloalkylene. In embodiments, $L^2$ is $R^{24}$-substituted $C_4$-$C_6$ cycloalkylene. In embodiments, $L^2$ is $R^{24}$-substituted $C_4$-$C_6$ cycloalkylene. In embodiments, $L^2$ is $R^{24}$-substituted or unsubstituted $C_4$ cycloalkylene. In embodiments, $L^2$ is $R^{24}$-substituted $C_4$ cycloalkylene. In embodiments, $L^2$ is $R^{24}$-substituted $C_4$ cycloalkylene. In embodiments, $L^2$ is $R^{24}$-substituted or unsubstituted $C_5$ cycloalkylene. In embodiments, $L^2$ is $R^{24}$-substituted $C_5$ cycloalkylene. In embodiments, $L^2$ is $R^{24}$-substituted $C_5$ cycloalkylene.

In embodiments, $L^2$ is $R^{24}$-substituted or unsubstituted 5 to 6 membered heterocycloalkylene. In embodiments, $L^2$ is $R^{24}$-substituted 5 to 6 membered heterocycloalkylene. In embodiments, $L^2$ is unsubstituted 5 to 6 membered heterocycloalkylene. In embodiments, $L^2$ is $R^{24}$-substituted or unsubstituted 5 membered heterocycloalkylene. In embodiments, $L^2$ is $R^{24}$-substituted 5 membered heterocycloalkylene. In embodiments, $L^2$ is unsubstituted 5 membered heterocycloalkylene. In embodiments, $L^2$ is $R^{24}$-substituted or unsubstituted 6 membered heterocycloalkylene. In embodiments, $L^2$ is $R^{24}$-substituted 6 membered heterocycloalkylene. In embodiments, $L^2$ is unsubstituted 6 membered heterocycloalkylene.

In embodiments, $L^2$ is $R^{24}$-substituted or unsubstituted phenylene. In embodiments, $L^2$ is $R^{24}$-substituted phenylene. In embodiments, $L^2$ is unsubstituted phenylene.

In embodiments, $L^2$ is $R^{24}$-substituted or unsubstituted 5 to 6 membered heteroarylene. In embodiments, $L^2$ is $R^{24}$-substituted 5 to 6 membered heteroarylene. In embodiments, $L^2$ is unsubstituted 5 to 6 membered heteroarylene. In embodiments, $L^2$ is $R^{24}$-substituted or unsubstituted 5 membered heteroarylene. In embodiments, $L^2$ is $R^{24}$-substituted 5 membered heteroarylene. In embodiments, $L^2$ is unsubstituted 5 membered heteroarylene. In embodiments, $L^2$ is $R^{24}$-substituted or unsubstituted 6 membered heteroarylene.

In embodiments, L² is R²⁴-substituted 6 membered heteroarylene. In embodiments, L² is unsubstituted 6 membered heteroarylene.

R²⁴ is independently oxo, halogen, —CX²⁴₃, —CHX²⁴₂, —CH₂X²⁴, —OCX²⁴₃, —OCH₂X²⁴, —OCHX²⁴₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C₅-C₆ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C₆-C₁₀ aryl, C₁₀ aryl, or phenyl), or unsubstituted heteroaryl (e.g., 5 to 10 membered heteroaryl, 5 to 9 membered heteroaryl, or 5 to 6 membered heteroaryl). Each X²⁴ is independently —F, —Cl, —Br, or —I.

In embodiments, R²⁴ is oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl. In embodiments, R²⁴ is independently oxo. In embodiments, R²⁴ is independently halogen. In embodiments, R²⁴ is independently —CF₃. In embodiments, R²⁴ is independently —CN. In embodiments, R²⁴ is independently —OH. In embodiments, R²⁴ is independently —NH₂. In embodiments, R²⁴ is independently —COOH. In embodiments, R²⁴ is independently —CONH₂. In embodiments, R²⁴ is independently —NO₂. In embodiments, R²⁴ is independently —SH. In embodiments, R²⁴ is independently —SO₃H. In embodiments, R²⁴ is independently —SO₄H. In embodiments, R²⁴ is independently —SO₂NH₂. In embodiments, R²⁴ is independently —NHNH₂. In embodiments, R²⁴ is independently —ONH₂. In embodiments, R²⁴ is independently —NHC=(O)NHNH₂. In embodiments, R²⁴ is independently —NHC=(O) NH₂. In embodiments, R²⁴ is independently —NHSO₂H. In embodiments, R²⁴ is independently —NHC=(O)H. In embodiments, R²⁴ is independently —NHC(O)—OH. In embodiments, R²⁴ is independently —NHOH. In embodiments, R²⁴ is independently —OCF₃. In embodiments, R²⁴ is independently —OCHF₂.

In embodiments, the compound has the formula:

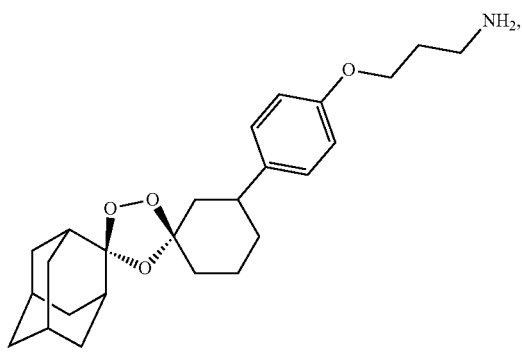

-continued

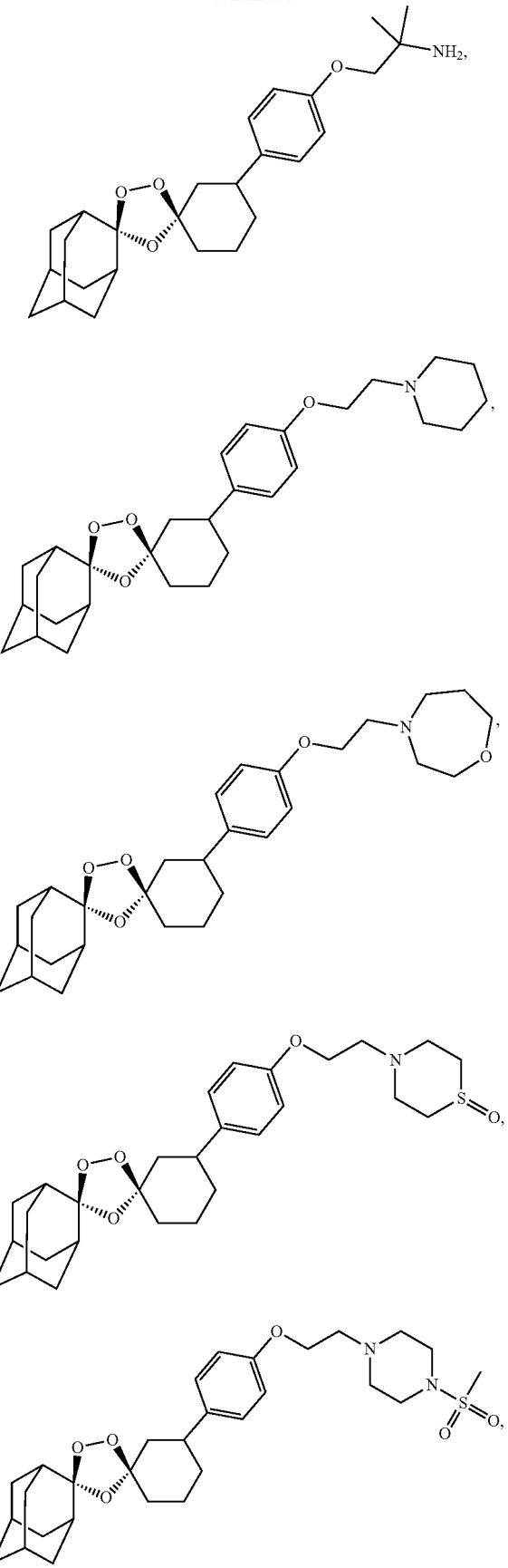

57
-continued
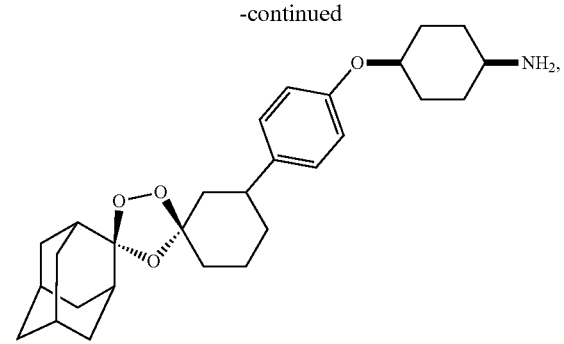
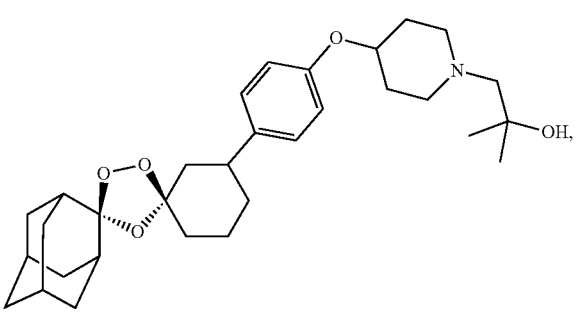
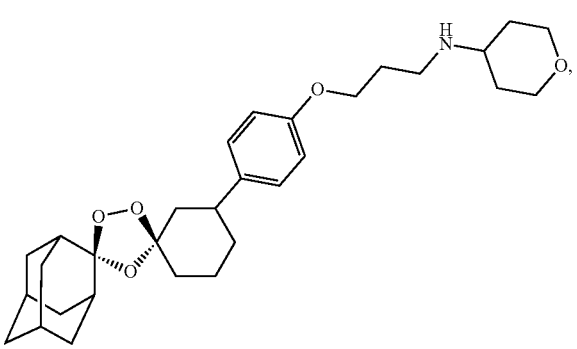
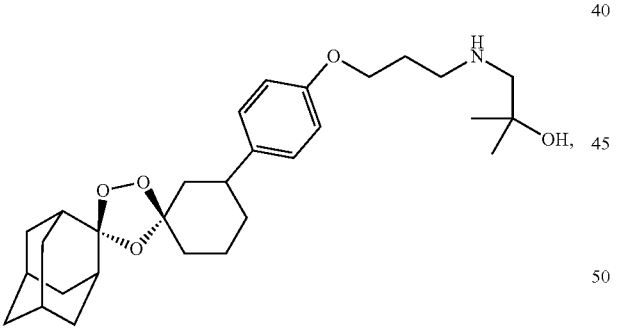
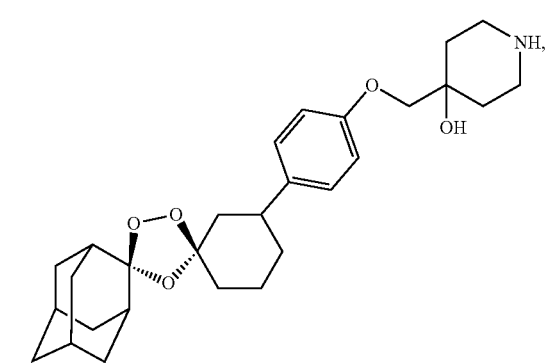
58
-continued
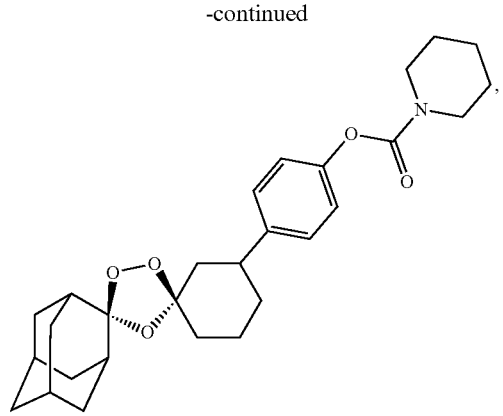
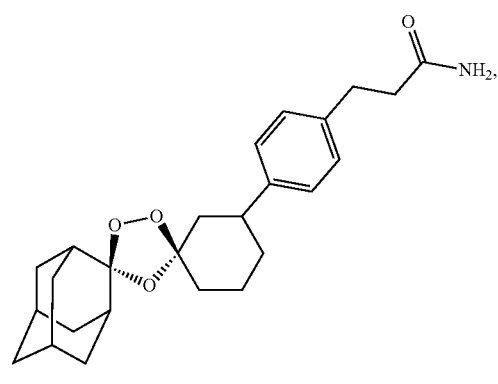
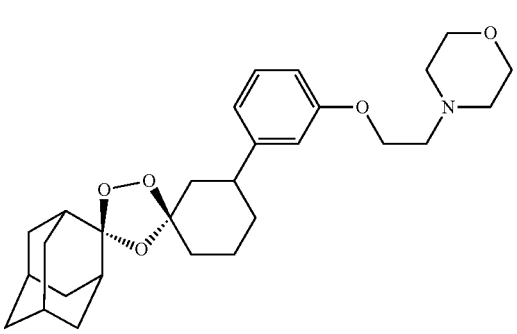
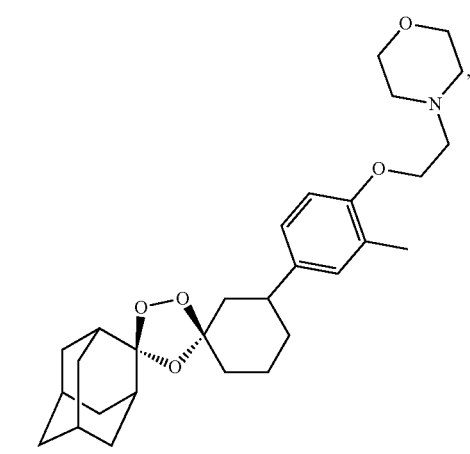

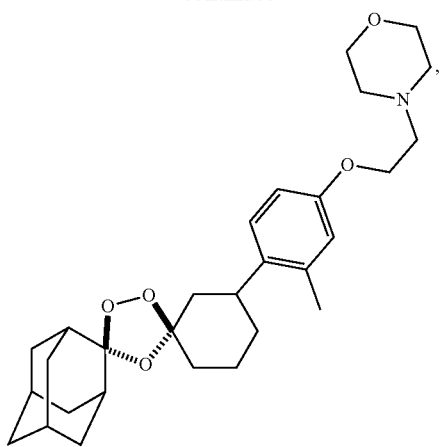
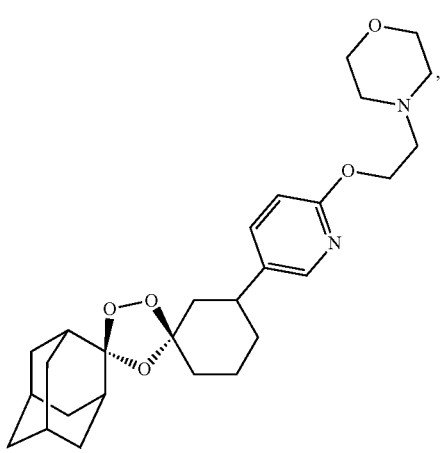
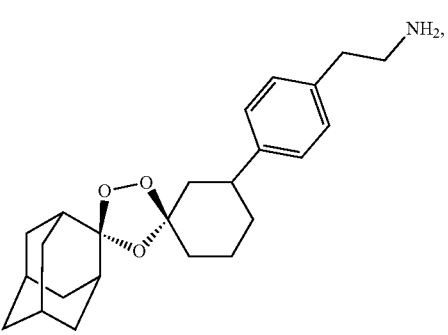
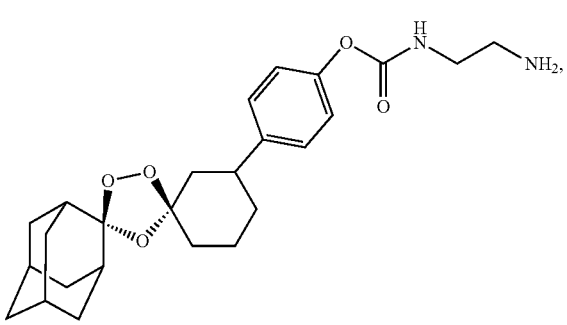
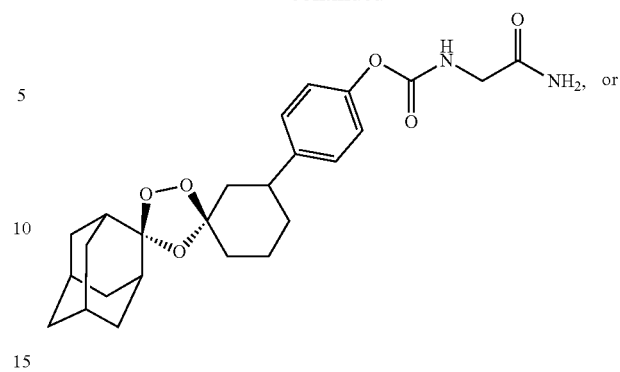
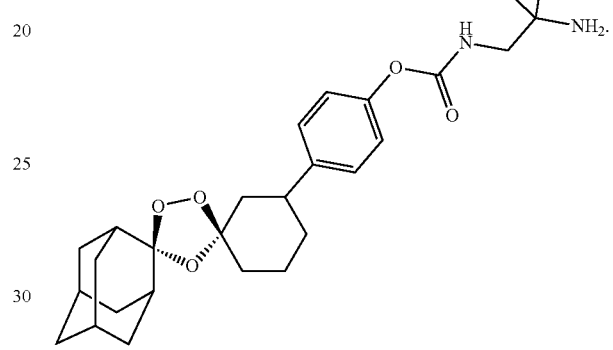
In embodiments, the compound has the formula:
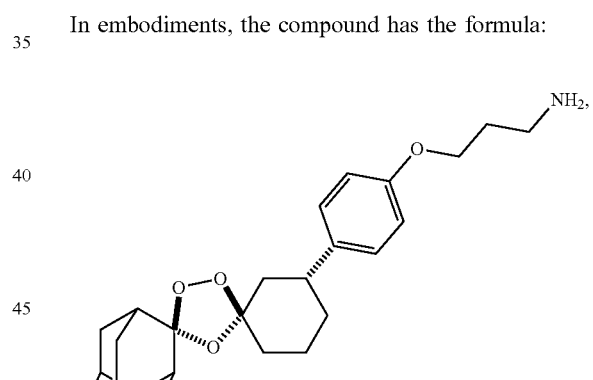
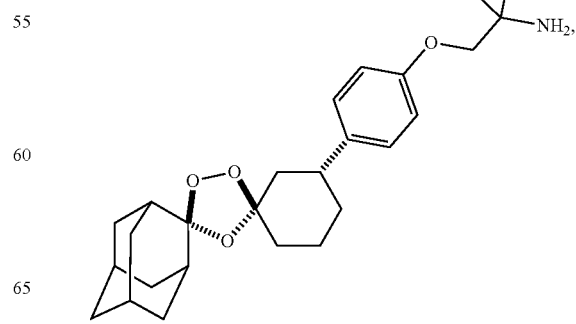

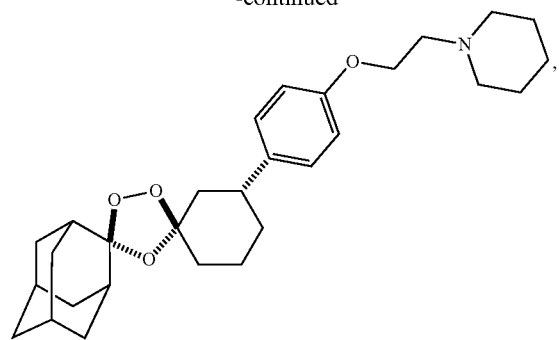
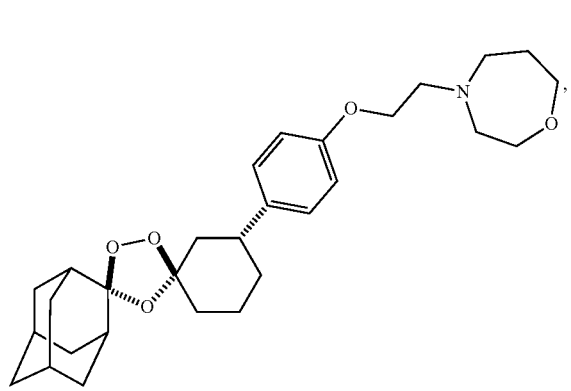
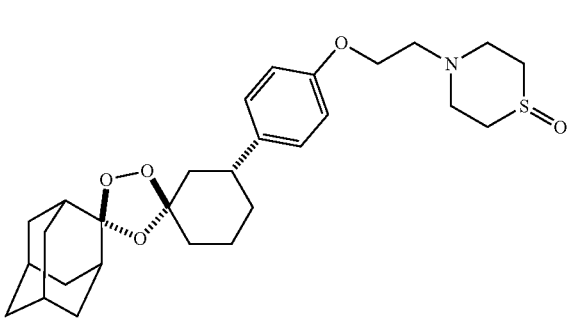
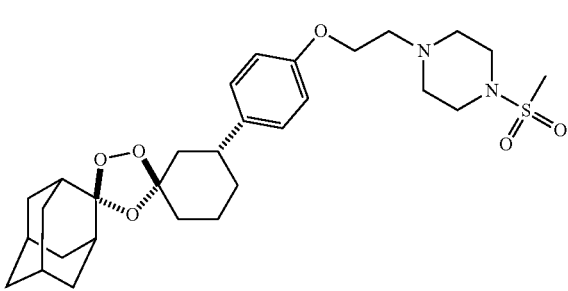
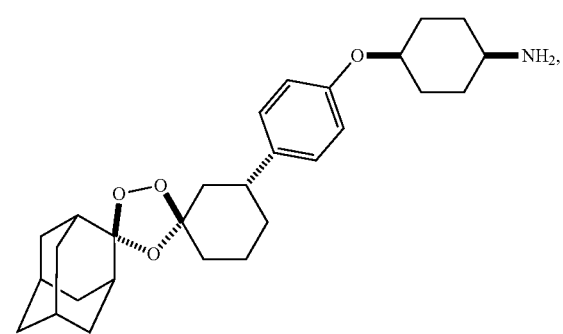
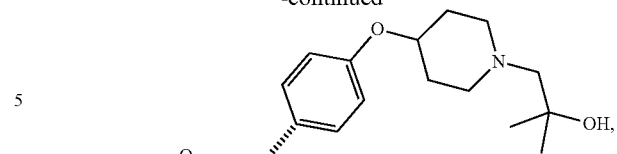
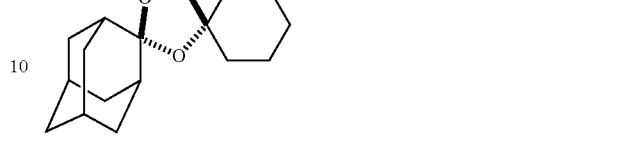
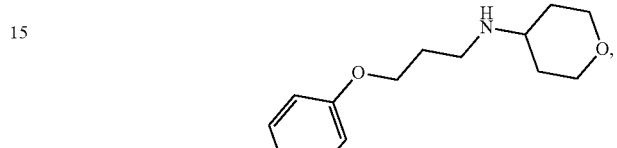
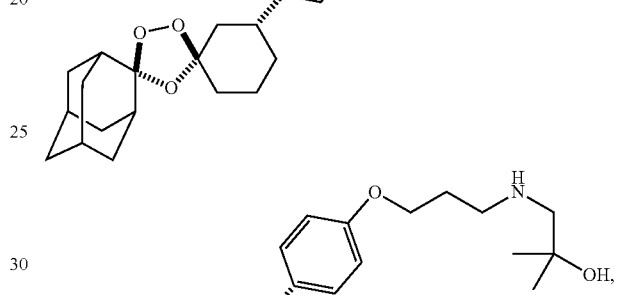
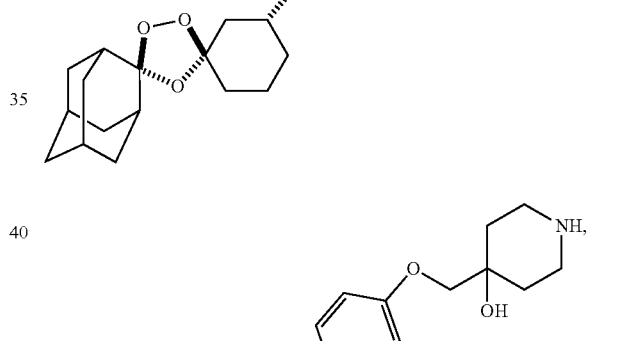
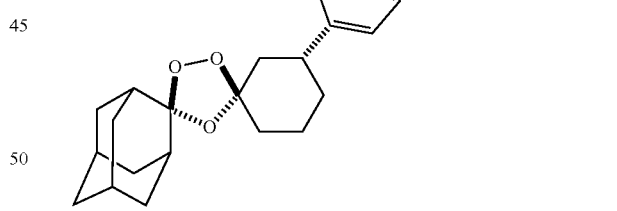
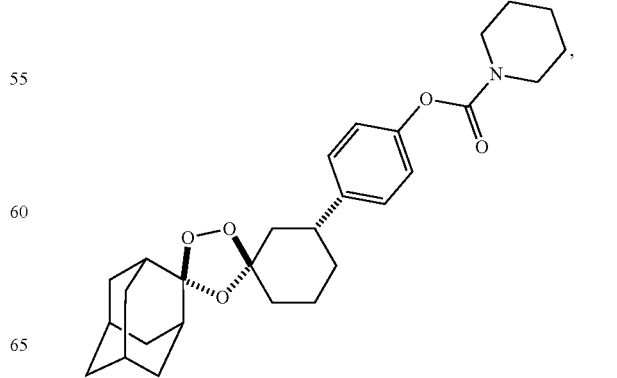

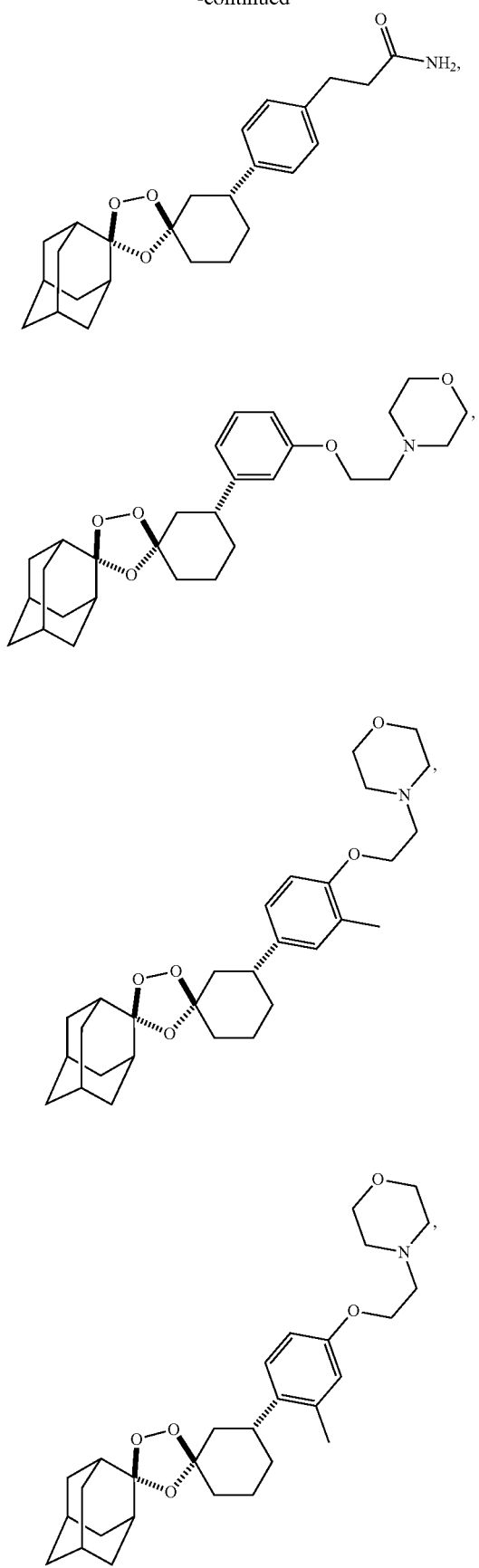
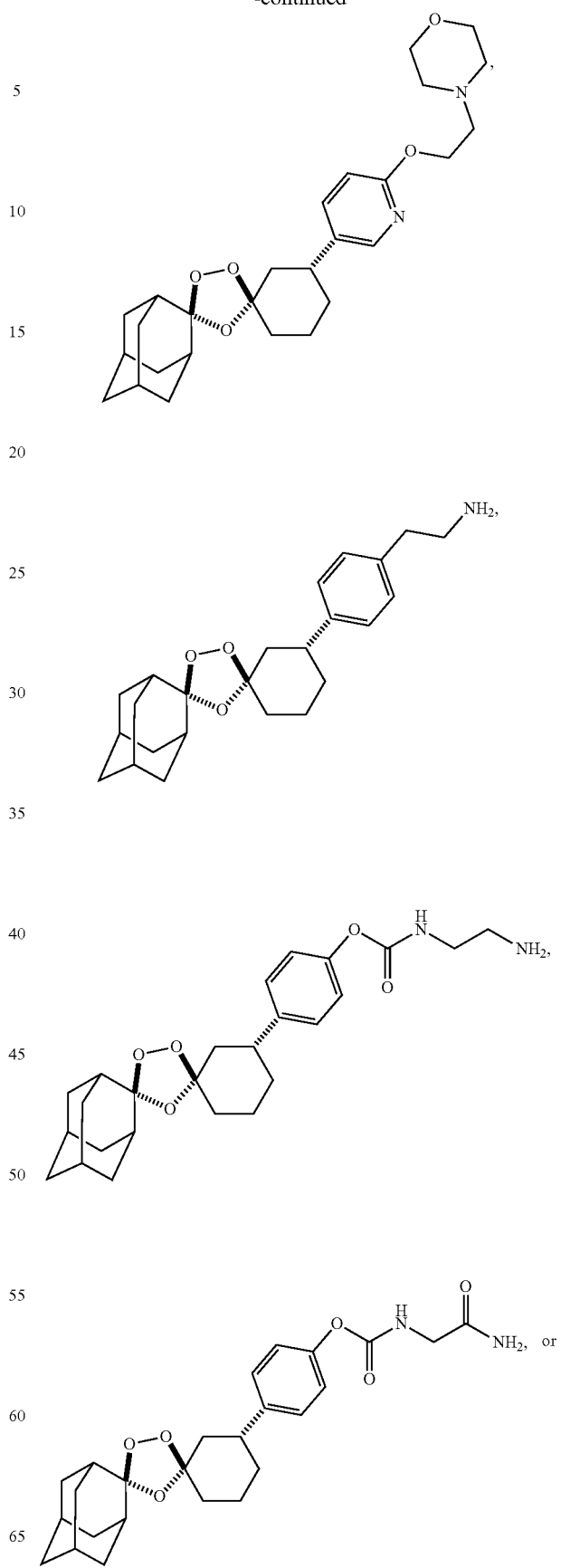

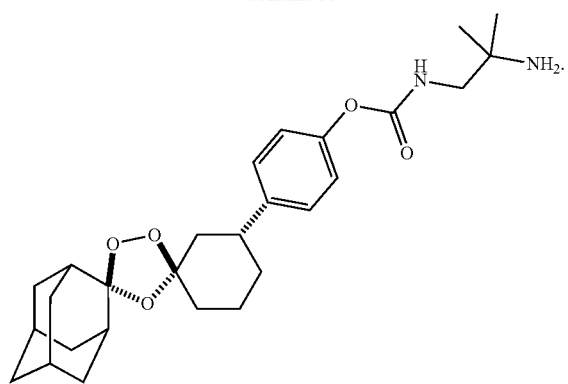
In embodiments, the compound has the formula:
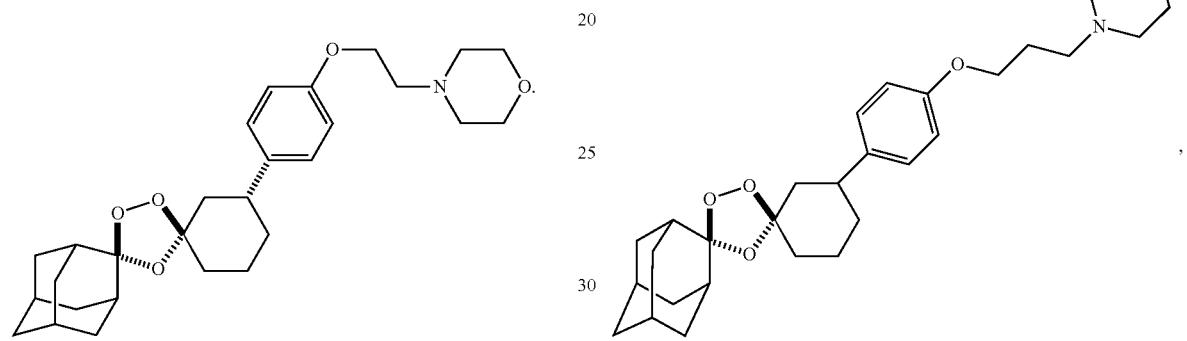
In embodiments, the compound has the formula:
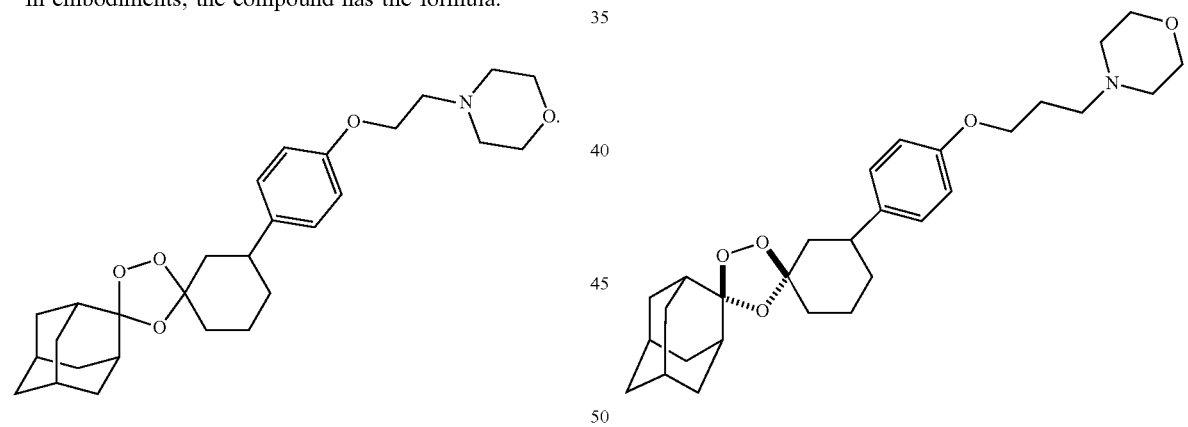
In embodiments, the compound has the formula:
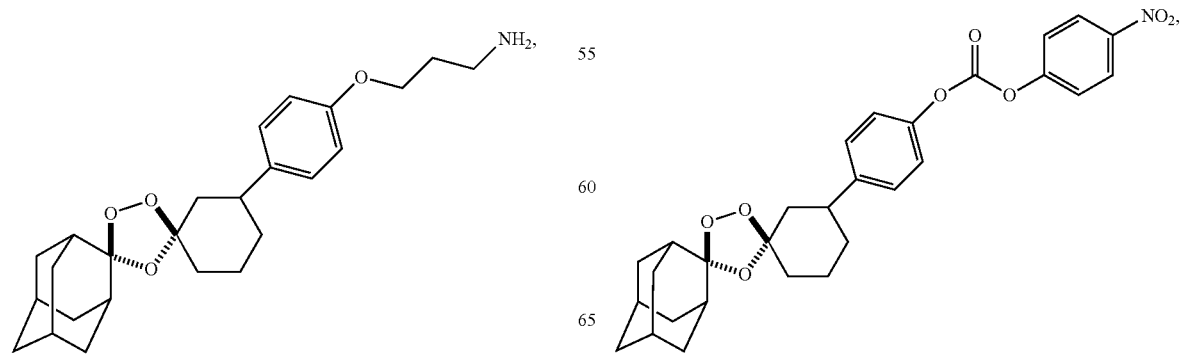
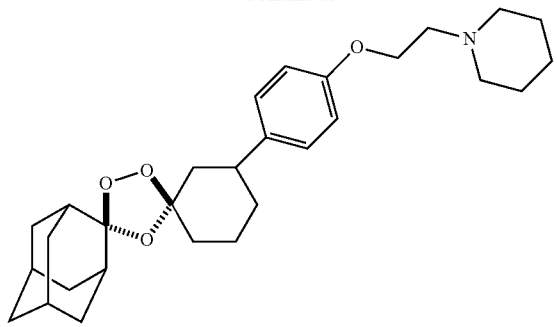
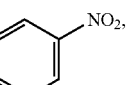

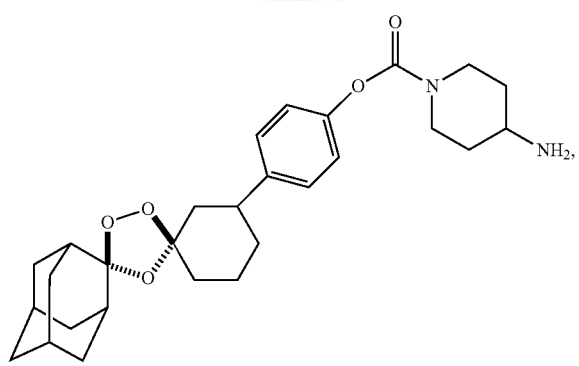
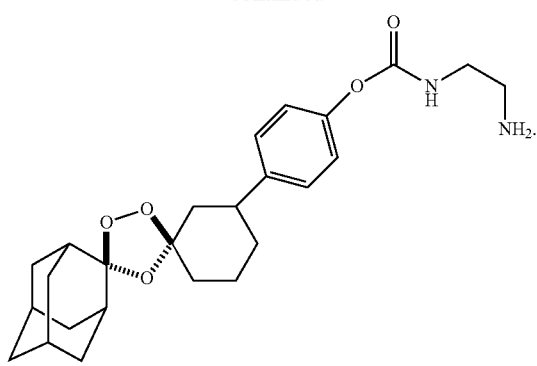
In embodiments, the compound has the formula:
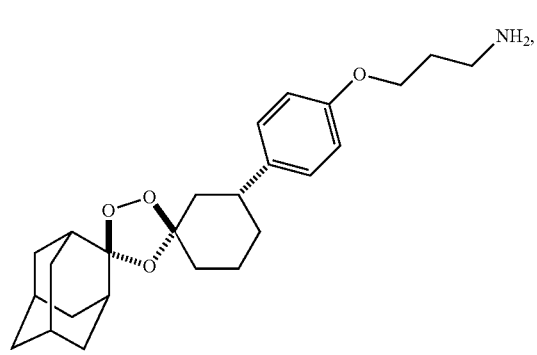
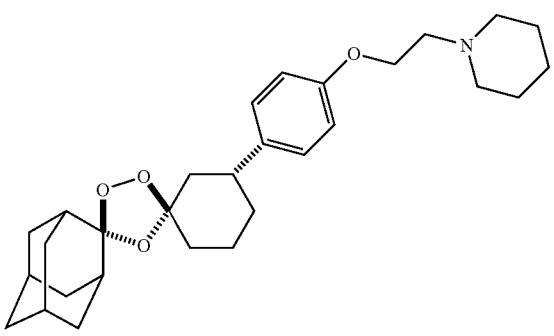
, or
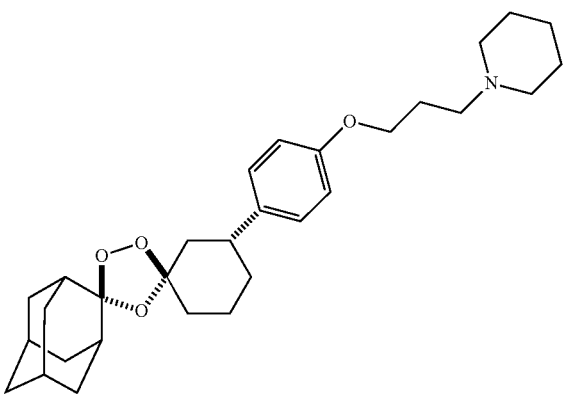
, 69
-continued
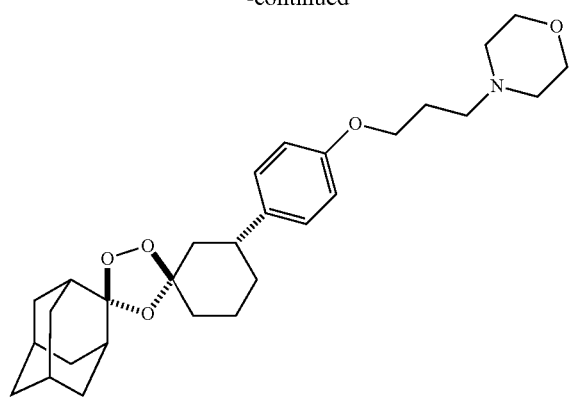
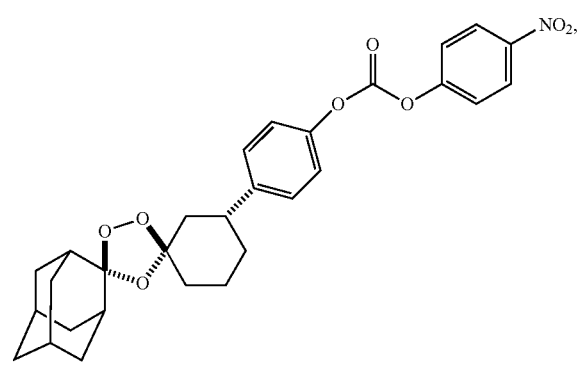
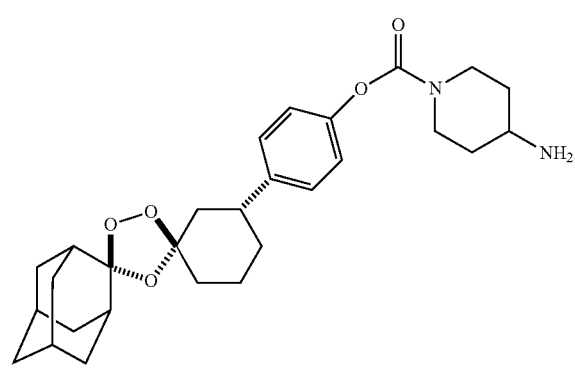
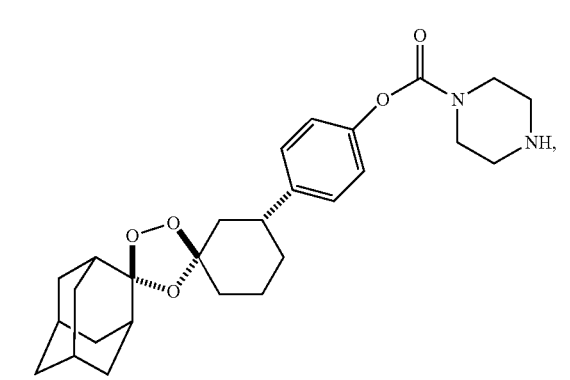
70
-continued
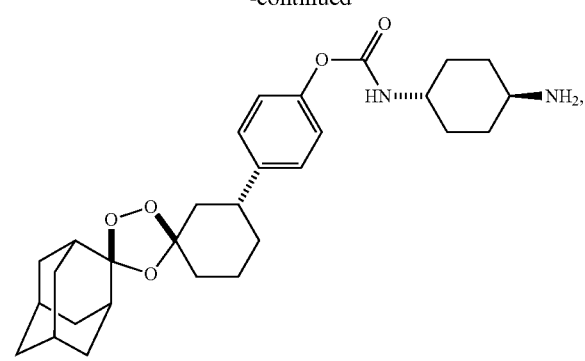
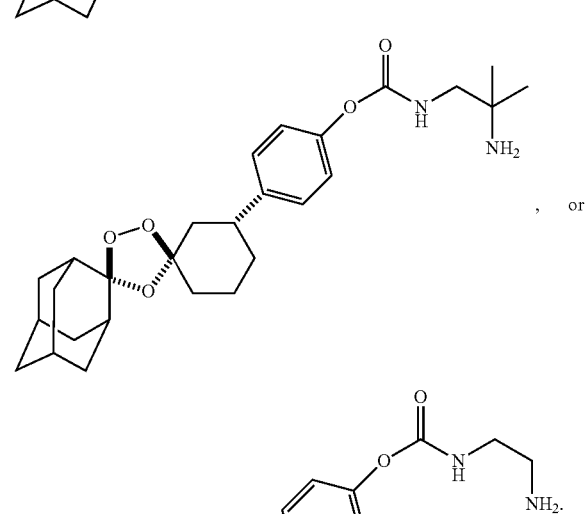
, or
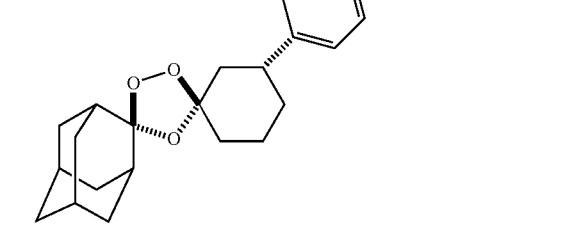
In embodiments, the compound has the formula:
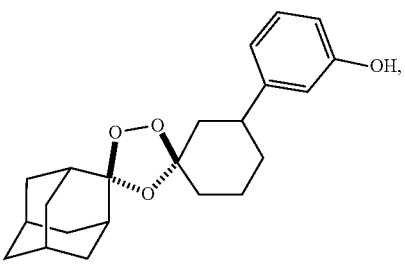
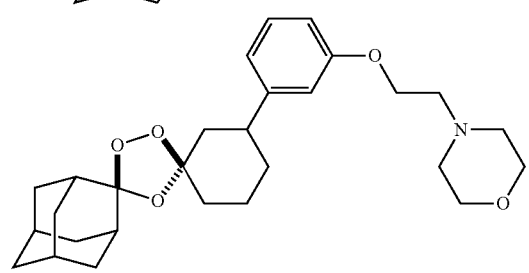
, -continued
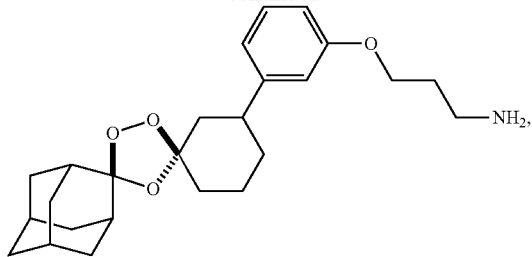
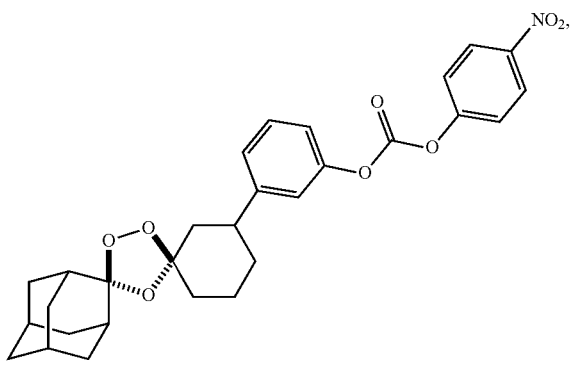
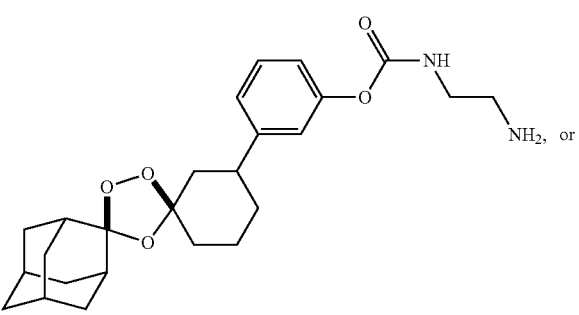
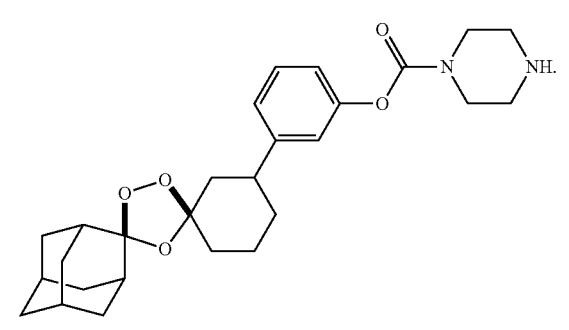
In embodiments, the compound has the formula:
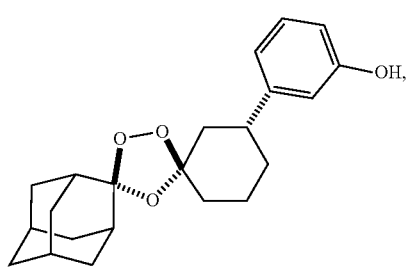
-continued
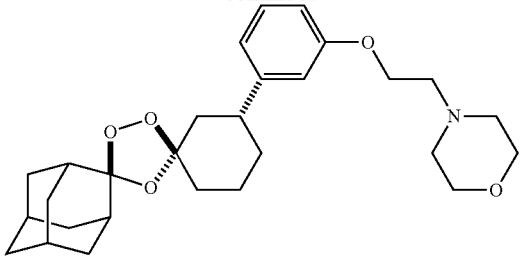
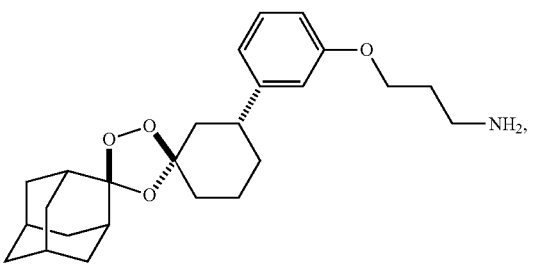
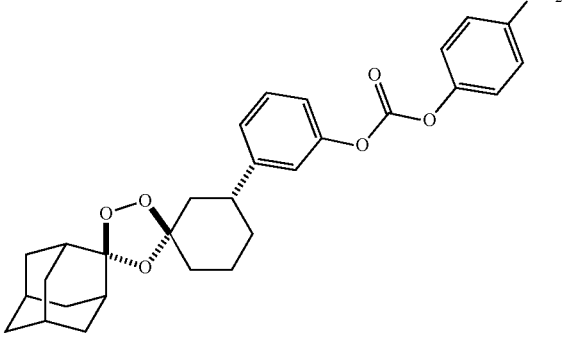
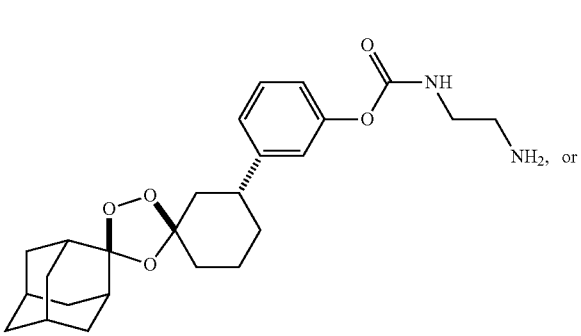
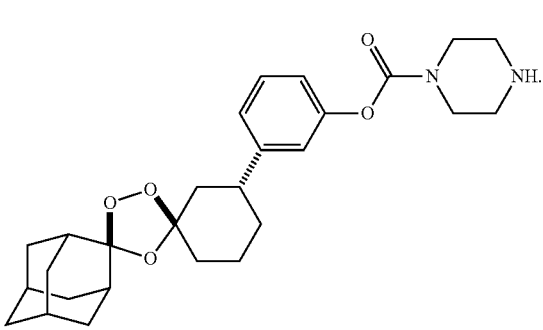

In embodiments, the compound has the formula:

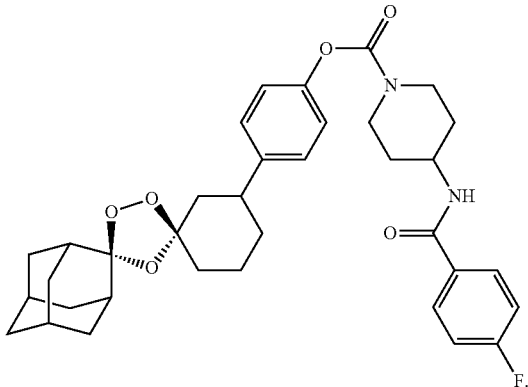

In embodiments, the compound has the formula:

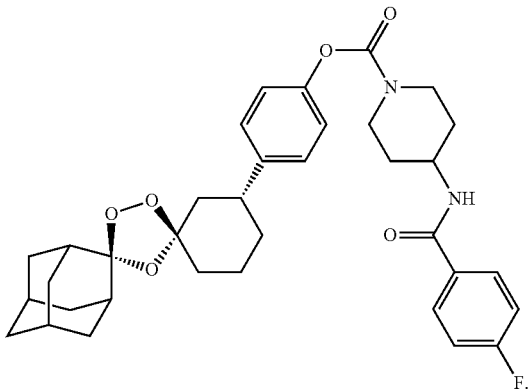

In an aspect is provided a compound having the formula:

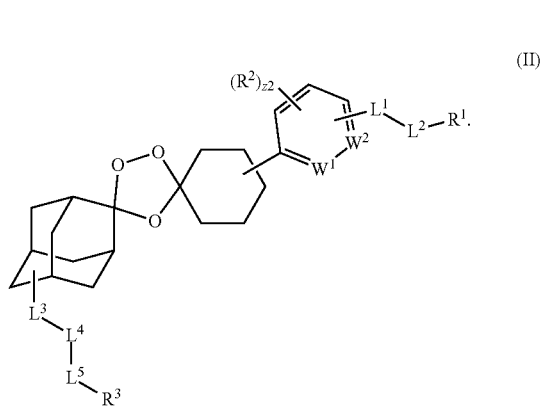

(II)

$W^1$, $W^2$, $L^1$, $L^2$, $R^1$, $R^2$, z2, $R^{1A}$, $R^{1B}$, $R^{1C}$, $R^{1D}$, X, $X^1$, $X^2$, n1, m1, and v1 are as described herein, including in embodiments.

$R^3$ is independently hydrogen, halogen, $-CX^3{}_3$, $-CHX^3{}_2$, $-CH_2X^3$, $-OCX^3{}_3$, $-OCH_2X^3$, $-OCHX^3{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

$L^3$, $L^4$, and $L^5$ are independently a bond, $-O-$, $-NH-$, $-OC(O)-$, $-C(O)O-$, $-NHC(O)-$, $-C(O)NH-$, $-OC(O)O-$, $-OC(O)NH-$, $-NHC(O)O-$, $-NHC(O)NH-$, $-S-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, -$L^3$-$L^4$-$L^5$- is $-C(O)NHCH_2CH_2CH_2NHC(O)Ph-$. In embodiments, -$L^3$-$L^4$-$L^5$- is bond. In embodiments, -$L^3$-$L^4$-$L^5$- is $-O-$. In embodiments, -$L^3$-$L^4$-$L^5$- is $-NH-$. In embodiments, -$L^3$-$L^4$-$L^5$- is $-OC(O)-$. In embodiments, -$L^3$-$L^4$-$L^5$- is $-C(O)O-$. In embodiments, -$L^3$-$L^4$-$L^5$- is $-NHC(O)-$. In embodiments, -$L^3$-$L^4$-$L^5$- is $-C(O)NH-$. In embodiments, -$L^3$-$L^4$-$L^5$- is $-OC(O)O-$. In embodiments, -$L^3$-$L^4$-$L^5$- is $-OC(O)NH-$. In embodiments, -$L^3$-$L^4$-$L^5$- is $-NHC(O)O-$. In embodiments, -$L^3$-$L^4$-$L^5$- is $-NHC(O)NH-$. In embodiments, -$L^3$-$L^4$-$L^5$- is $-S-$.

In embodiments, -$L^3$-$L^4$-$L^5$- is

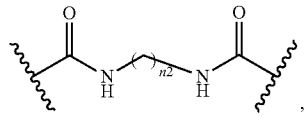

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, -$L^3$-$L^4$-$L^5$- is

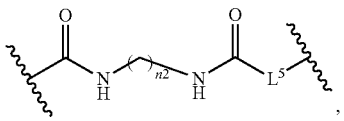

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, -$L^3$-$L^4$-$L^5$- is

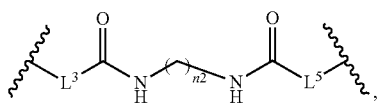

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, the compound has the formula:

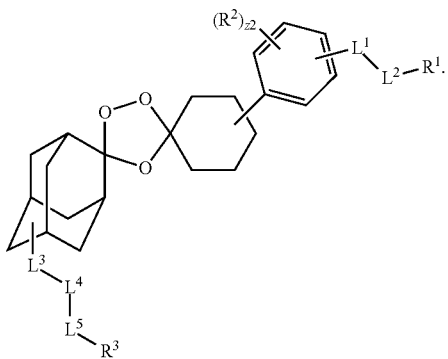

In embodiments, $L^3$ is independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, $R^{25}$-substituted or unsubstituted alkylene (e.g., $C_1$-$C_8$ alkylene, $C_1$-$C_6$ alkylene, or $C_1$-$C_4$ alkylene), $R^{25}$-substituted or unsubstituted heteroalkylene (e.g., 2 to 8 membered heteroalkylene, 2 to 6 membered heteroalkylene, or 2 to 4 membered heteroalkylene), $R^{25}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{25}$-substituted or unsubstituted heterocycloalkylene (e.g., 3 to 8 membered heterocycloalkylene, 3 to 6 membered heterocycloalkylene, or 5 to 6 membered heterocycloalkylene), $R^{25}$-substituted or unsubstituted arylene (e.g., $C_6$-$C_{10}$ arylene, $C_{10}$ arylene, or phenylene), or $R^{25}$-substituted or unsubstituted heteroarylene (e.g., 5 to 10 membered heteroarylene, 5 to 9 membered heteroarylene, or 5 to 6 membered heteroaryl). In embodiments, $L^3$ is independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroaryl).

$R^{25}$ is independently oxo, halogen, —$CX^{25}_3$, —$CHX^{25}_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{25}$ is independently oxo, halogen, —$CF_3$, —$CHF_2$, —$CH_2F$, —$OCF_3$, —$OCH_2F$, —$OCHF_2$, —$CCl_3$, —$CHCl_2$, —$CH_2Cl$, —$OCCl_3$, —$OCH_2Cl$, —$OCHCl_2$, —$CBr_3$, —$CHBr_2$, —$CH_2Br$, —$OCBr_3$, —$OCH_2Br$, —$OCHBr_2$, —$CI_3$, —$CHI_2$, —$CH_2I$, —$OCI_3$, —$OCH_2I$, —$OCHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each $X^{25}$ is independently —F, —Cl, —Br, or —I.

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, a substituted $L^4$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^4$ is substituted with a plurality of groups selected from substituent groups, size-limited substituent groups, and lower substituent groups; each substituent group, size-limited substituent group, and/or lower substituent group may optionally be different. In embodiments, a substituted $L^5$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^5$ is substituted with a plurality of groups selected from substituent groups, size-limited substituent groups, and lower substituent groups; each substituent group, size-limited substituent group, and/or lower substituent group may optionally be different.

In embodiments, $L^3$ is $R^{25}$-substituted or unsubstituted alkylene (e.g., $C_1$-$C_8$ alkylene, $C_1$-$C_6$ alkylene, or $C_1$-$C_4$ alkylene). In embodiments, $L^3$ is $R^{25}$-substituted alkylene (e.g., $C_1$-$C_8$ alkylene, $C_1$-$C_6$ alkylene, or $C_1$-$C_4$ alkylene). In embodiments, $L^3$ is an unsubstituted alkylene (e.g., $C_1$-$C_8$ alkylene, $C_1$-$C_6$ alkylene, or $C_1$-$C_4$ alkylene).

In embodiments, $L^3$ is $R^{25}$-substituted or unsubstituted heteroalkylene (e.g., 2 to 8 membered heteroalkylene, 2 to 6 membered heteroalkylene, or 2 to 4 membered heteroalkylene). In embodiments, $L^3$ is $R^{25}$-substituted heteroalkylene (e.g., 2 to 8 membered heteroalkylene, 2 to 6 membered heteroalkylene, or 2 to 4 membered heteroalkylene). In embodiments, $L^3$ is an unsubstituted heteroalkylene (e.g., 2 to 8 membered heteroalkylene, 2 to 6 membered heteroalkylene, or 2 to 4 membered heteroalkylene).

In embodiments, $L^3$ is $R^{25}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^3$ is $R^{25}$-substituted cycloalkylene (e.g., $C_3$-$C_8$ cycloalkylene, $C_3$-$C_6$ cycloalkylene, or $C_5$-$C_6$ cycloalkylene). In embodiments, $L^3$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^3$ is $R^{25}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^3$ is $R^{25}$-substituted heterocycloalkylene (e.g., 3 to 8 membered heterocycloalkylene, 3 to 6 membered heterocycloalkylene, or 5 to 6 membered heterocycloalkylene). In embodiments, $L^3$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^3$ is $R^{25}$-substituted or unsubstituted arylene (e.g., $C_6$-$C_{10}$ arylene, $C_{10}$ arylene, or phenylene). In embodiments, $L^3$ is $R^{25}$-substituted arylene (e.g., $C_6$-$C_{10}$ arylene, $C_{10}$ arylene, or phenylene). In embodiments, $L^3$ is an unsubstituted arylene (e.g., $C_6$-$C_{10}$ arylene, $C_{10}$ arylene, or phenylene).

In embodiments, $L^3$ is $R^{25}$-substituted or unsubstituted heteroarylene (e.g., 5 to 10 membered heteroarylene, 5 to 9 membered heteroarylene, or 5 to 6 membered heteroarylene). In embodiments, $L^3$ is $R^{25}$-substituted heteroarylene (e.g., 5 to 10 membered heteroarylene, 5 to 9 membered heteroarylene, or 5 to 6 membered heteroarylene). In embodiments, $L^3$ is an unsubstituted heteroarylene (e.g., 5 to 10 membered heteroarylene, 5 to 9 membered heteroarylene, or 5 to 6 membered heteroarylene).

In embodiments, $L^3$ is $R^{25}$-substituted or unsubstituted $C_1$-$C_6$ alkylene. In embodiments, $L^3$ is $R^{25}$-substituted $C_1$-$C_6$ alkylene. In embodiments, $L^3$ is unsubstituted $C_1$-$C_6$ alkylene. In embodiments, $L^3$ is $R^{25}$-substituted or unsubstituted $C_2$-$C_6$ alkylene. In embodiments, $L^3$ is $R^{25}$-substituted $C_2$-$C_6$ alkylene. In embodiments, $L^3$ is unsubstituted $C_2$-$C_6$ alkylene. In embodiments, $L^3$ is $R^{25}$-substituted or unsubstituted $C_1$ alkylene. In embodiments, $L^3$ is $R^{25}$-substituted $C_1$ alkylene. In embodiments, $L^3$ is unsubstituted $C_1$ alkylene. In embodiments, $L^3$ is $R^{25}$-substituted or unsubstituted $C_2$ alkylene. In embodiments, $L^3$ is $R^{25}$-substituted $C_2$ alkylene. In embodiments, $L^3$ is unsubstituted $C_2$ alkylene. In embodiments, $L^3$ is $R^{25}$-substituted or unsubstituted $C_3$ alkylene. In embodiments, $L^3$ is $R^{25}$-substituted $C_3$ alkylene. In embodiments, $L^3$ is unsubstituted $C_3$ alkylene. In embodiments, $L^3$ is $R^{25}$-substituted or unsubstituted $C_4$ alkylene. In embodiments, $L^3$ is $R^{25}$-substituted $C_4$ alkylene. In embodiments, $L^3$ is unsubstituted $C_4$ alkylene. In embodiments, $L^3$ is $R^{25}$-substituted or unsubstituted $C_5$ alkylene. In embodiments, $L^3$ is $R^{25}$-substituted $C_5$ alkylene. In embodiments, $L^3$ is unsubstituted $C_5$ alkylene. In embodiments, $L^3$ is $R^{25}$-substituted or unsubstituted $C_6$ alkylene. In embodiments, $L^3$ is $R^{25}$-substituted $C_6$ alkylene. In embodiments, $L^3$ is unsubstituted $C_6$ alkylene.

In embodiments, $L^3$ is $R^{25}$-substituted or unsubstituted 2 to 8 membered heteroalkylene. In embodiments, $L^3$ is $R^{25}$-substituted 2 to 8 membered heteroalkylene. In embodiments, $L^3$ is unsubstituted 2 to 8 membered heteroalkylene. In embodiments, $L^3$ is $R^{25}$-substituted or unsubstituted 2 membered heteroalkylene. In embodiments, $L^3$ is $R^{25}$-substituted 2 membered heteroalkylene. In embodiments, $L^3$ is unsubstituted 2 membered heteroalkylene. In embodiments, $L^3$ is $R^{25}$-substituted or unsubstituted 3 membered heteroalkylene. In embodiments, $L^3$ is $R^{25}$-substituted 3 membered heteroalkylene. In embodiments, $L^3$ is unsubstituted 3 membered heteroalkylene. In embodiments, $L^3$ is $R^{25}$-substituted or unsubstituted 4 membered heteroalkylene. In embodiments, $L^3$ is $R^{25}$-substituted 4 membered heteroalkylene. In embodiments, $L^3$ is unsubstituted 4 membered heteroalkylene. In embodiments, $L^3$ is $R^{25}$-substituted or unsubstituted 5 membered heteroalkylene. In embodiments, $L^3$ is $R^{25}$-substituted 5 membered heteroalkylene. In embodiments, $L^3$ is unsubstituted 5 membered heteroalkylene. In embodiments, $L^3$ is $R^{25}$-substituted or unsubstituted 6 membered heteroalkylene. In embodiments, $L^3$ is $R^{25}$-substituted 6 membered heteroalkylene. In embodiments, $L^3$ is unsubstituted 6 membered heteroalkylene. In embodiments, $L^3$ is $R^{25}$-substituted or unsubstituted$^3$ membered heteroalkylene. In embodiments, $L^3$ is $R^{25}$-substituted$^3$ membered heteroalkylene. In embodiments, $L^3$ is unsubstituted$^3$ membered heteroalkylene.

In embodiments, $L^3$ is $R^{25}$-substituted or unsubstituted $C_4$-$C_6$ cycloalkylene. In embodiments, $L^3$ is $R^{25}$-substituted $C_4$-$C_6$ cycloalkylene. In embodiments, $L^3$ is $R^{25}$-substituted $C_4$-$C_6$ cycloalkylene. In embodiments, $L^3$ is $R^{25}$-substituted or unsubstituted $C_4$ cycloalkylene. In embodiments, $L^3$ is $R^{25}$-substituted $C_4$ cycloalkylene. In embodiments, $L^3$ is $R^{25}$-substituted $C_4$ cycloalkylene. In embodiments, $L^3$ is $R^{25}$-substituted or unsubstituted $C_5$ cycloalkylene. In embodiments, $L^3$ is $R^{25}$-substituted $C_5$ cycloalkylene. In embodiments, $L^3$ is $R^{25}$-substituted $C_5$ cycloalkylene.

In embodiments, $L^3$ is $R^{25}$-substituted or unsubstituted 5 to 6 membered heterocycloalkylene. In embodiments, $L^3$ is $R^{25}$-substituted 5 to 6 membered heterocycloalkylene. In embodiments, $L^3$ is unsubstituted 5 to 6 membered heterocycloalkylene. In embodiments, $L^3$ is $R^{25}$-substituted or unsubstituted 5 membered heterocycloalkylene. In embodiments, $L^3$ is $R^{25}$-substituted 5 membered heterocycloalkylene. In embodiments, $L^3$ is unsubstituted 5 membered heterocycloalkylene. In embodiments, $L^3$ is $R^{25}$-substituted or unsubstituted 6 membered heterocycloalkylene. In embodiments, $L^3$ is $R^{25}$-substituted 6 membered heterocycloalkylene. In embodiments, $L^3$ is unsubstituted 6 membered heterocycloalkylene.

In embodiments, $L^3$ is $R^{25}$-substituted or unsubstituted phenylene. In embodiments, $L^3$ is $R^{25}$-substituted phenylene. In embodiments, $L^3$ is unsubstituted phenylene.

In embodiments, $L^3$ is $R^{25}$-substituted or unsubstituted 5 to 6 membered heteroarylene. In embodiments, $L^3$ is $R^{25}$-substituted 5 to 6 membered heteroarylene. In embodiments, $L^3$ is unsubstituted 5 to 6 membered heteroarylene. In embodiments, $L^3$ is $R^{25}$-substituted or unsubstituted 5 membered heteroarylene. In embodiments, $L^3$ is $R^{25}$-substituted 5 membered heteroarylene. In embodiments, $L^3$ is unsubstituted 5 membered heteroarylene. In embodiments, $L^3$ is $R^{25}$-substituted or unsubstituted 6 membered heteroarylene. In embodiments, $L^3$ is $R^{25}$-substituted 6 membered heteroarylene. In embodiments, $L^3$ is unsubstituted 6 membered heteroarylene.

In embodiments, $L^4$ independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, $R^{26}$-substituted or unsubstituted alkylene (e.g., $C_1$-$C_8$ alkylene, $C_1$-$C_6$ alkylene, or $C_1$-$C_4$ alkylene), $R^{26}$-substituted or unsubstituted heteroalkylene (e.g., 2 to 8 membered heteroalkylene, 2 to 6 membered heteroalkylene, or 2 to 4 membered heteroalkylene), $R^{26}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{26}$-substituted or unsubstituted heterocycloalkylene (e.g., 3 to 8 membered heterocycloalkylene, 3 to 6 membered heterocycloalkylene, or 5 to 6 membered heterocycloalkylene), $R^{26}$-substituted or unsubstituted arylene (e.g., $C_6$-$C_{10}$ arylene, $C_{10}$ arylene, or phenyl), or $R^{26}$-substituted or unsubstituted heteroarylene (e.g., 5 to 10 membered heteroarylene, 5 to 9 membered heteroarylene, or 5 to 6 membered heteroaryl). In embodiments, $L^4$ independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenyl), or unsubstituted heteroarylene (e.g., 5 to 10 membered heteroarylene, 5 to 9 membered heteroarylene, or 5 to 6 membered heteroaryl).

$R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each $X^{26}$ is independently —F, —Cl, —Br, or —I.

In embodiments, $L^4$ is $R^{26}$-substituted or unsubstituted alkylene (e.g., $C_1$-$C_8$ alkylene, $C_1$-$C_6$ alkylene, or $C_1$-$C_4$ alkylene). In embodiments, $L^4$ is $R^{26}$-substituted alkylene (e.g., $C_1$-$C_8$ alkylene, $C_1$-$C_6$ alkylene, or $C_1$-$C_4$ alkylene). In embodiments, $L^4$ is an unsubstituted alkylene (e.g., $C_1$-$C_8$ alkylene, $C_1$-$C_6$ alkylene, or $C_1$-$C_4$ alkylene).

In embodiments, $L^4$ is $R^{26}$-substituted or unsubstituted heteroalkylene (e.g., 2 to 8 membered heteroalkylene, 2 to 6 membered heteroalkylene, or 2 to 4 membered heteroalkylene). In embodiments, $L^4$ is $R^{26}$-substituted heteroalkylene (e.g., 2 to 8 membered heteroalkylene, 2 to 6 membered heteroalkylene, or 2 to 4 membered heteroalkylene). In embodiments, $L^4$ is an unsubstituted heteroalkylene (e.g., 2 to 8 membered heteroalkylene, 2 to 6 membered heteroalkylene, or 2 to 4 membered heteroalkylene).

In embodiments, $L^4$ is $R^{26}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is $R^{26}$-substituted cycloalkylene (e.g., $C_3$-$C_8$ cycloalkylene, $C_3$-$C_6$ cycloalkylene, or $C_5$-$C_6$ cycloalkylene). In embodiments, $L^4$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^4$ is $R^{26}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is $R^{26}$-substituted heterocycloalkylene (e.g., 3 to 8 membered heterocycloalkylene, 3 to 6 membered heterocycloalkylene, or 5 to 6 membered heterocycloalkylene). In embodiments, $L^4$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^4$ is $R^{26}$-substituted or unsubstituted arylene (e.g., $C_6$-$C_{10}$ arylene, $C_{10}$ arylene, or phenylene). In embodiments, $L^4$ is $R^{26}$-substituted arylene (e.g., $C_6$-$C_{10}$ arylene, $C_{10}$ arylene, or phenylene). In embodiments, $L^4$ is an unsubstituted arylene (e.g., $C_6$-$C_{10}$ arylene, $C_{10}$ arylene, or phenylene).

In embodiments, $L^4$ is $R^{26}$-substituted or unsubstituted heteroarylene (e.g., 5 to 10 membered heteroarylene, 5 to 9 membered heteroarylene, or 5 to 6 membered heteroarylene). In embodiments, $L^4$ is $R^{26}$-substituted heteroarylene (e.g., 5 to 10 membered heteroarylene, 5 to 9 membered heteroarylene, or 5 to 6 membered heteroarylene). In embodiments, $L^4$ is an unsubstituted heteroarylene (e.g., 5 to 10 membered heteroarylene, 5 to 9 membered heteroarylene, or 5 to 6 membered heteroarylene).

In embodiments, $L^4$ is $R^{26}$-substituted or unsubstituted $C_1$-$C_6$ alkylene. In embodiments, $L^4$ is $R^{26}$-substituted $C_1$-$C_6$ alkylene. In embodiments, $L^4$ is unsubstituted $C_1$-$C_6$ alkylene. In embodiments, $L^4$ is $R^{26}$-substituted or unsubstituted $C_2$-$C_6$ alkylene. In embodiments, $L^4$ is $R^{26}$-substituted $C_2$-$C_6$ alkylene. In embodiments, $L^4$ is unsubstituted $C_2$-$C_6$ alkylene. In embodiments, $L^4$ is $R^{26}$-substituted or unsubstituted $C_1$ alkylene. In embodiments, $L^4$ is $R^{26}$-substituted $C_1$ alkylene. In embodiments, $L^4$ is unsubstituted $C_1$ alkylene. In embodiments, $L^4$ is $R^{26}$-substituted or unsubstituted $C_2$ alkylene. In embodiments, $L^4$ is $R^{26}$-substituted $C_2$ alkylene. In embodiments, $L^4$ is unsubstituted $C_2$ alkylene. In embodiments, $L^4$ is $R^{26}$-substituted or unsubstituted $C_3$ alkylene. In embodiments, $L^4$ is $R^{26}$-substituted $C_3$ alkylene. In embodiments, $L^4$ is unsubstituted $C_3$ alkylene. In embodiments, $L^4$ is $R^{26}$-substituted or unsubstituted $C_4$ alkylene. In embodiments, $L^4$ is $R^{26}$-substituted $C_4$ alkylene. In embodiments, $L^4$ is unsubstituted $C_4$ alkylene. In embodiments, $L^4$ is $R^{26}$-substituted or unsubstituted $C_5$ alkylene. In embodiments, $L^4$ is $R^{26}$-substituted $C_5$ alkylene. In embodiments, $L^4$ is unsubstituted $C_5$ alkylene. In embodiments, $L^4$ is $R^{26}$-substituted or unsubstituted $C_6$ alkylene. In embodiments, $L^4$ is $R^{26}$-substituted $C_6$ alkylene. In embodiments, $L^4$ is unsubstituted $C_6$ alkylene.

In embodiments, $L^4$ is $R^{26}$-substituted or unsubstituted 2 to 8 membered heteroalkylene. In embodiments, $L^4$ is $R^{26}$-substituted 2 to 8 membered heteroalkylene. In embodiments, $L^4$ is unsubstituted 2 to 8 membered heteroalkylene. In embodiments, $L^4$ is $R^{26}$-substituted or unsubstituted 2 membered heteroalkylene. In embodiments, $L^4$ is $R^{26}$-substituted 2 membered heteroalkylene. In embodiments, $L^4$ is unsubstituted 2 membered heteroalkylene. In embodiments, $L^4$ is $R^{26}$-substituted or unsubstituted 3 membered heteroalkylene. In embodiments, $L^4$ is $R^{26}$-substituted 3 membered heteroalkylene. In embodiments, $L^4$ is unsubstituted 3 membered heteroalkylene. In embodiments, $L^4$ is $R^{26}$-substituted or unsubstituted 4 membered heteroalkylene. In embodiments, $L^4$ is $R^{26}$-substituted 4 membered heteroalkylene. In embodiments, $L^4$ is unsubstituted 4 membered heteroalkylene. In embodiments, $L^4$ is $R^{26}$-substituted or unsubstituted 5 membered heteroalkylene. In embodiments, $L^4$ is $R^{26}$-substituted 5 membered heteroalkylene. In embodiments, $L^4$ is unsubstituted 5 membered heteroalkylene. In embodiments, $L^4$ is $R^{26}$-substituted or unsubstituted 6 membered heteroalkylene. In embodiments, $L^4$ is $R^{26}$-substituted 6 membered heteroalkylene. In embodiments, $L^4$ is unsubstituted 6 membered heteroalkylene. In embodiments, $L^4$ is $R^{26}$-substituted or unsubstituted 4 membered heteroalkylene.

In embodiments, $L^4$ is $R^{26}$-substituted⁴ membered heteroalkylene. In embodiments, $L^4$ is unsubstituted⁴ membered heteroalkylene.

In embodiments, $L^4$ is $R^{26}$-substituted or unsubstituted $C_4$-$C_6$ cycloalkylene. In embodiments, $L^4$ is $R^{26}$-substituted $C_4$-$C_6$ cycloalkylene. In embodiments, $L^4$ is $R^{26}$-substituted $C_4$-$C_6$ cycloalkylene. In embodiments, $L^4$ is $R^{26}$-substituted or unsubstituted $C_4$ cycloalkylene. In embodiments, $L^4$ is $R^{26}$-substituted $C_4$ cycloalkylene. In embodiments, $L^4$ is $R^{26}$-substituted $C_4$ cycloalkylene. In embodiments, $L^4$ is $R^{26}$-substituted or unsubstituted $C_5$ cycloalkylene. In embodiments, $L^4$ is $R^{26}$-substituted $C_5$ cycloalkylene. In embodiments, $L^4$ is $R^{26}$-substituted $C_5$ cycloalkylene.

In embodiments, $L^4$ is $R^{26}$-substituted or unsubstituted 5 to 6 membered heterocycloalkylene. In embodiments, $L^4$ is $R^{26}$-substituted 5 to 6 membered heterocycloalkylene. In embodiments, $L^4$ is unsubstituted 5 to 6 membered heterocycloalkylene. In embodiments, $L^4$ is $R^{26}$-substituted or unsubstituted 5 membered heterocycloalkylene. In embodiments, $L^4$ is $R^{26}$-substituted 5 membered heterocycloalkylene. In embodiments, $L^4$ is unsubstituted 5 membered heterocycloalkylene. In embodiments, $L^4$ is $R^{26}$-substituted or unsubstituted 6 membered heterocycloalkylene. In embodiments, $L^4$ is $R^{26}$-substituted 6 membered heterocycloalkylene. In embodiments, $L^4$ is unsubstituted 6 membered heterocycloalkylene.

In embodiments, $L^4$ is $R^{26}$-substituted or unsubstituted phenylene. In embodiments, $L^4$ is $R^{26}$-substituted phenylene. In embodiments, $L^4$ is unsubstituted phenylene.

In embodiments, $L^4$ is $R^{26}$-substituted or unsubstituted 5 to 6 membered heteroarylene. In embodiments, $L^4$ is $R^{26}$-substituted 5 to 6 membered heteroarylene. In embodiments, $L^4$ is unsubstituted 5 to 6 membered heteroarylene. In embodiments, $L^4$ is $R^{26}$-substituted or unsubstituted 5 membered heteroarylene. In embodiments, $L^4$ is $R^{26}$-substituted 5 membered heteroarylene. In embodiments, $L^4$ is unsubstituted 5 membered heteroarylene. In embodiments, $L^4$ is $R^{26}$-substituted or unsubstituted 6 membered heteroarylene. In embodiments, $L^4$ is $R^{26}$-substituted 6 membered heteroarylene. In embodiments, $L^4$ is unsubstituted 6 membered heteroarylene.

In embodiments, $L^5$ independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, $R^{27}$-substituted or unsubstituted alkylene (e.g., $C_1$-$C_8$ alkylene, $C_1$-$C_6$ alkylene, or $C_1$-$C_4$ alkylene), $R^{27}$-substituted or unsubstituted heteroalkylene (e.g., 2 to 8 membered heteroalkylene, 2 to 6 membered heteroalkylene, or 2 to 4 membered heteroalkylene), $R^{27}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{27}$-substituted or unsubstituted heterocycloalkylene (e.g., 3 to 8 membered heterocycloalkylene, 3 to 6 membered heterocycloalkylene, or 5 to 6 membered heterocycloalkylene), $R^{27}$-substituted or unsubstituted arylene (e.g., $C_6$-$C_{10}$ arylene, $C_{10}$ arylene, or phenyl), or $R^{27}$-substituted or unsubstituted heteroarylene (e.g., 5 to 10 membered heteroarylene, 5 to 9 membered heteroarylene, or 5 to 6 membered heteroaryl). In embodiments, $L^5$ independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenyl), or unsubstituted heteroarylene (e.g., 5 to 10 membered heteroarylene, 5 to 9 membered heteroarylene, or 5 to 6 membered heteroaryl).

$R^{27}$ is independently oxo, halogen, —$CX^{27}{}_3$, —$CHX^{27}{}_2$, —$CH_2X^{27}$, —$OCX^{27}{}_3$, —$OCH_2X^{27}$, —$OCHX^{27}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each $X^{27}$ is independently —F, —Cl, —Br, or —I.

In embodiments, $L^5$ is $R^{27}$-substituted or unsubstituted alkylene (e.g., $C_1$-$C_8$ alkylene, $C_1$-$C_6$ alkylene, or $C_1$-$C_4$ alkylene). In embodiments, $L^5$ is $R^{27}$-substituted alkylene (e.g., $C_1$-$C_8$ alkylene, $C_1$-$C_6$ alkylene, or $C_1$-$C_4$ alkylene). In embodiments, $L^5$ is an unsubstituted alkylene (e.g., $C_1$-$C_8$ alkylene, $C_1$-$C_6$ alkylene, or $C_1$-$C_4$ alkylene).

In embodiments, $L^5$ is $R^{27}$-substituted or unsubstituted heteroalkylene (e.g., 2 to 8 membered heteroalkylene, 2 to 6 membered heteroalkylene, or 2 to 4 membered heteroalkylene). In embodiments, $L^5$ is $R^{27}$-substituted heteroalkylene (e.g., 2 to 8 membered heteroalkylene, 2 to 6 membered heteroalkylene, or 2 to 4 membered heteroalkylene). In embodiments, $L^5$ is an unsubstituted heteroalkylene (e.g., 2 to 8 membered heteroalkylene, 2 to 6 membered heteroalkylene, or 2 to 4 membered heteroalkylene).

In embodiments, $L^5$ is $R^{27}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is $R^{27}$-substituted cycloalkylene (e.g., $C_3$-$C_8$ cycloalkylene, $C_3$-$C_6$ cycloalkylene, or $C_5$-$C_6$ cycloalkylene). In embodiments, $L^5$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^5$ is $R^{27}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is $R^{27}$-substituted heterocycloalkylene (e.g., 3 to 8 membered heterocycloalkylene, 3 to 6 membered heterocycloalkylene, or 5 to 6 membered heterocycloalkylene). In embodiments, $L^5$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^5$ is $R^{27}$-substituted or unsubstituted arylene (e.g., $C_6$-$C_{10}$ arylene, $C_{10}$ arylene, or phenylene). In embodiments, $L^5$ is $R^{27}$-substituted arylene (e.g., $C_6$-$C_{10}$ arylene, $C_{10}$ arylene, or phenylene). In embodiments, $L^5$ is an unsubstituted arylene (e.g., $C_6$-$C_{10}$ arylene, $C_{10}$ arylene, or phenylene).

In embodiments, $L^5$ is $R^{27}$-substituted or unsubstituted heteroarylene (e.g., 5 to 10 membered heteroarylene, 5 to 9 membered heteroarylene, or 5 to 6 membered heteroarylene). In embodiments, $L^5$ is $R^{27}$-substituted heteroarylene (e.g., 5 to 10 membered heteroarylene, 5 to 9 membered heteroarylene, or 5 to 6 membered heteroarylene). In embodiments, $L^5$ is an unsubstituted heteroarylene (e.g., 5 to 10 membered heteroarylene, 5 to 9 membered heteroarylene, or 5 to 6 membered heteroarylene).

In embodiments, $L^5$ is $R^{27}$-substituted or unsubstituted $C_1$-$C_6$ alkylene. In embodiments, $L^5$ is $R^{27}$-substituted $C_1$-$C_6$ alkylene. In embodiments, $L^5$ is unsubstituted $C_1$-$C_6$ alkylene. In embodiments, $L^5$ is $R^{27}$-substituted or unsubstituted $C_2$-$C_6$ alkylene. In embodiments, $L^5$ is $R^{27}$-substituted $C_2$-$C_6$ alkylene. In embodiments, $L^5$ is unsubstituted $C_2$-$C_6$ alkylene. In embodiments, $L^5$ is $R^{27}$-substituted or unsubstituted $C_1$ alkylene. In embodiments, $L^5$ is $R^{27}$-substituted $C_1$ alkylene. In embodiments, $L^5$ is unsubstituted $C_1$ alkylene. In embodiments, $L^5$ is $R^{27}$-substituted or unsubstituted $C_2$ alkylene. In embodiments, $L^5$ is $R^{27}$-substituted $C_2$ alkylene. In embodiments, $L^5$ is unsubstituted $C_2$ alkylene. In embodiments, $L^5$ is $R^{27}$-substituted or unsubstituted $C_3$ alkylene. In embodiments, $L^5$ is $R^{27}$-substituted $C_3$ alkylene. In embodiments, $L^5$ is unsubstituted $C_3$ alkylene. In embodiments, $L^5$ is $R^{27}$-substituted or unsubstituted $C_4$ alkylene. In embodiments, $L^5$ is $R^{27}$-substituted $C_4$ alkylene. In embodiments, $L^5$ is unsubstituted $C_4$ alkylene. In embodiments, $L^5$ is $R^{27}$-substituted or unsubstituted $C_5$ alkylene. In embodiments, $L^5$ is $R^{27}$-substituted $C_5$ alkylene. In embodiments, $L^5$ is unsubstituted $C_5$ alkylene. In embodiments, $L^5$ is $R^{27}$-substituted or unsubstituted $C_6$ alkylene. In embodiments, $L^5$ is $R^{27}$-substituted $C_6$ alkylene. In embodiments, $L^5$ is unsubstituted $C_6$ alkylene.

In embodiments, $L^5$ is $R^{27}$-substituted or unsubstituted 2 to 8 membered heteroalkylene. In embodiments, $L^5$ is $R^{27}$-substituted 2 to 8 membered heteroalkylene. In embodiments, $L^5$ is unsubstituted 2 to 8 membered heteroalkylene. In embodiments, $L^5$ is $R^{27}$-substituted or unsubstituted 2 membered heteroalkylene. In embodiments, $L^5$ is $R^{27}$-substituted 2 membered heteroalkylene. In embodiments, $L^5$ is unsubstituted 2 membered heteroalkylene. In embodiments, $L^5$ is $R^{27}$-substituted or unsubstituted 3 membered heteroalkylene. In embodiments, $L^5$ is $R^{27}$-substituted 3 membered heteroalkylene. In embodiments, $L^5$ is unsubstituted 3 membered heteroalkylene. In embodiments, $L^5$ is $R^{27}$-substituted or unsubstituted 4 membered heteroalkylene. In embodiments, $L^5$ is $R^{27}$-substituted 4 membered heteroalkylene. In embodiments, $L^5$ is unsubstituted 4 membered heteroalkylene. In embodiments, $L^5$ is $R^{27}$-substituted or unsubstituted 5 membered heteroalkylene. In embodiments, $L^5$ is $R^{27}$-substituted 5 membered heteroalkylene. In embodiments, $L^5$ is unsubstituted 5 membered heteroalkylene. In embodiments, $L^5$ is $R^{27}$-substituted or unsubstituted 6 membered heteroalkylene. In embodiments, $L^5$ is $R^{27}$-substituted 6 membered heteroalkylene. In embodiments, $L^5$ is unsubstituted 6 membered heteroalkylene. In embodiments, $L^5$ is $R^{27}$-substituted or unsubstituted 5 membered heteroalkylene. In embodiments, $L^5$ is $R^{27}$-substituted 5 membered heteroalkylene. In embodiments, $L^5$ is unsubstituted 5 membered heteroalkylene.

In embodiments, $L^5$ is $R^{27}$-substituted or unsubstituted $C_4$-$C_6$ cycloalkylene. In embodiments, $L^5$ is $R^{27}$-substituted $C_4$-$C_6$ cycloalkylene. In embodiments, $L^5$ is $R^{27}$-substituted $C_4$-$C_6$ cycloalkylene. In embodiments, $L^5$ is $R^{27}$-substituted or unsubstituted $C_4$ cycloalkylene. In embodiments, $L^5$ is $R^{27}$-substituted $C_4$ cycloalkylene. In embodiments, $L^5$ is $R^{27}$-substituted $C_4$ cycloalkylene. In embodiments, $L^5$ is $R^{27}$-substituted or unsubstituted $C_5$ cycloalkylene. In embodiments, $L^5$ is $R^{27}$-substituted $C_5$ cycloalkylene. In embodiments, $L^5$ is $R^{27}$-substituted $C_5$ cycloalkylene.

In embodiments, $L^5$ is $R^{27}$-substituted or unsubstituted 5 to 6 membered heterocycloalkylene. In embodiments, $L^5$ is $R^{27}$-substituted 5 to 6 membered heterocycloalkylene. In embodiments, $L^5$ is unsubstituted 5 to 6 membered heterocycloalkylene. In embodiments, $L^5$ is $R^{27}$-substituted or unsubstituted 5 membered heterocycloalkylene. In embodiments, $L^5$ is $R^{27}$-substituted 5 membered heterocycloalkylene. In embodiments, $L^5$ is unsubstituted 5 membered heterocycloalkylene. In embodiments, $L^5$ is $R^{27}$-substituted or unsubstituted 6 membered heterocycloalkylene. In embodiments, $L^5$ is $R^{27}$-substituted 6 membered heterocycloalkylene. In embodiments, $L^5$ is unsubstituted 6 membered heterocycloalkylene.

In embodiments, $L^5$ is $R^{27}$-substituted or unsubstituted phenylene. In embodiments, $L^5$ is $R^{27}$-substituted phenylene. In embodiments, $L^5$ is unsubstituted phenylene.

In embodiments, $L^5$ is $R^{27}$-substituted or unsubstituted 5 to 6 membered heteroarylene. In embodiments, $L^5$ is $R^{27}$-substituted 5 to 6 membered heteroarylene. In embodiments, $L^5$ is unsubstituted 5 to 6 membered heteroarylene. In embodiments, $L^5$ is $R^{27}$-substituted or unsubstituted 5 membered heteroarylene. In embodiments, $L^5$ is $R^{27}$-substituted 5 membered heteroarylene. In embodiments, $L^5$ is unsubstituted 5 membered heteroarylene. In embodiments, $L^5$ is $R^{27}$-substituted or unsubstituted 6 membered heteroarylene. In embodiments, $L^5$ is $R^{27}$-substituted 6 membered heteroarylene. In embodiments, $L^5$ is unsubstituted 6 membered heteroarylene.

In embodiments, $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). $X^3$ is independently —F, —Cl, —Br, or —I. In embodiments, $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), or unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^3$ is independently —F, —Cl, —Br, or —I.

$R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each $X^{28}$ is independently —F, —Cl, —Br, or —I.

$R^3$ is independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. In embodiments, $R^3$ is simultaneously a detectable moiety and independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. $X^3$ is independently —F, —Cl, —Br, or —I.

In embodiments, $R^3$ is a detectable moiety. In embodiments, $R^3$ is a radionuclide. In embodiments, $R^3$ is a positron emitting radionuclide (e.g., carbon-11, nitrogen-13, oxygen-15, fluorine-18, gallium-68, zirconium-89, or rubidium-82). In embodiments, $R^3$ is carbon-11, nitrogen-13, oxygen-15, or fluorine-18. In embodiments, $R^3$ is fluorine-18. In embodiments, $R^3$ is gallium-68, zirconium-89, rubidium-82, or iodine-124. In embodiments, $R^3$ is fluorine-19. In embodiments, $R^3$ is fluorine-18 or fluorine-19. In embodiments, $R^3$ is fluorine-18 and fluorine-19 (e.g., a plurality of the compound includes one or more compounds wherein $R^3$ is fluorine-18 and one or more compounds wherein $R^3$ is fluorine-19. In embodiments, $R^3$ is fluorine-18 or fluorine-19 (e.g., a compound includes fluorine-18 that becomes fluorine-19 over time due to radioactive decay; fluorine-18 has a half life of 109.8 minutes). $X^3$ is independently —F, —Cl, —Br, or —I.

In embodiments, $R^3$ is $R^{28}$-substituted or unsubstituted alkyl (e.g., $C_1$-$C_8$ alkyl, $C_1$-$C_6$ alkyl, or $C_1$-$C_4$ alkyl). In embodiments, $R^3$ is $R^{28}$-substituted alkyl (e.g., $C_1$-$C_8$ alkyl, $C_1$-$C_6$ alkyl, or $C_1$-$C_4$ alkyl). In embodiments, $R^3$ is an unsubstituted alkyl (e.g., $C_1$-$C_8$ alkyl, $C_1$-$C_6$ alkyl, or $C_1$-$C_4$ alkyl).

In embodiments, $R^3$ is $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^{28}$-substituted heteroalkyl (e.g., 2 to 8 membered heteroalkyl, 2 to 6 membered heteroalkyl, or 2 to 4 membered heteroalkyl). In embodiments, $R^3$ is an unsubstituted heteroalkyl (e.g., 2 to 8 membered heteroalkyl, 2 to 6 membered heteroalkyl, or 2 to 4 membered heteroalkyl).

In embodiments, $R^3$ is $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{28}$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^3$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^3$ is $R^{28}$-substituted or unsubstituted aryl (e.g., $C_6$-$C_{10}$ aryl, $C_{10}$ aryl, or phenyl). In embodiments, $R^3$ is $R^{28}$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl).

In embodiments, $R^3$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^3$ is $R^{28}$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^3$ is $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, radionuclides (e.g. carbon-11, nitrogen-13, oxygen-15, fluorine-18, rubidium-82), fluorodeoxyglucose (e.g. fluorine-18 labeled), fluorodeoxyglucose nucleotide or nucleoside (e.g. fluorine-18 labeled A, C, G, or T), gamma ray emitting radionuclides, positron-emitting radionuclide, or radiolabeled glucose.

In an aspect, is provided a compound having the formula:

(III)

L³, L⁴, L⁵, and R³, are as described herein, including in embodiments.

L⁶ is a bond, —O—, —NH—, —OC(O)—, —C(O)O—, —NHC(O)—, —C(O)NH—, —OC(O)O—, —OC(O)NH—, —NHC(O)O—, —NHC(O)NH—, —CH₂OC(O)—, —CH₂C(O)O—, —CH₂NHC(O)—, —CH₂C(O)NH—, —CH₂OC(O)O—, —CH₂OC(O)NH—, —CH₂NHC(O)O—, —CH₂NHC(O)NH—, or —S—.

L⁷ is a bond, substituted or unsubstituted alkylene, substituted or unsubstituted heteroalkylene, substituted or unsubstituted cycloalkylene, or substituted or unsubstituted heterocycloalkylene.

R⁴ and R⁵ are independently $C_{1-6}$ alkyl.

In embodiments, L⁷ independently a bond, R²⁹-substituted or unsubstituted alkylene (e.g., $C_1$-$C_8$ alkylene, $C_1$-$C_6$ alkylene, or $C_1$-$C_4$ alkylene), R²⁹-substituted or unsubstituted heteroalkylene (e.g., 2 to 8 membered heteroalkylene, 2 to 6 membered heteroalkylene, or 2 to 4 membered heteroalkylene), R²⁹-substituted or unsubstituted cycloalkylene (e.g., $C_3$-$C_8$ cycloalkylene, $C_3$-$C_6$ cycloalkylene, or $C_5$-$C_6$ cycloalkylene), R²⁹-substituted or unsubstituted heterocycloalkylene (e.g., 3 to 8 membered heterocycloalkylene, 3 to 6 membered heterocycloalkylene, or 5 to 6 membered heterocycloalkylene), R²⁹-substituted or unsubstituted arylene (e.g., $C_6$-$C_{10}$ arylene, $C_{10}$ arylene, or phenyl), or R²⁹-substituted or unsubstituted heteroarylene (e.g., 5 to 10 membered heteroarylene, 5 to 9 membered heteroarylene, or 5 to 6 membered heteroaryl). In embodiments, L⁷ independently a bond, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroaryl).

R²⁹ is independently oxo, halogen, —CX²⁹₃, —CHX²⁹₂, —CH₂X²⁹, —OCX²⁹₃, —OCH₂X²⁹, —OCHX²⁹₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). Each X²⁹ is independently —F, —Cl, —Br, or —I.

In embodiments, the compound has the formula:

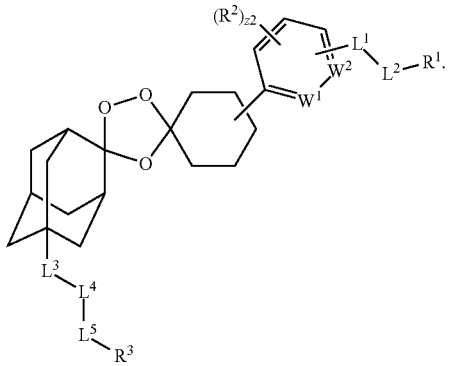
(IIa)

In an embodiment is provided a compound having the formula:

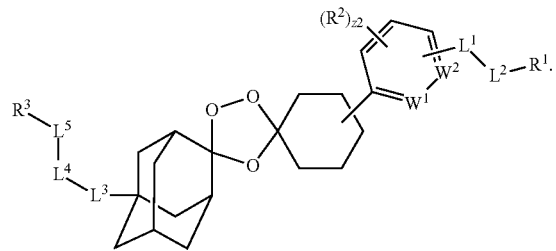
(IIb)

In embodiments, the compound has the formula:

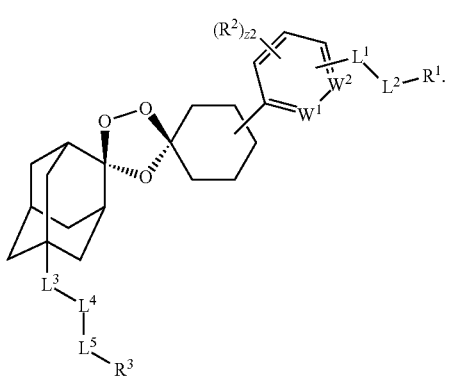
(IIc)

W¹, W², L¹, L², R¹, R², z2, L³, L⁴, L⁵, and R³ are as described herein, including in embodiments.

In embodiments, the compound has the formula:

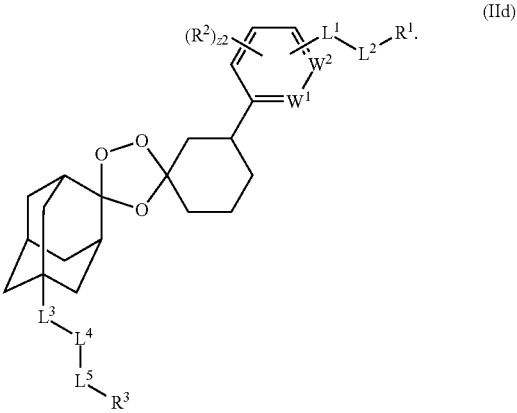
(IId)

W¹, W², L¹, L², R¹, R², z2, L³, L⁴, L⁵, and R³ are as described herein, including in embodiments.

In embodiments, the compound has the formula:

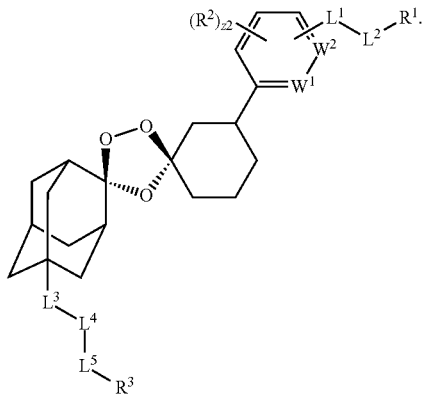
(IIe)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

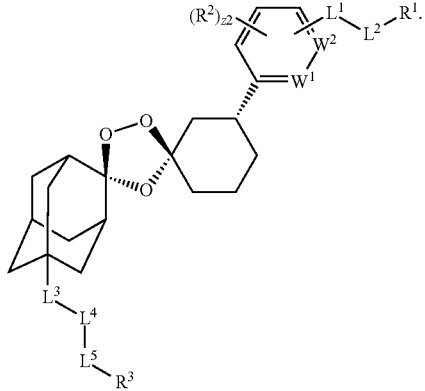
(IIf)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

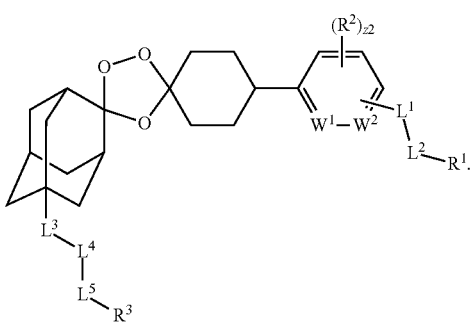
(IIg)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

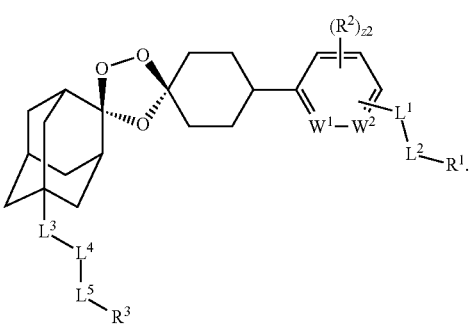
(IIh)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

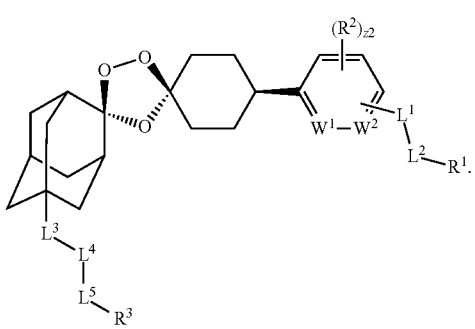
(IIi)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

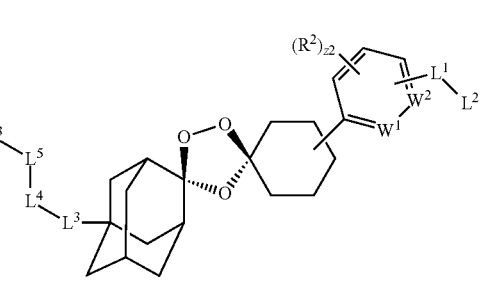
(IIj)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

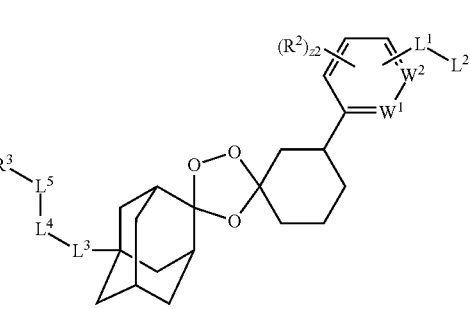
(IIk)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

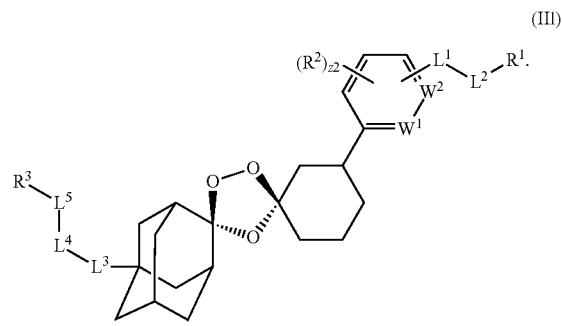
(III)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

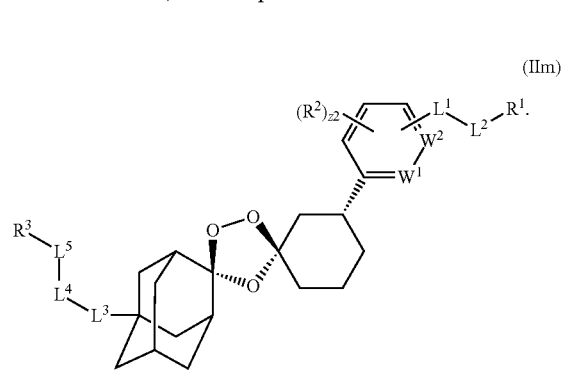
(IIm)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

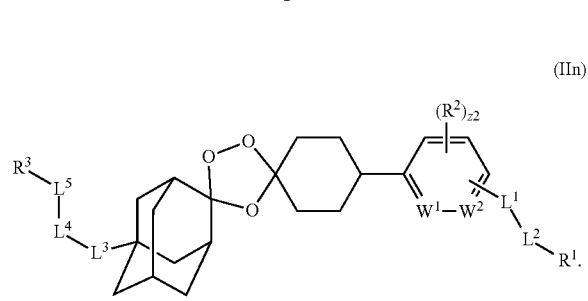
(IIn)

$W^1$, $W^2$, L, $L^2$, $R^1$, $R^2$, z2, $L^3$, $L^4$, $L^5$, and $R^3$ are as described herein, including in embodiments.

In embodiments, the compound has the formula:

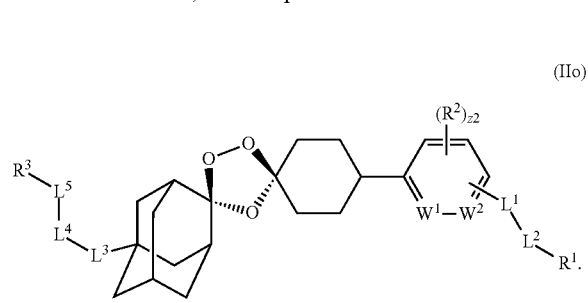
(IIo)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

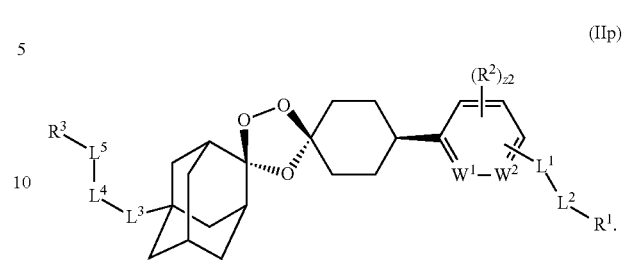
(IIp)

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

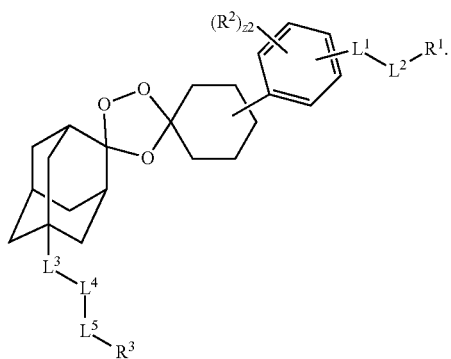

In an embodiment is provided a compound having the formula:

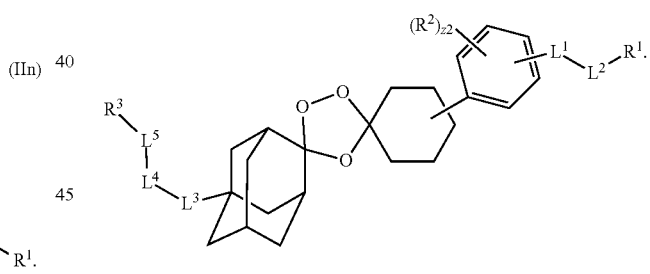

In embodiments, the compound has the formula:

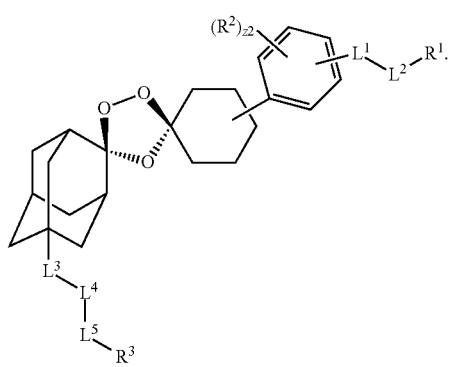

$L^1$, $L^2$, $R^1$, $R^2$, z2, $L^3$, $L^4$, $L^5$, and $R^3$ are as described herein, including in embodiments.

In embodiments, the compound has the formula:

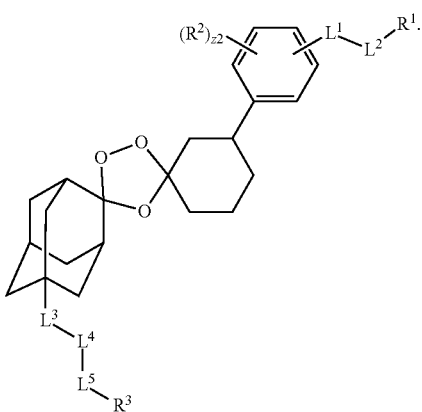

$W^1$, $W^2$, $L^1$, $L^2$, $R^1$, $R^2$, z2, $L^3$, $L^4$, $L^5$, and $R^3$ are as described herein, including in embodiments.

In embodiments, the compound has the formula:

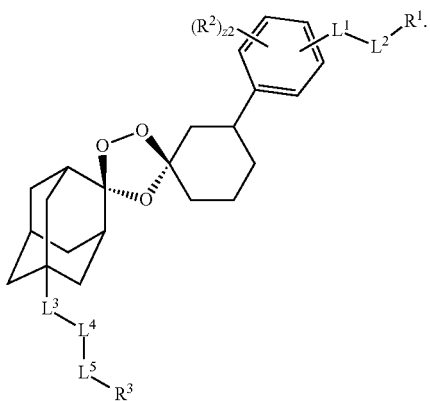

$L^1$, $L^2$, $R^1$, $R^2$, z2, $L^3$, $L^4$, $L^5$, and $R^3$ are as described herein, including in embodiments.

In embodiments, the compound has the formula:

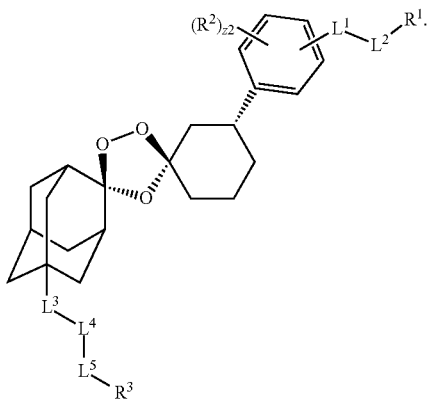

$L^1$, $L^2$, $R^1$, $R^2$, z2, $L^3$, $L^4$, $L^5$, and $R^3$ are as described herein, including in embodiments.

In embodiments, the compound has the formula:

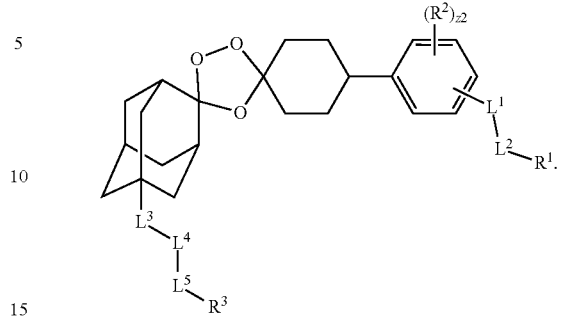

$L^1$, $L^2$, $R^1$, $R^2$, z2, $L^3$, $L^4$, $L^5$, and $R^3$ are as described herein, including in embodiments.

In embodiments, the compound has the formula:

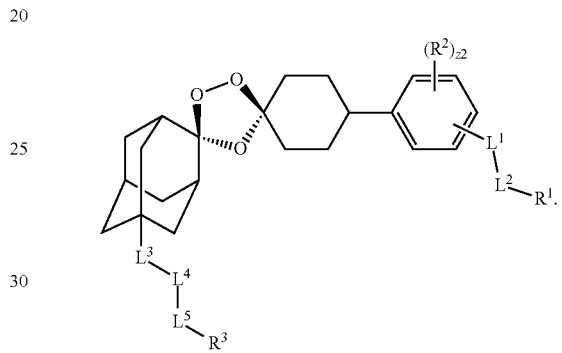

$L^1$, $L^2$, $R^1$, $R^2$, z2, $L^3$, $L^4$, $L^5$, and $R^3$ are as described herein, including in embodiments.

In embodiments, the compound has the formula:

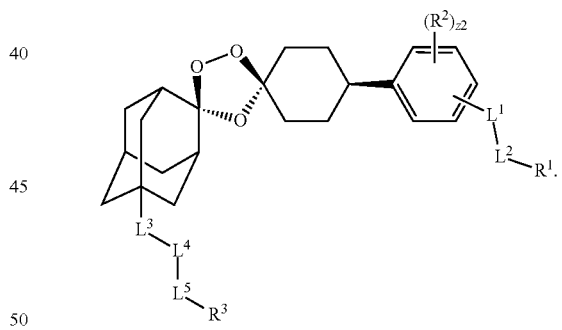

$L^1$, $L^2$, $R^1$, $R^2$, z2, $L^3$, $L^4$, $L^5$, and $R^3$ are as described herein, including in embodiments.

In embodiments, the compound has the formula:

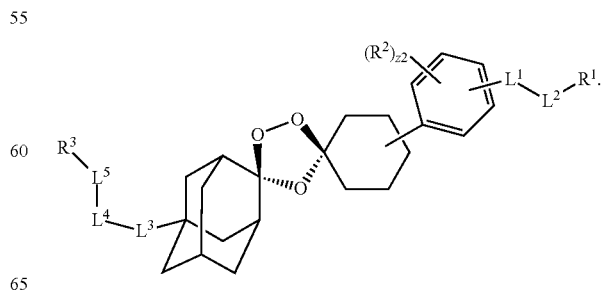

$L^1$, $L^2$, $R^1$, $R^2$, z2, $L^3$, $L^4$, $L^5$, and $R^3$ are as described herein, including in embodiments.

In embodiments, the compound has the formula:

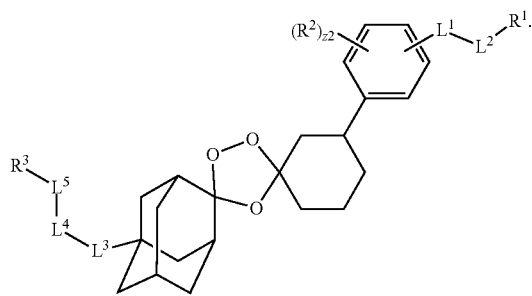

$L^1, L^2, R^1, R^2, z2, L^3, L^4, L^5,$ and $R^3$ are as described herein, including in embodiments.

In embodiments, the compound has the formula:

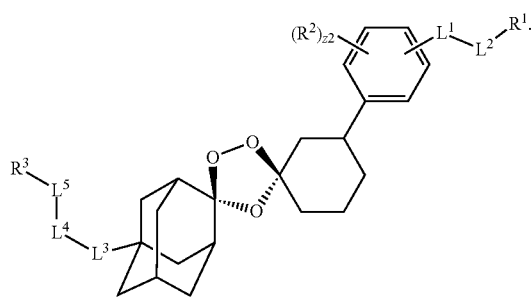

$L^1, L^2, R^1, R^2, z2, L^3, L^4, L^5,$ and $R^3$ are as described herein, including in embodiments.

In embodiments, the compound has the formula:

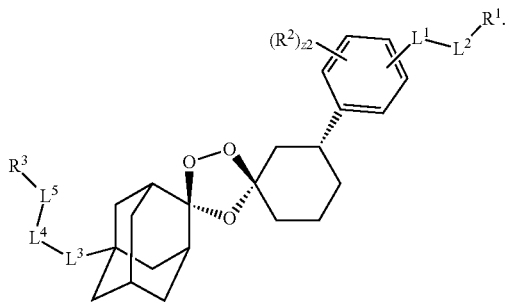

$L^1, L^2, R^1, R^2, z2, L^3, L^4, L^5,$ and $R^3$ are as described herein, including in embodiments.

In embodiments, the compound has the formula:

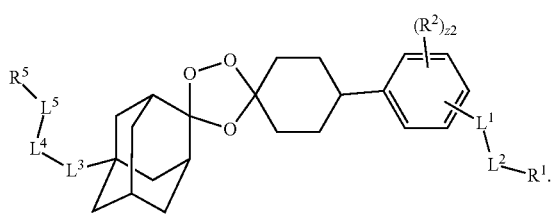

$L^1, L^2, R^1, R^2, z2, L^3, L^4, L^5,$ and $R^3$ are as described herein, including in embodiments.

In embodiments, the compound has the formula:

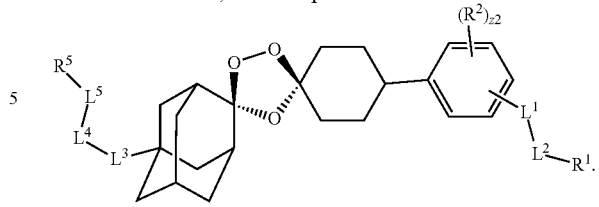

$L^1, L^2, R^1, R^2, z2, L^3, L^4, L^5,$ and $R^3$ are as described herein, including in embodiments.

In embodiments, the compound has the formula:

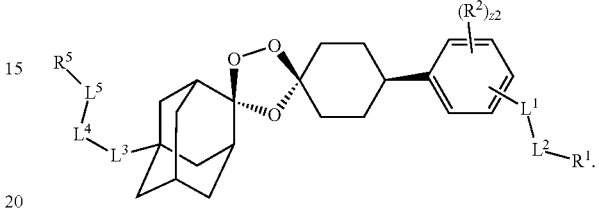

$L^1, L^2, R^1, R^2, z2, L^3, L^4, L^5,$ and $R^3$ are as described herein, including in embodiments.

In embodiments, the compound has the formula:

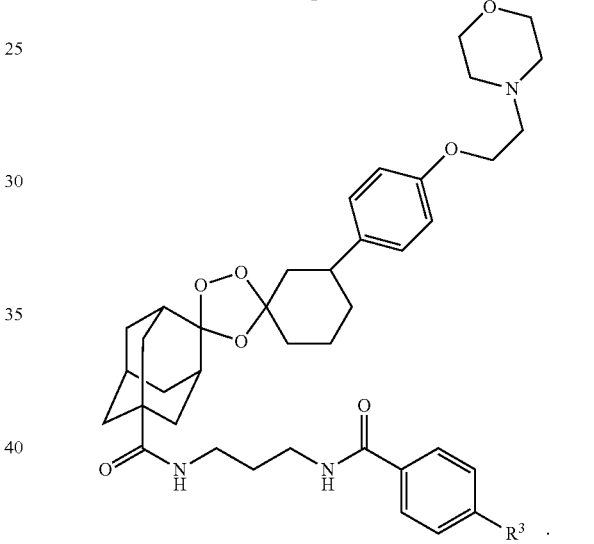

$R^3$ is as described herein, including in embodiments.

In embodiments, the compound has the formula:

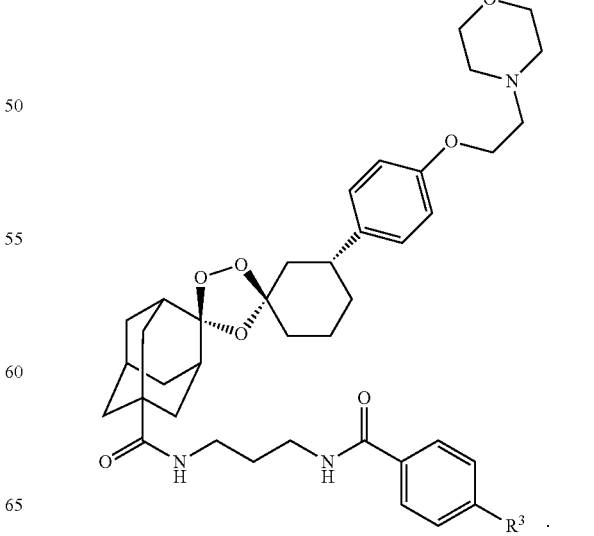

$R^3$ is as described herein, including in embodiments.

In embodiments, the compound has the formula:

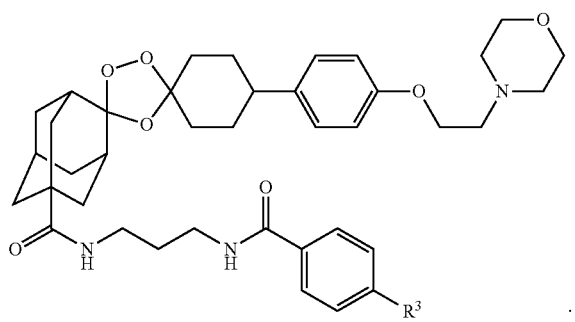

R³ is as described herein, including in embodiments.

In embodiments, the compound has the formula:

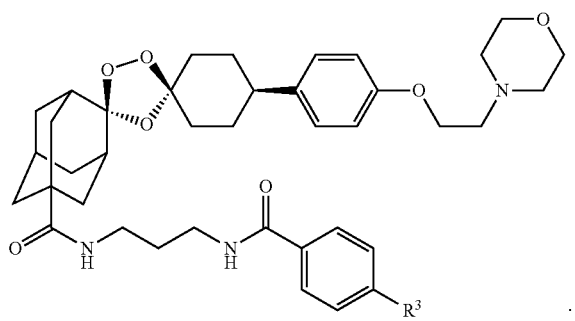

R³ is as described herein, including in embodiments.

In embodiments, the compound has the formula:

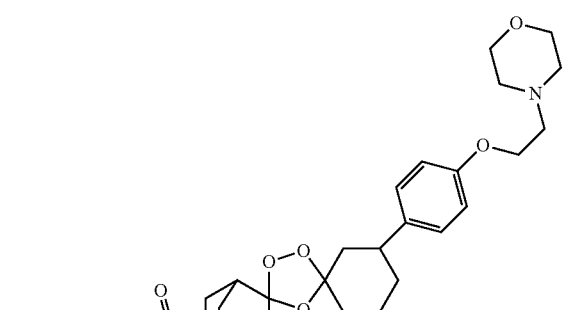
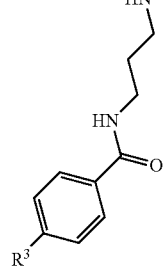

R³ is as described herein, including in embodiments.

In embodiments, the compound has the formula:

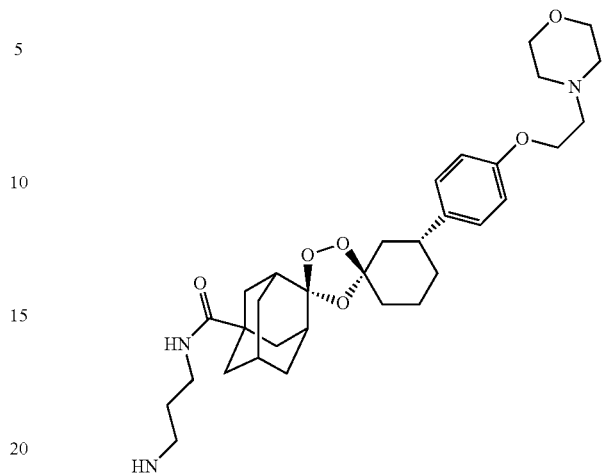

R³ is as described herein, including in embodiments.

In embodiments, the compound has the formula:

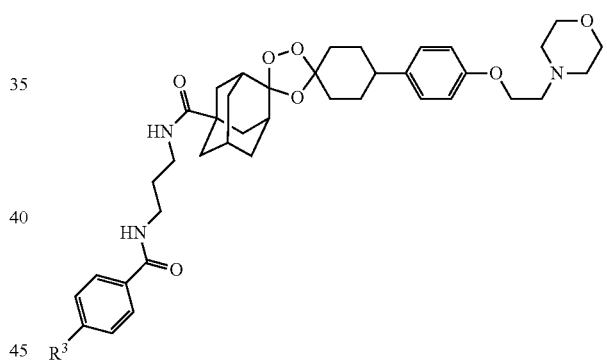

R³ is as described herein, including in embodiments.

In embodiments, the compound has the formula:

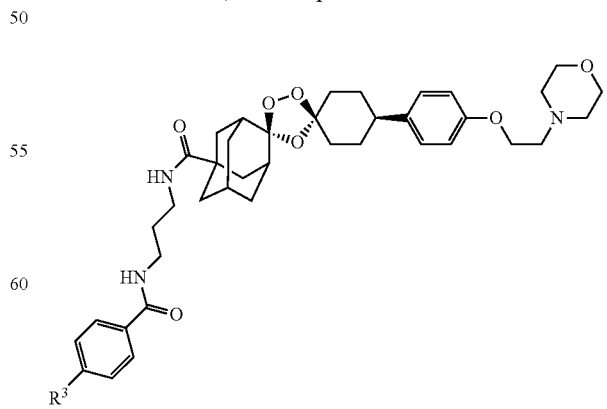

R³ is as described herein, including in embodiments.

In embodiments, the compound has the formula:

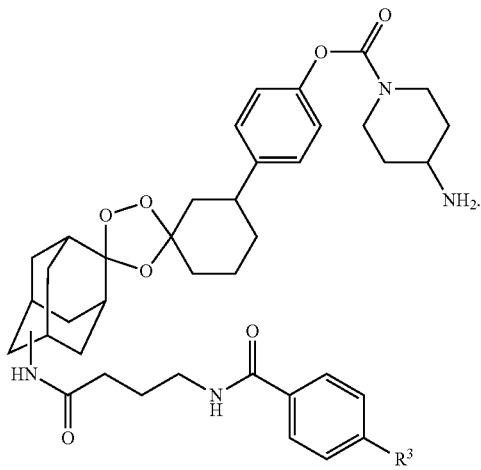

R³ is as described herein, including in embodiments.
In embodiments, the compound has the formula:

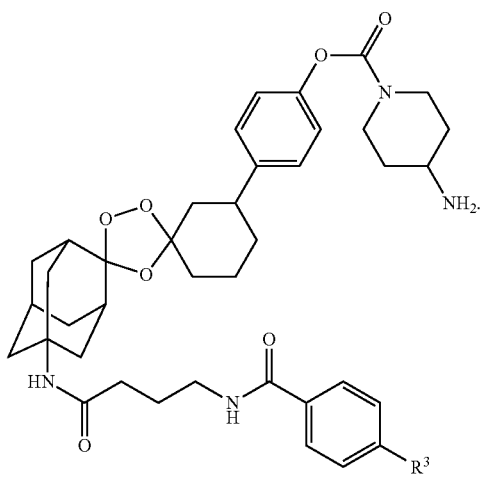

R³ is as described herein, including in embodiments.
In embodiments, the compound has the formula:

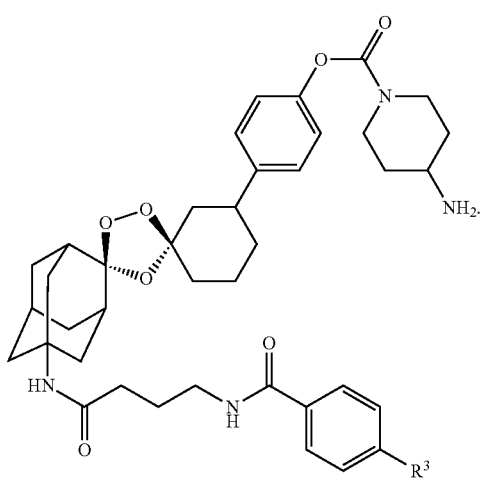

R³ is as described herein, including in embodiments.

In embodiments, the compound has the formula:

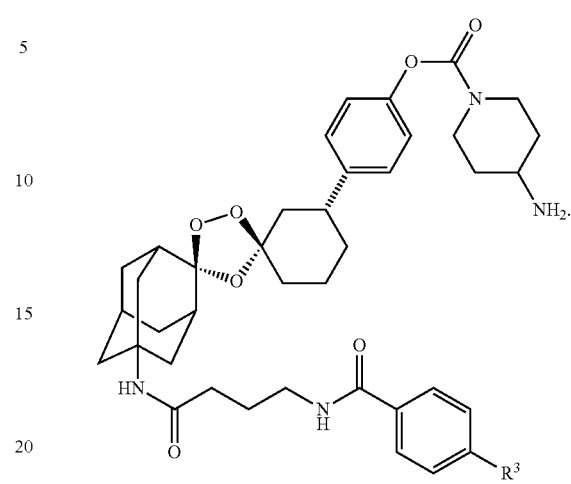

R³ is as described herein, including in embodiments.
In embodiments, the compound has the formula:

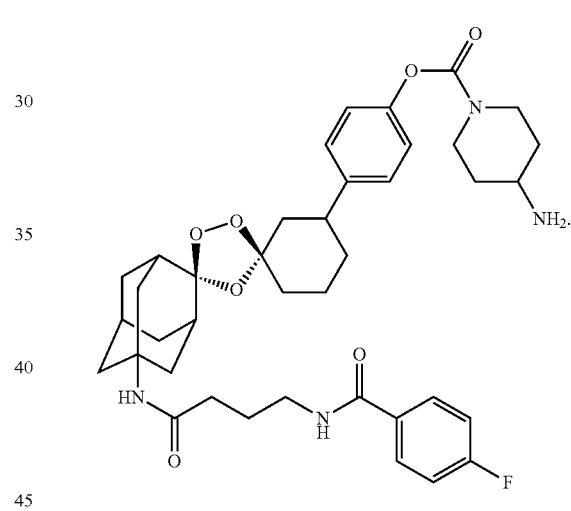

In embodiments, the compound has the formula:

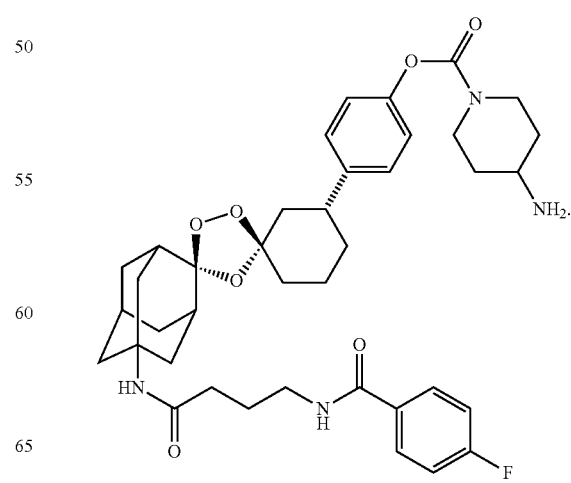

In embodiments, the compound has the formula:

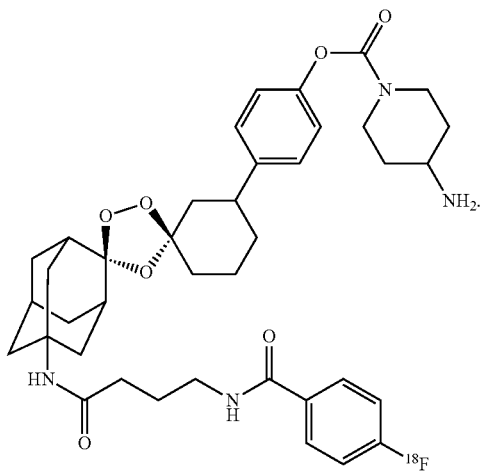

In embodiments, the compound has the formula:

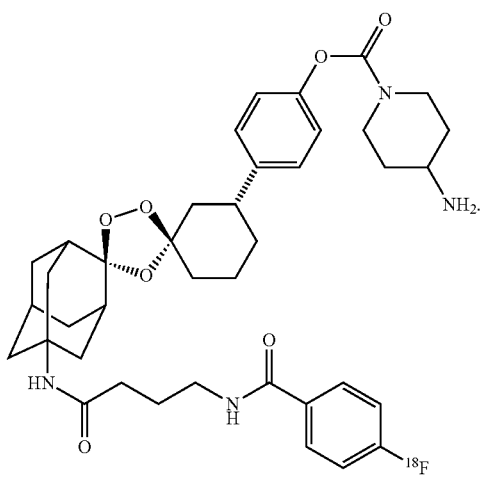

In embodiments, the compound has the formula:

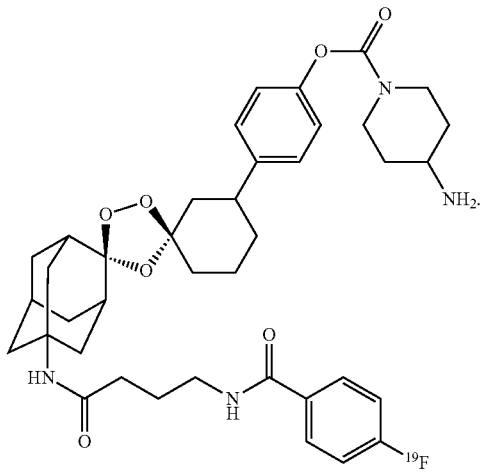

In embodiments, the compound has the formula:

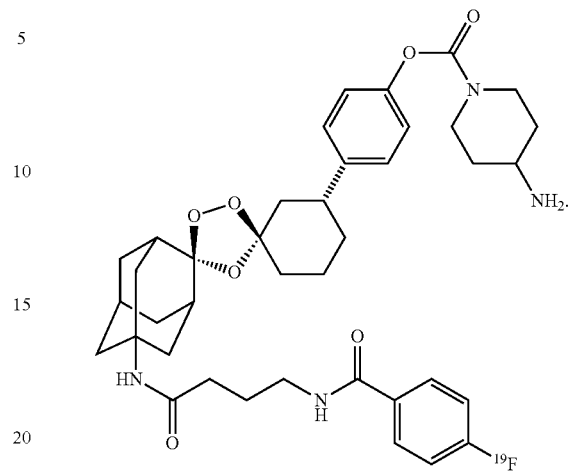

In embodiments, the compound has the formula:

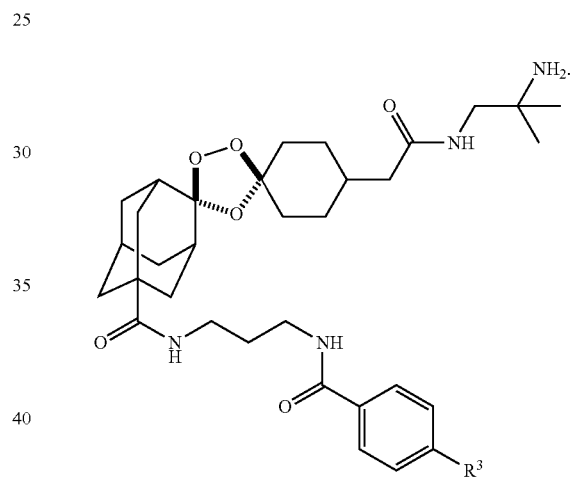

$R^3$ is as described herein, including in embodiments.

In embodiments, the compound has the formula:

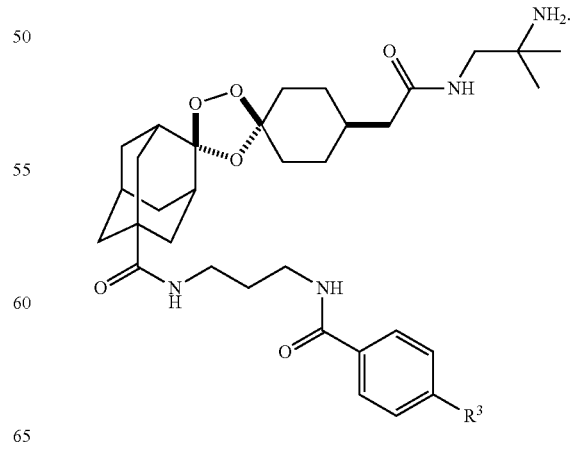

$R^3$ is as described herein, including in embodiments.

103
In embodiments, the compound has the formula:
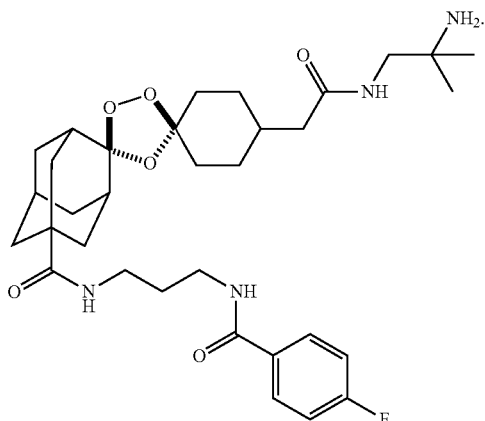
In embodiments, the compound has the formula:
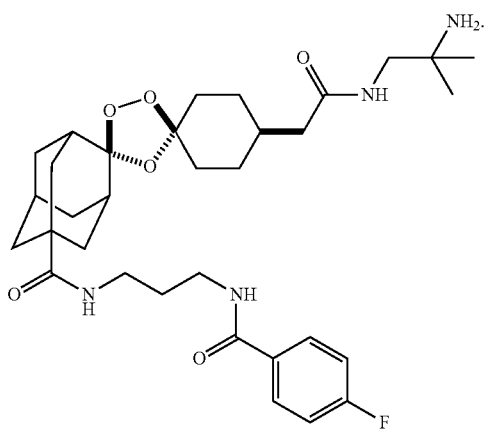
In embodiments, the compound has the formula:
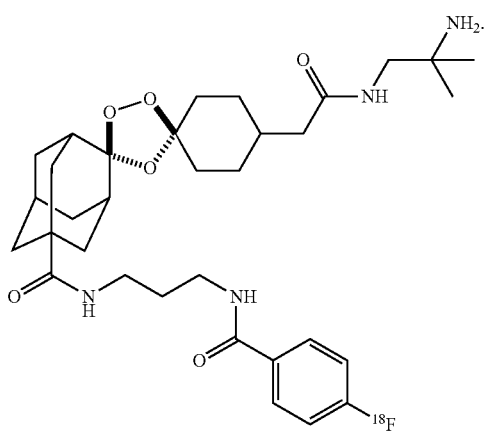
104
In embodiments, the compound has the formula:
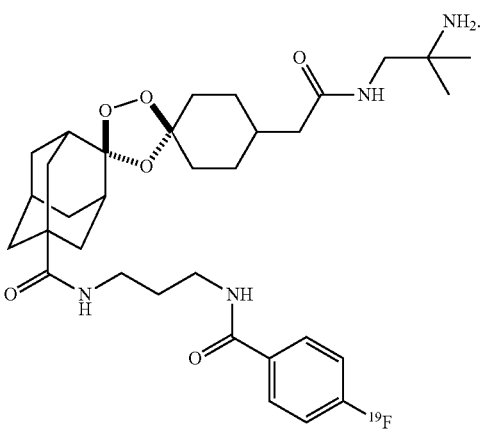
In embodiments, the compound has the formula:
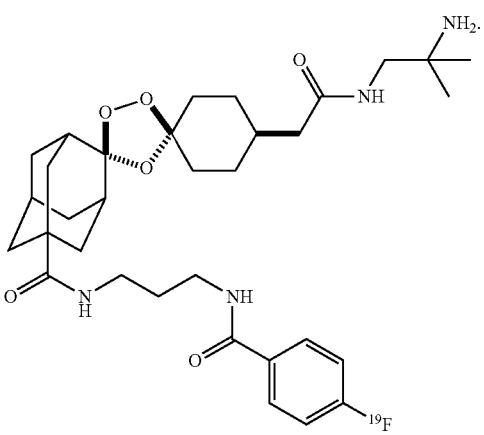

C. Pharmaceutical Compositions

In an aspect is provided a pharmaceutical composition including a pharmaceutically acceptable excipient and a compound described herein (including in an aspect, embodiment, table, example, or claim), or a pharmaceutically acceptable salt thereof.

In embodiments of the pharmaceutical compositions, the pharmaceutical composition includes a compound, or pharmaceutically acceptable salt thereof, as described herein (e.g. compound of formula I, or any embodiment thereof) in a therapeutically effective amount. In embodiments of the pharmaceutical compositions, the pharmaceutical composition includes a compound, or pharmaceutically acceptable salt thereof, as described herein (e.g. compound of formula I, or any embodiment thereof) in a detectable amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is an agent for treating malaria. In embodiments, the second agent is an anti-malaria agent (e.g., quinine, chloroquine, amodiaquine, pyrimethamine, proguanil, solfonamides, mefloquine, atovaquone, primaquine, artemisinin, halofantrine, doxycycline, or clindamycin). In embodiments, the second agent is an anti-infective agent.

D. Methods

In an aspect is provided a method of treating a disease in a patient in need of such treatment, said method including administering a therapeutically effective amount of a compound described herein (including in an aspect, embodiment, table, example, or claim), or a pharmaceutically acceptable salt thereof, to the patient.

In embodiments, the disease is associated with a cell or organism having an increased level of a reductant (e.g. biological reductant, or $Fe^{II}$) compared to a standard control (e.g. a subject without the disease, sample from a subject without the disease, or a subject with the disease but without administration of a therapeutically effective amount of a compound described herein). In embodiments, the disease is associated with a cell or organism having an increased $Fe^{II}$ level compared to a standard control (e.g. subject without the disease or sample from a subject without the disease). In some embodiments, the method of treating is a method of preventing. In some embodiments, the method of treating does not include preventing. In embodiments, the disease is cancer. In embodiments, the disease is malaria. In embodiments, the disease is a parasitic disease. In embodiments, the disease is schistosomiasis. In embodiments, the disease is helminthiasis. In embodiments, the disease is algid malaria, bilious malaria, cerebral malaria, congenital malaria, *falciparum* malaria, *Plasmodium* falciparummalaria, pernicious malaria, *ovale* malaria, *Plasmodium ovale* malaria, quartan malaria, *malariae* malaria, *Plasmodium malariae* malaria, quotidian malaria, tertian malaria, transfusion malaria, *vivax* malaria, or *Plasmodium vivax* malaria. In embodiments, the disease is hemochromatosis.

In embodiments, the compound has the formula:

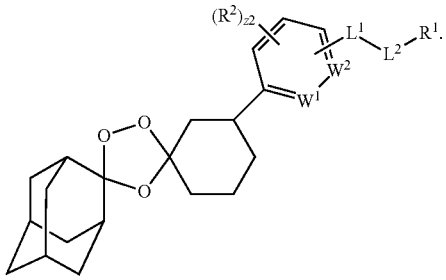

$W^1$ and $W^2$ are independently =N—, =C($R^2$)—, or =CH—.

$L^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, or —S—.

$L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

z2 is an integer from 0 to 4.

Each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl.

Each X, $X^1$, and $X^2$ is independently —F, —Cl, —Br, or —I.

n1 is independently an integer from 0 to 4.

m1 and v1 are independently 1 or 2.

In embodiments, the compound has the formula:

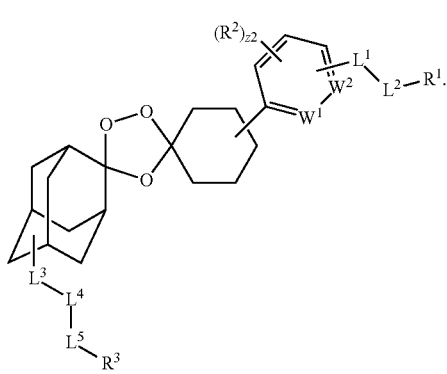

(II)

$W^1$, $W^2$, $L^1$, $L^2$, $R^1$, $R^2$, z2, $R^{1A}$, $R^{1B}$, $R^{1C}$, $R^{1D}$. X, $X^1$, $X^2$, n1, m1, and v1 are as described herein, including in embodiments.

$R^3$ is independently hydrogen, halogen, —$CX^3_3$, —$CHX^3_2$, —$CH_2X^3$, —$OCX^3_3$, —$OCH_2X_3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

$L^3$, $L^4$, and $L^5$ are independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, -$L^3$-$L^4$-$L^5$- is —C(O)$NHCH_2CH_2CH_2NHC(O)$Ph-. In embodiments, -$L^3$-$L^4$-$L^5$- is bond. In embodiments, -$L^3$-$L^4$-$L^5$- is —O—. In embodiments, -$L^3$-$L^4$-$L^5$- is —NH—. In embodiments, -$L^3$-$L^4$-$L^5$- is —OC(O)—. In embodiments, -$L^3$-$L^4$-$L^5$- is —C(O)O—. In embodiments, -$L^3$-$L^4$-$L^5$- is —NHC(O)—. In embodiments, -$L^3$-$L^4$-$L^5$- is —C(O)NH—. In embodiments, -$L^3$-$L^4$-$L^5$- is —OC(O)O—. In embodiments, -$L^3$-$L^4$-$L^5$- is —OC(O)NH—. In embodiments, -$L^3$-$L^4$-$L^5$- is —NHC(O)O—. In embodiments, -$L^3$-$L^4$-$L^5$- is —NHC(O)NH—. In embodiments, -$L^3$-$L^4$-$L^5$- is —S—.

In embodiments, -$L^3$-$L^4$-$L^5$- is

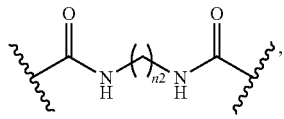

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, -$L^3$-$L^4$-$L^5$- is

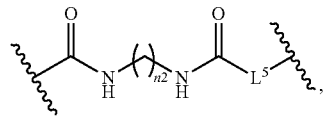

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, -$L^3$-$L^4$-$L^5$

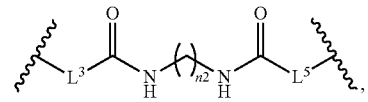

wherein n2 is an integer from 1 to 12. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12.

In embodiments, the compound has the formula:

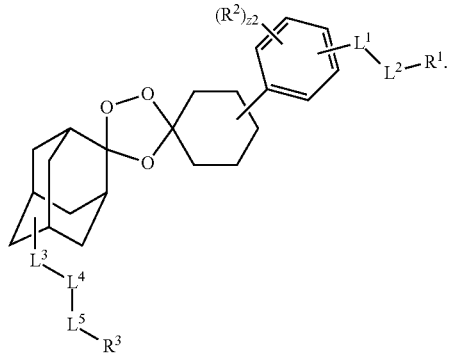

In an aspect is provided a method of detecting a disease associated with a cell or organism having an increased $Fe^{II}$ level compared to a standard control, in a subject, the method including administering an effective amount of a compound described herein (including in an aspect, embodiment, table, example, or claim), or a pharmaceutically acceptable salt thereof, to the subject and measuring the level of the compound in the subject. The method may include detecting the presence of the compound. The method may include detecting an increased level of the compound or detectable agent compared to the level of compound or detectable agent detected in a patient without the disease. In embodiments, the method includes determining if a subject has a disease associated with an organism or cell having an increased $Fe^{II}$ level compared to a standard control, by obtaining a biological sample from the patient, and administering an effective amount of a compound described herein (including in an aspect, embodiment, table, example, or claim), or a pharmaceutically acceptable salt thereof, to the subject, and measuring the level of the compound in the subject (e.g., by detecting the detectable moiety within the compound). If the level of the compound is above a threshold, it is determined that the subject has a disease associated with an organism or cell having an increased $Fe^{II}$ level.

In embodiments, the compound has the formula:

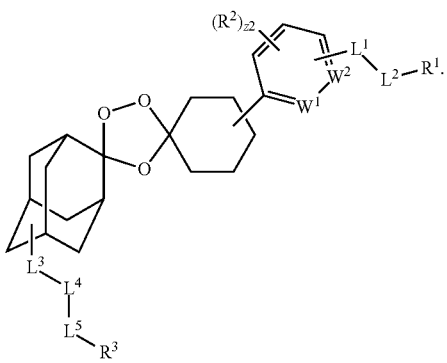

(II)

$W^1$, $W^2$, $L^1$, $L^2$, $R^1$, $R^2$, z2, $R^{1A}$, $R^{1B}$, $R^{1C}$, $R^{1D}$. X, $X^1$, $X^2$, n1, m1, and v1 are as described herein, including in embodiments. $L^3$, $L^4$, and $L^5$ are independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^3$ is a detectable moiety.

In embodiments, the compound has the formula:

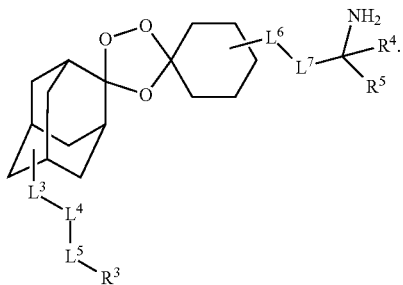

$L^3$, $L^4$, $L^5$, and $R^3$, are as described herein, including in embodiments.

$L^6$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, —CH$_2$OC(O)—, —CH$_2$C(O)O—, —CH$_2$NHC(O)—, —CH$_2$C(O)NH—, —CH$_2$OC(O)O—, —CH$_2$OC(O)NH—, —CH$_2$NHC(O)O—, —CH$_2$NHC(O)NH—, or —S—.

$L^7$ is a bond, substituted or unsubstituted alkylene, substituted or unsubstituted heteroalkylene, substituted or unsubstituted cycloalkylene, or substituted or unsubstituted heterocycloalkylene.

$R^4$ and $R^5$ are independently $C_{1-6}$ alkyl.

In embodiments, the compound has the formula:

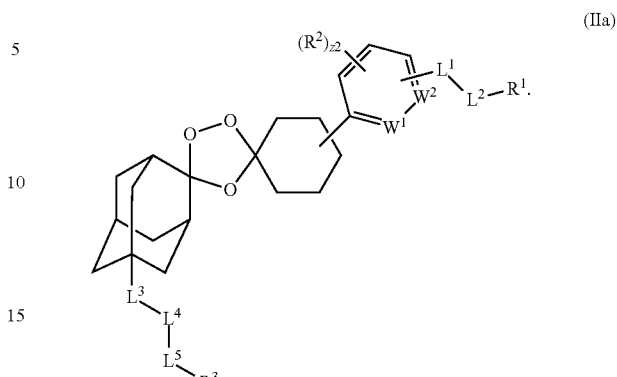

(IIa)

In an embodiment is provided a compound having the formula:

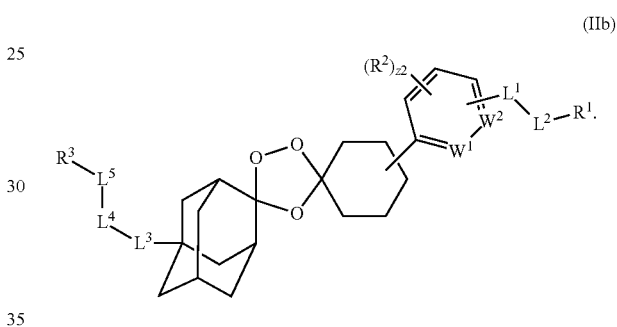

(IIb)

In an aspect is provided a method of identifying a patient having a disease associated with a cell or organism having an increased $Fe^{II}$ level compared to a standard control, the method including administering an effective amount of a compound described herein (including in an aspect, embodiment, table, example, or claim), or a pharmaceutically acceptable salt thereof, to the patient.

In embodiments, the method includes detecting a hypoxic cancer cell (e.g., a cancer cell undergoing hypoxia) or a necrotic cancer cell (e.g., a cancer cell undergoing necrosis). In embodiments, the method includes detecting iron ($Fe^{II}$).

In embodiments, the compound includes a detectable moiety. In embodiments, the detectable moiety is a fluorescent moiety. In embodiments, the detectable moiety is a moiety of a fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticle, USPIO nanoparticle aggregate, nanoparticle contrast agent, liposome or other delivery vehicle containing Gadolinium chelate ("Gd-chelate") molecules, Gadolinium, radioisotope (e.g. $^{32}$P), radionuclide (e.g. carbon-11, nitrogen-13, oxygen-15, fluorine-18, rubidium-82), fluorodeoxyglucose (e.g. fluorine-18 labeled), gamma ray emitting radionuclide, positron-emitting radionuclide, iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, fluorescent protein, xanthene derivative (e.g. fluorescein, rhodamine, Oregon green, eosin, or Texas red), cyanine or derivative (e.g. cyanine, indocarbocyanine, oxacarbocyanine, thiacarbocyanine or merocyanine), napththalene derivative (e.g. dansyl or prodan derivative), coumarin or a derivative, oxadiazole derivative (e.g. pyridyloxazole, nitrobenzoxadiazole or benzoxadiazole), anthracene derivative (e.g. anthraquinone, DRAQ5, DRAQ7, or CyTRAK Orange), pyrene derivative (e.g. cascade blue or derivative), oxazine derivative (e.g. Nile red, Nile blue, cresyl violet, oxazine 170), acridine derivative (e.g. proflavin, acridine orange, acridine yellow), arylmethine derivative (e.g. auramine, crystal violet, malachite green), tetrapyrrole derivative (e.g. porphin, phthalocyanine, bilirubin), CF Dye™, DRAQ™, CyTRAK™, BODIPY™, Alexa Fluor™, DyLight Fluor™, Atto™, Tracy™, FluoProbe™, Abberior Dye™, DY™ dyes, MegaStokes Dye™, Sulfo Cy™, Seta™ dyes, SeTau™ dye, Square Dye™, Quasar™ dyes, Cal Fluor™ dyes, SureLight Dye™, PerCP™, Phycobilisome™, APC™, APCXL™, RPE™, or BPE™. In embodiments, the detectable moiety is a radionuclide (e.g. carbon-11, nitrogen-13, oxygen-15, fluorine-18, rubidium-82). In embodiments, the detectable moiety is fluorine-18.

In embodiments, the method includes measuring the level of compound in the subject using positron emission tomography. In embodiments, the disease is cancer (e.g., leukemia, astrocytoma, or breast cancer), malaria, or an inflammatory disease.

In embodiments, the method includes reducing the activity or level of a parasite (e.g., a parasitic protozoan, a plasmodium parasite, or malarial parasite).

In embodiments, the compound should confer rapid parasite killing kinetics (with a time to reduce early ring viability by 50% ranging from with a rate ranging from 0.5 h to 8 h). In embodiments, the compound should confer rapid parasite killing kinetics (with a time to reduce early ring viability by 50% ranging from with a rate ranging from 1 h to 5 h). In embodiments, parasitic agents should retain a prolonged in vivo exposure profile (with a half-life ranging from 1 minute to 280 minutes). In embodiments, the compound should retain a prolonged in vivo exposure profile (with a half-life ranging from 1 minute to 480 minutes). In embodiments, the compound should retain a prolonged in vivo exposure profile (with a half-life ranging from 1 minute to 3 days).

EXAMPLES

A. Regioisomeric Analogs of Arterolane

We describe the first systematic study of antimalarial 1,2,4-trioxolanes bearing a substitution pattern regioisomeric to that of arterolane. A conformational analysis suggested that trans-3" substituted trioxolanes would exhibit Fe(II) reactivity and antiparasitic activity similar to that achieved with traditional cis-4" substitution. The chiral 3" analogs were prepared as single stereoisomers and evaluated alongside their 4" congeners against cultured malaria parasites and in a murine malaria model. As predicted, the trans-3" analogs exhibited in vitro antiplasmodial activity remarkably similar to that of their cis-4" comparators. In contrast, efficacy in the *Plasmodium berghei* mouse model differed dramatically for some of the congeneric pairs. The best of the novel 3" analogs (e.g., 12i in Scheme 4) outperformed not only the 4" comparator but arterolane itself, producing cures in mice after a single oral exposure. Overall, this study revealed new avenues for modulating Fe(II) reactivity and the pharmacokinetic and pharmacodynamic properties of 1,2,4-trioxolane antimalarials.

Despite recent progress in the control and treatment of malaria, this devastating disease still affects millions around the world and was estimated by the World Health Organization to have caused 429,000 deaths in 2015. The blood stage of infection is responsible for symptomatic disease, which is characterized by cyclical rounds of asexual replication of *Plasmodium* spp. parasites within host erythrocytes. To support its rapid proliferation in this stage of infection, the parasite depends on the catabolism of host hemoglobin as a source of amino acids. However, the consequent production of toxic free ferrous iron heme during this process represents an Achilles heel that is targeted in different ways by multiple classes of approved antimalarials, including quinolines and artemisinins.

The sesquiterpene artemisinin (qinghaosu, 1Z in FIG. 1) and its analogs dihydroartemisinin (DHA) and artesunate are employed in artemisinin-based combination therapies (ACT), the current WHO recommended front line therapy for uncomplicated malaria caused by *Plasmodium falciparum*, the most virulent human malaria parasite. Artemisinins exhibit a novel pharmacology that requires initial activation of a hindered endoperoxide bond by reduced iron sources in the parasite. The iron-dependence and likely involvement of carbon-centered radical intermediates in artemisinins pharmacology were first revealed in the early 1990s in elegant mechanistic work involving synthetic artemisinin derivatives.[1,2] Soon, more synthetically accessible chemotypes were identified that, like the artemisinins, bore a peroxide bond in a sterically hindered environment. Most notably, Vennerstrom and co-workers identified the 1,2,4-trioxolane-based pharmacophore that produced both arterolane[3] (OZ277, 2a in FIG. 1) and artefenomel[4] (OZ439, 3Z in FIG. 1). Clinical development of arterolane by Ranbaxy led to its approved in India and some African countries as a combination with piperaquine. Artefenomel was subsequently selected for clinical development on the basis of its much superior Fe(II) stability and in vivo PK/PD properties[5] and is currently in Phase 2 clinical trials.[6]

Recent chemoproteomic studies[7-9] from two different groups have confirmed the long-hypothesized pleiotropic action of the artemisinins and demonstrated[7] a remarkable concordance in the proteins covalently targeted by artemisinins and synthetic 1,2,4-trioxolanes. Hence, artemisinin and 1,2,4-trioxolane-derived affinity probes were shown to irreversibly label numerous proteins in the parasite, including those involved in energy acquisition, antioxidant response, and protein and DNA synthesis. Yet despite having many targets in the parasite, resistance to artemisinins has emerged in Southeast Asia and is now a significant clinical problem, especially with concomitant resistance to partner drugs.[10] The resistant phenotype results from mutations in the propeller domain of the PfKelch13 (K13) protein, which shares homology with the mammalian Keap1 protein.[11] This gain of function mutation appears to result in an enhanced stress response and a prolonged ring stage that allows K13 mutant parasites to better sustain the potent but short-lived insult conferred by artemisinins.[12] An obvious concern is whether K13 mutations will confer resistance to clinically used 1,2,4-trioxolanes, given their similar pharmacology. To answer this question,[13] Tilley and co-workers used a pulsed-exposure approach to study the killing kinetics of DHA, 2a in FIG. 1, and 3Z in FIG. 1 against a clinical K13-mutant strain and a genetically matched K13 revertant strain[14] bearing the wild type K13 allele. For all three agents, the time to reduce early ring viability by 50% ($t^\wedge_{50}$) was more than doubled in the K13 mutant strain when compared to the K13 revertant parasites. Interestingly, while DHA and 2a exhibited similar $t^\wedge_{50}$ values of ~3 h and ~1 h for the K13 mutant and revertant strains, respectively, 3Z exhibited notably slower killing, with $t^\wedge_{50}$ values of ~5 h and ~2 h. In the clinical setting however, where the half-life of 3Z (>48 h)[5] greatly exceeds that of DHA or 2a (~1 and ~2-3 h), the authors argue that 3Z should still be effective against K13 mutant parasites, despite its intrinsically slower rate of killing in vitro. The findings summarized above provide essential guidance for future optimization of endoperoxide antimalarials. New agents should confer rapid parasite killing kinetics while retaining a prolonged in vivo exposure profile to prevent escape of mutant K13 parasites and, ideally, to enable single-dose therapy for malaria.[9,13] Among currently available agents, 3Z meets this pharmacokinetic target whereas 2a and current artemisinins do not, due to short durations of exposure. However, 3Z may be inferior to both DHA and 2a in terms of intrinsic killing kinetics. Identifying new 1,2,4-trioxolanes that combine the best properties of the existing agents will require new means for the modulating endoperoxide reduction/activation by either endogenous labile Fe(II) or pathology-specific Fe(II) sources (free heme). Here we demonstrate that trans-3"-substitution of the cyclohexane ring, like traditional cis-4" substitution, provides a ready means to modulate Fe(II) reactivity in a pharmacologically relevant regime in vivo. Comparing congeneric sets of trans-3" and cis-4" analogs, we furthermore demonstrate that trans-3" analogs can exhibit in vivo PK/PD properties distinct from cis-4" comparators. Finally, we describe an efficient and stereocontroled synthesis of trans-3"-substituted 1,2,4-trioxolane analogs that will enable further lead optimization studies of this chemotype.

ABBREVIATIONS USED HEREIN: DHA, dihydroartemisinin; ACT, artemisinins combination therapy; WHO, World Health Organization; PK, pharmacokinetics; PD, pharmacodynamics; $CL_{int}$, intrinsic clearance; MLM, mouse liver microsome assay; QD, once-daily dosing; PD100, oral dose given once a day for 4 days that produces cures in all treated, P. berghei infected animals.

B. Design and Synthesis of Regioisomeric Analogs of Arterolane

The Fe(II) reactivity and resulting antimalarial effects of 2a and 3Z (FIG. 1) can be rationalized in terms of the conformational dynamics of the cyclohexane ring. In ground state conformer I (Scheme 1), the axial endoperoxide lies in the concave face of an aliphatic surface, with approach to the σ* orbital of the O—O bond effectively shielded by the four proximal axial hydrogen atoms of the adamantane and cyclohexane rings (Scheme 1). It is the peroxide-equatorial conformer II that exposes the O—O bond for inner-sphere coordination with Fe(II) and single-electron transfer leading to bond scission.[15,16] Consistent with this interpretation is the highly regioselective nature of peroxide cleavage, with reaction at the oxygen atom opposite the adamantane moiety predominating ($O^1$, Scheme 1).[16] The crucial role of cyclohexane ring conformation on Fe(II) reactivity allows the latter to be finely tuned by varying the nature and stereochemistry of the 4" substituent (i.e., $R^B$ in Scheme 1).[15] The optimal balance of Fe(II) reactivity and antiplasmodial effects was ultimately achieved in analogs bearing cis-$R^B$ substitution that stabilizes the un-reactive conformer I. A focus on cis-$R^B$ substitution during lead optimization efforts ultimately produced both of the clinical candidates from this class (2a and 3Z, FIG. 1). Moreover, the improved stability of $3Z^4$ as compared to 2a toward endogenous Fe(II) sources can be understood as arising from more severe 1,3-diaxial interactions in conformer II of compound 3Z due to the bulkier aryl $R^B$ side chain. Importantly, 3Z retains sufficient reactivity with free Fe(II) heme in parasites to confer a potent antimalarial effect.

Scheme 1. Conformational effects on Fe(II) reactivity in antimalarial 1,2,4-trioxolanes.

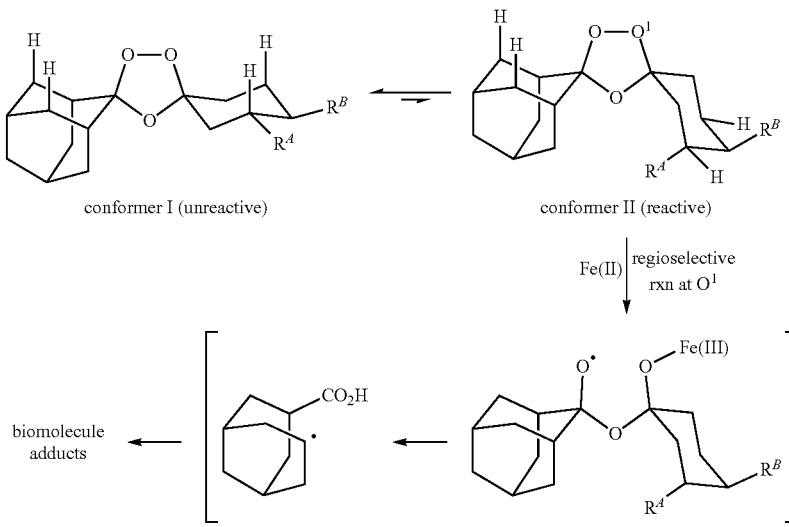

The ability to predict Fe(II) reactivity on conformational grounds is very appealing from a design perspective, and may prove useful in finding the right balance of in vivo stability toward endogenous Fe(II) sources (principally labile iron) and reactivity with Fe(II) heme to target both susceptible and resistant parasites. We considered that trans-3" substitution, nearly[17] unexplored previously, would modulate conformational dynamics in an analogous fashion as canonical cis-4" substitution ($R^A$ vs $R^B$, Scheme 1). In the case of trans-$R^A$ analogs however, 1,3-diaxial interactions in conformer II would involve both O and H atoms, as opposed to only H atoms in cis-$R^B$ analogs. Depending on the nature of the $R^A/R^B$ side chain then, distinct conformational dynamics of the cyclohexane ring might be expected, and this would confer distinct in vitro and in vivo activities. Other important properties such as solubility, metabolism, and clearance could also be affected by the switch to trans-$R^A$ substitution, which eliminates the internal symmetry present in 2a and 3Z (FIG. 1), producing a distinct topology. The arterolane (2a) scaffold was selected for initial studies. A late-stage amide coupling reaction would allow ready access to the matched $R^A/R^B$ analog pairs. As comparators, we selected several $R^B$-side chain derivatives that possess reasonable in vivo efficacy with oral dosing. Thus, 2a and nine additional $R^B$-side chain analogs (2b-j) were synthesized[19] from the acid intermediate 4[17] (Scheme 2) and amines (Scheme 2). We then turned our attention to construction of the analogous $R^A$-side chain variants.

Scheme 2[a] Synthesis of arterolane and related cis-4" analogs from key intermediate 4.

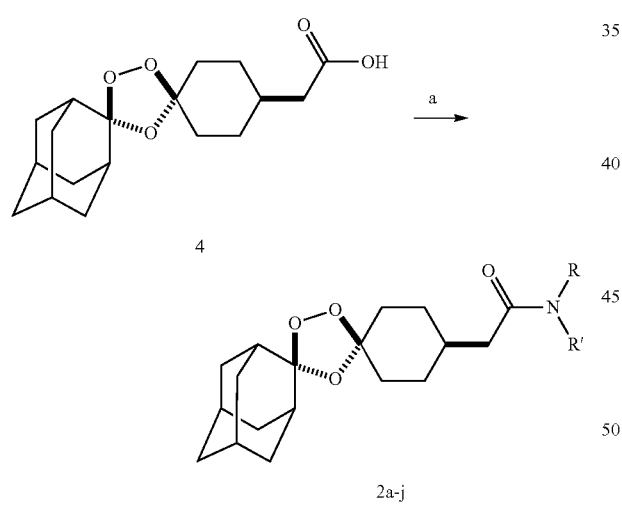

Reagents and conditions: (a) Ethyl chloroformate, Et$_3$N, CH$_2$Cl$_2$, −10° C., 75 min; R(R')NH, CH$_2$Cl$_2$, −10° C. to rt, 2-24 h, 71-95%. Reaction conditions adapted from Ref 19.

Unlike 2a-j (Scheme 2), which possess internal symmetry and are achiral, $R^A$ substitution leads to four possible stereoisomers. Since trans-$R^A$ stereochemistry was desired based on our conformational analysis, this left the trans-(R,R) and trans-(S,S) enantiomers as potential candidates for evaluation and we chose the trans-(R,R) stereoisomers for an initial study. Previously, we found[20] that the Griesbaum co-ozonolysis reaction of 3-substituted cyclohexanones proceeds with high (~90:10 dr) intrinsic diastereoselectivity and favors the desired trans stereoisomer. Preparing the desired trans-(R,R) stereoisomer then required starting from an appropriate non-racemic 3-cyclohexanone. Towards these ends, cyclohexanone 5 was prepared in 87% yield via catalytic asymmetric Michael addition of dimethyl malonate to 2-cyclohexen-1-one (Scheme 3).[21-23] Notably, this very practical synthesis of 5 (Scheme 3) has been performed on kilogram scales in a pre-manufacturing setting.[23] We confirmed the high enantiomeric purity of 5 (95% ee) by conversion to the ketal 6[24,25], the two diastereomers of which could be readily distinguished by $^{13}$C NMR spectroscopy.

Scheme 3[a] Enantiocontroled synthesis of ketone 7.

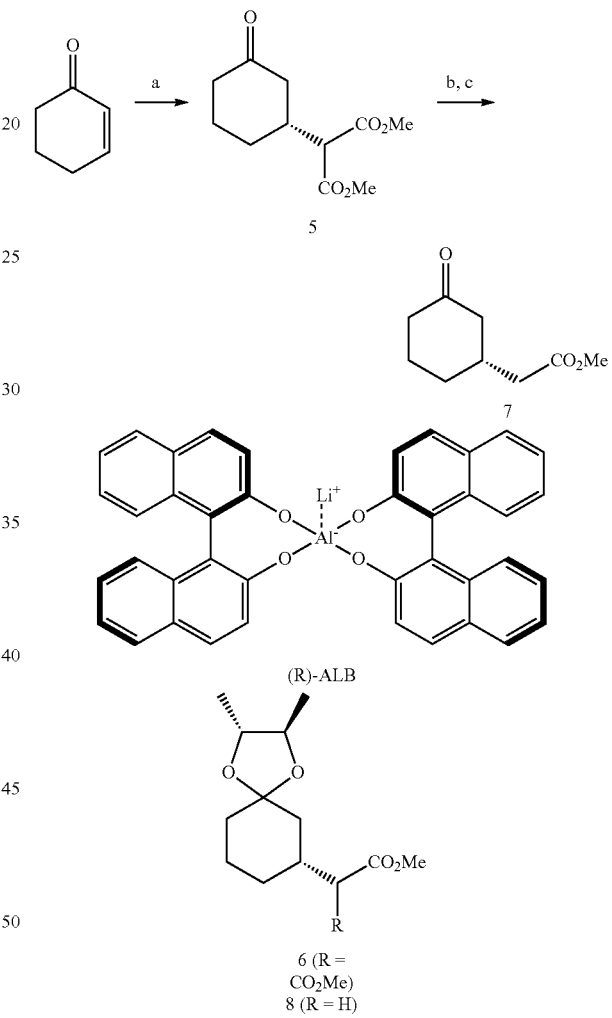

6 (R = CO$_2$Me)
8 (R = H)

[a] Reagents and conditions: (a) Dimethyl malonate, (R)-ALB (1 mol %), t-BuOK (0.9 equiv relative to ALB), 4 Å MS, THF, rt, 68 h, 87%; (b) NaOH, H$_2$O/THF (11:1) 0° C., 2 h; (c) DMSO, 160° C., 4 h, 85% over two steps.

A Krapcho decarboxylation was next considered as a means to produce the desired ester 7[26] from 5. However, to avoid the possibility of epimerization via retro-Michael/Michael addition of dimethyl malonate, a two-step procedure was utilized instead.[26] Thus, hydrolysis of 5 with NaOH at 0° C. afforded the mono carboxylate intermediate, which was immediately heated to 160° C. to facilitate decarboxylation. This afforded 7 in 85% yield over two steps. Conversion of 7 to ketal 8 confirmed that the hydrolysis/decarboxylation sequence had proceeded without erosion of enantiomeric purity (94% ee for 7). Griesbaum co-ozonolysis of 7 with two equivalents of oxime 9 at 0° C. using our optimized conditions,[20] afforded the 1,2,4-trioxolane intermediate 10 in nearly quantitative yield. Hydrolysis of ester 10 with NaOH then furnished the desired carboxylic acid 11 in excellent yield. From 11, the desired 3" amides 12a-k were prepared in 68-95% yields via formation of the mixed anhydride (ethyl chloroformate and Et$_3$N at −10° C.) and subsequent reaction with primary or secondary amines (Scheme 4). We were able to confirm that the Griesbaum co-ozonolysis of 7 and 9 had proceeded with good diastereoselectivity (dr=91:9) by the preparation of analog 12k in which trans and cis diastereomers could be readily distinguished by NMR.[20]

matography system. Compounds were visualized under UV light or through staining with permanganate, iodine, or most preferably for trioxolane analogs, Seebach's "Magic" stain (composed of the following: 2.5 g phosphomolybdic acid, 1.0 g cerium sulfate, 6 mL concentrated sulfuric acid, and 94 mL water). Solution containing crude reaction mixtures, as well as those solutions obtained upon work-up of the reaction, and chromatography fractions were first concentrated by rotary evaporation at temperatures under 40° C., at 20 Torr then subsequently placed under Hi-Vac at 0.5 Torr unless otherwise indicated. It is imperative to maintain water bath temperatures≤40° C. during rotary evaporation due to the thermal instability of trioxolanes at higher temperatures.

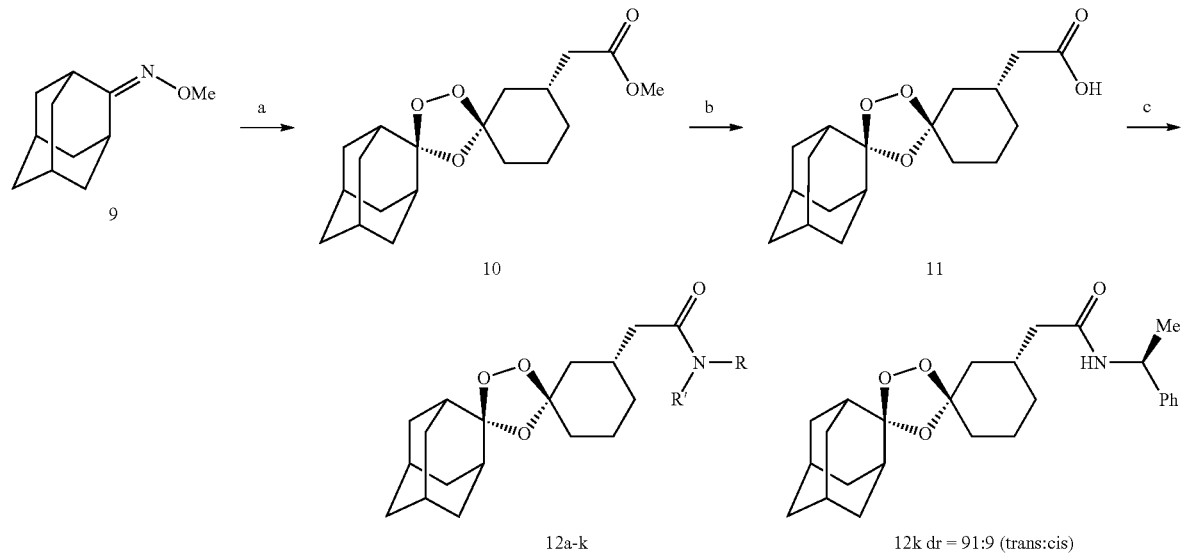

Scheme 4$^a$ Stereocontroled synthesis of 1,2,4-trioxolane analogs 12a-k.

Reagents and conditions: (a) 0.5 equiv. 7, O$_3$, CCl$_4$, 0° C., 3 h, 95%; (b) NaOH, EtOH/H$_2$O, 50° C., 4 h 95%; (c) Ethyl chloroformate, Et$_3$N, CH$_2$Cl$_2$, -10° C., 75 min; R(R')NH, CH$_2$Cl$_2$, -10° C. to rt, 2-24 h, 68-95%.

Known compounds were prepared according to literature procedures. The synthesis of new compounds 12a-k is described herein. All compounds tested in parasites or mice were judged to be of >95% purity as assessed using a Waters Micromass ZQ 4000, equipped with Waters 2795 Separation Module, Waters 2996 Photodiode Array Detector (254 nm), and Waters 2424 ELS detector. Separations were carried out with an XBridge BEH C18, 3.5 µm, 4.6×20 mm column, at ambient temperature (unregulated) using a mobile phase of water-methanol containing a constant 0.10% formic acid.

All reactions were performed under an Ar atmosphere using anhydrous solvents obtained from commercial suppliers in oven-dried round-bottom flasks containing Teflon coated stirrer bars, unless otherwise noted. All anhydrous solvents used were purchased from Sigma-Aldrich and used without further purification. Solvents to be employed in flash column chromatography and reaction work-up procedures were purchased from either Sigma-Aldrich or Fisher Scientific. All other reagents were obtained commercially and used without further purification, unless otherwise stated. Air and/or moisture sensitive reagents were transferred via syringe and were introduced into reaction vessels through rubber septa. Reactions were monitored using thin layer chromatography (TLC), performed on 0.25-mm EMD pre-coated glass-backed silica gel 60 F-254 plates. Column chromatography was performed on Silicycle Sili-prep cartridges using a Biotage Isolera Four automated flash chromatography system.

Instrumentation $^1$H NMR spectra were recorded on either a Varian INOVA 400 MHz spectrometer (with 5 mm Quad-Nuclear Z-Grad Probe), or a Bruker AvanceIII HD 400 MHz (with 5 mm BBFO Z-gradient Smart Probe), or a Bruker Avance DRX500 MHZ (with 5 mm quad-resonance Z-gradient QCI cryoprobe) calibrated to CH(D)Cl$_3$ as an internal reference (7.26 and 77.00 ppm for $^1$H and $^{13}$C NMR spectra, respectively). Data for $^1$H NMR spectra are reported in terms of chemical shift (δ, ppm), multiplicity, coupling constant (Hz), and integration. Data for $^{13}$C NMR spectra are reported in terms of chemical shift (δ, ppm), with multiplicity and coupling constants in the case of C—F coupling. The following abbreviations are used to denote the multiplicities: s=singlet; d=doublet; dd=doublet of doublets; dt=doublet of triplets; dq=doublet of quartets; ddd=doublet of doublet of doublets; t=triplet; td=triplet of doublets; tt=triplet of triplets; q=quartet; qd=quartet of doublets; quin=quintet; sex=sextet; m=multiplet. LC-MS and compound purity were determined using Waters Micromass ZQ 4000, equipped with a Waters 2795 Separation Module, Waters 2996 Photodiode Array Detector, and a Waters 2424 ELSD. Separations were carried out with an XBridge BEH C18, 3.5 µm, 4.6×20 mm column, at ambient temperature (unregulated) using a mobile phase of water-methanol containing a constant 0.1% formic acid.

Synthetic Procedures

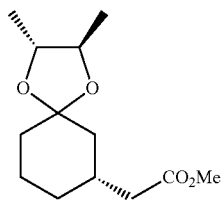 [SMILES: COC(=O)C[C@@H]1CCCC2(C1)O[C@H](C)[C@@H](C)O2]

Methyl 2-((2R,3R,7R)-2,3-dimethyl-1,4-dioxaspiro[4.5]decan-7-yl)acetate (8). To a solution of methyl (R)-2-(3-oxocyclohexyl)acetate (7) (0.060 g, 0.353 mmol, 1.0 equiv) in benzene (4 mL) was added (2R,3R)-(−)-2,3-butanediol (34 µL, 0.372 mmol 1.06 equiv) andp-toluenesulfonic acid monohydrate (5.6 mg, 0.029 mmol, 0.084 equiv). After stirring for 22 hours at room temperature, the reaction was diluted with EtOAc (10 mL) and quenched with sat. aq. NaHCO$_3$ (10 mL). Following separation of the layers, the organic layer was washed with additional sat. aq. NaHCO$_3$ (10 mL×2). The combined aqueous layers were then extracted with EtOAc (10 mL×2). The combined organic layers were then washed with Brine (10 mL), dried over anhydrous Na$_2$SO$_4$, filtered, and concentrated under reduced pressure. The residue was then purified through flash column chromatography (12 g silica gel cartridge, 0-7% EtOAc/Hexanes, product elutes during 4-5%) to yield 8 (68.5 mg, 80%) as a foamy solid. Analysis of the $^{13}$C NMR data showed a 97:3 ratio of diastereomers, which allowed us to infer the enantiomeric purity of 7 as 94% ee. $^1$H NMR (400 MHz, CDCl$_3$) δ (3.64, s, 3H), 3.63-3.57 (m, 2H), 2.20 (d, J=7.2 Hz, 2H), 2.17-2.04 (m, 1H), 1.80-1.63 (m, 4H), 1.62-1.48 (m, 1H), 1.47-1.35 (m, 1H), 1.27-1.14 (m, 7H), 0.97-0.82 (m, 1H); $^{13}$C NMR (100 MHz, CDCl$_3$) δ 173.0, 107.8, 78.1 (minor diastereomer), 78.0, 77.8, 77.7 (minor diastereomer), 51.3, 43.3 (minor diastereomer), 42.3, 41.2 (minor diastereomer), 41.1, 36.7, 35.7 (minor diastereomer), 32.6, 32.2 (minor diastereomer), 31.4, 22.8 (minor diastereomer), 22.5, 17.0, 16.9 (minor diastereomer), 16.8.

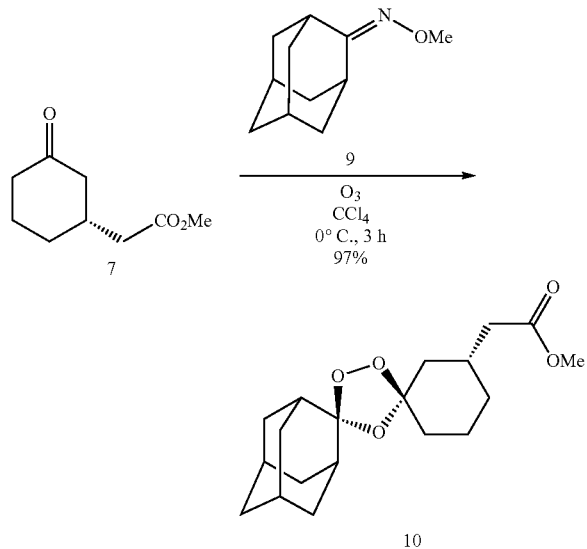

Methyl 2-((R,R)-dispiro[adamantane-2,3'-[1,2,4]trioxolane-5',1''-cyclohexan]-3''-yl)acetate (10). To a solution of ketone 7 (1.00 g, 5.88 mmol, 1.0 equiv) in carbon tetrachloride (100 mL) was added adamantyl oxime 9 (2.11 g, 11.75 mmol, 2.0 equiv). This solution was then cooled to 0° C. and O$_2$ was bubbled into the solution for 15 minutes. Ozone generation was then initiated (2 L/min, 40% power) and the ozone gas mixture bubbled into the solution, maintaining the reaction mixture at 0° C. After 95 mins, the reaction was judged incomplete by LCMS analysis and so an additional portion of oxime 9 (0.527 g, 2.94 mmol, 0.5 equiv) was added to the reaction. Ozone was bubbled into the solution for another 60 mins, after which time the reaction was judged complete. The reaction mixture was then purged with O$_2$ for 20 mins to remove any dissolved ozone, followed by sparging with argon gas to remove any oxygen from the solution. The solution was then concentrated under reduced pressure to provide a viscous oil. The residue was purified through flash column chromatography (180 g silica gel cartridge, 0-5% EtOAc/Hexanes) to yield 10 (1.91 g, 97%) as a foamy solid. $^1$H NMR (400 MHz, CDCl$_3$) δ 3.66 (s, 3H), 2.30-2.15 (m, 2H), 2.12-2.01 (m, 1H), 2.01-1.86 (m, 8H), 1.86-1.63 (m, 10H), 1.62-1.46 (m, 2H), 1.42 (t, J=12.9 Hz, 1H), 1.02-0.87 (m, 1H); $^{13}$C NMR (100 MHz, CDCl$_3$) δ 172.7, 111.3, 108.7, 51.4, 40.9, 40.6, 36.8, 36.4, 34.8, 34.7, 34.2, 32.5, 30.9, 26.8, 26.4, 22.6; MS (ESI) calculated for C$_{19}$H$_{28}$O$_5$Na [M+Na]$^+$ m/z 359.18, found 359.51.

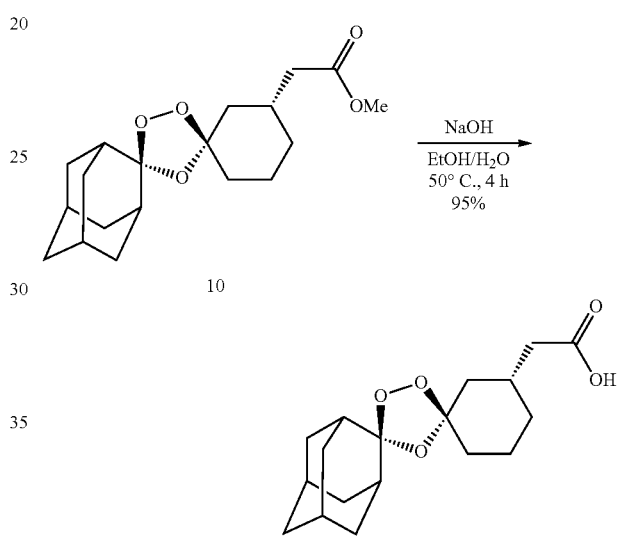

2-((R,R)-Dispiro[adamantane-2,3'-[1,2,4]trioxolane-5',1''-cyclohexan]-3''-yl)acetic acid (11). To a solution of ester 10 (1.78 g, 5.29 mmol, 1.0 equiv) in absolute ethanol (23.75 mL) and deionized water (1.25 mL) was added a solution of sodium hydroxide (0.65 g in 13.5 mL deionized water, 1.2 M NaOH, 3.0 equiv). The solution was placed in a preheated oil bath set to 50° C. and stirred at this temperature for 4 hours. The solution was then removed from the oil bath and allowed to cool to room temperature and then further cooled to 0° C. by placing the flask into an ice bath. Once the solution was chilled, the pH of the mixture was adjusted to pH=1 by slow addition of 1 M HCl, which led the product to separate as an oil. Dichloromethane (50 mL) was then added to the solution and the mixture was then transferred to a separatory funnel where the layers were separated. The aqueous layer was extracted further with CH$_2$Cl$_2$ (2×50 mL). The combined organic layers were then washed with brine, dried over anhydrous Na$_2$SO$_4$, filtered, and concentrated under reduced pressure. The residue was then purified by flash column chromatography (120 g silica gel cartridge, 0-50% EtOAc/Hexanes) to yield 11 (1.62 g, 95%) as a foamy solid. $^1$H NMR (400 MHz, CDCl$_3$) δ 2.37-2.21 (m, 2H), 2.14-2.03 (m, 1H), 2.03-1.87 (m, 8H), 1.87-1.64 (m, 10H), 1.64-1.41 (m, 3H), 1.07-0.92 (m, 1H); $^{13}$C NMR (100 MHz, CDCl$_3$) δ 178.6, 111.3, 108.6, 40.8, 40.5, 36.8, 36.4, 34.8, 34.8, 34.2, 32.3, 30.9, 26.9, 26.5, 22.6; MS (ESI) calculated for C$_{18}$H$_{26}$O$_5$Na [M+Na]$^+$ m/z 345.17, found 345.52.

General procedure for the preparation of analogs 12a-k.

Amide analogs 12a-j were prepared via the mixed anhydride intermediate S1, which was prepared as described below and then transferred in aliquots to separate solutions of requisite amines. Then general protocol is illustrated below for the preparation of 12b and 12e from 11 via intermediate 13.

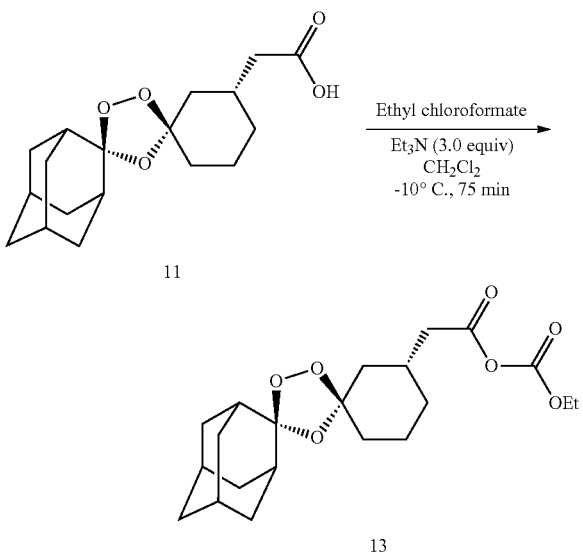

2-((R,R)-Dispiro[adamantane-2,3'-[1,2,4]trioxolane-5', 1"-cyclohexan]-3"-yl)acetic (ethyl carbonic) anhydride (13). To a solution of acid 11 (0.217 g, 0.673 mmol, 1.0 equiv) in CH$_2$Cl$_2$ (4.35 mL) was added triethylamine (281 μL, 2.016 mmol, 3.0 equiv). The mixture was then cooled to −10° C. in an ice/salt bath. Once cooled, a solution of ethyl chloroformate (74 μL, 0.774 mmol, 1.15 equiv) in CH$_2$Cl$_2$ (500 μL) was added dropwise to the solution. The vessel that had contained the ethyl chloroformate was rinsed with CH$_2$Cl$_2$ (150 μL), which was then added to the reaction. The reaction was allowed to proceed for 75 minutes, at which point it was deemed complete by thin layer chromatography.

Representative procedure for preparing analogs 12 from amines obtained in salt forms.

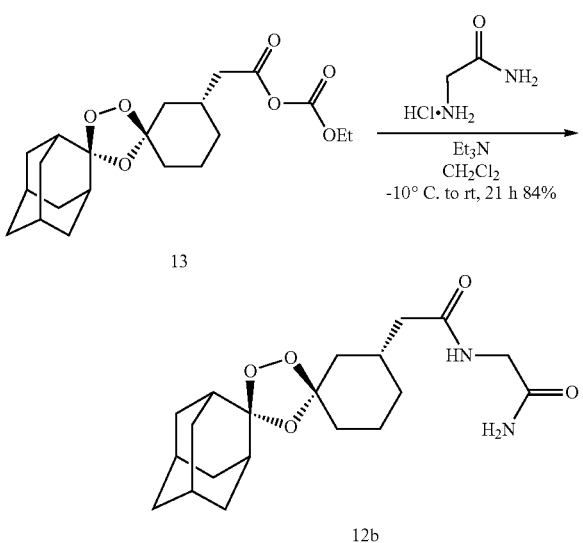

N-(2-Amino-2-oxoethyl)-2-((R,R)-dispiro[adamantane-2,3'-[1,2,4]trioxolane-5',1"-cyclohexan]-3"-yl)acetamide (12b). To a glass vial was added glycinamide HCl (34.6 mg, 0.310 mmol, 1.9 equiv), followed by CH$_2$Cl$_2$ (1.0 mL), and Et$_3$N (65 μL, 0.465 mmol, 2.9 equiv). This mixture was allowed to stir 15 mins at room temp and then cooled to −10° C. Once cooled, a solution of the freshly prepared mixed anhydride 13 (1.2 mL, 0.161 mmol, 1.0 equiv) was added to the vial. The reaction was allowed to stir at −10° C. for 10 mins, at which point it was removed from the bath and allowed to warm to room temp, where it was stirred for 21 h. The reaction was then diluted with CH$_2$Cl$_2$ (20 mL) and transferred to a separatory funnel where it was washed with sat aq. NaHCO$_3$ (10 mL×2), and brine (10 mL). The combined aqueous layers were then extracted with CH$_2$Cl$_2$ (10 mL). The combined organic layers were then dried over Na$_2$SO$_4$, filtered, and concentrated under reduced pressure. The residue was then purified via flash column chromatography (12 g silica gel cartridge), eluting with 0-50% EtOAc/Hexanes and then 0-20% MeOH (containing 0.7 N NH$_3$)/CH$_2$Cl$_2$ to yield 12b (51.1 mg, 84%) as a colorless thin film. $^1$H NMR (500 MHz, CDCl$_3$) δ 7.01-6.68 (m, 2H); 6.17-5.88 (m, 1H), 3.96 (d, J=4.2 Hz, 2H), 2.30-2.09 (m, 2H), 2.08-1.84 (m, 9H), 1.84-1.62 (m, 10H), 1.57 (td, J=13.5, 3.3 Hz, 1H), 1.52-1.43 (m, 1H), 1.38 (t, J=12.8 Hz, 1H), 1.01-0.86 (m, 1H); $^{13}$C NMR (125.7 MHz, CDCl$_3$) δ 172.5, 172.5 (minor diastereomer), 171.7, 171.6 (minor diastereomer), 111.7 (minor diastereomer), 111.3, 108.7, 43.1, 42.9 (minor diastereomer), 42.7, 40.8, 40.4 (minor diastereomer), 36.7, 36.3, 36.3, 36.2 (minor diastereomer), 34.9 (minor diastereomer), 34.8, 34.7, 34.7, 34.2, 34.0 (minor diastereomer), 33.0, 32.7 (minor diastereomer), 31.1 (minor diastereomer), 30.9, 26.8, 26.4, 22.7, 22.4 (minor diastereomer); MS (ESI) calculated for C$_{20}$H$_{30}$N$_2$O$_5$Na [M+Na]$^+$ m/z 401.21, found 401.60.

Representative procedure for preparing analogs 12 from amines obtained as free bases.

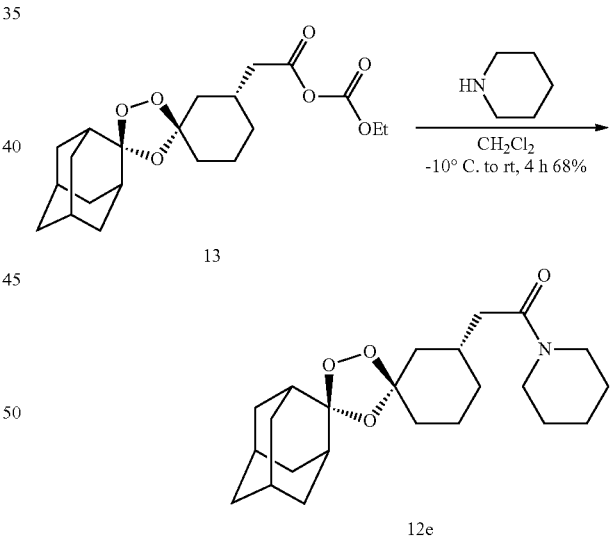

2-((R,R)-Dispiro[adamantane-2,3'-[1,2,4]trioxolane-5', 1"-cyclohexan]-3"-yl)-1-(piperidin-1-yl)ethan-1-one (12e). To a solution of piperidine (39 μL, 0.388 mmol, 2.4 equiv) in CH$_2$Cl$_2$ (1.0 mL) cooled at −10° C. was added a solution of the freshly prepared mixed anhydride 13 (1.2 mL, 0.161 mmol, 1.0 equiv). The reaction was allowed to stir at −10° C. for 5 mins, at which point it was removed from the bath and allowed to warm to room temp, where it was stirred for 4 h. The clear colorless solution was then diluted with CH$_2$Cl$_2$ (20 mL) and transferred to a separatory funnel where it was washed with sat aq. NaHCO$_3$ (10 mL×2), and Brine (10 mL). The combined aqueous layers were then extracted with CH$_2$Cl$_2$ (10 mL). The combined organic layers were then dried over Na$_2$SO$_4$, filtered, and concentrated under reduced pressure. The residue was then purified through flash column chromatography (12 g silica gel cartridge), eluting with 0-30% EtOAc/Hexanes (desired product eluted between 10-20% EtOAc/Hex) to yield 12e (42.4 mg, 68%) as a colorless thin film. $^1$H NMR (500 MHz, CDCl$_3$) δ 3.66-3.44 (m, 2H), 3.44-3.30 (m, 2H), 2.33-2.15 (m, 2H), 2.07-1.85 (m, 9H), 1.85-1.59 (m, 13H), 1.59-1.47 (m, 5H), 1.46-1.38 (m, 1H), 1.01-0.89 (m, 1H); $^{13}$C NMR (125.7 MHz, CDCl$_3$) δ 169.9 (minor diastereomer), 169.7, 111.5 (minor diastereomer), 111.2, 108.9 (minor diastereomer), 108.8, 47.0, 46.9 (minor diastereomer), 42.6, 40.9, 40.8 (minor diastereomer), 40.4, 39.9 (minor diastereomer), 36.7, 36.6 (minor diastereomer), 36.3, 36.3, 34.9 (minor diastereomer), 34.8, 34.7, 34.7, 34.3, 34.1 (minor diastereomer), 32.7, 32.5 (minor diastereomer), 31.7 (minor diastereomer), 31.3, 26.8, 26.6, 26.4, 25.6, 24.6 (minor diastereomer), 24.5, 22.7, 22.6 (minor diastereomer); MS (ESI) calculated for C$_{23}$H$_{36}$NO$_4$ [M+H]$^+$ m/z 390.26, found 390.63.

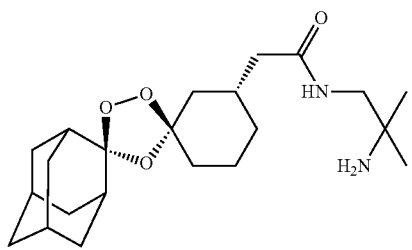

N-(2-Amino-2-methylpropyl)-2-((R,R)-dispiro[adamantane-2,3'-[1,2,4]trioxolane-5',1''-cyclohexan]-3''-yl)acetamide (12a). Prepared according to the standard procedure and purified by flash column chromatography (12 g silica gel cartridge, 0-50% EtOAc/Hexanes, followed by 0-20% MeOH (containing 0.7 N NH$_3$)/CH$_2$Cl$_2$, and desired product eluted during 20% MeOH (containing 0.7 N ammonia)/CH$_2$Cl$_2$) to yield 12a (51.8 mg, 82%) as a colorless thin film. $^1$H NMR (500 MHz, CDCl$_3$) δ 6.20 (br s, 1H), 3.23-3.03 (m, 2H), 2.18-2.07 (m, 2H), 2.07-1.83 (m, 9H), 1.83-1.60 (m, 12H), 1.60-1.44 (m, 2H), 1.39 (t, J=12.6 Hz, 1H), 1.10 (s, 6H), 1.01-0.87 (m, 1H); $^{13}$C NMR (125.7 MHz, CDCl$_3$) δ 172.0 (minor diastereomer), 171.7, 111.6 (minor diastereomer), 111.2, 108.8 (minor diastereomer), 108.7, 50.2 (minor diastereomer), 50.1, 44.0, 43.6 (minor diastereomer), 40.8, 40.3 (minor diastereomer), 36.7, 36.3, 36.3, 36.2 (minor diastereomer), 34.8 (minor diastereomer), 34.8 (minor diastereomer), 34.7, 34.7, 34.2, 33.3, 32.6 (minor diastereomer), 31.3 (minor diastereomer), 31.1, 28.4 (minor diastereomer), 28.4, 26.8, 26.4, 22.7, 22.3 (minor diastereomer); MS (ESI) calculated for C$_{22}$H$_{37}$N$_2$O$_4$ [M+H]$^+$ m/z 393.28, found 393.66.

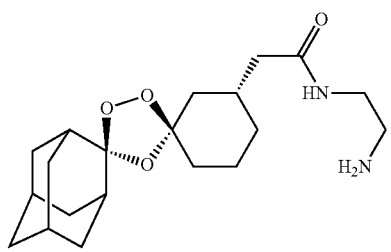

N-(2-Aminoethyl)-2-((R,R)-dispiro[adamantane-2,3'-[1,2,4]trioxolane-5',1''-cyclohexan]-3''-yl)acetamide (12c). Prepared according to the standard procedure and purified by flash column chromatography (12 g silica gel cartridge), eluting with 0-50% EtOAc/Hexanes, followed by 0-20% MeOH (containing 0.7 N NH$_3$)/CH$_2$Cl$_2$ to yield 12c (43.4 mg, 74%) as a colorless thin film. $^1$H NMR (400 MHz, CDCl$_3$) δ 6.28 (br s, 1H), 3.39-3.19 (m, 2H), 2.82 (t, J=5.5 Hz, 2H), 2.18-2.06 (m, 2H), 2.06-1.83 (m, 11H), 1.83-1.61 (m, 10H), 1.61-1.34 (m, 3H), 1.00-0.86 (m, 1H); $^{13}$C NMR (100 MHz, CDCl$_3$) δ 171.9, 111.6 (minor diastereomer), 111.2, 108.7, 43.7, 41.6, 41.2, 40.7, 36.7, 36.3, 36.3, 34.7, 34.7, 34.2, 33.2, 31.0, 26.8, 26.4, 22.7; MS (ESI) calculated for C$_{20}$H$_{33}$N$_2$O$_4$ [M+H]$^+$ m/Z 365.24, found 365.62.

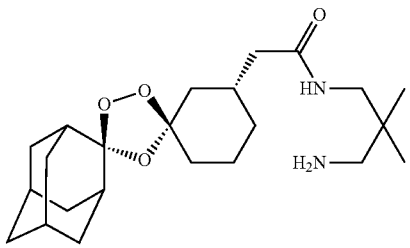

N-(3-Amino-2,2-dimethylpropyl)-2-((R,R)-dispiro[adamantane-2,3'-[1,2,4]trioxolane-5',1''-cyclohexan]-3''-yl)acetamide (12d). Prepared according to the standard procedure and purified by flash column chromatography (12 g silica gel cartridge), eluting with 0-50% EtOAc/Hexanes, followed by 0-20% MeOH (containing 0.7 N NH$_3$)/CH$_2$Cl$_2$, to yield 12d (49.2 mg, 75%) as a colorless thin film. $^1$H NMR (500 MHz, CDCl$_3$) δ 7.20 (br s, 1H), 6.97 (br s, 1H, minor diastereomer), 3.26-3.06 (m, 2H), 2.54 (s, 2H), 2.16-2.05 (m, 2H), 2.05-1.84 (m, 9H), 1.84-1.62 (m, 12H), 1.62-1.52 (m, 1H), 1.52-1.43 (m, 1H), 1.38 (t, J=13.5 Hz, 1H), 1.00-0.82 (m, 7H); $^{13}$C NMR (125.7 MHz, CDCl$_3$) δ 171.8 (minor diastereomer), 171.5, 111.6 (minor diastereomer), 111.2, 108.8 (minor diastereomer), 108.7, 51.5, 51.3 (minor diastereomer), 48.6, 48.2 (minor diastereomer), 44.1, 43.7 (minor diastereomer), 40.8, 40.3 (minor diastereomer), 36.7, 36.3, 36.3, 36.3 (minor diastereomer), 34.9 (minor diastereomer), 34.9 (minor diastereomer), 34.7, 34.7, 34.2, 33.2, 32.7 (minor diastereomer), 31.3 (minor diastereomer), 31.2, 26.8, 26.4, 23.7, 23.6 (minor diastereomer), 23.5, 22.8, 22.3 (minor diastereomer); MS (ESI) calculated for C$_{23}$H$_{39}$N$_2$O$_4$ [M+H]$^+$ m/z 407.29, found 407.64.

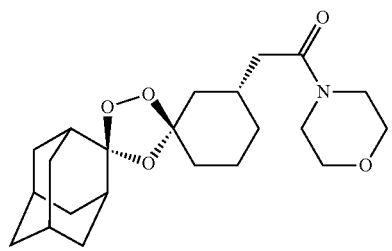

2-((R,R)-Dispiro[adamantane-2,3'-[1,2,4]trioxolane-5',1''-cyclohexan]-3''-yl)-1-morpholinoethan-1-one (12f). Prepared according to the standard procedure and purified by flash column chromatography (12 g silica gel cartridge), eluting with 0-75% EtOAc/Hexanes to yield 12f (53.4 mg, 85%) as a colorless thin film. $^1$H NMR (500 MHz, CDCl$_3$)

δ 3.73-3.56 (m, 6H), 3.53-3.37 (m, 2H), 2.25 (d, J=7.1 Hz, 2H), 2.11-1.85 (m, 9H), 1.85-1.62 (m, 10H), 1.62-1.47 (m, 2H), 1.43 (t, J=12.6 Hz, 1H), 1.03-0.89 (m, 1H); $^{13}$C NMR (125.7 MHz, CDCl$_3$) δ 170.3 (minor diastereomer), 170.1, 111.6 (minor diastereomer), 111.2, 108.7 (minor diastereomer), 108.7, 66.9, 66.7, 46.3, 46.2 (minor diastereomer), 41.8, 40.9, 40.7 (minor diastereomer), 39.9, 39.3 (minor diastereomer), 36.7, 36.6 (minor diastereomer), 36.3, 36.3 (minor diastereomer), 34.9 (minor diastereomer), 34.8, 34.7, 34.7, 34.7 (minor diastereomer), 34.2, 34.1 (minor diastereomer), 32.6, 32.3 (minor diastereomer), 31.6 (minor diastereomer), 31.3, 26.8, 26.4, 22.7 22.4 (minor diastereomer); MS (ESI) calculated for C$_{22}$H$_{34}$NO$_5$ [M+H]$^+$ m/z 392.24, found 392.59.

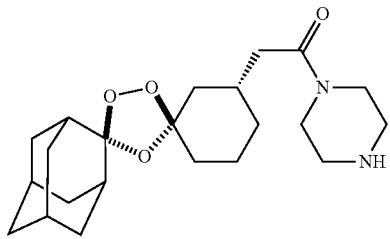

2-((R,R)-Dispiro[adamantane-2,3'-[1,2,4]trioxolane-5',1''-cyclohexan]-3''-yl)-1-(piperazin-1-yl)ethan-1-one (12g). Prepared according to the standard procedure and purified by flash column chromatography (12 g silica gel cartridge), eluting with 0-50% EtOAc/Hexanes, followed by 0-20% MeOH (containing 0.7 N NH$_3$)/CH$_2$Cl$_2$, to yield 12 g (50.6 mg, 80%) as a colorless thin film. $^1$H NMR (500 MHz, CDCl$_3$) δ 3.67-3.52 (m, 2H), 3.51-3.37 (m, 2H), 2.94-2.68 (m, 5H), 2.29-2.19 (m, 2H), 2.07-1.84 (m, 9H), 1.84-1.60 (m, 10H), 1.60-1.45 (m, 2H), 1.41 (t, J=12.7 Hz, 1H), 1.02-0.87 (m, 1H); $^{13}$C NMR (125.7 MHz, CDCl$_3$) δ 170.2 (minor diastereomer), 170.0, 111.5 (minor diastereomer), 111.2, 108.8 (minor diastereomer), 108.7, 46.7, 46.6 (minor diastereomer), 46.1, 45.7, 45.4 (minor diastereomer), 42.2, 40.9, 40.7 (minor diastereomer), 40.0, 39.5 (minor diastereomer), 36.7, 36.3, 36.3 (minor diastereomer), 34.9 (minor diastereomer), 34.7, 34.7, 34.2, 34.1 (minor diastereomer), 32.6, 32.4 (minor diastereomer), 31.6 (minor diastereomer), 31.2, 26.8, 26.4, 22.7, 22.5 (minor diastereomer); MS (ESI) calculated for C$_{22}$H$_{35}$N$_2$O$_4$ [M+H]$^+$ m/z 391.26, found 391.64.

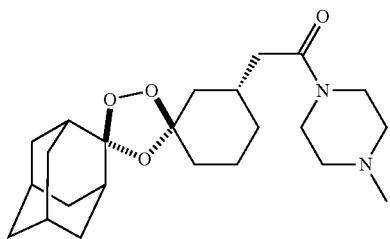

2-((R,R)-Dispiro[adamantane-2,3'-[1,2,4]trioxolane-5',1''-cyclohexan]-3''-yl)-1-(4-methylpiperazin-1-yl)ethan-1-one (12h). Prepared according to the standard procedure and purified by flash column chromatography (12 g silica gel cartridge), eluting with 0-50% EtOAc/Hexanes, followed by 0-20% MeOH (containing 0.7 N NH$_3$)/CH$_2$Cl$_2$, to yield 12h (59.7 mg, 92%) as a white thin film. $^1$H NMR (400 MHz, CDCl$_3$) δ 3.73-3.51 (m, 2H), 3.51-3.37 (m, 2H), 2.41-2.30 (m, 5H), 2.27 (s, 3H), 2.23 (d, J=7.0 Hz, 2H), 2.06-1.83 (m, 9H), 1.83-1.60 (m, 10H), 1.60-1.34 (m, 2H), 1.03-0.85 (m, 1H); $^{13}$C NMR (100 MHz, CDCl$_3$) δ 169.8, 111.1, 108.7 (minor diastereomer), 108.7, 55.1, 54.7, 54.6, 46.1 (minor diastereomer), 45.9, 45.7, 41.3, 40.8, 40.1, 36.7, 36.3, 36.2 (minor diastereomer), 34.7, 34.7, 34.6 (minor diastereomer), 34.2, 32.6, 31.2, 26.8, 26.4, 22.7; MS (ESI) calculated for C$_{23}$H$_{37}$N$_2$O$_4$ [M+H]$^+$ m/z 405.28, found 405.69.

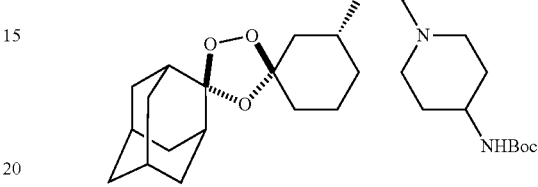

tert-Butyl (1-(2-((R,R)-dispiro[adamantane-2,3'-[1,2,4]trioxolane-5',1''-cyclohexan]-3''-yl)acetyl)piperidin-4-yl)carbamate (14). Prepared according to the standard procedure and purified by flash column chromatography (12 g silica gel cartridge), eluting with 0-75% EtOAc/Hexanes to yield 14 (78.4 mg, 99%) as a white solid. $^1$H NMR (500 MHz, CDCl$_3$) δ 4.67-4.28 (m, 1H), 3.90-3.51 (m, 2H), 3.16-3.01 (m, 1H), 2.79-2.57 (m, 1H), 2.41-2.14 (m, 2H), 2.10-1.83 (m, 11H), 1.83-1.17 (m, 24H), 1.01-0.88 (m, 1H); $^{13}$C NMR (125.7 MHz, CDCl$_3$) δ 170.0 (minor diastereomer), 169.9 (minor diastereomer), 169.8, 169.8, 155.0, 111.5 (minor diastereomer), 111.4, 111.2, 108.8, 108.7, 79.5, 79.3, 47.8, 47.6, 44.9, 44.6, 41.0, 40.7, 40.5, 40.4, 40.2, 39.8 (minor diastereomer), 39.5 (minor diastereomer), 36.7, 36.3, 36.3, 35.0 (minor diastereomer), 34.9 (minor diastereomer), 34.8, 34.8, 34.7, 34.7, 34.7, 34.6, 34.3, 34.1, 33.2 (minor diastereomer), 33.1, 33.1 (minor diastereomer), 33.0, 32.7, 32.6, 32.4 (minor diastereomer), 32.3, 32.2 (minor diastereomer), 32.1, 31.7 (minor diastereomer), 31.6 (minor diastereomer), 31.4, 31.2, 28.3, 26.8, 26.8, 26.4, 22.8, 22.7, 22.5 (minor diastereomer), 22.5 (minor diastereomer); MS (ESI) calculated for C$_{28}$H$_{45}$N$_2$O$_6$ [M+H]$^+$ m/z 505.33, found 505.17.

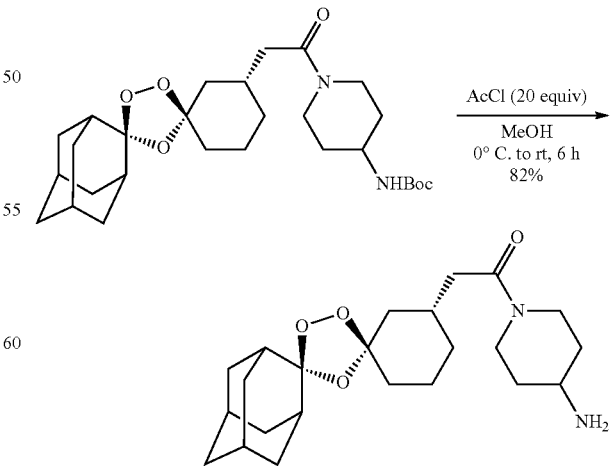

1-(4-Aminopiperidin-1-yl)-2-((R,R)-dispiro[adamantane-2,3'-[1,2,4]trioxolane-5',1''-cyclohexan]-3''-yl)ethan-1-one (12i). To a solution of intermediate 14 (16.5 mg, 0.0327 mmol, 1 equiv) in methanol (1.6 mL) cooled to 0° C. in an ice bath, was added acetyl chloride (47 µL, 0.674 mmol, 21 equiv) dropwise via microsyringe. The solution was allowed to stir for 10 minutes at 0° C., after which the solution was removed from the bath and allowed to warm to room temperature. After stirring for 6 h, the reaction was deemed complete by LCMS and TLC. Following dilution with dichloromethane (5 mL), sat aq. NaHCO$_3$ (5 mL) was added to neutralize any acid in the flask. The solution was then concentrated under reduced pressure to remove all volatile solvents. To the resulting slurry was added dichloromethane (15 mL) and water (3 mL). After separating the layers, the organic layer was washed with sat aq. NaHCO$_3$ (10 mL×2). The combined aqueous layers were then back extracted with dichloromethane (10 mL×2). The combined organic layers were washed with brine (10 mL), anhydrous Na$_2$SO$_4$, filtered, and concentrated under reduced pressure. The residue was then purified through flash column chromatography (12 g silica gel cartridge), eluting with 0-50% EtOAc/Hexanes, followed by 0-20% MeOH (containing 0.7 N NH$_3$)/CH$_2$Cl$_2$, to yield 12i (10.8 mg, 82%) as a thin film. $^1$H NMR (400 MHz, CDCl$_3$) δ 4.50 (t, J=11.5 Hz, 1H), 3.81 (d, J=12.1 Hz, 1H), 3.19-2.85 (m, 4H), 2.68 (q, J=12.0 Hz, 1H), 2.35-2.18 (m, 2H), 2.11-1.84 (m, 10H), 1.84-1.20 (m, 16H), 1.04-0.88 (m, 1H); $^{13}$C NMR (100 MHz, CDCl$_3$) δ 170.1 (minor diastereomer), 169.9, 111.6 (minor diastereomer), 111.2, 108.8 (minor diastereomer), 108.8, 48.7, 48.6, 44.6, 44.5, 44.4 (minor diastereomer), 41.0, 40.9, 40.5, 40.4 (minor diastereomer), 40.3, 40.2, 36.7, 36.3, 35.0 (minor diastereomer), 34.7, 34.4 (minor diastereomer), 34.3, 34.3, 32.8, 32.7, 32.5 (minor diastereomer), 31.3, 26.8, 26.4, 22.7, 22.6 (minor diastereomer); MS (ESI) calculated for C$_{23}$H$_{37}$N$_2$O$_4$ [M+H]$^+$ m/z 405.28, found 405.13.

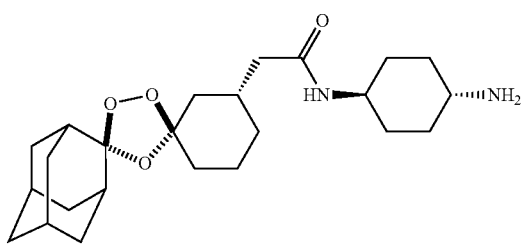

N-((trans)-4-Aminocyclohexyl)-2-((R,R)-dispiro[adamantane-2,3'-[1,2,4]trioxolane-5',1"-cyclohexan]-3"-yl)acetamide (12j). As this reaction was performed in THF and CH$_2$Cl$_2$, an updated procedure has been provided. First step: To a solution of acid 11 (0.0526 g, 0.1632 mmol, 1.0 equiv) in tetrahydrofuran (1.0 mL) and triethylamine (68 µL, 0.4895 mmol, 3.0 equiv) cooled to −10° C. was added a solution of ethyl chloroformate (20 µL, 0.2039 mmol, 1.25 equiv) in tetrahydrofuran (100 µL) dropwise. The vessel that had contained the ethyl chloroformate was rinsed with tetrahydrofuran (100 µL), and this solution added to the reaction mixture. The reaction was allowed to proceed for 70 minutes, at which time a large amount of white precipitate had formed, and the reaction was judged complete by TLC.

Second step: The soluble material from the first step, containing mixed anhydride 13, was removed from the flask via syringe and added directly to a solution of trans-1,4-diaminocyclohexane (0.0951 mg, 0.8158 mmol, 5.0 equiv) in tetrahydrofuran (1.0 mL) cooled at −10° C. The flask used to prepare S1 was rinsed with additional tetrahydrofuran (0.400 mL) and the solution added to the amine reaction mixture. The reaction was stirred at −10° C. for 10 mins, removed from the cooling bath and stirred for 3 h. The cloudy white solution was then diluted with CH$_2$Cl$_2$ (20 mL) and transferred to a separatory funnel and washed with sat aq. NaHCO$_3$ (10 mL×2), and brine (10 mL). The combined aqueous layers were then extracted with CH$_2$Cl$_2$ (10 mL). Finally, the combined organic layers were washed with brine (1×10 mL), dried over Na$_2$SO$_4$, filtered, and concentrated under reduced pressure. The crude product was purified by flash column chromatography (12 g silica gel cartridge), eluting with 0-50% EtOAc/Hexanes, followed by 0-20% MeOH (containing 0.7 N NH$_3$)/CH$_2$Cl$_2$, to yield 12j (47.5 mg, 70%) as a colorless thin film. $^1$H NMR (500 MHz, CDCl$_3$) δ 5.46-5.40 (m, 1H, minor diastereomer), 5.40-5.31 (m, 1H), 3.79-3.64 (m, 1H), 2.72-2.59 (m, 1H), 2.11-2.04 (m, 1H), 2.04-1.92 (m, 9H), 1.92-1.75 (m, 9H), 1.75-1.62 (m, 9H), 1.61-1.33 (m, 3H), 1.30-1.09 (m, 3H), 0.98-0.84 (m, 1H); $^{13}$C NMR (125.7 MHz, CDCl$_3$) δ 171.0 (minor diastereomer), 170.7, 111.6 (minor diastereomer), 111.2, 108.8 (minor diastereomer), 108.7, 49.9 (minor diastereomer), 49.9, 47.7, 43.9, 43.4 (minor diastereomer), 40.7, 39.8 (minor diastereomer), 36.7, 36.4, 36.3, 36.3 (minor diastereomer), 35.0, 34.9 (minor diastereomer), 34.8, 34.7, 34.7, 34.2, 33.3, 32.7 (minor diastereomer), 31.8, 31.8, 31.1 (minor diastereomer), 30.9, 26.8, 26.4, 22.7, 22.0 (minor diastereomer); MS (ESI) calculated for C$_{24}$H$_{39}$N$_2$O$_4$ [M+H]$^+$ m/z 419.29, found 419.74.

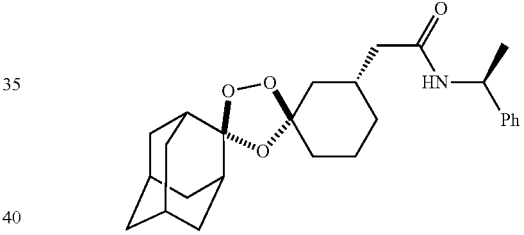

2-((R,R)-dispiro[adamantane-2,3'-[1,2,4]trioxolane-5',1"-cyclohexan]-3"-yl)-N-((S)-1-phenylethyl)acetamide (12k). Prepared according to the standard procedure and purified by flash column chromatography (12 g silica gel cartridge), eluting with 0-50% EtOAc/Hexanes to yield 12k (64.7 mg, 98%) as a white foam. $^1$H NMR (400 MHz, MeOD) δ 8.42 (d, J=8.04 Hz, 0.3H, this is likely the NH of the amide undergoing exchange with the NMR solvent, hence the integration value of less than one hydrogen), 7.35-7.26 (m, 4H), 7.24-7.17 (m, 1H), 5.09-4.93 (m, 1H), 2.21-2.11 (m, 1H), 2.11-2.05 (m, 1H), 2.04-1.93 (m, 3H), 1.93-1.62 (m, 16H), 1.62-1.50 (m, 1H), 1.48-1.40 (m, 4H), 1.39-1.28 (m, 1H), 1.02-0.88 (m, 1H); $^{13}$C NMR (100 MHz, CDCl$_3$) δ 170.8 (minor diastereomer), 170.5, 143.1, 128.6, 127.2, 126.1, 111.5 (minor diastereomer), 111.2, 108.8 (minor diastereomer), 108.7, 48.5, 43.8, 43.4 (minor diastereomer), 40.7, 40.1 (minor diastereomer), 36.7, 36.6 (minor diastereomer), 36.3, 36.2 (minor diastereomer), 35.7 (minor diastereomer), 34.8 (minor diastereomer), 34.8, 34.7, 34.7, 34.2, 33.3, 32.7 (minor diastereomer), 31.3 (minor diastereomer), 31.0, 26.8, 26.4, 25.7 (minor diastereomer), 24.6 (minor diastereomer), 22.6, 22.2 (minor diastereomer), 21.6; MS (ESI) calculated for C$_{26}$H$_{36}$NO$_4$ [M+H]$^+$ m/426.26, found 426.06.

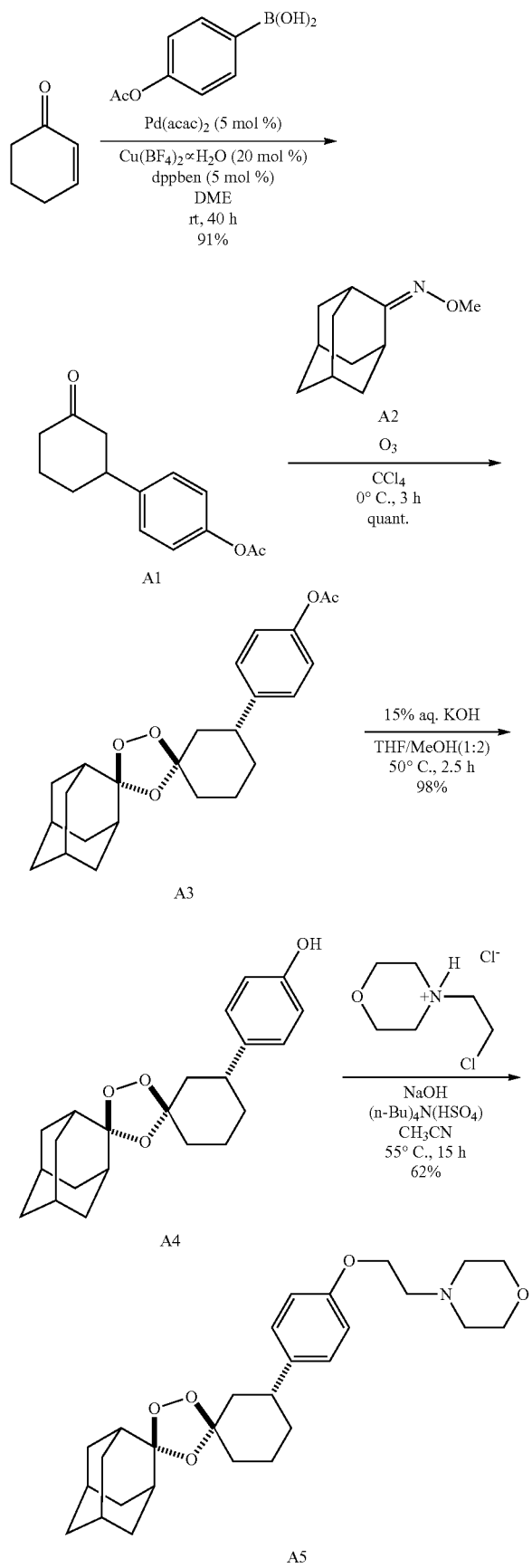

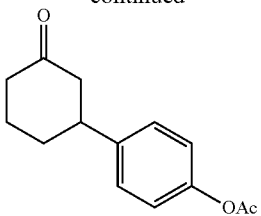

3-(4-acetoxyphenyl)cyclohexan-1-one (A1)

To an oven-dried round bottom flask containing a Teflon-coated magnetic stir bar under an Ar(g) atmosphere was added palladium(II) acetylacetonate (0.156 g, 0.506 mmol, 0.05 equiv), 1,2-bis(diphenylphosphino)benzene (0.231 g, 0.506 mmol, 0.05 equiv), copper(II) tetrafluoroborate hydrate (0.484 g, 2.025 mmol, 0.2 equiv), and 4-acetoxyphenylboronic acid (2.789 g, 15.185 mmol, 1.5 equiv). To the mixture of solid materials was added anhydrous dimethoxyethane (60 mL). At this point, the solution appeared dark brown in color. To the stirring solution was then added 2-cyclohexen-1-one (1 mL, 10.122 mmol, 1.0 equiv) via syringe at room temperature. Within 5 minutes the solution had turned lime green in color. The solution was allowed to stir at room temperature for 16 hours. Based on LCMS and TLC analysis, it was determined that the reaction was incomplete and the following reagents were added: palladium(II) acetylacetonate (0.078 g, 0.256 mmol, 0.025 equiv), 1,2-bis(diphenylphosphino)benzene (0.115 g, 0.258 mmol, 0.025 equiv), copper(II) tetrafluoroborate hydrate (0.242 g, 1.020 mmol, 0.1 equiv), and 4-acetoxyphenylboronic acid (1.394 g, 7.746 mmol, 0.75 equiv). The reaction was then allowed to stir at room temperature for an additional 24 hours, at which point it was determined to be complete. The mixture was then concentrated under reduced pressure to yield a dark green oil. To this oil was added EtOAc (100 mL) followed by DI $H_2O$ (50 mL). Following separation of the layers, the organic layer was washed with additional DI $H_2O$ (50 mL). The organic layer was then filtered through a pad of Celite to remove all insoluble inorganic material. The pad was then rinsed with EtOAc (50 mL×4). The aqueous layer was extracted with EtOAc, and the resulting organic solution was filtered through the same pad of Celite. The pad was then again rinsed with EtOAc (50 mL×2). The clear yellow solution was concentrated under reduced pressure to yield a yellow oil. The residue was then purified through flash column chromatography (220 g HP silica gel cartridge, 0-20% EtOAc/Hexanes, product eluted during 10-15% EtOAc/Hex) to yield A1 (2.133 g, 91%) as a foamy solid. $^1$H NMR (400 MHz, $CDCl_3$) δ 7.22 (d, J=8.5 Hz, 2H), 7.04 (d, J=8.5 Hz, 2H), 3.08-2.93 (m, 1H), 2.64-2.55 (m, 1H), 2.55-2.42 (m, 2H), 2.42-2.32 (m, 1H), 2.29 (s, 3H), 2.19-2.03 (m, 2H), 1.90-1.70 (m, 2H); $^{13}$C NMR (100 MHz, $CDCl_3$) δ 210.8, 169.6, 149.2, 141.8, 127.5, 121.7, 48.9, 44.1, 41.1, 32.7, 25.4, 21.1; MS (ESI) calculated for $C_{12}H_{15}O_2$ [M+H]$^+$ m/z 191.11, found 190.90. This mass corresponds to loss of the acetate, followed by protonation of the phenoxide to yield the phenol.

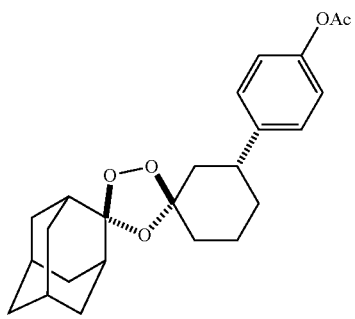

4-(dispiro[adamantane-2,3'-[1,2,4]trioxolane-5',1"-cyclohexan]-3"-yl)phenyl acetate (A3)

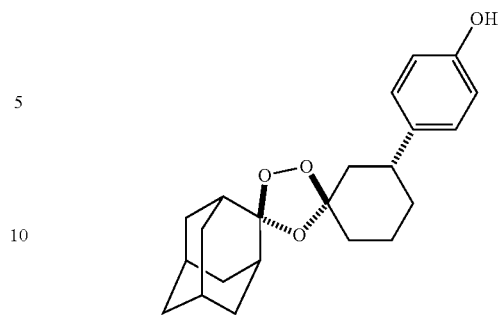

4-(dispiro[adamantane-2,3'-[1,2,4]trioxolane-5',1"-cyclohexan]-3"-yl)phenol (A4)

To a solution of adamantan-2-one O-methyl oxime (9) (3.226 g, 17.996 mmol, 2.0 equiv) in 100 mL carbon tetrachloride was added ketone A1 (2.09 g, 8.998 mmol, 1.0 equiv) as a solution in carbon tetrachloride (80 mL). This solution was then cooled to 0° C. and subsequently sparged with $O_2$ for 10 minutes. The reaction was kept at 0° C. while ozone was then bubbled (2 L/min, 35% power). After stirring for 35 mins, the reaction was deemed to be incomplete based on LCMS analysis and additional oxime (0.806 g, 4.499 mmol, 0.5 equiv) was added in a single portion to the reaction. Ozone was bubbled through the reaction for another 60 mins, at which point the reaction was found to still be incomplete. As such, additional oxime (0.806 g, 4.499 mmol, 0.5 equiv) was added in a single portion to the reaction. Additionally, at this point, the ozone power was increased to 40% and the ozone was continued to be bubbled through the reaction for another 80 mins. Based on LCMS and TLC analysis, the reaction was now found to be complete. The reaction was then purged with $O_2$ for 10 minutes in an effort to remove any dissolved ozone, followed by sparging with argon gas for 10 minutes to remove any dissolved oxygen. The solution was then concentrated under reduced pressure to provide an extremely viscous oil. The residue was purified through flash column chromatography (220 g silica gel cartridge, 0-10% EtOAc/Hexanes, product eluted during 4% EtOAc/Hex) to yield A3 (3.60 g, 100%) as a thick colorless oil, which solidified to a white solid upon standing in the refrigerator. The diastereoselectivity of the Griesbaum coozonolysis was determined to be 8.1:1 in favor of the trans diastereomer. $^1$H NMR (400 MHz, $CDCl_3$) δ 7.24-7.18 (m, 2H), 7.05-6.98 (m, 2H), 2.95 (tt, J=12.7, 3.1 Hz, 1H, minor diastereomer), 2.81 (tt, J=12.8, 3.3 Hz, 1H), 2.29 (s, 3H), 2.18-2.09 (m, 1H), 2.04-1.55 (m, 20H), 1.44-1.30 (m, 1H); $^{13}$C NMR (100 MHz, $CDCl_3$) δ 169.6, 148.9, 143.3 (minor diastereomer), 143.1, 127.7, 121.4, 111.8 (minor diastereomer), 111.3, 108.9, 46.9 (minor diastereomer), 42.1, 41.6 (minor diastereomer), 41.3, 41.0 (minor diastereomer), 39.2 (minor diastereomer), 36.7, 36.4, 36.3 (minor diastereomer), 35.0 (minor diastereomer), 34.9 (minor diastereomer), 34.8, 34.7, 34.1, 34.0 (minor diastereomer), 33.5 (minor diastereomer), 32.7, 27.4 (minor diastereomer), 26.9 (minor diastereomer), 26.8, 26.4, 23.5, 21.1; MS (ESI) calculated for $C_{24}H_{30}O_5Na$ [M+Na]$^+$ m/z 421.20, found 420.95.

To a solution of trioxolane A3 (3.53 g, 8.858 mmol, 1.0 equiv) in anhydrous THF (35 mL) and MeOH (70 mL) was added 15% aqueous KOH (15 mL, 40.100 mmol, 4.53 equiv). The solution was then placed in an oil bath that had been preheated to 50° C., and was allowed to stir at this temperature for 2.5 hours. During this time, the solution turned from a clear colorless solution to one that was dark brown in color. Upon determination of reaction completion by LCMS and TLC, the solution was removed from the oil bath and allowed to cool to room temperature. The mixture was then concentrated under reduced pressure to remove all volatile organic materials, which produced a viscous brown solution. To this was then added $H_2O$ (30 mL), which resulted in the formation of a yellow precipitate. Glacial acetic acid was then added to this solution until pH was around 4. This resulted in the formation of large tan colored solids to form. Some of the precipitate sank to the bottom of the flask, whereas some was observed to float on top of the solution as well. As a result, the aqueous solution was decanted by pouring the water onto a fritted funnel. The solid material collected on the frit was then dissolved with EtOAc and this solution was then added to the remaining solid in the original flask from which the aqueous solution was decanted out of. To this flask was added additional EtOAc (100 mL) to fully dissolve all of the solid material. This solution was then washed with DI $H_2O$ (40 mL×2), Brine (40 mL), dried over anhydrous $Na_2SO_4$, filtered, and concentrated under reduced pressure to yield a thick brown oil. The residue was then purified through flash column chromatography (120 g HP silica gel cartridge, 0-20% EtOAc/Hexanes, product eluted during 7-10% EtOAc/Hex) to yield A4 (3.08 g, 98%) as a foamy solid. At this point, the diastereoselectivity was determined to be 15.3:1 in favor of the trans diastereomer. $^1$H NMR (400 MHz, $CDCl_3$) δ 7.12-7.02 (m, 2H), 6.81-6.72 (m, 2H), 4.95 (br s, 1H), 2.89 (tt, J=12.6, 3.3 Hz, 1H, minor diastereomer), 2.74 (tt, J=12.8, 3.3 Hz, 1H), 2.15-2.08 (m, 1H), 2.05-1.64 (m, 19H), 1.64-1.55 (m, 1H), 1.40-1.28 (m, 1H); $^{13}$C NMR (100 MHz, $CDCl_3$) δ 153.9, 138.0, 127.8, 115.2, 111.4, 109.1; 42.3, 41.8 (minor diastereomer), 41.0, 40.7 (minor diastereomer), 36.8, 36.4, 35.0 (minor diastereomer), 34.9 (minor diastereomer), 34.8, 34.7, 34.2, 33.0, 26.8, 26.5, 23.5, 21.1 (minor diastereomer); MS (ESI) calculated for $C_{22}H_{27}O_4$[M−H]$^-$ m/z 355.19, found 355.15.

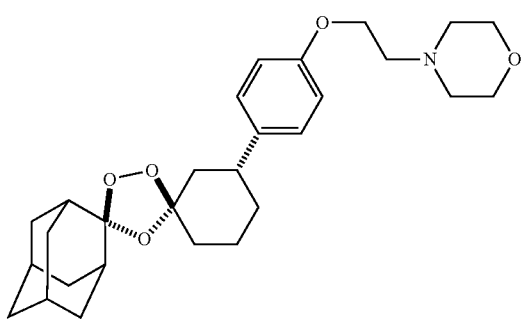

4-(2-(4-(dispiro[adamantane-2,3'-[1,2,4]trioxolane-5',1''-cyclohexan]-3''-yl)phenoxy)ethyl)morpholine (A5)

To a solution of phenol A4 (100 mg, 0.281 mmol, 1.0 equiv) in dry CH₃CN (4 mL) was added tetrabutylammonium hydrogen sulfate (19.1 mg, 0.056 mmol, 0.2 equiv) and powdered NaOH (44.9 mg, 1.122 mmol, 4.0 equiv). The flask was then rinsed with dry CH₃CN (1 mL) to wash all of the solid material off the sides of the flask. This mixture was then allowed to stir at room temperature for 30 minutes, at which point 4-(2-chloroethyl)morpholine hydrochloride (104.4 mg, 0.561 mmol, 2.0 equiv) was added to the solution. The mixture was then placed in an oil bath that had been preheated to 55° C., and was allowed to stir at this temperature for 14.5 hours. Following determination of reaction completion by TLC and LCMS analysis, the solution was then removed from the oil bath and allowed to cool to room temperature. Upon cooling, the mixture was diluted with EtOAc (20 mL) prior to the addition of H₂O (10 mL), which served to dissolve all of the inorganic solids present. Following separation of the layers, the aqueous layer was extracted with EtOAc (20 mL). However, this resulted in the formation of an emulsion. For this reason, Brine (10 mL) was added to the mixture to help clear the emulsion. The combined organic layers were then washed with Brine (10 mL), dried over anhydrous Na₂SO₄, filtered, and concentrated under reduced pressure. The residue was then purified through flash column chromatography (25 g silica gel cartridge, 0-100% EtOAc/Hexanes, product eluted during 40-100% EtOAc/Hex) to yield A5 (82 mg, 62%) as a clear colorless oil. It is important to note that a solubility issue was observed during the column as the material stopped eluting until the polarity was dramatically increased. The material was therefore initially collected as two separate fractions and characterized separately. Ultimately, the two fractions were determined to be identical to one another and were therefore pooled together. Additionally, at this point, the compound appeared to exist as a single diastereomer based on the obtained NMR data. $^1$H NMR (400 MHz, CDCl₃) δ 7.11 (d, J=8.6 Hz, 2H), 6.84 (d, J=8.6 Hz, 2H), 4.09 (t, J=5.7 Hz, 2H), 3.74 (t, J=4.7 Hz, 4H), 2.79 (t, J=5.7 Hz, 2H), 2.79-2.68 (m, 1H), 2.58 (t, J=4.5 Hz, 4H), 2.15-2.06 (m, 1H), 2.04-1.87 (m, 7H), 1.87-1.54 (m, 13H), 1.40-1.24 (m, 1H); $^{13}$C NMR (100 MHz, CDCl₃) δ 157.0, 138.1, 127.6, 114.5, 111.3, 109.0, 66.8, 65.7, 57.6, 54.0, 42.3, 41.0, 36.7, 36.4, 34.8, 34.7, 34.1, 32.9, 26.8, 26.4, 23.5; MS (ESI) calculated for C₂₈H₄₀NO₅ [M+H]⁺ m/z 470.29, found 470.09.

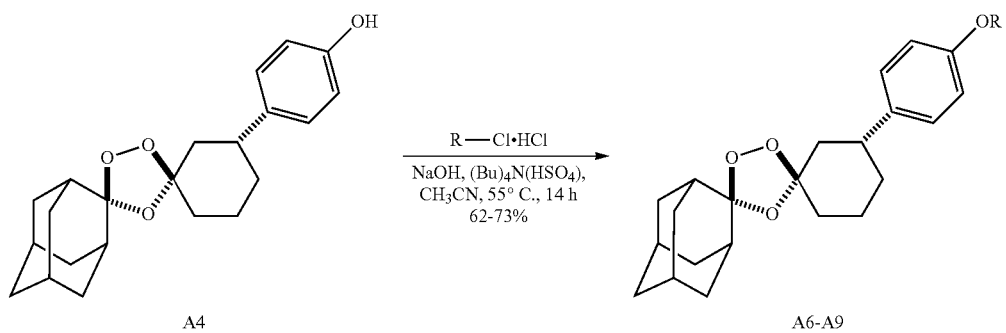

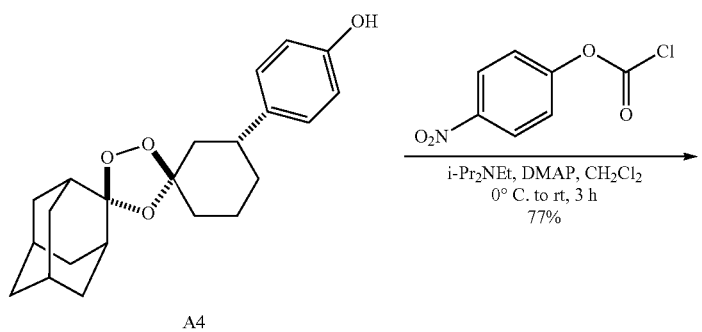

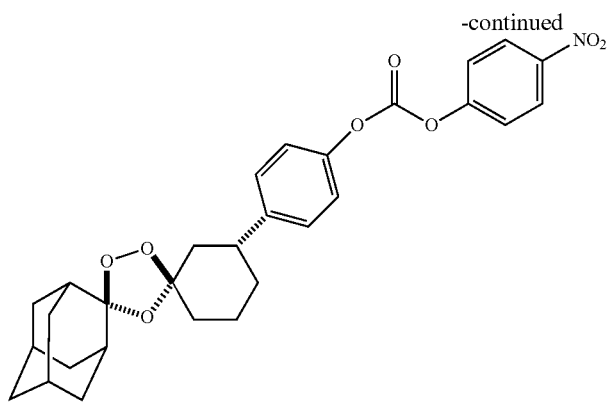

A10

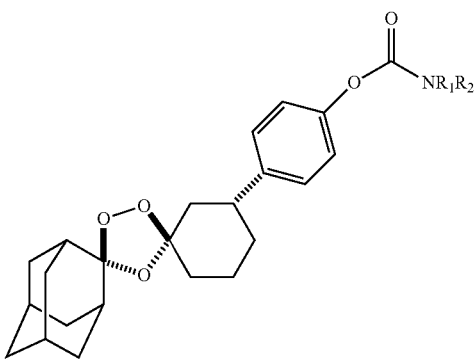

A11-A15

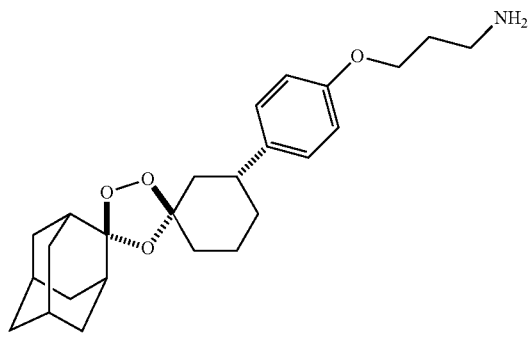

3-{p-(Dispiro[cyclohexane-1,3'-[1,2,4]trioxolane-5', 2''-tricyclo[3.3.1.1$^{3,7}$]decan]-3-yl)phenoxy}propylamine (A6)

To a solution of phenol A4 (80 mg, 0.22 mmol, 1.0 equiv) in dry CH$_3$CN (4 mL) was added tetrabutylammonium hydrogen sulfate (16.0 mg, 0.05 mmol, 0.21 equiv) and powdered NaOH (32 mg, 0.80 mmol, 3.6 equiv). This mixture was then allowed to stir at room temperature for 30 minutes, at which point 1-Amino-3-chloropropane hydrochloride (58 mg, 0.45 mmol, 2.0 equiv) was added to the solution. The mixture was then placed in an oil bath that had been preheated to 55° C., and was allowed to stir at this temperature for 14 hours. Following determination of reaction completion by TLC and LCMS analysis, the solution was then removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH/CH$_2$Cl$_2$, and desired product eluted during 20% MeOH, to yield the desired product (65.0 mg, 70%) as a yellow solid. $^1$H NMR (400 MHz, CHLOROFORM-d) δ 7.13 (d, J=8.52 Hz, 2H), 6.85 (d, J=8.52 Hz, 2H), 3.96-4.13 (m, 2H), 2.94 (t, J=6.70 Hz, 2H), 2.67-2.89 (m, 1H), 2.20-2.28 (m, 2H), 2.09-2.15 (m, 1H), 1.91-2.04 (m, 8H), 1.66-1.86 (m, 12H), 1.50-1.66 (m, 1H), 1.22-1.49 (m, 2H); 13C NMR (100 MHz, CHLOROFORM-d) δ 157.4, 138.1, 127.8, 114.5, 111.5, 109.3, 76.8, 66.0, 42.5, 41.2, 39.3, 36.9, 36.6, 36.5, 35.0, 35.0, 34.9, 34.9, 34.3, 33.2, 32.7, 27.0, 26.6, 23.7; MS (ESI) calculated for C$_{25}$H$_{36}$NO$_4$ [M+H]$^+$ m/z 414.26, found 414.17.

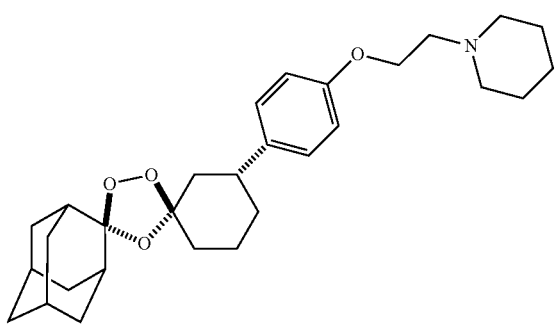

3-[p-(2-Piperidinoethoxy)phenyl]dispiro[cyclohexane-1,3'-[1,2,4]trioxolane-5',2"-tricyclo[3.3.1.1$^{3,7}$]decane](A7)

To a solution of phenol A4 (80 mg, 0.22 mmol, 1.0 equiv) in dry CH$_3$CN (4 mL) was added tetrabutylammonium hydrogen sulfate (16.0 mg, 0.05 mmol, 0.21 equiv) and powdered NaOH (32 mg, 0.80 mmol, 3.6 equiv). This mixture was then allowed to stir at room temperature for 30 minutes, at which point 1-(2-chloroethyl)piperidine hydrochloride (83.0 mg, 0.45 mmol, 2.0 equiv) was added to the solution. The mixture was then placed in an oil bath that had been preheated to 55° C., and was allowed to stir at this temperature for 14 hours. Following determination of reaction completion by TLC and LCMS analysis, the solution was then removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH/CH$_2$Cl$_2$, and desired product eluted during 5% MeOH, to yield the desired product (68.0 mg, 63%) as a yellow oil. $^1$H NMR (400 MHz, CHLOROFORM-d) δ 7.09 (d, J=8.52 Hz, 2H), 6.83 (d, J=8.52 Hz, 2H), 4.09 (t, J=5.97 Hz, 2H), 2.68-2.80 (m, 3H), 2.48-2.56 (m, 4H), 2.06-2.11 (m, 1H), 1.89-2.01 (m, 7H), 1.74-1.83 (m, 6H), 1.59-1.72 (m, 12H), 1.41-1.47 (m, 2H); $^{13}$C NMR (100 MHz, CHLOROFORM-d) δ 157.2, 138.1, 127.7, 114.6, 111.4, 109.2, 65.8, 57.9, 55.0, 42.4, 41.1, 36.9, 36.5, 36.5, 34.9, 34.8, 34.8, 34.3, 33.1, 27.0, 26.6, 25.9, 24.2, 23.6; MS (ESI) calculated for C$_{29}$H$_{42}$NO$_4$ [M+H]$^+$ m/z 468.31, found 468.30.

3-[p-(3-Piperidinopropoxy)phenyl]dispiro[cyclohexane-1,3'-[1,2,4]trioxolane-5',2"-tricyclo[3.3.1.1$^{3,7}$]decane] (A8)

To a solution of phenol A4 (80 mg, 0.22 mmol, 1.0 equiv) in dry CH$_3$CN (4 mL) was added tetrabutylammonium hydrogen sulfate (16.0 mg, 0.05 mmol, 0.21 equiv) and powdered NaOH (32 mg, 0.80 mmol, 3.6 equiv). This mixture was then allowed to stir at room temperature for 30 minutes, at which point 1-(3-chloropropyl)piperidine hydrochloride (89.0 mg, 0.45 mmol, 2.0 equiv) was added to the solution. The mixture was then placed in an oil bath that had been preheated to 55° C., and was allowed to stir at this temperature for 14 hours. Following determination of reaction completion by TLC and LCMS analysis, the solution was then removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH/CH$_2$Cl$_2$, and desired product eluted during 10% MeOH, to yield the desired product (68.0 mg, 63%) as a yellow oil. $^1$H NMR (400 MHz, CHLOROFORM-d) δ 7.06 (d, J=8.52 Hz, 2H), 6.79 (d, J=8.77 Hz, 2H), 3.95 (t, J=6.21 Hz, 2H), 2.65-2.73 (m, 1H), 2.45-2.58 (m, 6H), 1.86-2.08 (m, 11H), 1.72-1.81 (m, 6H), 1.60-1.70 (m, 11H), 1.40-1.48 (m, 2H); $^{13}$C NMR (100 MHz, CHLOROFORM-d) δ 157.3, 137.9, 127.6, 114.4, 111.3, 109.1, 66.2, 55.9, 54.4, 42.3, 41.0, 36.8, 36.4, 36.4, 34.8, 34.8, 34.7, 34.2, 33.0, 26.9, 26.5, 26.4, 25.4, 24.0, 23.5; MS (ESI) calculated for C$_{30}$H$_{44}$NO$_4$ [M+H]$^+$ m/z 482.33, found 482.35.

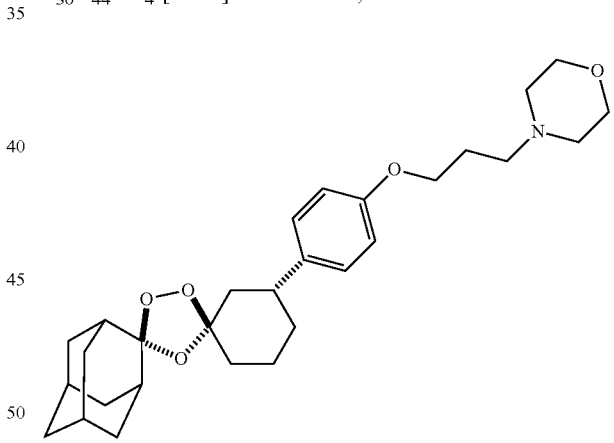

3-[p-(3-Morpholinopropoxy)phenyl]dispiro[cyclohexane-1,3'-[1,2,4]trioxolane-5',2"-tricyclo[3.3.1.1$^{3,7}$]decane] (A9)

To a solution of phenol A4 (80 mg, 0.22 mmol, 1.0 equiv) in dry CH$_3$CN (4 mL) was added tetrabutylammonium hydrogen sulfate (16.0 mg, 0.05 mmol, 0.21 equiv) and powdered NaOH (32 mg, 0.80 mmol, 3.6 equiv). This mixture was then allowed to stir at room temperature for 30 minutes, at which point 4-(3-chloropropyl)morpholine (73.0 mg, 0.45 mmol, 2.0 equiv) was added to the solution. The mixture was then placed in an oil bath that had been preheated to 55° C., and was allowed to stir at this temperature for 14 hours. Following determination of reaction

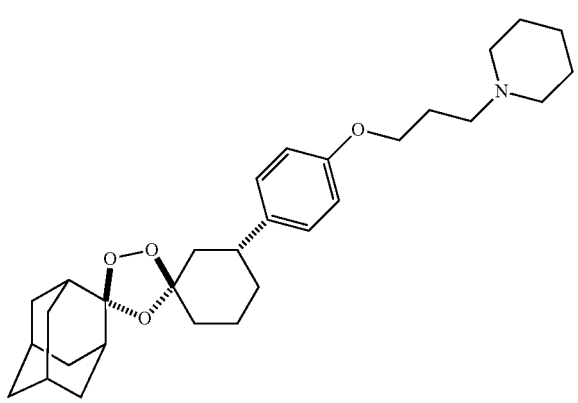

completion by TLC and LCMS analysis, the solution was then removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH/CH$_2$Cl$_2$, and desired product eluted during 5% MeOH, to yield the desired product (77.0 mg, 71%) as a colorless oil. $^1$H NMR (400 MHz, CHLOROFORM-d) δ 7.07-7.11 (m, 2H), 6.79-6.83 (m, 2H), 3.98 (t, J=6.33 Hz, 2H), 3.67-3.72 (m, 5H), 3.59 (t, J=6.57 Hz, 1H), 2.68-2.75 (m, 1H), 2.41-2.52 (m, 7H), 2.05-2.11 (m, 1H), 1.88-2.00 (m, 9H), 1.75-1.83 (m, 5H), 1.63-1.71 (m, 6H), 1.30-1.38 (m, 1H); $^{13}$C NMR (100 MHz, CHLOROFORM-d) δ 157.4, 137.9, 127.6, 114.5, 111.3, 109.1, 77.5, 77.2, 76.8, 67.0, 66.1, 55.8, 55.6, 53.8, 53.8, 43.1, 42.4, 41.1, 36.8, 36.5, 36.4, 34.9, 34.9, 34.8, 34.8, 34.2, 33.1, 29.6, 26.9, 26.5, 23.6; MS (ESI) calculated for C$_{29}$H$_{42}$NO$_4$ [M+H]$^+$ m/z 484.31, found 484.22.

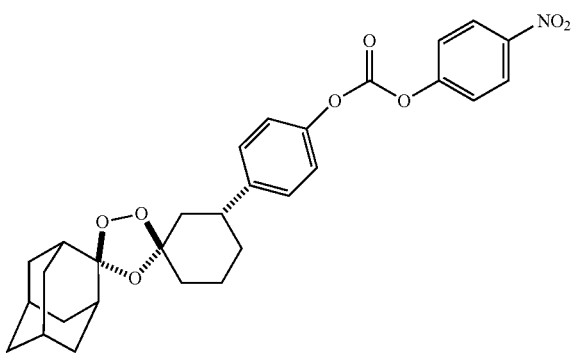

3-[p-(p-Nitrophenoxycarbonyloxy)phenyl]dispiro [cyclohexane-1,3'-[1,2,4]trioxolane-5',2"-tricyclo [3.3.1.1$^{3,7}$]decane] (A10)

To an oven-dried round bottom flask containing a magnetic stir bar under an Ar(g) atmosphere was phenol A4 (0.150 mg, 0.42 mmol, 1.0 equiv) dissolved in dichloromethane (10 mL), N,N-diisopropylethylamine (0.22 mL, 1.26 mmol, 3.00 equiv), and 4-dimethylaminopyridine (0.062 g, 0.51 mmol, 1.2 equiv). The mixture was cooled to 0° C. while 4-nitrophenyl chloroformate (0.254 g, 1.26 mmol, 3.00 equiv) was added as a solid in one portion. The solution was allowed to stir at room temperature for 3 hours. The reaction was then diluted with H$_2$O (100 mL) and subsequently extracted with EtOAc (100 mL). The organic layer was washed repeatedly by potassium carbonate solution until the aqueous layer was colorless and no longer yellow (meaning that all of the p-nitrophenol had been successfully removed from the organic layer). The organic layer was dried over anhydrous Na$_2$SO$_4$, filtered, and concentrated under reduced pressure to yield thick yellow oil. The residue was then purified through flash column chromatography (80 g silica gel cartridge, 0-25% EtOAc/Hexanes, product eluted during 10% EtOAc/Hex) to yield the desired product (170 mg, 77%) as a colorless solid. $^1$H NMR (400 MHz, CHLOROFORM-d) δ 8.29-8.34 (m, 2H), 7.49 (d, J=9.01 Hz, 2H), 7.20-7.30 (m, 4H), 2.85 (tt, J=3.01, 12.69 Hz, 1H), 2.16 (br d, J=13.15 Hz, 1H), 1.91-2.05 (m, 7H), 1.65-1.88 (m, 13H), 1.37-1.45 (m, 1H); $^{13}$C NMR (100 MHz, CHLOROFORM-d) δ 155.4, 151.2, 149.0, 145.6, 144.3, 128.1, 125.4, 121.8, 120.7, 111.5, 108.9, 42.1, 41.4, 36.8, 36.5, 34.9, 34.8, 34.2, 32.8, 26.9, 26.5, 23.5. MS (ESI) calculated for C$_{29}$H$_{31}$NNaO$_8$ [M+Na]$^+$ m/z 544.19, found 544.23.

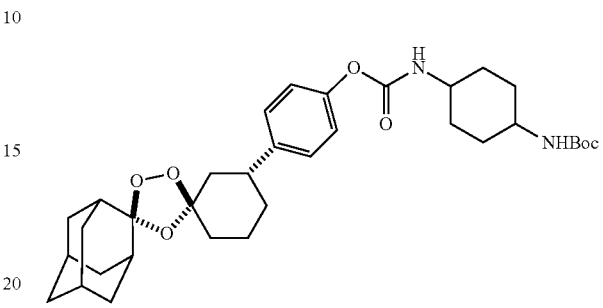

3-{p-[4-(tert-Butoxycarbonylamino)cyclohexylaminocarbonyloxy]phenyl}dispiro[cyclohexane-1,3'-[1,2,4]trioxolane-5',2"-tricyclo[3.3.1.1$^{3,7}$]decane]. To a solution of intermediate A10 (63 mg, 0.12 mmol, 1.0 equiv) in dichloromethane (2.0 mL) was added Et$_3$N (24 µL, 0.17 mmol, 1.5 equiv), followed by 4-(N-boc-amino)piperidine (38 mg, 0.19 mmol, 1.5 equiv) at room temperature. The bright yellow mixture was then allowed to stir at room temperature for 5 h, at which point, the reaction was judged complete by TLC and LCMS. The reaction was then diluted with H$_2$O (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous Na$_2$SO$_4$, filtered, and concentrated under reduced pressure. The residue was then purified through flash column chromatography (25 g silica gel cartridge, 0-25% EtOAc/Hexanes, product eluted during 20% EtOAc/Hex) to yield the desired product (53 mg, 75%) as a colorless oil. $^1$H NMR (400 MHz, CHLOROFORM-d) δ 7.16-7.20 (m, 1H), 6.99-7.03 (m, 2H), 4.61 (br d, J=6.82 Hz, 1H), 4.13-4.25 (m, 2H), 3.66 (br s, 1H), 2.93-3.16 (m, 2H), 2.75-2.83 (m, 1H), 2.12 (br d, J=13.39 Hz, 1H), 1.89-2.05 (m, 9H), 1.59-1.86 (m, 14H), 1.44-1.51 (m, 9H), 1.33-1.44 (m, 3H); $^{13}$C NMR (100 MHz, CHLOROFORM-d) δ 155.2, 153.8, 149.7, 142.6, 127.6, 121.6, 111.4, 109.0, 79.6, 47.7, 43.3, 43.2, 42.2, 41.3, 36.8, 36.5, 34.9, 34.8, 34.2, 32.9, 32.6, 28.5, 26.9, 26.5, 23.5. MS (ESI) calculated for C$_{33}$H$_{46}$N$_2$NaO$_7$ [M+H]$^+$ m/z 605.32, found 605.28.

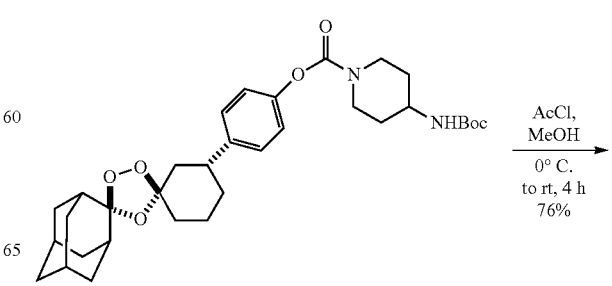

141

-continued

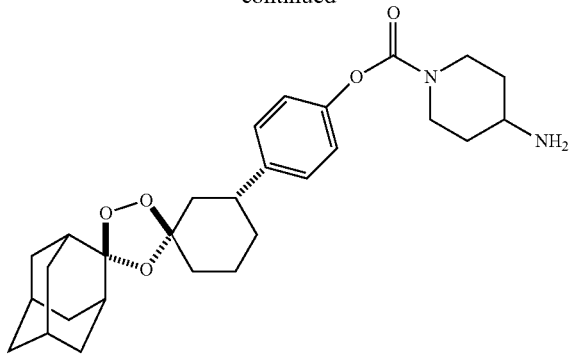

3-[p-(4-Aminocyclohexylaminocarbonyloxy)phenyl] dispiro[cyclohexane-1,3'-[1,2,4]trioxolane-5',2"-tricyclo[3.3.1.1$^{3,7}$]decane] (A11)

To a solution of 3-{p-[4-(tert-Butoxycarbonylamino)cy-clohexylaminocarbonyloxy]phenyl}dispiro[cyclohexane-1, 3'-[1,2,4]trioxolane-5',2"-tricyclo[3.3.1.1$^{3,7}$]decane] (19.0 mg, 0.0327 mmol, 1 equiv) in methanol (1.6 mL) cooled to 0° C. in an ice bath, was added acetyl chloride (47 μL, 0.674 mmol, 21 equiv) dropwise via microsyringe. The solution was allowed to stir for 10 minutes at 0° C., after which the solution was removed from the bath and allowed to warm to room temperature. After stirring for 4 h, the reaction was deemed complete by LCMS and TLC. Following dilution with dichloromethane (5 mL), sat aq. NaHCO$_3$ (5 mL) was added to neutralize any acid in the flask. After separating the layers, the organic layer was washed with sat aq. NaHCO$_3$ (10 mL×2). The combined aqueous layers were then back extracted with dichloromethane (10 mL×2). The combined organic layers were washed with brine (10 mL), anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH (containing 0.7 N NH$_3$)/CH$_2$Cl$_2$, and desired product eluted during 20% MeOH (containing 0.7 N NH$_3$)/CH$_2$Cl$_2$], to yield the desired product (11.0 mg, 76%) as a colorless oil. $^1$H NMR (400 MHz, CHLOROFORM-d) δ 7.13 (d, J=8.28 Hz, 1H), 6.95 (d, J=8.52 Hz, 2H), 4.13-4.26 (m, 2H), 2.94-3.03 (m, 2H), 2.82-2.90 (m, 1H), 2.68-2.76 (m, 1H), 2.05 (br d, J=13.64 Hz, 1H), 1.82-1.96 (m, 10H), 1.58-1.79 (m, 13H), 1.50-1.58 (m, 1H), 1.39-1.49 (m, 2H), 1.29 (br dd, J=2.92, 12.42 Hz, 1H); $^{13}$C NMR (100 MHz, CHLOROFORM-d) δ 153.9, 149.5, 142.7, 127.6, 121.6, 111.4, 109.0, 48.4, 42.1, 41.3, 36.4, 34.7, 34.1, 34.8, 26.8, 26.4, 23.5. MS (ESI) calculated for C$_{27}$H$_{37}$N$_2$O$_5$ [M+H]$^+$ m z 483.29, found 483.24.

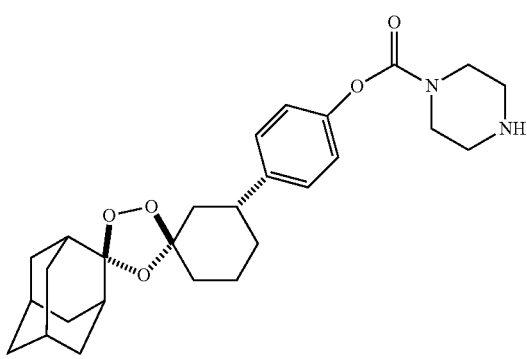

142 p-(Dispiro[cyclohexane-1,3'-[1,2,4]trioxolane-5',2"-tricyclo[3.3.1.1$^{3,7}$]decan]-3-yl)phenyl 1-piperazin-ecarboxylate (A12)

To a solution of intermediate A10 (60 mg, 0.12 mmol, 1.0 equiv) in dichloromethane (2.0 mL) was added Et$_3$N (24 μL, 0.17 mmol, 1.5 equiv), followed by piperazine (18.0 mg, 0.19 mmol, 1.5 equiv) at room temperature. The bright yellow mixture was then allowed to stir at room temperature for 5 h, at which point, the reaction was judged complete by TLC and LCMS. The reaction was then diluted with H$_2$O (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH (containing 0.7 N NH$_3$)/CH$_2$Cl$_2$, and desired product eluted during 5% MeOH (containing 0.7 N NH$_3$)/CH$_2$Cl$_2$], to yield the desired product (43.0 mg, 76%) as a colorless solid. $^1$H NMR (400 MHz, CHLOROFORM-d) δ 7.19 (d, J=8.52 Hz, 1H), 7.03 (d, J=8.52 Hz, 2H), 3.55-3.71 (m, 4H), 3.16-3.20 (m, 1H), 2.93-2.98 (m, 4H), 2.80 (tt, J=3.10, 12.60 Hz, 1H), 2.13 (br d, J=13.39 Hz, 1H), 1.89-2.03 (m, 7H), 1.78-1.87 (m, 5H), 1.64-1.76 (m, 7H), 1.59-1.64 (m, 1H), 1.31-1.42 (m, 1H); $^{13}$C NMR (100 MHz, CHLOROFORM-d) δ 153.8, 149.6, 142.7, 127.6, 121.6, 111.4, 109.0, 42.1, 41.3, 36.4, 34.8, 34.2, 34.8, 26.9, 26.5, 23.5. MS (ESI) calculated for C$_{27}$H$_{37}$N$_2$O$_5$ [M+H]$^+$ m/z 469.27, found 469.17.

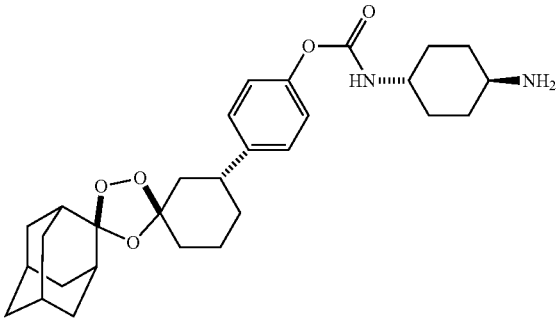

3-[p-(4-Aminocyclohexylaminocarbonyloxy)phenyl] dispiro[cyclohexane-1,3'-[1,2,4]trioxolane-5',2"-tricyclo[3.3.1.1$^{3,7}$]decane] (A13)

To a solution of intermediate A10 (58 mg, 0.11 mmol, 1.0 equiv) in dichloromethane (2.0 mL) was added Et$_3$N (24 μL, 0.17 mmol, 1.5 equiv), followed by (1r,4r)-cyclohexane-1, 4-diamine (19 mg, 0.17 mmol, 1.5 equiv) at room temperature. The bright yellow mixture was then allowed to stir at room temperature for 5 h, at which point, the reaction was judged complete by TLC and LCMS. The reaction was then diluted with H$_2$O (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous $Na_2SO_4$, filtered, and concentrated under reduced pressure. The residue was then purified through flash column chromatography (12 g silica gel cartridge, 0-100% EtOAc/Hexanes, followed by 0-20% MeOH (containing 0.7 N $NH_3$)/$CH_2Cl_2$, and desired product eluted during 20% MeOH (containing 0.7 $NH_3$)/$CH_2Cl_2$], to yield the desired product (43.0 mg, 76%) as a white solid. $^1H$ NMR (400 MHz, CHLOROFORM-d) δ 7.13 (br d, J=8.28 Hz, 2H), 6.98 (br d, J=8.28 Hz, 2H), 3.44 (br s, 1H), 2.96 (br s, 2H), 2.74 (br t, J=12.66 Hz, 1H), 2.55-2.66 (m, 1H), 1.99-2.09 (m, 3H), 1.83-1.98 (m, 9H), 1.61-1.82 (m, 13H), 1.12-1.37 (m, 6H); $^{13}C$ NMR (100 MHz, CHLOROFORM-d) δ 149.3, 142.6, 127.6, 127.5, 121.5, 115.3, 111.4, 111.3, 109.0, 49.7, 49.5, 42.1, 41.3, 36.7, 36.4, 34.8, 34.7, 34.6, 34.1, 32.8, 31.7, 26.8, 26.5, 23.5. MS (ESI) calculated for $C_{29}H_{41}N_2O_5$ $[M+H]^+$ m/z 497.30, found 497.28.

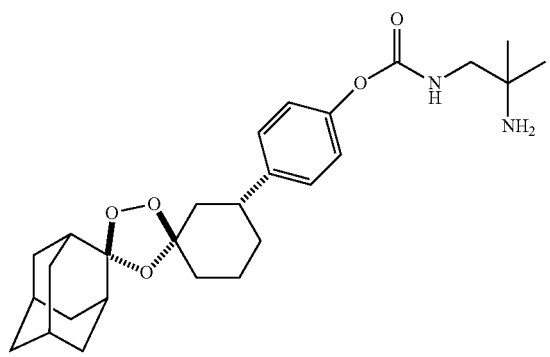

3-[p-(2-Amino-2-methylpropylaminocarbonyloxy) phenyl]dispiro[cyclohexane-1,3'-[1,2,4]trioxolane-5', 2"-tricyclo[3.3.1.1$^{3,7}$]decane] (A14)

To a solution of intermediate A10 (52.0 mg, 0.10 mmol, 1.0 equiv) in dichloromethane (2.0 mL) was added $Et_3N$ (21 μL, 0.15 mmol, 1.5 equiv), followed by 2-methylpropane-1,2-diamine (16 μL, 0.15 mmol, 1.5 equiv) at room temperature. The bright yellow mixture was then allowed to stir at room temperature for 5 h, at which point, the reaction was judged complete by TLC and LCMS. The reaction was then diluted with $H_2O$ (100 mL) and subsequently extracted with EtOAc (100 mL). The organic layer was washed repeatedly with potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous $Na_2SO_4$, filtered, and concentrated under reduced pressure. The residue was then purified through flash column chromatography (12 g silica gel cartridge, 0-100% EtOAc/Hexanes, followed by 0-20% MeOH (containing 0.7 N $NH_3$)/$CH_2Cl_2$, and desired product eluted during 15% MeOH (containing 0.7 N $NH_3$)/$CH_2Cl_2$], to yield the desired product (43.0 mg, 76%) as a white solid. $^1H$ NMR (400 MHz, CHLOROFORM-d) δ 7.14-7.19 (m, 2H), 7.09-7.14 (m, 2H), 3.34 (br s, 2H), 2.78 (br t, J=12.66 Hz, 1H), 2.07-2.13 (m, 1H), 1.93-2.04 (m, 7H), 1.65-1.86 (m, 14H), 1.59-1.64 (m, 1H), 1.37-1.46 (m, 1H), 1.39 (s, 4H), 1.27-1.33 (m, 2H); $^{13}C$ NMR (100 MHz, CHLOROFORM-d) δ 156.2, 149.4, 143.0, 127.9, 122.1, 115.4, 111.5, 109.1, 56.1, 42.5, 42.3, 41.4, 41.1, 36.5, 34.9, 34.3, 34.3, 33.2, 34.9, 27.0, 26.6, 23.7, 23.7, 23.6. MS (ESI) calculated for $C_{29}H_{41}N_2O_5$ $[M+H]^+$ m/z 471.29, found 471.27.

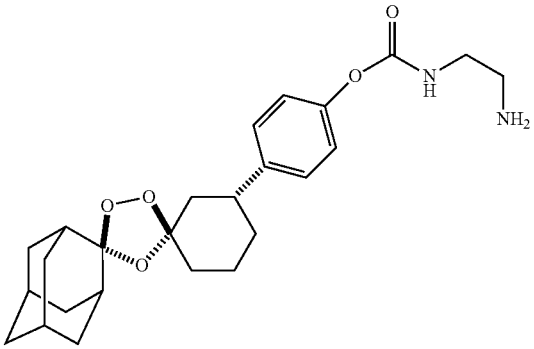

3-[p-(2-Aminoethylaminocarbonyloxy)phenyl] dispiro[cyclohexane-1,3'-[1,2,4]trioxolane-5',2"-tricyclo[3.3.1.1$^{3,7}$]decane] (A15)

To a solution of intermediate A11 (52.0 mg, 0.10 mmol, 1.0 equiv) in dichloromethane (2.0 mL) was added $Et_3N$ (21 μL, 0.15 mmol, 1.5 equiv), followed by ethylenediamine (12 μL, 0.18 mmol, 1.5 equiv) at room temperature. The bright yellow mixture was then allowed to stir at room temperature for 5 h, at which point, the reaction was judged complete by TLC and LCMS. The reaction was then diluted with $H_2O$ (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous $Na_2SO_4$, filtered, and concentrated under reduced pressure. The residue was then purified through flash column chromatography (12 g silica gel cartridge, 0-100% EtOAc/Hexanes, followed by 0-20% MeOH (containing 0.7 N $NH_3$)/$CH_2Cl_2$, and desired product eluted during 20% MeOH (containing 0.7 N $NH_3$)/$CH_2Cl_2$], to yield the desired product (43.0 mg, 76%) as a white foam. $^1H$ NMR (400 MHz, CHLOROFORM-d) δ 7.03-7.06 (m, 2H), 6.77-6.80 (m, 1H), 3.37 (br s, 1H), 2.93-3.01 (m, 1H), 2.66-2.83 (m, 1H), 2.08-2.15 (m, 1H), 1.90-2.03 (m, 8H), 1.76-1.87 (m, 6H), 1.56-1.75 (m, 8H), 1.30-1.39 (m, 1H); $^{13}C$ NMR (100 MHz, CHLOROFORM-d) δ 154.9, 137.3, 127.8, 121.6, 115.5, 111.4, 109.3, 42.5, 41.1, 41.0, 36.9, 36.5, 34.9, 34.8, 34.3, 34.2, 33.1, 33.1, 27.0, 26.6, 23.6. MS (ESI) calculated for $C_{29}H_{41}N_2O_5$ $[M+H]^+$ m/z 443.25, found 443.20.

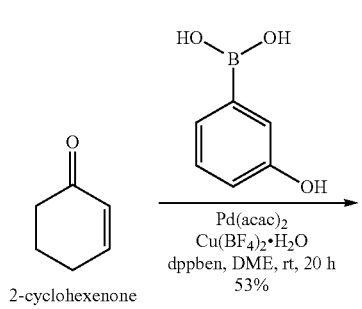

145
-continued

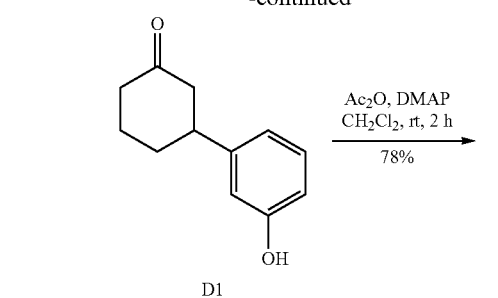
D1

Ac₂O, DMAP
CH₂Cl₂, rt, 2 h
78%

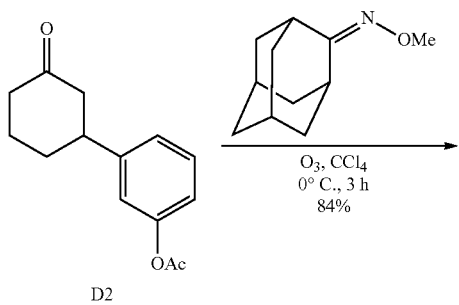
D2

O₃, CCl₄
0° C., 3 h
84%

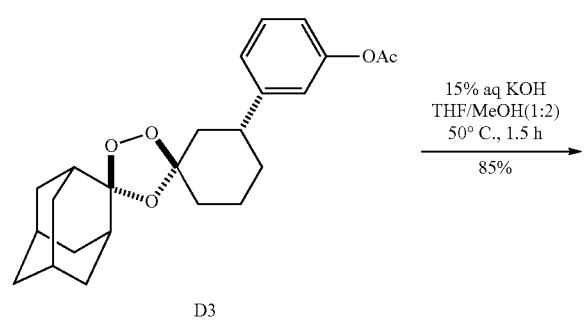
D3

15% aq KOH
THF/MeOH(1:2)
50° C., 1.5 h
85%

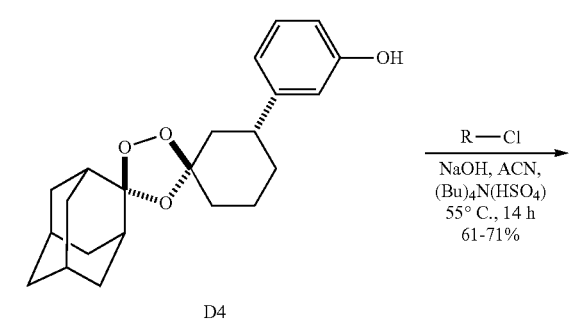
D4

R—Cl
NaOH, ACN,
(Bu)₄N(HSO₄)
55° C., 14 h
61-71%

D5-D6

146
-continued

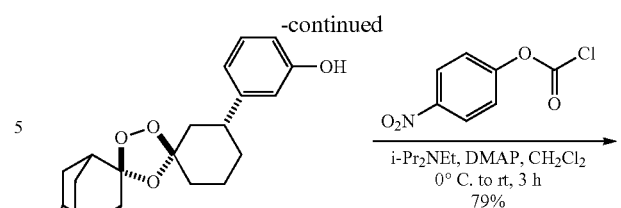
D4 i-Pr₂NEt, DMAP, CH₂Cl₂
0° C. to rt, 3 h
79%

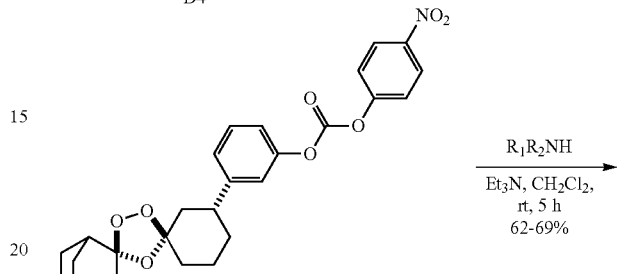
D7

R₁R₂NH
Et₃N, CH₂Cl₂,
rt, 5 h
62-69%

D8-D9

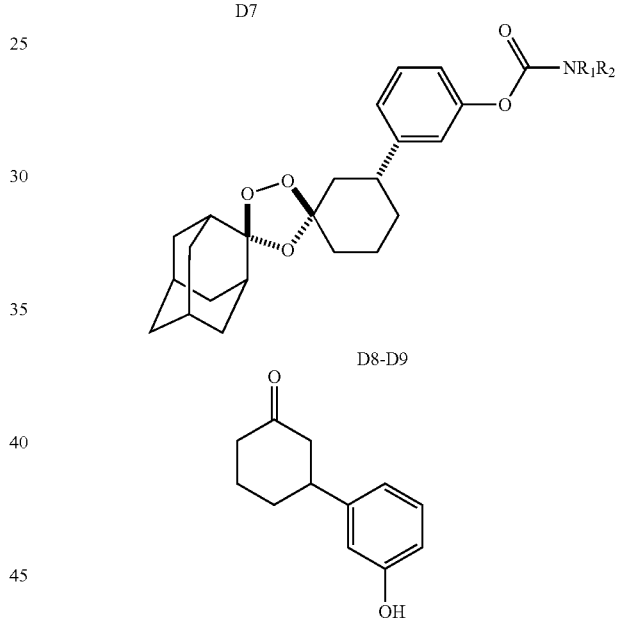

3-(3-hydroxyphenyl)cyclohexan-1-one (D1)

To an oven-dried round bottom flask containing a magnetic stir bar under an Ar(g) atmosphere was added palladium(II) acetylacetonate (0.158 g, 0.52 mmol, 0.05 equiv), 1,2-bis(diphenylphosphino)benzene (0.232 g, 0.520 mmol, 0.05 equiv), copper(II) tetrafluoroborate hydrate (0.531 g, 2.081 mmol, 0.2 equiv), and 3-hydroxyphenylboronic acid (2.511 g, 18.21 mmol, 1.75 equiv). To the mixture of solid materials was added anhydrous dimethoxyethane (60 mL). To the stirring solution was then added 2-cyclohexen-1-one (1.0 g, 10.33 mmol, 1.0 equiv) via syringe at room temperature. The solution was allowed to stir at room temperature for 20 hours. Based on LCMS and TLC analysis, it was determined that the reaction was complete. The mixture was then concentrated under reduced pressure to yield a dark green oil. To this oil was added EtOAc (100 mL) followed by H₂O (50 mL). Following separation of the layers, the organic layer was washed with additional DI H₂O (50 mL). The organic layer was then filtered through a pad of Celite to remove all insoluble inorganic material. The pad was then rinsed with EtOAc (50 mL×4). The aqueous layer was extracted with EtOAc, and the resulting organic solution was filtered through the same pad of Celite. The pad was then again rinsed with EtOAc (50 mL×2). The clear yellow solution was concentrated under reduced pressure to yield a yellow oil. The residue was then purified through flash column chromatography (120 g silica gel cartridge, product eluted during 35-40% EtOAc/Hex) to yield C1 (1.44 g, 73%) as a colorless oil. $^1$H NMR (400 MHz, CDCl$_3$) δ 7.33 (s, 1H), 7.16 (t, J=8.04 Hz, 1H), 6.72-6.77 (m, 3H), 2.88-2.97 (m, 1H), 2.43-2.61 (m, 3H), 2.32-2.41 (m, 1H), 2.08-2.15 (m, 1H), 2.02 (br d, J=11.69 Hz, 1H), 1.67-1.84 (m, 2H); $^{13}$C NMR (100 MHz, CDCl$_3$) δ 213.6, 156.3, 146.0, 129.8, 118.5, 113.8, 113.7, 48.7, 44.6, 41.1, 32.5, 25.4; MS (ESI) calculated for $C_{12}H_{13}O_2$[M−H$^-$] m/z 189.09, found 188.99.

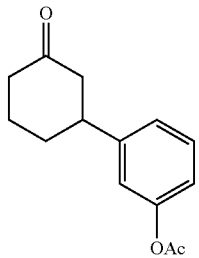 [SMILES: CC(=O)Oc1cccc(C2CCCC(=O)C2)c1]

m-(3-Oxocyclohexyl)phenyl acetate (D2)

To an oven-dried round bottom flask containing a magnetic stir bar under an Ar(g) atmosphere was added 3-(3-hydroxyphenyl)cyclohexan-1-one (0.525 g, 2.76 mmol, 1.0 equiv), dichloromethane (7 mL), acetic anhydride (0.29 mL, 3.04 mmol, 1.1 equiv), and 4-dimethylaminopyridine (0.337 g, 2.76 mmol, 1 equiv). The solution was allowed to stir at room temperature for 2 hours. The reaction was then diluted with H$_2$O (100 mL) and subsequently extracted with EtOAc (100 mL). The organic layer was dried over anhydrous Na$_2$SO$_4$, filtered, and concentrated under reduced pressure to yield a thick yellow oil. The residue was then purified through flash column chromatography (80 g silica gel cartridge, 0-25% EtOAc/Hexanes, product eluted during 20% EtOAc/Hex) to yield m-(3-oxocyclohexyl)phenyl acetate (503 mg, 78%) as a white solid. $^1$H NMR (400 MHz, CDCl$_3$) δ 7.15-7.24 (m, 1H), 6.97-7.02 (m, 1H), 6.87-6.92 (m, 2H), 2.85-2.94 (m, 1H), 2.40-2.51 (m, 2H), 2.23-2.35 (m, 2H), 2.17-2.20 (m, 3H), 1.90-2.02 (m, 2H), 1.57-1.75 (m, 2H); $^{13}$C NMR (100 MHz, CDCl$_3$) 210.5, 169.0, 150.5, 145.7, 129.2, 123.7, 119.0, 119.4, 48.1, 43.8, 40.6, 32.0, 24.9, 20.6; MS (ESI) calculated for $C_{14}H_{16}NaO_3$ [M+Na]$^+$ m/z 255.10, found 255.04.

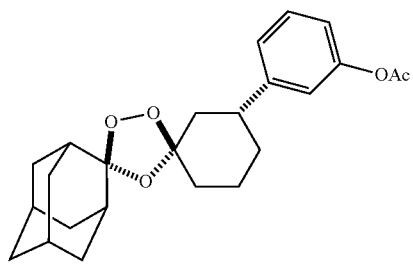

m-{(1R,3R)-Dispiro[cyclohexane-1,3'-[1,2,4]trioxolane-5',2"-tricyclo[3.3.1.1$^{3,7}$]decan]-3-yl}phenyl acetate (D3)

A solution of adamantan-2-one O-methyl oxime (9) (772 mg, 4.31 mmol, 2.0 equiv) and m-(3-oxocyclohexyl)phenyl acetate (500 mg, 2.15 mmol, 1.0 equiv) in 50 mL carbon tetrachloride was cooled to 0° C. and subsequently sparged with O$_2$ for 10 minutes. The reaction was kept at 0° C. while ozone was then bubbled (2 L/min, 35% power). After stirring for 2 hrs, the reaction was deemed to be incomplete based on LCMS analysis and additional oxime (193 mg, 1.08 mmol, 0.5 equiv) was added in a single portion to the reaction. Ozone was bubbled through the reaction for another 60 mins, at which point the reaction was found to be complete. The reaction was then purged with O$_2$ for 10 minutes in an effort to remove any dissolved ozone, followed by sparging with argon gas for 10 minutes to remove any dissolved oxygen. The solution was then concentrated under reduced pressure to provide an extremely viscous oil. The residue was purified through flash column chromatography (80 g silica gel cartridge, 0-10% EtOAc/Hexanes, product eluted during 8% EtOAc/Hex) to yield D3 (724 mg, 84%) as a thick colorless oil, which solidified to a white solid under high vacuum. The diastereoselectivity of the Griesbaum coozonolysis was determined to be 7.4:1 in favor of the trans diastereomer. $^1$H NMR (400 MHz, CDCl$_3$) δ 7.28-7.35 (m, 1H), 7.10 (d, J=7.79 Hz, 1H), 6.93-6.96 (m, 2H), 2.98 (tt, J=12.7, 3.1 Hz, 1H, minor diastereomer), 2.83 (tt, J=12.8, 3.3 Hz, 1H), 2.30-2.32 (m, 3H), 2.14-2.20 (m, 1H), 2.07-2.12 (m, 1H), 1.90-2.05 (m, 7H), 1.61-1.89 (m, 12H), 1.39 (dq, J=3.17, 12.42 Hz, 1H); $^{13}$C NMR (100 MHz, CDCl$_3$) δ 169.5, 169.5 (minor diastereomer), 150.9, 147.6 (minor diastereomer), 147.4, 129.4, 124.4, 124.3 (minor diastereomer), 120.0 (minor diastereomer), 120.0, 119.5, 111.9 (minor diastereomer), 111.4, 109.0 (minor diastereomer), 108.9, 47.0, 42.0, 41.7, 41.5, 41.4, 39.3, 36.8, 36.5, 36.5, 36.4, 35.1, 35.0, 34.8, 34.8, 34.2, 34.1, 33.4, 32.6, 27.5, 27.0, 26.9, 26.5, 23.5, 21.2; MS (ESI) calculated for $C_{24}H_{30}O_5$Na [M+Na]$^+$ m/z 421.20, found 421.14.

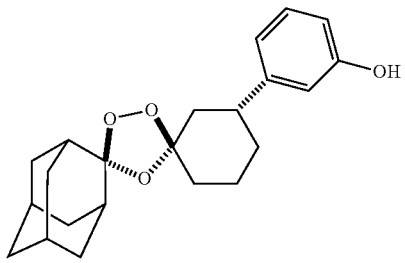

m-(Dispiro[cyclohexane-1,3'-[1,2,4]trioxolane-5',2"-tricyclo[3.3.1.1$^{3,7}$]decan]-3-yl)phenol (D4)

To a solution of (724 mg, 1.0 equiv) in anhydrous THF (7 mL) and MeOH (14 mL) was added 15% aqueous KOH (3 mL, 4.5 equiv). The solution was then placed in an oil bath that had been preheated to 50° C., and was allowed to stir at this temperature for 1.5 hours, and the solution then allowed to cool to room temperature. The mixture was then concentrated under reduced pressure, to this was then added H$_2$O (30 mL). Citric acid was then added to this solution until pH~4, and extracted with EtOAc (100 mL). The organic layer was then washed with brine, dried over anhydrous Na$_2$SO$_4$, filtered, and concentrated under reduced pressure, the residue was then purified through flash column chromatography (80 g silica gel cartridge, 0-50% EtOAc/Hexanes, product eluted during 30%) to yield the product (550 mg, 85%) as a thick colorless oil, which solidified to a white solid under high vacuum. At this point, the diastereoselectivity was determined to be 8.2:1 in favor of the trans diastereomer. $^1$H NMR (400 MHz, CDCl$_3$) δ ≡ 7.14-7.18 (m, 1H), 6.76-6.79 (m, 1H), 6.67-6.71 (m, 2H), 5.38 (br s, 1H), 2.98 (tt, J=12.7, 3.1 Hz, 1H, minor diastereomer), 2.83 (tt, J=12.8, 3.3 Hz, 1H), 2.10-2.16 (m, 1H), 1.89-2.04 (m, 7H), 1.65-1.86 (m, 12H), 1.58-1.65 (m, 1H), 1.30-1.41 (m, 1H); $^{13}$C NMR (100 MHz, CHLOROFORM-d) δ 155.8 (minor diastereomer), 155.8, 147.9 (minor diastereomer), 147.7, 129.7, 119.3, 113.9, 113.3, 113.3 (minor diastereomer), 112.0 (minor diastereomer), 111.6, 109.3, 42.1, 41.8, 41.6, 41.6, 36.9, 36.5, 35.1, 35.0, 34.9, 34.9, 34.8, 34.3, 34.2, 33.4, 32.7, 27.0, 27.0, 26.6, 23.6; MS (ESI) calculated for C$_{22}$H$_{27}$O$_4$[M−H]$^−$ m/z 355.19, found 355.13.

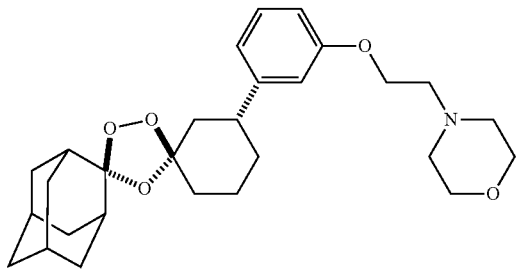

3-[m-(2-Morpholinoethoxy)phenyl]dispiro[cyclohexane-1,3'-[1,2,4]trioxolane-5',2"-tricyclo[3.3.1.1$^{3,7}$]decane] (D5)

To a solution of phenol D4 (60.0 mg, 0.17 mmol, 1.0 equiv) in dry CH$_3$CN (4 mL) was added tetrabutylammonium hydrogen sulfate (16.0 mg, 0.05 mmol, 0.3 equiv) and powdered NaOH (24.0 mg, 0.60 mmol, 3.6 equiv). This mixture was then allowed to stir at room temperature for 30 minutes, at which point 4-(2-chloroethyl)morpholine hydrochloride (63.0 mg, 0.34 mmol, 2.0 equiv) was added to the solution. The mixture was then placed in an oil bath that had been preheated to 55° C., and was allowed to stir at this temperature for 14 hours. Following determination of reaction completion by TLC and LCMS analysis, the solution was then removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-50% EtOAc/Hexanes, followed by 0-20% MeOH/CH$_2$Cl$_2$, and desired product eluted during 2% MeOH, to yield the desired product (48.0 mg, 61%) as a light yellow oil. Additionally, at this point, the compound appeared to exist as a single diastereomer based on the obtained NMR data.

$^1$H NMR (400 MHz, CHLOROFORM-d) δ 7.18-7.24 (m, 1H), 6.72-6.83 (m, 3H), 4.09-4.14 (m, 2H), 3.71-3.79 (m, 4H), 2.73-2.85 (m, 3H), 2.56-2.65 (m, 4H), 1.89-2.15 (m, 9H), 1.78-1.87 (m, 5H), 1.65-1.75 (m, 6H), 1.56-1.65 (m, 1H), 1.32-1.44 (m, 1H); $^{13}$C NMR (100 MHz, CHLOROFORM-d) δ 158.8, 147.4, 129.5, 119.4, 113.4, 112.1, 111.4, 109.0, 73.2, 66.9, 65.6, 57.7, 54.1, 42.1, 42.0, 41.3, 36.8, 36.5, 35.8, 34.9, 34.8, 34.3, 32.7, 31.0, 26.9, 26.5, 25.9, 23.6; MS (ESI) calculated for C$_{28}$H$_{40}$NO$_5$ [M+H]$^+$ m/z 470.29, found 470.22.

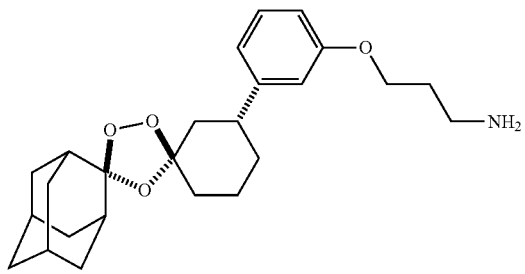

3-{m-(Dispiro[cyclohexane-1,3'-[1,2,4]trioxolane-5', 2"-tricyclo[3.3.1.1$^{3,7}$]decan]-3-yl) phenoxy}propylamine (D6)

To a solution of phenol D4 (50 mg, 0.14 mmol, 1.0 equiv) in dry CH$_3$CN (4 mL) was added tetrabutylammonium hydrogen sulfate (10.0 mg, 0.03 mmol, 0.3 equiv) and powdered NaOH (20.0 mg, 0.50 mmol, 3.6 equiv). This mixture was then allowed to stir at room temperature for 30 minutes, at which point 1-amino-3-chloropropane hydrochloride (38.0 mg, 0.28 mmol, 2.0 equiv) was added to the solution. The mixture was then placed in an oil bath that had been preheated to 55° C., and was allowed to stir at this temperature for 14 hours. When the reaction was judged complete by TLC and LCMS analysis, the solution was removed from the oil bath and allowed to cool to room temperature. Upon cooling, the mixture was diluted with EtOAc (20 mL) prior to the addition of H$_2$O (10 mL), which served to dissolve all of the inorganic solids present. Following separation of the layers, the aqueous layer was extracted with EtOAc (20 mL). The organic layer was then washed with brine (10 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH (containing 0.7 N NH$_3$)/CH$_2$Cl$_2$, and desired product eluted during 18% MeOH (containing 0.7 N NH$_3$)/CH$_2$Cl$_2$], to yield the product (41.0 mg, 71%) as a colorless oil. Additionally, at this point, the compound appeared to exist as a single diastereomer based on the obtained NMR data. $^1$H NMR (400 MHz, CHLOROFORM-d) δ 7.10-7.17 (m, 1H), 6.67-6.77 (m, 3H), 4.03 (brt, J=5.60 Hz, 2H), 3.20 (brt, J=7.18 Hz, 2H), 2.31 (br s, 1H), 2.08 (br d, J=13.15 Hz, 1H), 1.91-2.00 (m, 7H), 1.66-1.77 (m, 18H); MS (ESI) calculated for C$_{25}$H$_{36}$NO$_4$ [M+H]$^+$ m/z 414.26, found 414.29.

3-[m-(p-Nitrophenoxycarbonyloxy)phenyl]dispiro[cyclohexane-1,3'-[1,2,4]trioxolane-5',2"-tricyclo[3.3.1.13,7]decane] (D7)

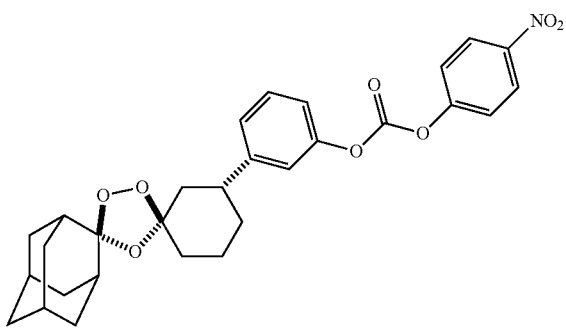

To an oven-dried round bottom flask containing a magnetic stir bar under an Ar(g) atmosphere was added phenol D4 (0.300 mg, 0.84 mmol, 1.0 equiv), dichloromethane (10 mL), N,N-diisopropylethylamine (0.48 mL, 2.74 mmol, 3.25 equiv), and 4-dimethylaminopyridine (0.123 g, 1.01 mmol, 1.2 equiv). The mixture was cooled to 0° C. while 4-nitrophenyl chloroformate (0.551 g, 2.74 mmol, 3.25 equiv) was added as a solid in one portion. The solution was allowed to stir at room temperature for 3 hours. The reaction was then diluted with DI H$_2$O (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The organic layer was dried over anhydrous Na$_2$SO$_4$, filtered, and concentrated under reduced pressure to yield a thick yellow oil. The residue was then purified through flash column chromatography (80 g silica gel cartridge, 0-25% EtOAc/Hexanes, product eluted during 8% EtOAc/Hex) to yield the desired product (347 mg, 79%) as a colorless solid. $^1$H NMR (400 MHz, CHLOROFORM-d) δ 8.31-8.36 (m, 2H), 7.49-7.53 (m, 2H), 7.35-7.41 (m, 1H), 7.12-7.19 (m, 3H), 3.01 (tt, J=3.32, 12.63 Hz, 1H), 2.87 (tt, J=3.32, 12.63 Hz, 1H), 2.15-2.21 (m, 1H), 1.77-2.05 (m, 13H), 1.65-1.75 (m, 5H), 1.59-1.65 (m, 1H), 1.39-1.46 (m, 1H); 13C NMR (100 MHz, CHLOROFORM-d) δ 155.4, 151.2, 150.9, 148.2, 148.0, 145.7, 129.8, 125.5, 125.4, 121.9, 119.2, 118.6, 112.0 (minor diastereomer), 111.6, 108.9, 42.0, 41.7, 41.5, 36.9, 36.5, 35.0, 34.9, 34.9, 34.2, 33.5, 32.7, 27.0, 27.0, 26.6, 23.5. MS (ESI) calculated for C$_{29}$H$_{31}$NNaO$_8$ [M+Na]$^+$ m/z 544.19, found 544.02.

3-[m-(2-Aminoethylaminocarbonyloxy)phenyl]dispiro[cyclohexane-1,3'-[1,2,4]trioxolane-5',2"-tricyclo[3.3.1.1$^{3,7}$]decane] (D8)

To a solution of intermediate D7 (60 mg, 0.12 mmol, 1.0 equiv) in dichloromethane (2.0 mL) was added Et$_3$N (24 μL, 0.17 mmol, 1.5 equiv), followed by ethylenediamine (12 μL, 0.17 mmol, 1.5 equiv) at room temperature. The bright yellow mixture was then allowed to stir at room temperature for 5 h, at which point, the reaction was judged complete by TLC and LCMS. The reaction was then diluted with H$_2$O (100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous Na$_2$SO$_4$, filtered, and concentrated under reduced pressure. The residue was then purified through flash column chromatography (12 g silica gel cartridge, 0-100% EtOAc/Hexanes, followed by 0-20% MeOH (containing 0.7 N NH$_3$)/CH$_2$Cl$_2$, and desired product eluted during 20% MeOH (containing 0.7 N NH$_3$)/CH$_2$Cl$_2$], to yield the desired product (38.0 mg, 75%) as a colorless oil. $^1$H NMR (400 MHz, CHLOROFORM-d) δ 7.22-7.27 (m, 1H), 7.03 (br d, J=7.55 Hz, 1H), 6.91-7.01 (m, 2H), 3.51 (br s, 2H), 3.13 (br s, 2H), 2.06-2.13 (m, 1H), 1.88-2.01 (m, 6H), 1.83-1.88 (m, 1H), 1.74-1.83 (m, 5H), 1.58-1.73 (m, 8H), 1.27-1.46 (m, 2H), 1.15-1.27 (m, 1H); MS (ESI) calculated for C$_{25}$H$_{35}$N$_2$O$_5$ [M+H]$^+$ m/z 443.25, found 443.28.

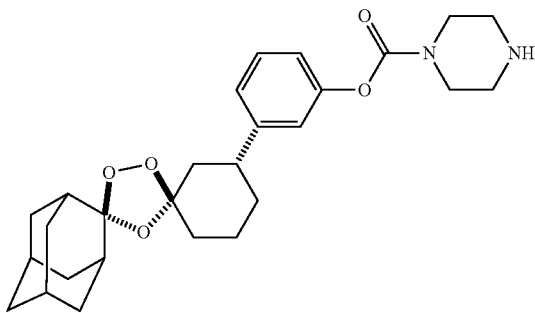

m-(Dispiro[cyclohexane-1,3'-[1,2,4]trioxolane-5',2"-tricyclo[3.3.1.1$^{3,7}$]decan]-3-yl)phenyl 1-piperazinecarboxylate (D9).

To a solution of intermediate D7 (60 mg, 0.12 mmol, 1.0 equiv) in dichloromethane (2.0 mL) was added Et$_3$N (24 μL, 0.17 mmol, 1.5 equiv), followed by piperazine (18.0 mg, 0.19 mmol, 1.5 equiv) at room temperature. The bright yellow mixture was then allowed to stir at room temperature for 5 h, at which point, the reaction was judged complete by TLC and LCMS. The reaction was then diluted with H$_2$O

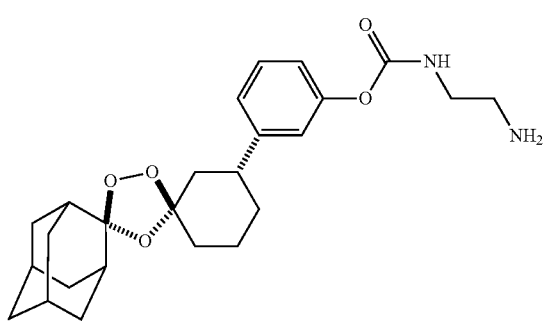

(100 mL) and subsequently extracted with EtOAc (100 mL). The organic layer was washed repeatedly by potassium carbonate solution until the aqueous layer was colorless and no longer yellow (indicating successful removal of p-nitrophenol from the organic layer). The combined aqueous layers were then back extracted with EtOAc (30 mL). The combined organic layers were then washed with brine (20 mL), dried over anhydrous $Na_2SO_4$, filtered, and concentrated under reduced pressure. The residue was then purified through flash column chromatography (12 g silica gel cartridge, 0-100% EtOAc/Hexanes, followed by 0-20% MeOH (containing 0.7 N $NH_3$)/$CH_2Cl_2$, and desired product eluted near 10% MeOH (containing 0.7 N $NH_3$)/$CH_2Cl_2$, to yield the desired product (41.0 mg, 76%) as a colorless oil. $^1$H NMR (400 MHz, CHLOROFORM-d) δ 7.22-7.32 (m, 1H), 7.04 (d, J=7.79 Hz, 1H), 6.92-6.96 (m, 2H), 3.62-3.75 (m, 2H), 3.60-3.77 (m, 1H), 3.51 (br s, 2H), 3.44-3.58 (m, 1H), 2.97-3.06 (m, 3H), 2.80 (tt, J=3.17, 12.66 Hz, 1H), 2.13 (br d, J=13.39 Hz, 1H), 2.01-2.10 (m, 1H), 1.87-2.01 (m, 6H), 1.77-1.85 (m, 4H), 1.63-1.73 (m, 7H), 1.43-1.63 (m, 1H), 1.31-1.42 (m, 1H), 1.19-1.31 (m, 1H); $^{13}$C NMR (100 MHz, CHLOROFORM-d) δ 153.8, 151.5, 147.4, 129.4, 124.1, 120.1, 119.7, 111.5, 109.1, 45.3, 44.0, 42.0, 41.8, 36.9, 36.6, 36.5, 36.5, 34.9, 34.9, 34.3, 32.8, 29.8, 27.0, 26.6, 23.6; MS (ESI) calculated for $C_{27}H_{37}N_2O_5$ [M+H]$^+$ m/z 469.27, found 469.17.

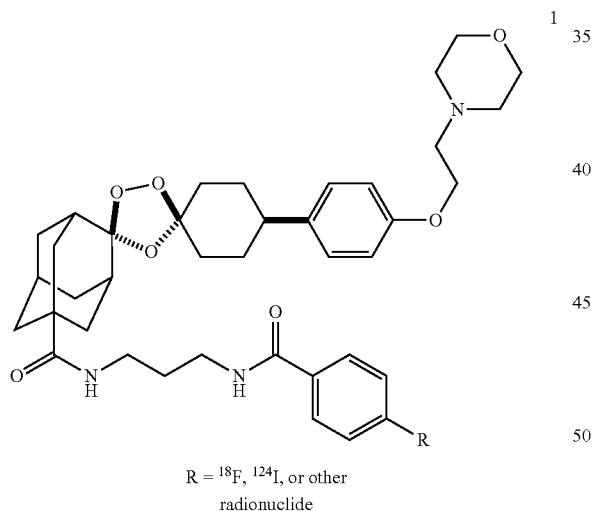

R = $^{18}$F, $^{124}$I, or other radionuclide

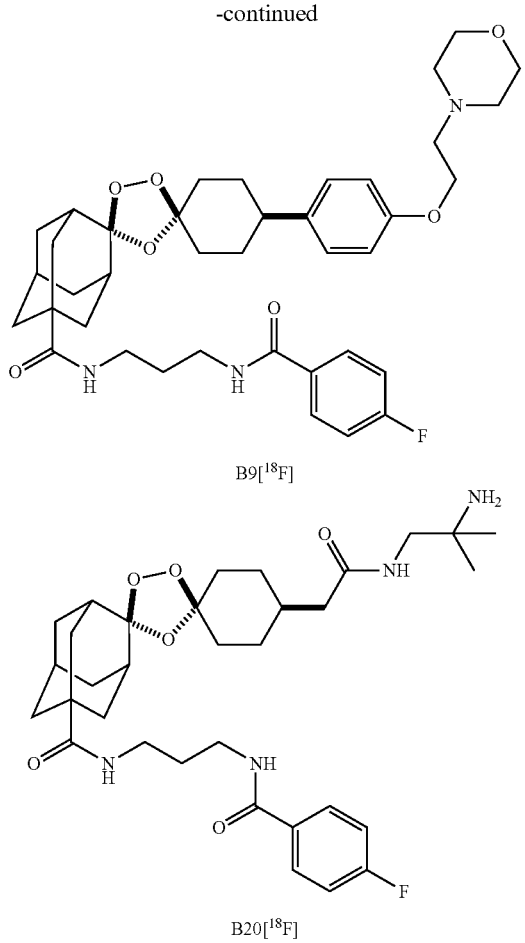

B9[$^{18}$F]

B20[$^{18}$F]

Figure 2:
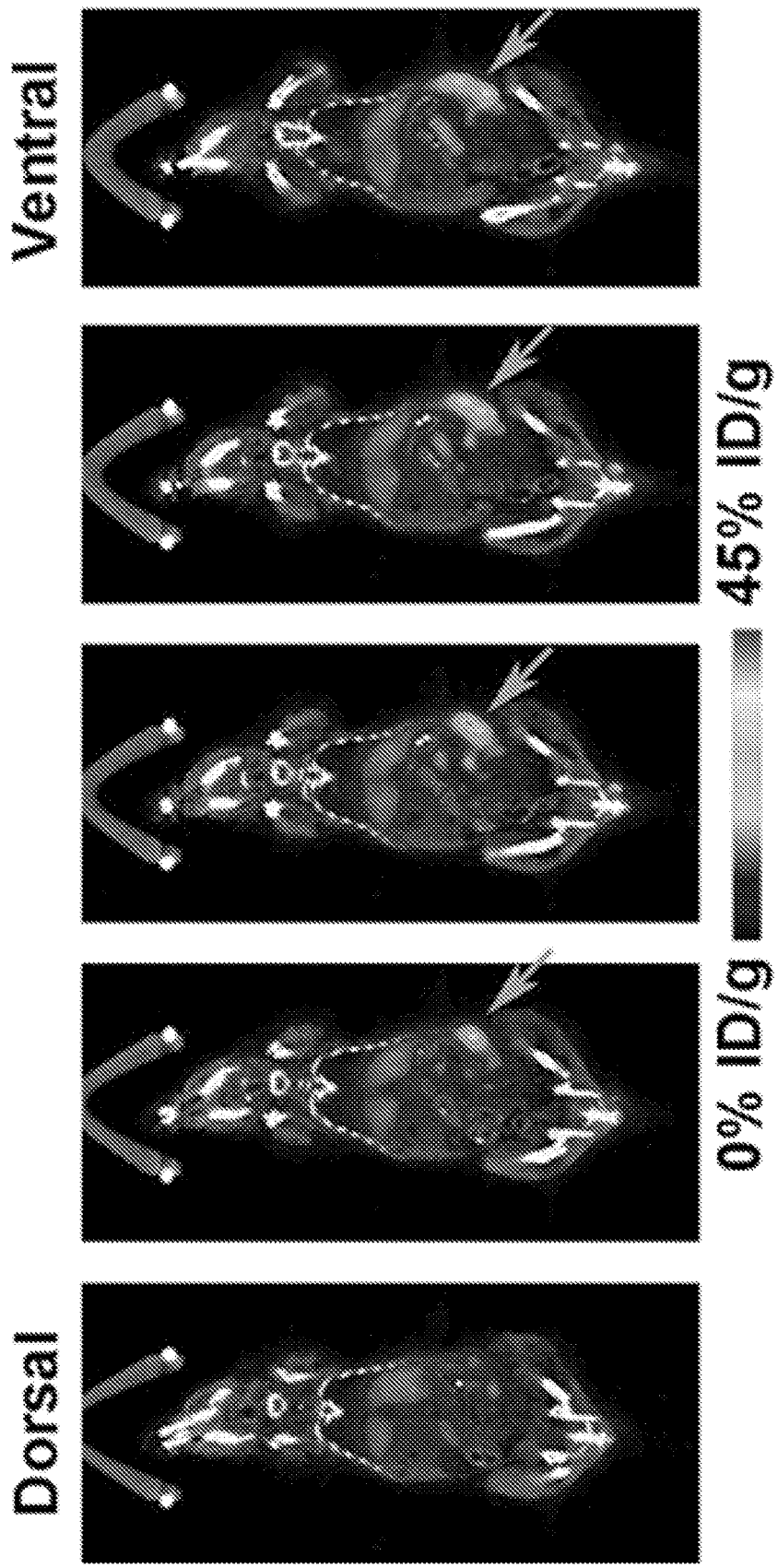
FIG. 2 PET images of PC-3 xenograft mouse treated with modified derivative of artefenomel (R=18F) via tail vein injection.

Compounds 1 and specific examples B8[$^{18}$F] and B20[$^{18}$F] above are PET imaging reagent with applications in cancer, infectious disease, and inflammation. A PET experiment with B9 in a mouse PC-3 xenograft showed accumulation in the small intestine (FIG. 2). Additional, more quantitative, biodistribution data (e.g., biodistribution data for probes B9 and B20) is included in FIGS. 5-8. These compound possesses good stability in animals but can react and become sequestered in tissues where free Fe(II) is encountered. The imaging reagents above provides a new paradigm for imaging diverse cancer types based on metabolic changes in iron metabolism in tumors and other aspects of tumor biology (hypoxia, necrosis, macrophage infiltration). Imaging primary tumors and metastases and other therapeutic conditions involving aberrant production of labile Fe(II) such as inflammation and infection.

Synthesis of B9

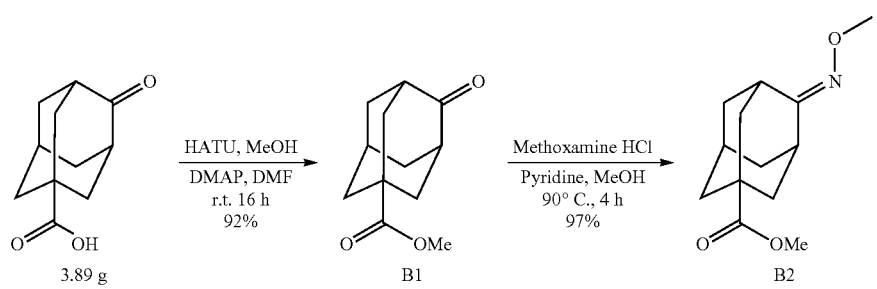

-continued
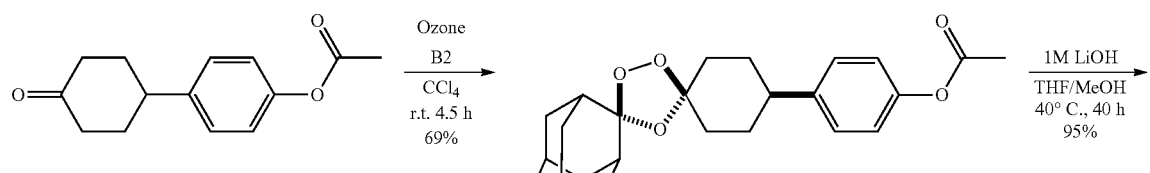
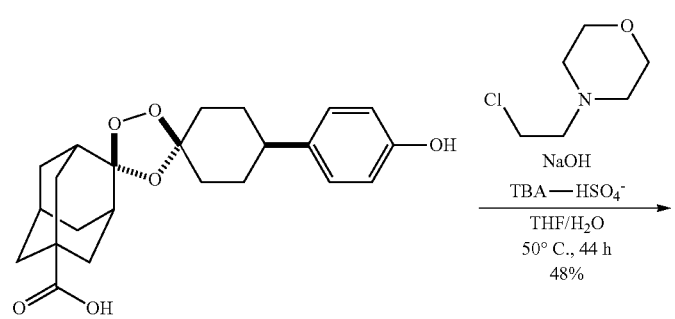
B4
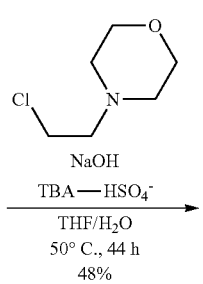
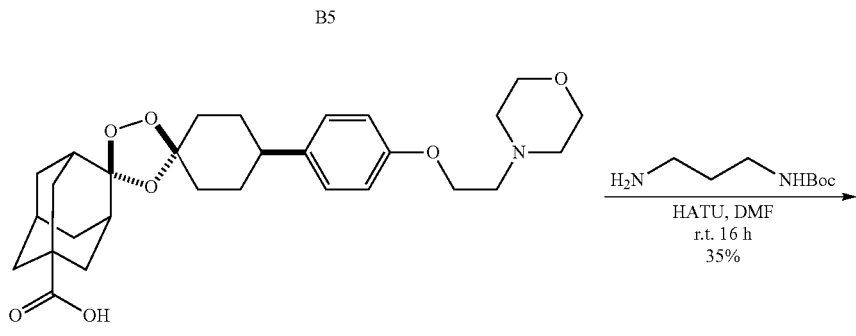
B5
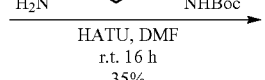
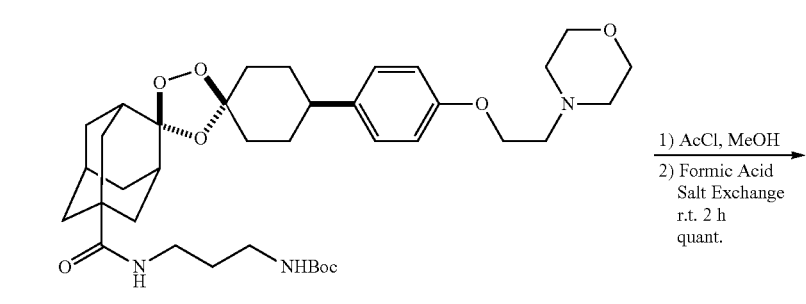
B6
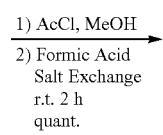
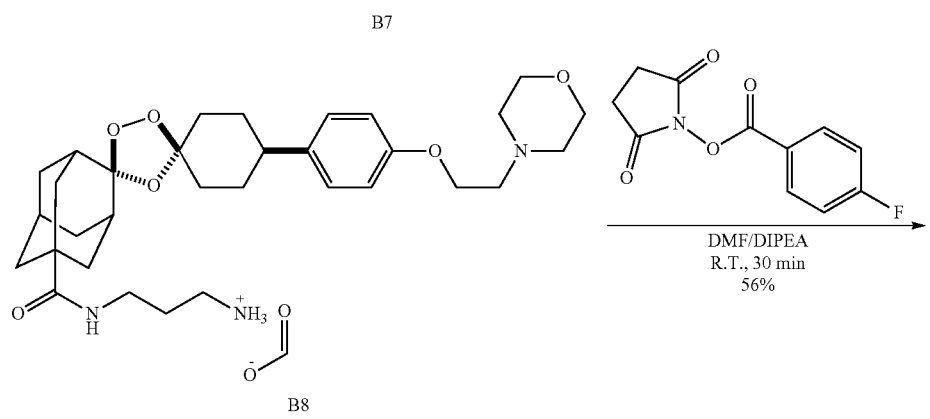
B7
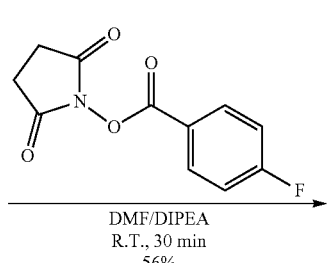
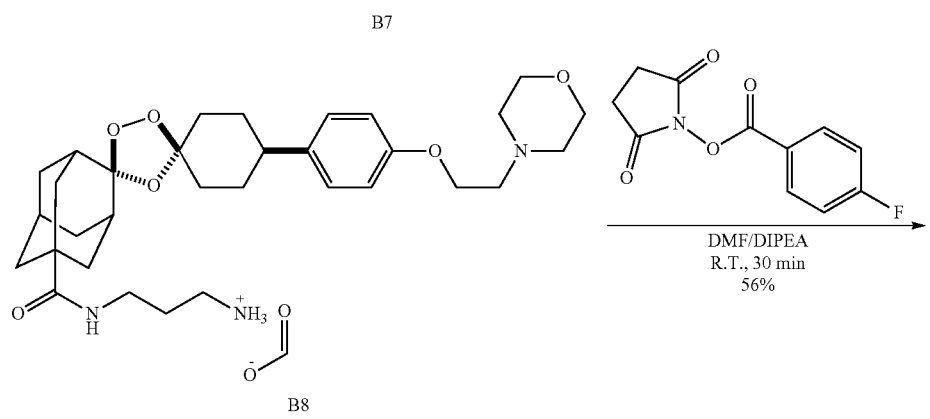
B8

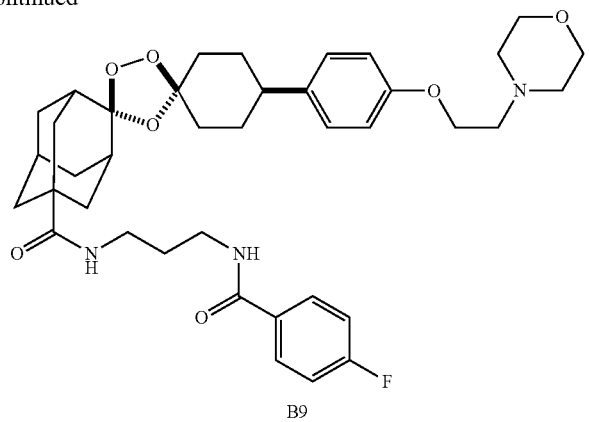

B9

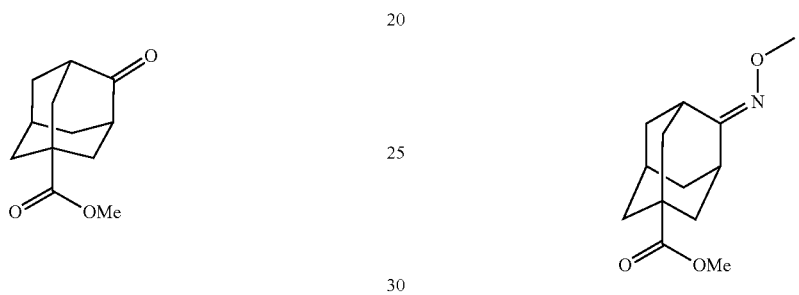

methyl 4-oxoadamantane-1-carboxylate (B1)

methyl-4-(methoxyimino)adamantane-1-carboxylate (B2)

To a round bottom flask containing a Teflon-coated magnetic stir bar under an Ar(g) atmosphere was added 4-oxoadamantane-1-carboxylic acid (3.885 g, 20.0 mmol, 1.0 equiv.), HATU (9.219 g, 24.0 mmol, 1.2 equiv.), N,N-dimethylformamide (80 mL), methanol (8.103 ml, 200.0 mmol, 10.0 equiv.), and 4-dimethylaminopyridine (1.222 g, 10.0 mmol, 0.5 equiv.). After addition of the HATU, the solution turned a dark orange color. The solution was allowed to at room temperature for 16 hours, at which time TLC staining with KMnO$_4$ and LCMS analysis indicated the reaction was complete. To the reaction mixture was added water (75 mL). The aqueous layer was then extracted with ethyl acetate (3×75 mL). The organic layers were collected and washed with brine (3×75 mL) to remove excess DMF. The aqueous phase was then extracted again with ethyl acetate and washed with brine as before. The combined organic phases were then dried over magnesium sulfate and filtered under vacuum. The solution was concentrated under reduced pressure to give a dark brown solution containing residual DMF. This crude product was purified through flash column chromatography (330 g HP silica gel cartridge, 0-20% EtOAc/Hexanes, product eluted near 20% EtOAc/Hex) to yield B1 (3.869 g, 93%) as a white, crunchy solid. NMR spectra of this material were consistent with those reported in the literature for this compound.

To a sealed tube containing a Teflon-coated magnetic stir bar under an Ar(g) atmosphere was added adamantanone B1 (3.800 g, 18.2 mmol, 1.0 equiv.) and methanol (36 mL.). This solution was stirred until all solid had dissolved, then pyridine (2.946 ml, 36.5 mmol, 2.0 equiv.) and methoxylamine HCl (1.711 g, 20.1 mmol, 1.1 equiv.) were added sequentially. The solution was again stirred at room temperature under argon until all of the solid went into solution. The reaction was placed in an oil bath that had been preheated to 90° C. and stirred for 4 hours. The solution was then allowed to cool at which point TLC and LCMS showed the reaction was complete. The mixture was concentrated under reduced pressure to give a white slurry. Following the addition of EtOAc (50 mL) and water (50 mL), the organic layer was separated and washed with KHSO$_4$ (2×50 mL) and brine (1×50 mL). The organic layer was dried over MgSO$_4$, filtered, and concentrated under reduced pressure to afford B2 as a white fluffy powder (4.19 g, 97%). NMR was consistent with literature values.

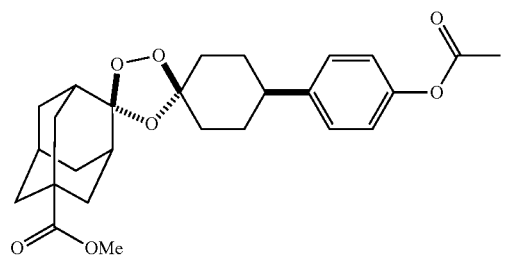

methyl-4"-(4-acetoxyphenyl)dispiro[adamantane-2, 3'-[1,2,4]trioxolane-5',1"-cyclohexane]-5-carboxylate (B4)

To a round bottom flask containing a Teflon-coated magnetic stir bar open to the atmosphere was added oxime B2 (1.277 g, 5.4 mmol, 1.0 equiv.) and 4-(4-acetoxyphenyl)cyclohexan-1-one (1.250 g, 5.4 mmol, 1.0 equiv.). To the mixture of solid materials was added carbon tetrachloride (100 mL). This solution was cooled to 0° C. and subsequently sparged with $O_2$ for 10 minutes. The reaction was kept at 0° C. while ozone was then bubbled (2 L/min, 35% power). After stirring for 75 minutes, TLC and LCMS showed only starting material and no product formation. It was noted that the starting material had precipitated from solution and dichloromethane (5 mL) was added to produce a solution. After stirring for 60 minutes, the reaction was still determined to be incomplete by TLC and additional oxime B2 (350 mg, 1.5 mmol, 0.3 equiv.) was added to the reaction mixture in one portion. Ozone was bubbled through the mixture for 60 minutes at which point the reaction was judged incomplete by TLC. An additional portion of oxime B2 (300 mg, 1.3 mmol, 0.2 equiv.) was added and ozone again bubbled through the reaction for 60 minutes at which the reaction was purged with $O_2$ for 10 minutes to remove any dissolved ozone, followed by sparging with argon gas for 10 minutes. The reaction mixture was then concentrated under reduced vacuum to give a white slurry. This crude mixture was purified by flash column chromatography (120 g HP silica gel cartridge, 0-10% EtOAc/Hexanes, product eluted during 10% EtOAc/Hex) to yield B4 (1.68 g, 69%) as an off-white foam. Analysis by LCMS and NMR indicates a mixture of diasteromers in a ratio of approximately 8:1. $^1$H NMR (400 MHz, CDCl3) δ 7.25 (d, 8 Hz, 2H, minor diastereomer), 7.21 (d, 8 Hz, 2H, major), 7.05-6.97 (m, 2H), 3.70-3.65 (m, 3H), 2.62-2.51 (m, 1H), 2.29 (s, 3H), 2.26-2.19 (m, 2H), 2.17-1.79 (m, 16H), 1.77-1.64 (m, 4H); $^{13}$C NMR (100 MHz, CDCl3) δ 177.1, 176.1 (minor diastereomer), 169.5, 148.8, 143.4, 127.6, 121.3, 110.1, 108.5, 51.9, 51.6 (minor diastereomer), 42.2, 40.2, 40.0, 39.8, 39.4, 38.2, 38.0 (minor diastereomer), 37.7, 36.2, 36.1 (minor diastereomer), 35.9, 35.8 (minor diastereomer), 34.5, 33.6, 31.3, 27.2, 26.5, 26.1, 24.6, 21.0; MS (ESI) calculated for $C_{26}H_{32}O_7$[M+Na]+ m/z 479.20, found 479.08.

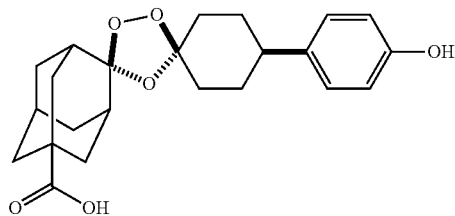

4"-(4-hydroxyphenyl)dispiro[adamantane-2,3'-[1,2,4]trioxolane-5',1"-cyclohexane]-5-carboxylic acid (B5)

To a round bottom flask containing a Teflon-coated magnetic stir bar open to the atmosphere was added trioxolane B4 (1.685 g, 3.7 mmol, 1.0 equiv.) dissolved in anhydrous tetrahydrofuran (40 mL) and methanol (40 mL). To this stirring solution was 1M lithium hydroxide in water (14.8 ml, 14.8 mmol, 4.0 equiv.). The reaction was placed into an oil bath that had been preheated to 40° C. and monitored by LCMS. After 19 hours, additional 1M LiOH was added to the reaction mixture (5 mL, 5.0 mmol, 1.4 equiv). After stirring at 40° C. for an additional 19 hours, the reaction was judged complete by LCMS. The reaction was then concentrated under reduced pressure to give a white slurry. Water (75 mL) and EtOAc (75 mL) were added to the crude mixture and the mixture transferred to an Erlenmeyer flask containing a Teflon-coated magnetic stir bar and cooled to 0° C. The pH of this stirring mixture was adjusted to pH~1 by dropwise addition of 1N HCl. The organic layer was collected and the aqueous layer was extracted with EtOAc (2×75 mL). The combined organic layers were then washed with brine (1×50 mL), and the organic layer was concentrated under reduced pressure to yield B5 (1.4 g, 95%) as a white powder. $^1$H NMR (400 MHz, DMSO-d6) δ 12.18 (br s, 1H), 7.21 (br s, 1H), 7.05-6.96 (m, 2H), 6.71-6.64 (m, 2H), 2.50-2.40 (m, 1H), 2.14-1.97 (m, 5H), 2.17-1.79 (m, 14H), 1.58-1.43 (m, 2H); $^{13}$C NMR (100 MHz, DMSO-d6) δ 177.6, 176.9 (minor diastereomer), 155.5, 136.1 127.4 (minor diastereomer), 127.3 115.0, 109.7, 108.4, 45.3, 40.7, 39.7, 38.8, 38.4, 37.7, 37.6 (minor diastereomer), 37.5, 37.3, 36.0, 35.9 (minor diastereomer), 35.5, 35.4 (minor diastereomer), 34.1, 33.2, 31.4, 26.8, 26.0, 25.6; MS (ESI) calculated for $C_{23}H_{28}O_6$[M–H]– m/z 399.18, found 399.23.

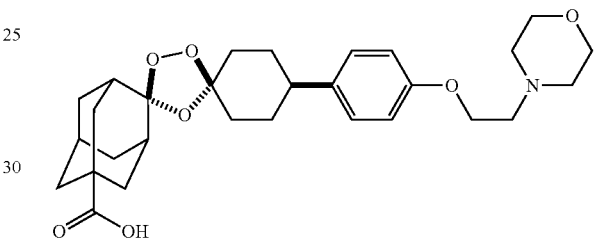

4"-(4-(2-morpholinoethoxy)phenyl)dispiro[adamantane-2,3'-[1,2,4]trioxolane-5',1"-cyclohexane]-5-carboxylic acid (B6)

To a round bottom flask containing a Teflon-coated magnetic stir bar under Ar(g) was added trioxolane B5 (1.40 g, 3.5 mmol, 1.0 equiv.), 1M sodium hydroxide (31.5 ml, 31.5 mmol, 9.0 equiv.) and tetrabutylammonium bisulfate (0.237 g, 0.7 mmol, 0.2 equiv.). This mixture was allowed to stir for 30 minutes at room temperature under argon, at which point 4-(2-chloroethyl)morpholine hydrochloride (1.301 g, 7.0 mmol, 2.0 equiv.) was added. The reaction was placed into an oil bath that had been preheated to 50° C. and and monitored by LCMS. Additional 4-(2-chloroethyl)morpholine hydrochloride (3 equiv) and 1M NaOH (1 equiv) were added over the subsequent two days until LCMS indicated complete consumption of starting material and some esterification side product. To saponify this side product, 1M NaOH (21 mL, 21 mmol, 6 eq) was added and the reaction allowed to stir at 50° C. for 4 hrs. At this point the reaction was determined to be complete by LCMS and the solution was concentrated under reduced vacuum to give a white slurry. To this crude mixture was added water (75 mL) and EtOAc (75 mL). Following the addition of EtOAc, a white precipitate formed and was collected by filtration and dried to afford the desired product B6 (880 mg, 1.71 mmol, 49%) as a white powder. This material was used without further purification. $^1$H NMR (400 MHz, CDCl3) δ 8.60 (br s, 1H), 7.18-7.09 (m, 2H), 6.88-6.80 (m, 2H), 4.16-4.08 (m, 2H), 3.80-3.71 (m, 4H), 2.85 (t, 5.2 Hz, 2H), 2.72-2.63 (m, 4H), 2.54-2.45 (m, 1H), 2.27-2.17 (m, 2H), 2.14-1.78 (m, 15H), 1.77-1.63 (m, 4H); $^{13}$C NMR (100 MHz, CDCl3) δ 181.3, 181.0 (minor diastereomer), 156.9, 138.6, 127.7, 114.5, 110.3, 108.7, 66.4, 66.3 (minor diastereomer), 65.1, 65.0

(minor diastereomer), 57.4, 53.7, 53.6 (minor diastereomer), 42.1, 42.0, 41.4, 39.7, 39.2, 38.1, 38.0, 36.3, 36.1, 35.9, 34.7, 34.6 (minor diastereomer), 34.2, 33.7, 31.7 (minor diastereomer), 31.6, 26.6, 26.2; MS (ESI) calculated for $C_{29}H_{39}NO_7$ [M+H]+ m/z 514.28, found 514.18.

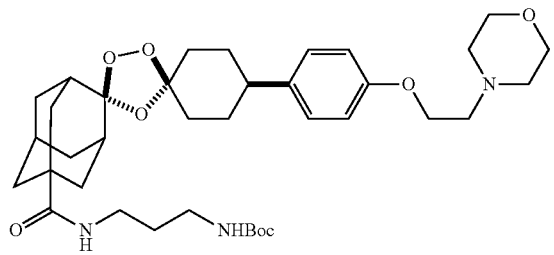

(tert-butyl N-{3-[(4"-{4-[2-(morpholin-4-yl)ethoxy]phenyl}dispiro[adamantane-2,2'-[1,2,4]trioxolane-4',1"-cyclohexane]-7-yl)formamido]propyl}carbamate (B7)

To a round bottom flask containing a Teflon-coated magnetic stir bar under Ar(g) was added trioxolane B6 (800 mg, 1.6 mmol, 1.0 equiv.), HATU (710 mg, 1.9 mmol, 1.2 equiv.), N,N-diisopropylethylamine (0.678 ml, 3.9 mmol, 2.5 equiv.) and N,N-dimethylformamide (15 mL). This dark orange solution stirred at room temperature under argon for 5 minutes before N-Boc-1,3-propanediamine (326 mg, 1.9 mmol, 1.2 equiv.) was added in one portion. The reaction was allowed to stir at room temperature for 16 hours at which point LCMS confirmed that the reaction had reached completion. The crude reaction was purified by preparatory HPLC (Waters XBridge C18 column, 25-70% methanol/water with 0.05% formic acid) to afford the product B7 as a white powder as two separable major diastereomers related by the relative orientation of the peroxo bridge and the adamantane-bound side chain. One of the two diastereomers was characterized by NMR and MS. $^1$H NMR (400 MHz, CDCl3) δ 7.14-7.09 (m, 2H), 6.86-6.82 (m, 2H), 4.09 (t, 5.8 Hz, 2H), 3.74 (t, 4.6 Hz, 4H), 3.30 (q, 6.3 Hz, 2H), 3.19-3.12 (m, 2H), 2.80 (t, 5.8 Hz, 2H), 2.61-2.55 (m, 4H), 2.55-2.45 (m, 1H), 2.23-2.16 (m, 2H), 2.14-2.09 (m, 2H), 2.07-1.77 (m, 15H), 1.77-1.56 (m, 6H), 1.46 (s, 9H); $^{13}$C NMR (100 MHz, CDCl3) δ 177.3, 157.1, 156.7, 138.5, 127.6, 114.5, 110.3, 108.9, 66.9, 65.7, 57.7, 54.0, 42.0, 39.8, 38.5, 38.0, 36.9, 36.7, 36.2, 34.7, 33.7, 31.6, 28.4, 26.4; MS (ESI) calculated for $C_{37}H_{55}N_3O_8$ [M+H]+ m/z 670.41, found 670.35.

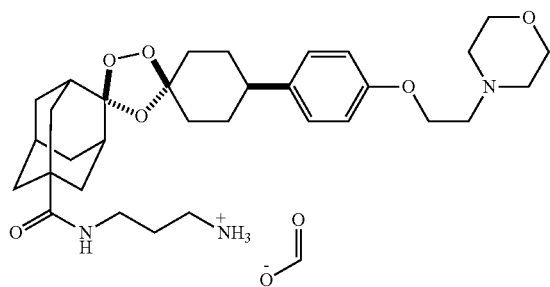

N-(3-azaniumylpropyl)-4"-{4-[2-(morpholin-4-yl)ethoxy]phenyl}dispiro[adamantane-2,2'-[1,2,4]trioxolane-4',1"-cyclohexane]-7-carboxamide formate (B8)

To a round bottom flask containing a Teflon-coated magnetic stir bar under Ar (g) was added trioxolane B7 (225 mg, 0.3 mmol, 1.0 equiv.) and methanol (7.5 mL). To this stirring solution was added acetyl chloride (716 ul, 10.1 mmol, 30.0 equiv.) dropwise over 5 minutes. The reaction was allowed to stir at room temperature for 140 minutes at which point the reaction was determined to be complete by LCMS. To quench the reaction, the pH was adjusted to pH 7 by addition of saturated $NaHCO_3$ solution (10 mL). The mixture was concentrated under reduced pressure to give a white slurry. To this slurry was added 1M $Na_2CO_3$ (20 mL) and dichloromethane (40 mL). The organic layer was collected and the aqueous layer was extracted with dichloromethane (2×25 mL). The combined organic layers were transferred to an Erlenmeyer flask equipped with a stir bar to which was added water (75 mL). This stirring mixture was cooled to 0° C. and the pH was adjusted to ~1 by addition of formic acid. The resulting emulsion was allowed to stand until the layers had separated. The aqueous layer was collected and washed with dichloromethane (2×40 mL). The product B8 (218 mg, quant.) was obtained as a white fluffy solid following lyophilization of the aqueous layer. Characterization was of a mixture of isomers. $^1$H NMR (400 MHz, CDCl3) δ 7.13-7.04 (m, 2H), 6.86-6.77 (m, 2H), 4.07-4.02 (m, 2H), 3.71-3.66 (m, 4H), 3.37-3.28 (m, 2H), 2.77-2.72 (m, 2H), 2.56-2.51 (m, 4H), 2.50-2.40 (m, 1H), 2.16-2.09 (m, 2H), 2.07-1.74 (m, 19H), 1.72-1.55 (m, 4H); $^{13}$C NMR (100 MHz, CDCl3) δ 177.2, 157.0, 138.3, 127.5, 114.3, 110.2, 108.6, 66.8, 65.7, 57.6, 54.0, 41.8, 39.6, 39.2, 38.4, 37.8, 36.6, 36.1, 36.0, 34.5, 33.6, 31.5, 26.3; MS (ESI) calculated for $C_{32}H_{47}N_3O_8$ [M+H]+ m/z 570.35, found 570.21.

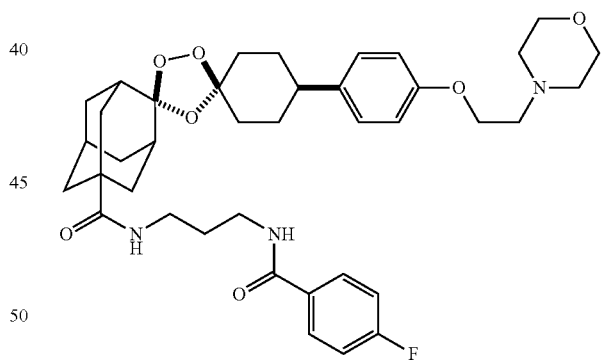

N-(3-(4-fluorobenzamido)propyl)-4"-(4-(2-morpholinoethoxy)phenyl)dispiro[adamantane-2,3'-[1,2,4]trioxolane-5',1"-cyclohexane]-5-carboxamide (B9[$^{19}$F]). This procedure specifically describes the synthesis of the cold ($^{19}$F) standard B9[$^{19}$F]. To a round bottom flask containing a Teflon-coated magnetic stir bar under Ar(g) was added trioxolane salt B8 (10 mg, 0.018 mmol, 1.0 equiv.), N,N-diisopropylethylamine (0.006 ml, 0.033 mmol, 1.9 equiv.) and N,N-dimethylformamide (0.2 mL). To this stirring solution was added succinimidyl 4-[$^{19}$F]-benzoate (SFB, 4 mg, 0.018 mmol, 1.0 equiv.) in one portion. The reaction was lowered into an oil bath that had been preheated to 50° C. and was allowed to stir under argon for 30 minutes. At this point, the reaction was determined to be complete by LCMS. The crude reaction was purified by preparatory HPLC (Waters XBridge C18 column, 40-70% methanol/water with 0.05% formic acid) to afford the product B9[$^{19}$F] as a white powder (7 mg, 58%). $^1$H NMR (400 MHz, CDCl3) δ 7.95-7.88 (m, 2H), 7.17-7.09 (m, 4H), 6.87-6.82 (m, 2H), 4.14-4.07 (m, 2H), 3.78-3.71 (m, 4H), 3.48-3.34 (m, 4H), 3.19-3.12 (m, 2H), 2.84-2.77 (m, 2H), 2.63-2.56 (m, 2H), 2.56-2.46 (m, 1H), 2.24-1.65 (m, 23H); MS (ESI) calculated for $C_{39}H_{50}FN_3O_7$[M+H]+ m/z 692.37, found 692.34.

Synthesis of N-(3-(4-[$^{18}$F]fluorobenzamido)propyl)-4"-(4-(2-morpholinoethoxy)phenyl)dispiro[adanantane-2,3'-[1,2,4]trioxolane-5',1"-cyclohexane]-5-carboxamide (B91[F])

Succinimidyl 4-fluorobenzoate partially enriched in $^{18}$F (S$^{18}$FB) was prepared by the UCSF cyclotron core. To a 3 mL vial containing a dried S$^{18}$FB (20-100 mCi) was added a solution of trioxolane salt 138 (5 mg, 0.09 mmol, 1.0 equiv.), and N,N-diisopropylethylamine (0.025 ml, 0.14 mmol, 16 equiv.) in N,N-dimethylformamide (0.5 mL). The vial was gently shaken and then was allowed to stand at room temperature for 30 minutes. At this point, the solution was diluted with de-ionized H$_2$O containing 0.1% formic acid (1.5 mL). This crude mixture was purified by preparative HPLC (Waters XBridge C18 column, 5-95% acetonitrile/water with 0.1% formic acid). The appropriate peak (having the same retention time as cold standard) was collected and diluted with 30 mL H$_2$O (0.1% formic acid) and then passed through a sep-pak C18 cartridge, within which the desired compound is sequestered. Next the sep-pak cartridge is washed with 10 mL H$_2$O and then ethanol, which causes B9[F] to elute from the cartridge. The ethanol solution of B9[$^{18}$F] is then concentrated by evaporation of ethanol under a stream of air or inert gas. The product is then dissolved in 10% vol/vol DMSO/0.4% vol/vol Tween 80 in 20 mM phosphate buffer, pH 3. At this point, the yield (typically 60-70%) is determined based on total radioactivity.

Synthesis of B20[$^{19}$F]

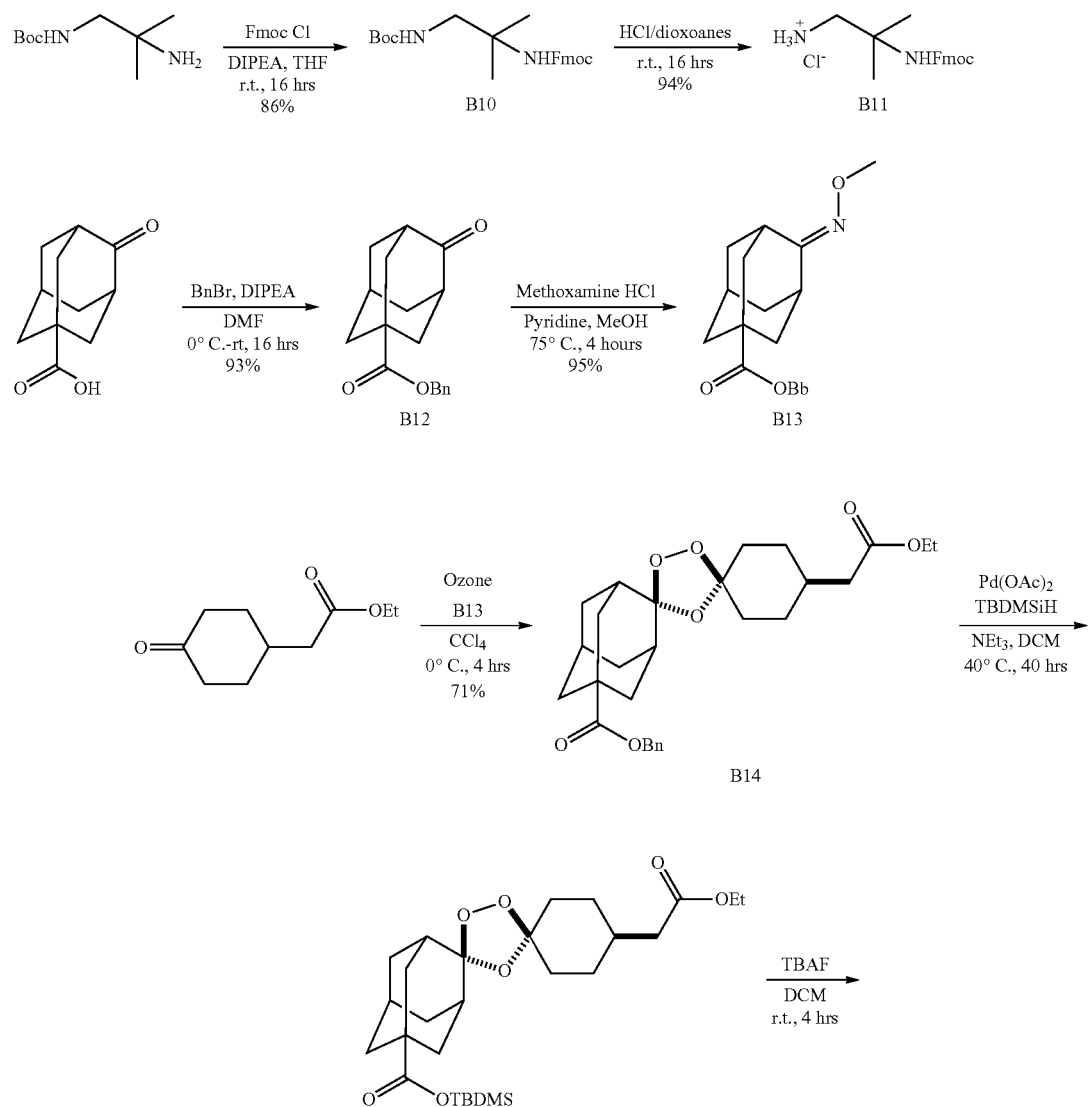

-continued
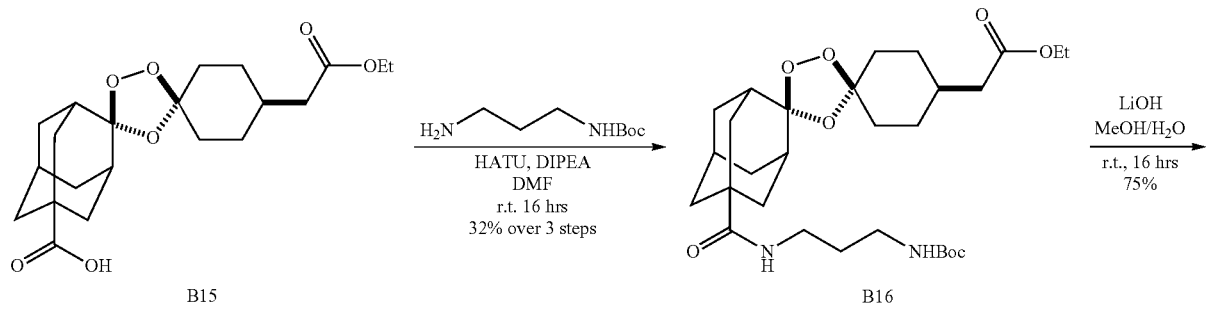
B15      B16
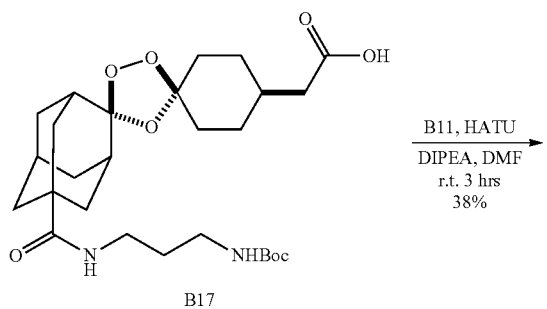
B17
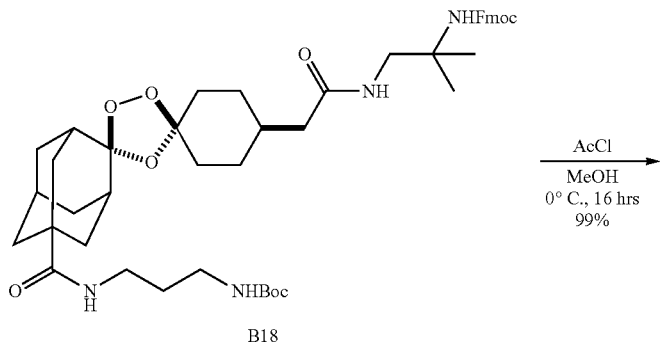
B18
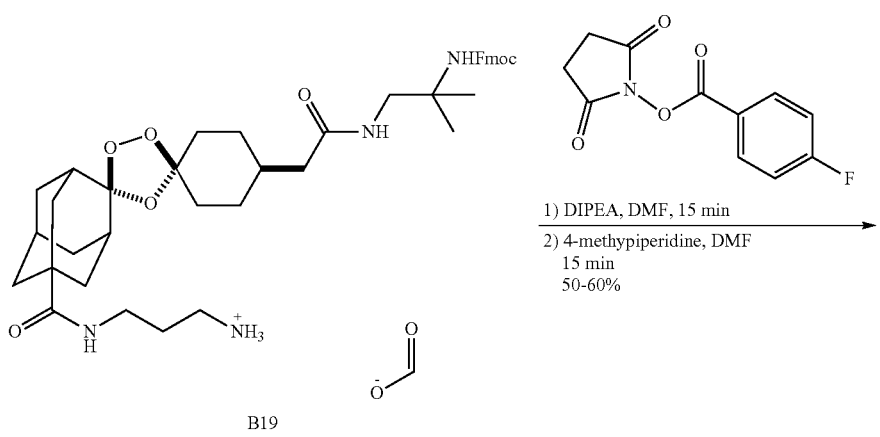
B19

-continued

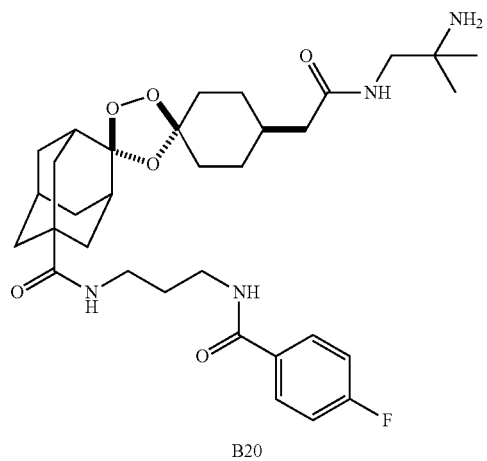

B20

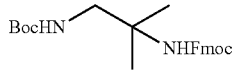

(9H-Fluoren-9-yl)methyl N-(1-{[(tert-butoxy)carbonyl]amino}-2-methylpropan-2-yl)carbamate (B10)

To a round bottom flask containing a Teflon-coated magnetic stir bar under an Ar(g) atmosphere was added tert-butyl N-(2-amino-2-methylpropyl)carbamate (200 mg, 1.1 mmol, 1.0 equiv.), tetrahydrofuran (10.000 ml, 123.3 mmol, 116.1 equiv.) and N,N-diisopropylethylamine (0.555 ml, 3.2 mmol, 3.0 equiv.). This stirring solution was brought to 0° C. before addition of 9-Fluorenylmethyl chloroformate (330 mg, 1.3 mmol, 1.2 equiv.) in one portion. The reaction was allowed to warm to RT overnight, at which point TLC shows complete consumption of starting material. Organic solvent was removed under reduced pressure. This crude product was purified by flash column chromatography (0-25% EtOAc/Hexanes) to yield B10 (373 mg, 86%). $^1$H NMR (400 MHz, CHLOROFORM-d) δ ppm 1.28 (s, 6H) 1.48 (s, 9H) 3.20-3.34 (m, 2H) 4.03-4.08 (m, 1H) 4.13 (dd, J=6.57, 1.95 Hz, 1H) 4.21 (t, J=1.00 Hz, 1H) 7.30-7.37 (m, 2H) 7.41 (m, 2H) 7.58-7.66 (m, 2H) 7.78 (m, 2H). $^{13}$C NMR (100 MHz, CHLOROFORM-d) δ ppm 25.06, 28.67, 47.67, 50.65, 65.81, 120.20, 124.97, 127.32, 127.90, 141.62, 144.46; MS (ESI) calculated for $C_{24}H_3N_2O_4$ [M+Na]$^+$ m/z 433.21, found 433.14.

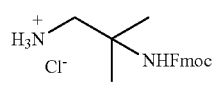

2-((((9H-Fluoren-9-yl)methoxy)carbonyl)amino)-2-methylpropan-1-aminium chloride (B11)

To a round bottom flask containing a Teflon-coated magnetic stir bar under an Ar(g) atmosphere was added B10 (373 mg, 0.9 mmol, 1 eq) and 1,4-dioxane (4 mL). This stirring solution was cooled to 0° C. at which point hydrochloric acid (1.0 ml, 4.0 mmol, 4.4 equiv.) was added dropwise. The solution stirred at 0° C. for 4 hours. Based on LCMS analysis, the reaction was judged complete. Organic solvent was removed under reduced pressure to give amine B311 (265 mg, 95%) as the chloride salt. This material was used in subsequent reactions without further purification.

Benzyl 4-oxoadamantane-1-carboxylate (B12)

To a round bottom flask containing a Teflon-coated magnetic stir bar under an Ar(g) atmosphere was added 4-oxoadamantane-1-carboxylic acid (1.000 g, 5.1 mmol, 1.0 equiv.), N,N-dimethylformamide (10.0 ml, 129.7 mmol, 25.2 equiv.) and N,N-diisopropylethylamine (1.794 ml, 10.3 mmol, 2.0 equiv). This stirring solution was brought to 0° C. at which point benzyl bromide (0.734 ml, 6.2 mmol, 1.2 equiv.) was added in one portion. The solution immediately turned brown. The reaction mixture was allowed to warm to room temperature of 16 hours at which point TLC and LCMS analysis confirmed reaction was complete. Water (75 mL) was added to the mixture and the aqueous layer was then extracted with ethyl acetate (2×75 mL). The organic layers were collected and washed with brine (3×50 mL). The combined organic phases were dried over magnesium sulfate, filtered and concentrated to give a dark brown solution that contained residual DMF. This crude product was purified by silica flash column chromatography (0-25% EtOAc/Hexanes gradient) to yield B12 (1.32 g, 90%). NMR was consistent with literature values. MS (ESI) calculated for $C_{18}H_{20}O_3$[M+H]$^+$ m/z 285.14, found 285.21.

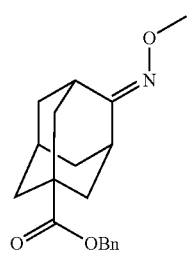 [SMILES: CON=C1C2CC3CC1CC(C(=O)OCc1ccccc1)(C3)C2]

Benzyl 4-(methoxyimino)adamantane-1-carboxylate (B13)

To a sealed tube containing a Teflon-coated magnetic stir bar under an Ar(g) atmosphere was added adamantanone B12 (1.750 g, 5.6 mmol, 1.0 equiv.) and methanol (6 mL.). This solution was stirred until all solid had dissolved, then pyridine (0.993 ml, 12.3 mmol, 2.0 equiv.) and methoxylamine HCl (1.711 g, 20.1 mmol, 1.1 equiv.) were added sequentially. The solution was again stirred at room temperature under argon until all of the solid went into solution. The reaction mixture was placed in an oil bath that had been preheated to 75° C. and stirred for 4 hours. The solution was allowed to cool at which point TLC and LCMS showed the reaction was complete. The mixture was then concentrated under reduced to give a white slurry. EtOAc (50 mL) and water (50 mL) were added and the organic layer was collected and washed with KHSO$_4$ (2×50 mL) and brine (1×50 mL). The organic layer was dried over MgSO$_4$, filtered, and concentrated under reduced to afford B13 as a white fluffy powder (1.770 g, 93%). $^1$H NMR (400 MHz, CHLOROFORM-d) δ ppm 1.76-1.95 (m, 4H) 1.99-2.16 (m, 7H) 2.64 (br s, 1H) 3.56 (br s, 1H) 3.81 (s, 3H) 5.10 (s, 2H) 7.27-7.40 (m, 5H); $^{13}$C NMR (100 MHz, CHLOROFORM-d) δ ppm 27.54, 28.64, 35.46, 36.43, 37.83, 37.86, 38.53, 39.88, 40.68, 60.96, 66.00, 127.65, 128.00, 128.43, 136.05, 164.27, 175.87. MS (ESI) calculated for C$_{19}$H$_{23}$NO$_3$ [M+H]+ m/z 314.17, found 314.04.

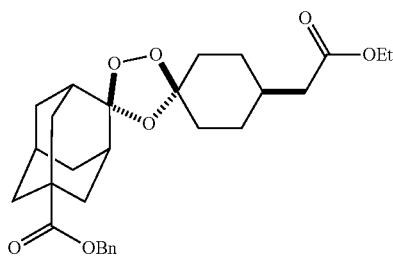

Benzyl (2r,3S,4"S,5S,5's,7S)-4"-(2-ethoxy-2-oxoethyl)dispiro[adamantane-2,3'-[1,2,4]trioxolane-5',1"-cyclohexane]-5-carboxylate (B14)

To a round bottom flask containing a Teflon-coated magnetic stir bar open to the atmosphere was added oxime B13 (765 mg, 2.4 mmol, 0.9 equiv.) and ethyl 2-(4-oxocyclohexyl)acetate (0.500 g, 2.7 mmol, 1.0 equiv.) To the mixture of solid materials was added carbon tetrachloride (25 mL). This solution was cooled to 0° C. and sparged with oxygen for 10 minutes, after which ozone was bubbled into the solution (2 L/min, 35% power). After stirring for 60 minutes, TLC and LCMS showed incomplete reaction and so additional oxime B13 (400 mg, 1.3 mmol, 0.5 equiv.) was added to the reaction in one portion. Ozone was bubbled through the reaction for 60 minutes at which point additional oxime (400 mg, 1.3 mmol, 0.5 equiv.) was added in one portion. Ozone was again bubbled through the reaction for 60 minutes at which point the reaction was purged with O$_2$ for 10 minutes to remove any dissolved ozone, followed by sparging with argon gas for 10 minutes. The reaction mixture was concentrated under reduced vacuum to give a white slurry. This crude mixture was purified through flash column chromatography (80 g HP silica gel cartridge, 0-20% EtOAc/Hexanes to yield B14 (857 mg, 65%) as an off-white foam. $^1$H NMR (400 MHz, CHLOROFORM-d) δ ppm 1.23-1.29 (m, 4H) 1.58-1.78 (m, 7H) 1.79-2.02 (m, 11H) 2.12-2.29 (m, 5H) 4.13 (m, 2H) 5.10 (m, 2H) 5.31 (s, 1H) 7.28-7.40 (m, 5H); $^{13}$C NMR (100 MHz, CHLOROFORM-d) δ ppm 14.28, 26.18, 26.56, 29.87, 33.13, 33.64, 33.87, 35.88, 36.18, 36.19, 38.19, 39.55, 39.95, 40.88, 60.27, 66.00, 76.62, 77.24, 108.86, 110.17, 127.69, 127.78, 128.01, 128.04, 128.52, 136.33, 172.75, 176.42; MS (ESI) calculated for C$_{28}$H$_{36}$O$_7$[M+Na]+ m/z 507.23, found 507.24.

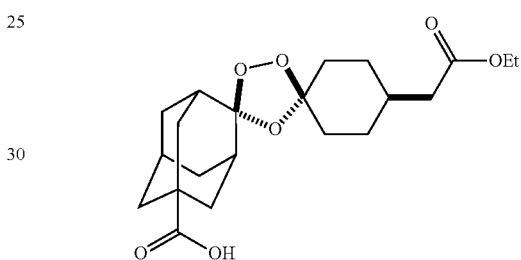

(1R,2r,3S,4"S,5S,5's,7S)-4"-(2-ethoxy-2-oxoethyl)dispiro[adamantane-2,3'-[1,2,4]trioxolane-5',1"-cyclohexane]-5-carboxylic acid (B15)

To a sealed tube containing a Teflon-coated magnetic stir bar and blanketed in argon was added trioxolane B14 (740 mg, 1.5 mmol, 1.0 equiv.), Palladium (II) Acetate (686 mg, 3.1 mmol, 2.0 equiv.), tert-butyldimethylsilane (0.500 ml, 3.1 mmol, 2.0 equiv.), triethylamine (1.171 ml, 8.4 mmol, 5.5 equiv.) and dry dichloromethane (10 mL). The tube was then sealed and placed in an oil bath preheated to 40° C. and allowed to stir for 16 hours at which time the reaction was still incomplete. After stirring for another 8 hours more tert-butyldimethylsilane (0.250 ml, 1.5 mmol, 1.0 equiv.) was added and the tube sealed under argon and heated for another 16 hours at 40° C. At this point, a black precipitate has formed in the reaction tube and LCMS shows complete consumption of starting material. The reaction was filtered over celite and the filtrated concentrated to give a yellow oil. This material was transferred to a 200 mL flask charged with a stir bar to which was added dichloromethane (15 mL) and a 1M tetrabutyl ammonium fluoride solution in THF (4.953 ml, 5.0 mmol, 4.0 equiv.). This reaction was allowed to stir at room temperature for 3 hours at which point LCMS confirmed complete consumption of the butyldimethylsilyl ester intermediate and formation of the free carboxylic acid. Organic solvent was removed under reduced pressure to give an orange/yellow oil. EtOAc (50 mL) and water (50 mL) were added and the solution transferred to a separatory funnel. The organic layer was separated and washed with water (2×50 mL) and brine (2×50 mL). This material was used without further purification in the next step. MS (ESI) calculated for $C_{21}H_{30}O_7[M-H]+$ m/z 393.20, found 393.25.

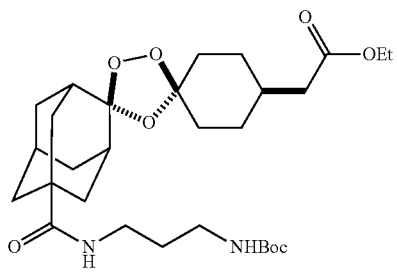

Ethyl 2-((1R,2r,3S,4"S,5S,5's,7S)-5-((3-((tert-butoxycarbonyl)amino)propyl)carbamoyl)dispiro[adamantane-2,3'-[1,2,4]trioxolane-5',1"-cyclohexan]-4"-yl)acetate (B16)

To a scintillation vial containing a Teflon-coated magnetic stir bar under Ar(g) was added crude carboxylic acid B15 (304 mg, 0.8 mmol, 1 eq), N-Boc-1,3-propanediamine (131 mg, 0.8 mmol, 1.0 equiv.) and HATU (322 mg, 0.8 mmol, 1.1 equiv.). To this solid mixture was added N,N-dimethylformamide (10 ml) and N,N-diisopropylethylamine (0.300 ml, 1.7 mmol, 2.3 equiv.) to afford a bright yellow solution. The reaction mixture was allowed to stir at room temperature for 16 hours at which point the solution had turned bright red and reaction was judged complete by LCMS. Water (30 mL) and EtOAc (30 mL) were then added and the solution transferred to a separatory funnel. The organic layer was collected and the aq layer was extracted with EtOAc (2×30 mL). The organic layers were collected and washed with water (1×25 mL) and brine (3×25 mL), dried over $MgSO_4$, filtered, and concentrated to give a red oil. The reaction was purified by silica flash chromatography (30-50% EtOAc/hexanes) to give the product B16 (262 mg, 62%) as a white powder. $^1$H NMR (400 MHz, CHLOROFORM-d) δ ppm 1.16-1.21 (m, 6H) 1.37 (s, 8H) 1.46-2.02 (m, 22H) 2.04-2.17 (m, 3H) 3.01-3.11 (m, 2H) 3.21 (s, 2H) 4.05 (qd, J=7.14, 2.44 Hz, 2H); $^{13}$C NMR (100 MHz, CHLOROFORM-d) δ ppm 14.06, 20.83, 26.21, 26.58, 28.23, 29.65, 29.94, 32.93, 33.50, 33.65, 33.67, 35.46, 35.86, 36.02, 36.31, 36.41, 36.76, 38.32, 39.21, 39.62, 40.65, 53.31, 60.05, 78.93, 108.62, 110.04, 156.48, 170.91, 172.53, 177.14; MS (ESI) calculated for $C_{29}H_{46}N_2O_8$ $[M+H]^+$ m/z 551.32, found 551.24.

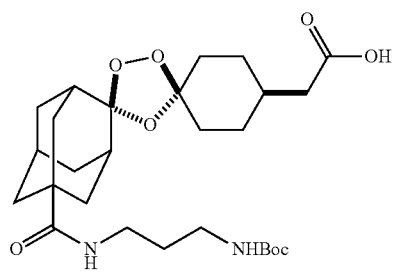

2-((1R,2r,3S,4"S,5S,5's,7S)-5-((3-((tert-butoxycarbonyl)amino)propyl)carbamoyl) dispiro[adamantane-2,3'-[1,2,4]trioxolane-5',1"-cyclohexan]-4"-yl)acetic acid (B17)

To a scintillation vial equipped with a magnetic stir bar under Ar(g) was added trioxolane B16 (230 mg, 0.4 mmol, 1.0 equiv.) and tetrahydrofuran (5.0 ml) To this solution was added methanol (5 ml) and lithium hydroxide (1.0 M, 2.0 mL, 2.0 mmol, 4.8 equiv.). This solution was allowed to stir at room temperature for 16 hours, at which time the reaction was judged complete. Solvent was then removed under reduced pressure to give a white slurry. Water (50 mL) and EtOAc (50 mL) were added and the mixture transferred to a flask containing a magnetic stir bar. The stirring solution was cooled to 0° C., at which point the pH was adjusted to ~1 by dropwise addition of 1N HCl. After transferring to a separatory flask, the organic layer was collected and the aqueous layer was extracted with EtOAc (2×75 mL). The combined organic layers were collected, dried over $MgSO_4$ and filtered. Solvent was removed under reduced pressure to give a white powder. This was further purified by silica flash chromatography (5% MeOH/$CH_2Cl_2$) to give carboxylic acid B17 (163 mg, 75%) as a white powder. $^1$H NMR (400 MHz, DMSO-d6) δ ppm 1.02-1.17 (m, 2H) 1.36 (s, 9H) 1.40-1.53 (m, 2H) 1.54-1.92 (m, 19H) 1.92-2.00 (m, 3H) 2.09 (d, J=6.33 Hz, 2H) 2.81-2.93 (m, 2H) 2.97-3.06 (m, 2H); $^{13}$C NMR (100 MHz, CDCl3) δ 177.3, 157.1, 156.7, 138.5, 127.6, 114.5, 110.3, 108.9, 66.9, 65.7, 57.7, 54.0, 42.0, 39.8, 38.5, 38.0, 36.9, 36.7, 36.2, 34.7, 33.7, 31.6, 28.4, 26.4; $^{13}$C NMR (100 MHz, DMSO-d6) δ ppm 21.05, 26.13, 26.51, 28.33, 29.62, 32.58, 33.51, 35.79, 35.91, 36.22, 36.29, 36.34, 37.40, 38.02, 38.80, 39.20, 40.38, 77.67, 108.68, 110.04, 155.73, 173.73, 176.09; MS (ESI) calculated for $C_{27}H_{42}N_2O_8$ $[M-H]^+$ m/z 521.29, found 521.55.

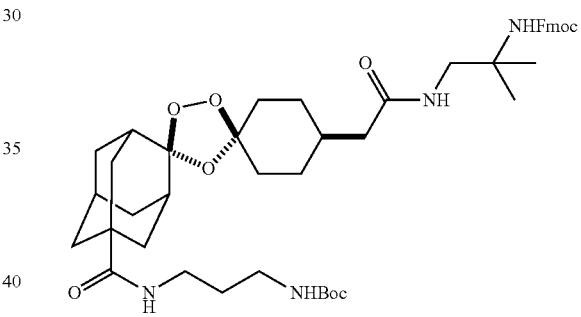

tert-Butyl (3-((1R,2r,3S,4"S,5S,5's,7S)-4"-(2-((2-((((9H-fluoren-9-yl)methoxy)carbonyl)amino)-2-methylpropyl)amino)-2-oxoethyl)dispiro[adamantane-2,3'-[1,2,4]trioxolane-5',1"-cyclohexane]-5-carboxamido)propyl)carbamate (B18)

To a scintillation vial equipped with a magnetic stir bar under Ar(g) was added carboxylic acid B17 (161 mg, 0.3 mmol, 1.0 equiv.), HATU (129 mg, 0.3 mmol, 1.1 equiv.), DMSO (5 mL) and N,N-diisopropylethylamine (0.160 ml, 0.9 mmol, 3.0 equiv.). Amine B11 (107 mg, 0.3 mmol, 1.0 equiv.) was then added. The solution was allowed to stir at room temperature for 3 hours, at which time the reaction was judged complete by LCMS. The crude reaction was purified by preparatory HPLC (Waters XBridge C18 column, 40-95% methanol/water+0.05% formic acid) to afford the product B18 (96 mg, 38%) as an off-white powder. $^1$H NMR (400 MHz, METHANOL-d4) δ ppm 1.23 (s, 8H) 1.39 (s, 9H) 1.50-2.19 (m, 24H) 2.92-3.21 (m, 4H) 3.24-3.29 (m, 2H) 4.13 (s, 1H) 4.23 (s, 2H) 7.20-7.40 (m, 4H) 7.59 (s, 2H) 7.66-7.83 (m, 2H); $^{13}$C NMR (100 MHz, METHANOL-d4) δ ppm 23.81, 27.45, 29.45, 29.57, 33.32, 33.57, 36.11, 36.19, 47.02, 48.51, 65.86, 108.61, 119.58, 126.78, 127.38, 144.04; MS (ESI) calculated for $C_{46}H_{62}N_4O_9$ $[M+H]^+$ m/z 815.45, found 815.49.

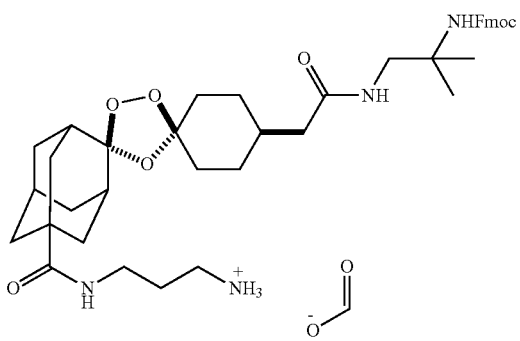

3-((1R,2r,3S,4"S,5S,5's,7S)-4"-(2-((2-((((9H-fluoren-9-yl)methoxy)carbonyl)amino)-2-methylpropyl)amino)-2-oxoethyl)dispiro[adamantane-2,3'-[1,2,4]trioxolane-5',1"-cyclohexane]-5-carboxamido)propan-1-aminium formate (B19)

To a scintillation vial containing a Teflon-coated magnetic stir bar under Ar(g) was added trioxolane B18 (96 mg, 0.1 mmol, 1.0 equiv.) and methanol (10 mL). To this stirring solution was added acetyl chloride (300 ul, 4.3 mmol, 35.0 equiv.) dropwise over 5 minutes. The reaction was allowed to stir at room temperature for 16 hours at which point the reaction was determined to be complete by LCMS. To quench the reaction, the pH was adjusted to pH 7 through addition of saturated $NaHCO_3$ solution (10 mL). The mixture was concentrated under reduced pressure to give a white slurry. To this slurry was added 1M $Na_2CO_3$ (10 mL) and $CH_2Cl_2$ (20 mL). The organic layer was collected and the aqueous layer was extracted with $CH_2Cl_2$ (2×20 mL). The combined organic layers were transferred to a flask equipped with a stir bar to which was added water (75 mL). This stirring mixture was cooled to 0° C. and the pH was adjusted to ~1 by dropwise addition of formic acid. The aqueous layer was collected and washed with $CH_2Cl_2$ (2×40 mL). The product B19 (89 mg, quant.) was obtained as a off-white fluffy solid following lyophilization of the aqueous layer. $^1H$ NMR (400 MHz, METHANOL-d4) δ ppm 1.02 (s, 2H) 1.32 (s, 5H) 1.64-1.79 (m, 8H) 1.80-2.07 (m, 12H) 2.11-2.21 (m, 3H) 3.25 (td, J=6.57, 2.43 Hz, 2H) 3.39 (t, J=6.70 Hz, 2H) 7.10-7.29 (m, 2H) 7.80-8.04 (m, 2H); MS (ESI) calculated for $C_{32}H_{47}N_3O_8$ $[M+H]^+$ m/z 715.40, found 715.36.

(1R,2r,3S,4"S,5S,5's,7S)-4"-(2-((2-amino-2-methylpropyl)amino)-2-oxoethyl)-N-(3-(4-fluorobenzamido)propyl)dispiro[adamantane-2,3'-[1,2,4]trioxolane-5',1"-cyclohexane]-5-carboxamide (B20 [$^{19}$F])

This specifically describes the synthesis of the non-radioactive standard. To a scintillation vial containing a Teflon-coated magnetic stir bar under Ar(g) was added trioxolane salt B19 (10 mg, 0.018 mmol, 1.0 equiv.) and succinimidyl 4-[$^{19}$F]-benzoate (SFB, 5 mg, 0.027 mmol, 1.5 equiv.). To this solid mixture was added N,N-diisopropylethylamine (0.010 ml, 0.1 mmol, 4.0 equiv.) and N,N-dimethylformamide (1.0 mL). The amidation reaction was monitored by LCMS and judged complete after 15 minutes. Next, the reaction mixture, was treated with a 40% solution of 4-methylpiperidine in DMF (1 mL) to remove the Fmoc protecting group, which by LCMS was complete after 15 minutes. The crude reaction was purified by silica flash chromatography (5% $MeOH/CH_2Cl_2$+0.7N $NH_3$) to afford the product B20[$^{19}$F] as a white powder (5 mg, 50%). $^1H$ NMR (400 MHz, CDCl3) δ 7.95-7.88 (m, 2H), 7.17-7.09 (m, 4H), 6.87-6.82 (m, 2H), 4.14-4.07 (m, 2H), 3.78-3.71 (m, 4H), 3.48-3.34 (m, 4H), 3.19-3.12 (m, 2H), 2.84-2.77 (m, 2H), 2.63-2.56 (m, 2H), 2.56-2.46 (m, 1H), 2.24-1.65 (m, 23H), $^{19}F$ NMR (376 MHz, METHANOL-d4) δ ppm −110.78 (s, 1° F.); MS (ESI) calculated for $C_{33}H_{47}FN_4O_6$ $[M+H]^+$ m/z 615.34, found 615.25.

(1R,2r,3S,4"S,5S,5's,7S)-4"-(2-((2-amino-2-methylpropyl)amino)-2-oxoethyl)-N-(3-(4-$^{18}$F-fluorobenzamido)propyl)dispiro[adamantane-2,3'-[1,2,4]trioxolane-5',1"-cyclohexane]-5-carboxamide All work with radionuclides is performed in a Sofie Elixys Flex/Chem. Succinimidyl 4-[$^{18}$F]-benzoate (S[$^{18}$F]B) is prepared according to previous literature and Sofie protocol. To a 3 mL vial containing S[$^{18}$F]B (20-100 mCi) was added a solution of trioxolane B19 (5 mg, 0.07 mmol, 1.0 equiv.) and 1 mL of a 1% solution of N,N-diisopropylethylamine in DMF. The vial was gently shaken then was allowed to stand at room temperature for 15 minutes. At this point, 1 mL of a 40% solution of 4-methylpiperidine in DMF was added and the vial was gently shaken and allowed to stand at room temperature for 15 minutes. The solution was diluted with $H_2O$ containing 0.1% formic acid (1.5 mL). This crude mixture was purified by preparatory HPLC (Waters XBridge C18 column, 5-95% acetonitrile/water with 0.1% formic acid) and concentrated using a Waters Sep-Pak C18 cartridge. The product is eluted from the cartridge using ethanol and concentrated under a stream of air or inert gas. At this point, yield is typically 60-70% based on total radioactivity.

Synthesis of B21

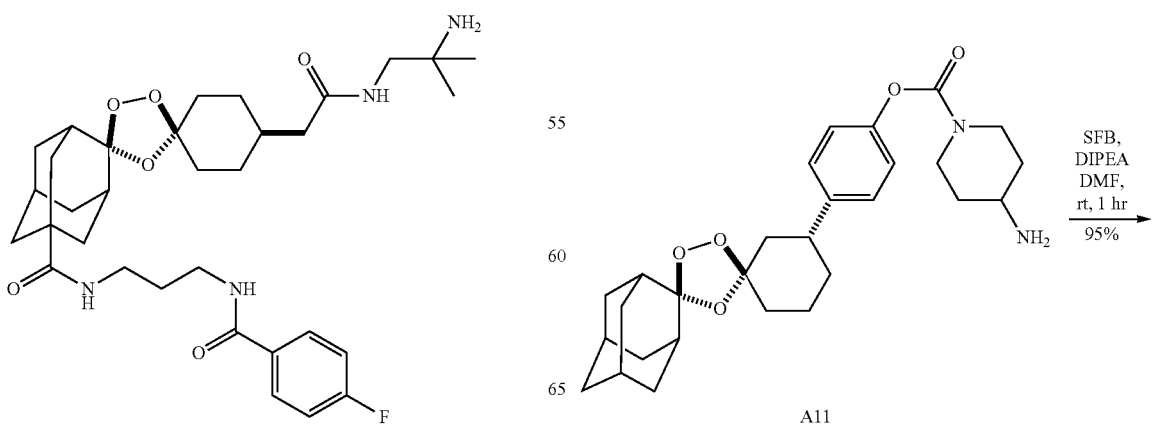

176

4-((1R,3R,3"R,5R,5'R,7R)-dispiro[adamantane-2,3'-[1,2,4]trioxolane-5',1"-cyclohexan]-3"-yl)phenyl 4-(4-fluorobenzamido)piperidine-1-carboxylate (B21)

This specifically describes the synthesis of the cold standard. For the synthesis of the hot material, necessary modifications will need to be made to the purification step for safety and time requirements. To a scintillation vial containing a Teflon-coated magnetic stir bar and SFB (3 mg, 0.012 mmol, 1.2 equiv.) under Ar(g) was added trioxolane A11 (5 mg, 0.010 mmol, 1.0 equiv.) in a solution of N,N-diisopropylethylamine (0.010 ml, 0.1 mmol, 5.4 equiv.) and N,N-dimethylformamide (1.0 mL). Monitoring by LCMS, the reaction appears complete after 15 minutes. The crude reaction was purified preparatory HPLC (Waters XBridge C18 column, 70-95% methanol/water with 0.05% formic acid) to afford the product B21 as a white solid (3 mg, 48%). 1H NMR (400 MHz, CDCl3) δ 7.95-7.88 (m, 2H), 7.17-7.09 (m, 4H), 6.87-6.82 (m, 2H), 4.14-4.07 (m, 2H), 3.78-3.71 (m, 4H), 3.48-3.34 (m, 4H), 3.19-3.12 (m, 2H), 2.84-2.77 (m, 2H), 2.63-2.56 (m, 2H), 2.56-2.46 (m, 1H), 2.24-1.65 (m, 23H); MS (ESI) calculated for $C_{35}H_{41}FN_2O_6[M+Na]^+$ m/z 627.28, found 627.29.

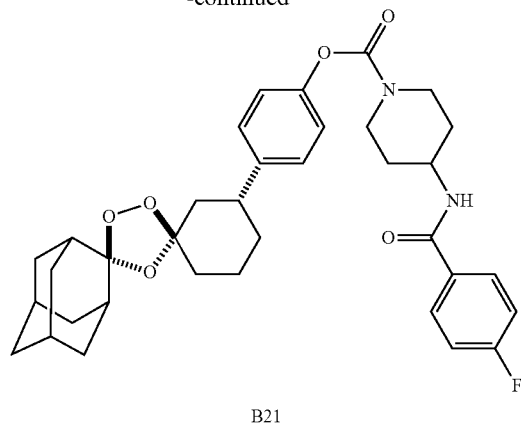

B21

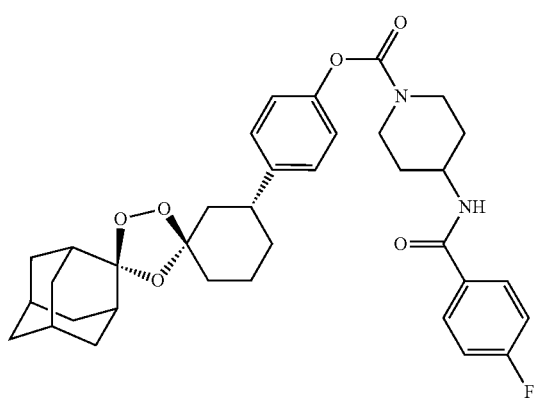

Synthesis of B32

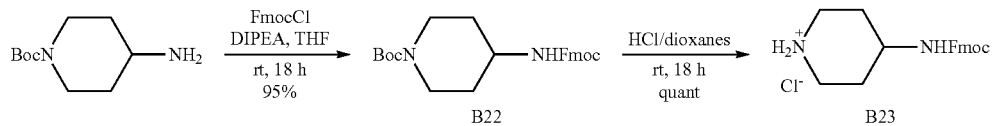

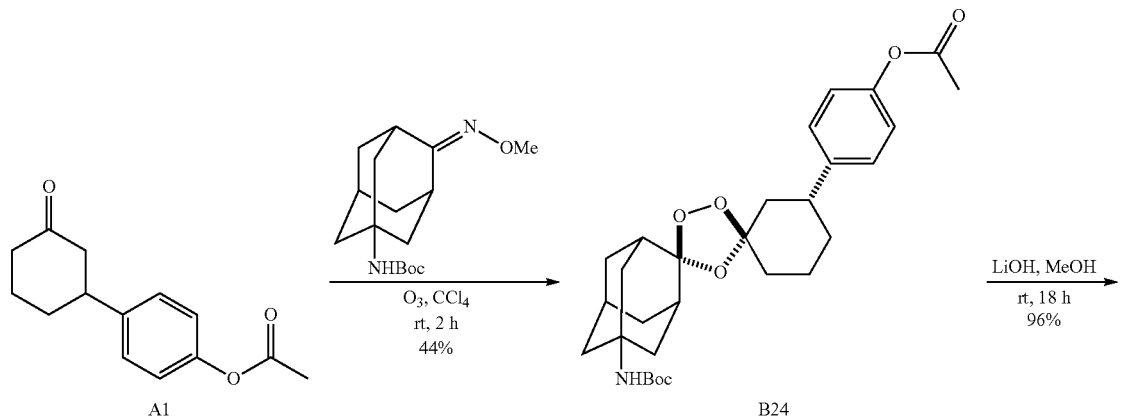

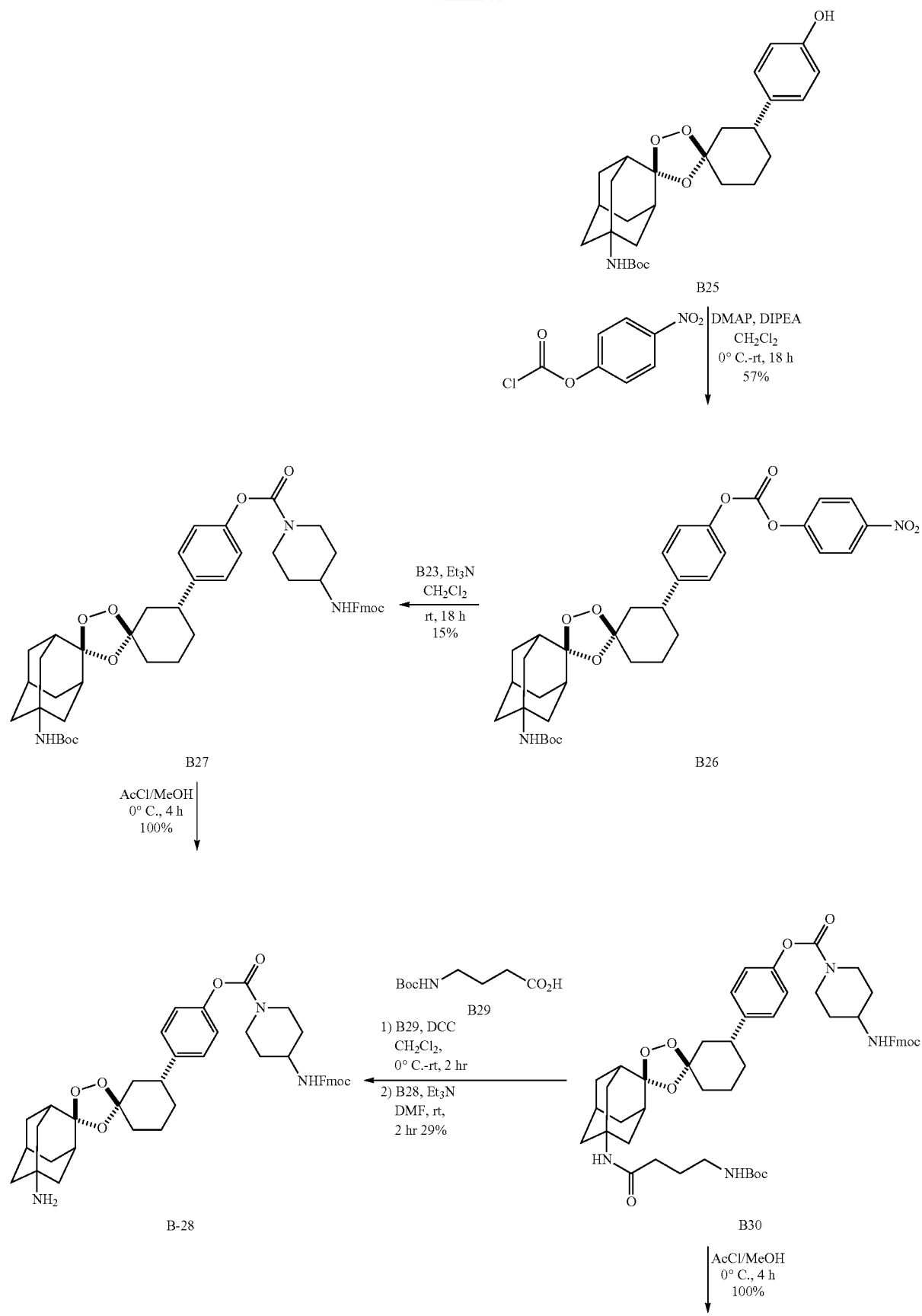

-continued

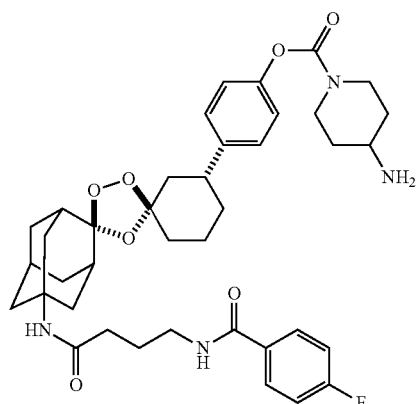

B32

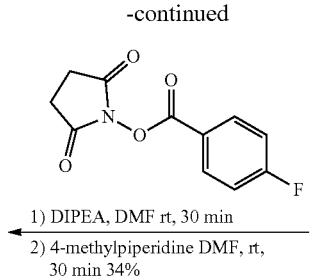

1) DIPEA, DMF rt, 30 min
2) 4-methylpiperidine DMF, rt, 30 min 34%

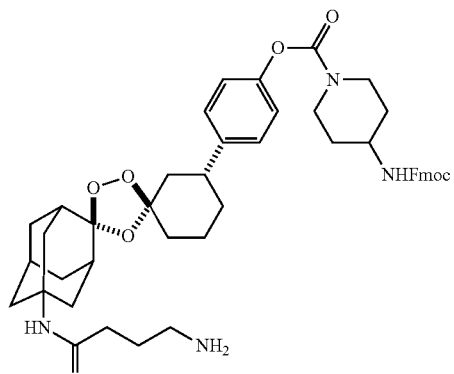

31

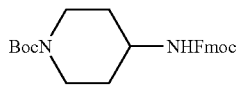

(9H-fluoren-9-yl)methyl N-(1-{[(tert-butoxy)carbonyl]amino}-2-methylpropan-2-yl)carbamate (B22)

To a round bottom flask containing a Teflon-coated magnetic stir bar under an Ar(g) atmosphere was added tert-butyl 4-aminopiperidine-1-carboxylate (950 mg, 4.7 mmol, 1.0 equiv.), tetrahydrofuran (15 ml) and N,N-diisopropylethylamine (1.65 ml, 9.5 mmol, 2 equiv.). This stirring solution was brought to 0° C. before addition of 9-Fluorenylmethyl chloroformate (1.473 g, 5.7 mmol, 1.2 equiv.) in two portions. The reaction was allowed to warm to RT overnight, at which point TLC shows complete consumption of starting material. Organic solvent was removed under reduced pressure. This crude product was purified through flash column chromatography (0-25% EtOAc/Hexanes) to yield B22 (1.853 g, 95%) as a colorless oil. MS (ESI) calculated for $C_{25}H_{30}N_2O_4$ [M+H]$^+$ m/z 423.23, found 423.22.

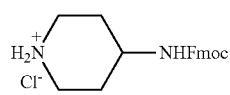

(9H-fluoren-9-yl)methyl N-(piperidin-4-yl)carbamate hydrochloride (B23)

To a round bottom flask containing a Teflon-coated magnetic stir bar under an Ar(g) atmosphere was added B22 (1.50 g, 3.55 mmol, 1 eq) and 1,4-dioxane (10 ml). This stirring solution was cooled to 0° C. at which point 4N hydrochloric acid in dioxanes (15, 60.0 mmol, 16.9 equiv.) was added slowly. The solution stirred at 0° C. for 4 hours. Based on LCMS analysis, the reaction was complete. Organic solvent was removed under reduced pressure to give amine B23 (1.27 g, 100%) as the chloride salt. MS (ESI) calculated for $C_{20}H_{22}N_2O_2$ [M+H]$^+$ m/z 323.18, found 323.14.

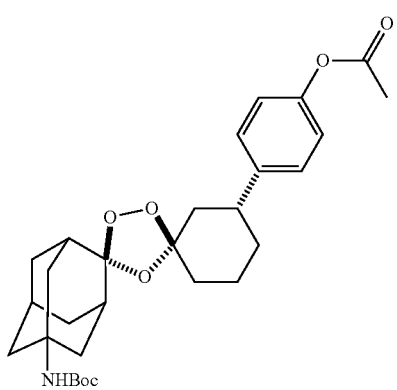

4-((1R,2r,3S,3"R,5S,5'R,7S)-5-((tert-butoxycarbonyl)amino)dispiro[adamantane-2,3'-[1,2,4]trioxolane-5',1"-cyclohexan]-3"-yl)phenyl acetate (B24)

To a round bottom flask containing a Teflon-coated magnetic stir bar open to the atmosphere was added tert-butyl N-[4-(methoxyimino)adamantan-1-yl]carbamate (500 mg, 1.7 mmol, 1.0 equiv.) and 3-(4-acetoxyphenyl)cyclohexan-1-one (592 mg, 2.5 mmol, 1.5 equiv.). To the mixture was added carbon tetrachloride (50 ml). This solution was cooled to 0° C. and subsequently sparged with oxygen for 10 minutes. The reaction was kept at 0° C. while ozone was then bubbled (2 L/min, 35% power). After stirring for 90 minutes, TLC and LCMS showed consumption of oxime and formation of product. The reaction was purged with $O_2$ for 10 minutes in an effort to remove any dissolved ozone, followed by sparging with Ar(g) for 10 minutes. The reaction mixture was concentrated under reduced vacuum. This crude mixture was purified through flash column chromatography (0-20% EtOAc/Hexanes) to yield B24 (308 mg, 35%) as a colorless oil. 1H NMR (400 MHz, CHLOROFORM-d) δ ppm 1.45 (m, 11H) 1.53-1.78 (m, 5H) 1.78-2.23 (m, 17H) 2.29 (s, 3H) 2.75-2.84 (m, 1H) 6.99-7.03 (m, 2H) 7.18-7.22 (m, 2H); 13C NMR (100 MHz, CHLOROFORM-d) δ ppm 21.10, 23.44, 27.51, 27.87, 28.41, 32.68, 33.48, 34.03, 37.05, 37.27, 38.74, 38.87, 38.95, 41.22, 42.01, 49.16, 49.53, 109.21, 110.22, 121.40, 127.66, 143.01, 148.93, 169.58. MS (ESI) calculated for $C_{29}H_{39}NO_7$ [M+H]$^+$ m/z 514.28, found 514.36.

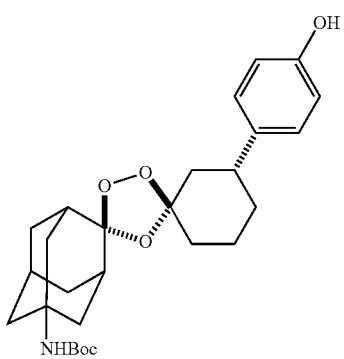

tert-butyl ((1R,2r,3S,3"R,5S,5'R,7S)-3"-(4-hydroxyphenyl)dispiro[adamantane-2,3'-[1,2,4]trioxolane-5',1"-cyclohexan]-5-yl)carbamate (B25)

To a scintillation vial charged with a Teflon-coated magnetic stir bar and containing trioxolane B24 (260 mg, 0.5 mmol, 1.0 equiv) was added methanol (5 mL) and 1N lithium hydroxide in water (2.5 mL, 2.5 mmol, 5 equiv). This suspension was allowed to stir for 16 hours at room temperature at which point product can be seen by LCMS and TLC. Solvent was removed under reduced pressure to give a white slurry to which saturated ammonium chloride (50 mL) and EtOAc (50 mL) were added. The organic layer was collected and the aqueous layer was further extracted with EtOAc (2×30 mL). Organic layers were collected, washed with brine (1×25 mL) and solvent was removed under reduced pressure to yield phenol B25 (228 mg, 96%). 1H NMR (400 MHz, CHLOROFORM-d) δ ppm 1.25-1.36 (m, 1H) 1.43 (s, 10H) 1.53-1.73 (m, 5H) 1.76-2.25 (m, 18H) 2.67-2.77 (m, 1H) 4.40 (br s, 1H) 6.76-6.81 (m, 2H) 7.05 (s, 1H) 7.06-7.09 (m, 1H); 13C NMR (100 MHz, CHLOROFORM-d) δ ppm 23.48, 27.53, 28.43, 32.95, 33.46, 33.50, 34.07, 37.06, 37.26, 38.81, 38.95, 40.95, 42.21, 46.41, 49.61, 77.20, 109.45, 110.12, 115.24, 127.76, 137.71, 154.07; MS (ESI) calculated for $C_{27}H_{37}NO_6$ [M+H]$^+$ m/z 472.27, found 472.36.

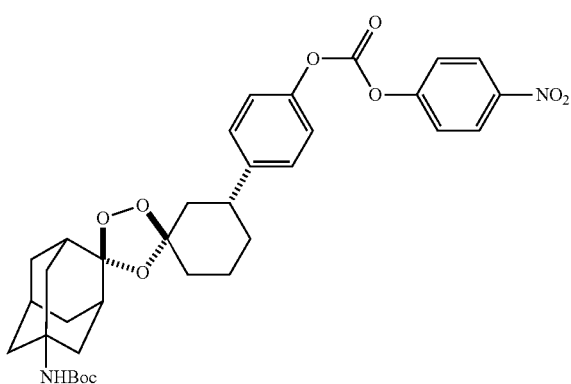

tert-butyl ((1R,2r,3S,3"R,5S,5'R,7S)-3"-(4-(((4-nitrophenoxy)carbonyl)oxy)phenyl) dispiro[adamantane-2,3'-[1,2,4]trioxolane-5',1"-cyclohexan]-5-yl)carbamate (B26)

To a scintillation vial containing a Teflon-coated magnetic stir bar under Ar(g) was added phenol B25 (304 mg, 0.8 mmol, 1 eq), 4-Nitrophenyl chloroformate (0.286 g, 1.4 mmol, 3.2 equiv.), 4-dimethylaminopyridine (62 mg, 0.5 mmol, 1.2 equiv.), N,N-diisopropylethylamine (0.259 ml, 1.5 mmol, 3.5 equiv.) and dichloromethane (4 mL). The solution was allowed to stir at room temperature for 16 hours at which point the reaction had progressed to completion based on TLC analysis. To the solution was added EtOAc (75 mL), which was subsequently washed with 1M sodium carbonate (5×30 mL). The organic layers were collected and washed with water (1×25 mL) and brine (3×25 mL). The organic layer was collected, dried over MgSO$_4$, filtered and concentrated under reduced pressure to give a light yellow oil. The reaction was purified by silica flash chromatography (0-15% EtOAc/hexanes) to give afford product B26 (153 mg, 57%) as a white foam. 1H NMR (400 MHz, CHLOROFORM-d) δ ppm 1.18-1.27 (m, 1H) 1.30-1.47 (m, 10H) 1.50-2.22 (m, 22H) 2.74-2.93 (m, 1H) 7.14-7.24 (m, 4H) 7.42-7.49 (m, 2H) 8.25-8.31 (m, 2H); 13C NMR (100 MHz, CHLOROFORM-d) δ ppm 23.38, 27.47, 27.83, 28.38, 32.64, 33.45, 33.96, 37.01, 37.21, 38.79, 38.89, 41.20, 41.86, 41.92, 49.55, 53.39, 79.00, 109.10, 110.21, 120.57, 121.67, 125.33, 127.93, 144.04, 145.50, 148.93, 151.07, 155.24, 162.73,

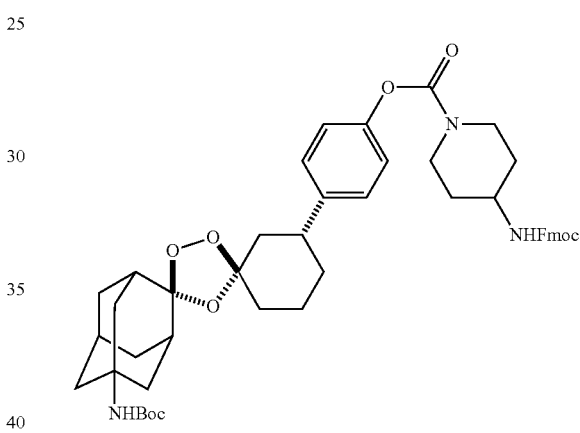

4-((1R,2r,3S,3' 'R,5S,5'R,7S)-5-((tert-butoxycarbonyl)amino)dispiro[adamantane-2,3'-[1,2,4]trioxolane-5',1"-cyclohexan]-3"-yl)phenyl 4-((((9H-fluoren-9-yl)methoxy)carbonyl)amino)piperidine-1-carboxylate (B27)

To a scintillation vial equipped with a magnetic stir bar under Ar(g) was added trioxolane B26 (0.140 g, 0.2 mmol, 1.0 equiv.), triethylamine (0.123 ml, 0.9 mmol, 4.0 equiv.) and dichloromethane (5 mL). To this stirring solution was added amine B23 (118 mg, 0.3 mmol, 1.5 equiv.). This solution was allowed to stir at room temperature for 16 hours at which point the reaction appears complete based on LCMS analysis. The reaction was purified by preparatory HPLC (Waters XBridge C18 column, 60-90% methanol/water+0.05% formic acid) to afford trioxolane B27 (28 mg, 16%) as a white solid. 1H NMR (400 MHz, CHLOROFORM-d) δ ppm 1.25-1.31 (m, 1H) 1.39-1.51 (m, 10H) 1.52-1.75 (m, 6H) 1.76-2.27 (m, 19H) 2.63-2.90 (m, 1H) 2.93-3.19 (m, 2H) 3.63-3.81 (m, 1H) 4.19-4.29 (m, 2H) 4.35-4.42 (m, 1H) 4.43-4.48 (m, 1H) 4.59-4.78 (m, 1H) 6.99-7.05 (m, 2H) 7.15-7.22 (m, 2H) 7.31-7.36 (m, 2H) 7.39-7.45 (m, 2H) 7.60 (d, J=7.30 Hz, 2H) 7.78 (d, J=7.30 Hz, 2H); 13C NMR (100 MHz, CHLOROFORM-d) δ ppm 23.45, 28.42, 32.08, 32.40, 32.77, 33.49, 34.06, 37.27, 38.88, 41.22, 41.95, 42.01, 43.22, 47.27, 48.22, 49.56, 66.50, 109.31, 110.20, 119.97, 121.54, 124.93, 127.04, 127.53, 127.70, 141.33, 142.49, 143.84, 149.59, 153.69, 155.53; MS (ESI) calculated for $C_{48}H_{57}N_3O_9$ [M+Na]$^+$ m/z 842.40, found 842.47.

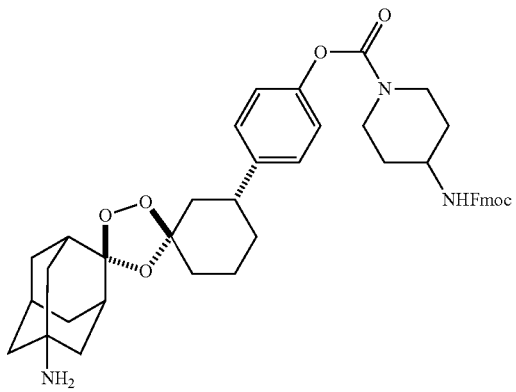

4-((1R,2r,3S,3"R,5S,5'R,7S)-5-aminodispiro[adamantane-2,3'-[1,2,4]trioxolane-5',1"-cyclohexan]-3"-yl)phenyl 4-((((9H-fluoren-9-yl)methoxy)carbonyl)amino)piperidine-1-carboxylate (B28)

To a scintillation vial equipped with a magnetic stir bar under Ar(g) was added trioxolane B27 (28 mg, 0.03 mmol, 1.0 equiv.) and methanol (2 mL). This solution was cooled to 0° C., at which point acetyl chloride (0.07 mL, 1.0 mmol, 30 equiv.) was added. The solution was allowed to stir at 0° C. After 4 hours, the reaction appears to be complete based on LCMS analysis. Organic solvent was removed under reduced pressure to afford the product B28 (96 mg, 38%) as an off-white solid; MS (ESI) calculated for $C_{43}H_{49}N_3O_7$ [M+H]$^+$ m/z 720.36, found 720.42

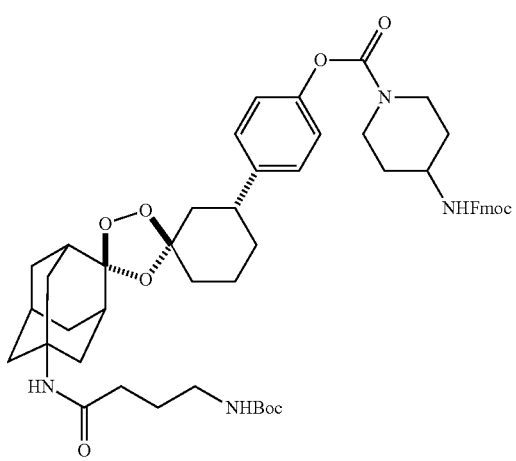

4-((1R,2r,3S,3"R,5S,5'R,7S)-5-(4-((tert-butoxycarbonyl)amino)butanamido) dispiro[adamantane-2,3'-[1,2,4]trioxolane-5',1"-cyclohexan]-3"-yl)phenyl 4-((((9H-fluoren-9-yl)methoxy)carbonyl)amino) piperidine-1-carboxylate (B30)

To a scintillation vial equipped with a magnetic stir bar under Ar(g) was added N-hydroxysuccinimide (3 mg, 0.03 mmol, 1.0 equiv.), gamma-(Boc-amino)butyric acid (6 mg, 0.03 mmol, 1 equiv.) and dichloromethane (1 mL). This solution was cooled to 0° C. at which point N,N'-dicyclohexylcarbodiimide (6 mg, 0.03 mmol, 1.0 equiv.) was added in one portion. This solution was allowed to warm to RT and stirred for 2 hrs at which point TLC confirms reaction complete. To this solution was added a solution of amine B28 (20 mg, 0.03 mmol, 1.0 equiv.) dissolved in N,N-dimethylformamide (1 mL) and triethylamine (0.019 ml, 0.12 mmol, 4.0 equiv.). The solution was allowed to stir at room temperature for 2 hours at which point the reaction appears complete based on LCMS analysis. The crude reaction was purified by silica flash chromatography (0-50% EtOAc/Hexanes) to afford B30 (7 mg, 28%) as a colorless oil. 1H NMR (400 MHz, CHLOROFORM-d) δ ppm 0.05-0.09 (m, 1H) 1.26-1.50 (m, 15H) 1.51-1.65 (m, 3H) 1.67-1.93 (m, 16H) 1.95-2.17 (m, 15H) 2.70-2.85 (m, 1H) 3.01-3.22 (m, 4H) 3.61-3.86 (m, 1H) 4.19-4.28 (m, 2H) 4.42-4.49 (m, 2H) 4.70-4.83 (m, 2H) 7.01 (d, J=7.49 Hz, 2H) 7.18 (d, J=8.52 Hz, 2H) 7.30-7.36 (m, 2H) 7.38-7.45 (m, 2H) 7.60 (d, J=7.55 Hz, 2H) 7.78 (d, J=7.55 Hz, 2H); MS (ESI) calculated for $C_{52}H_{64}N_4O_{10}$ [M+H]$^+$ m/z 905.47, found 905.41.

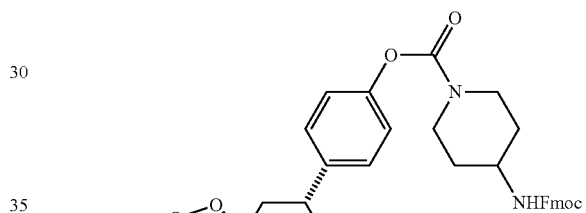

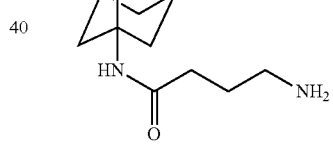

4-((1R,2r,3S,3"R,5S,5'R,7S)-5-(4-aminobutanamido) dispiro[adamantane-2,3'-[1,2,4]trioxolane-5',1"-cyclohexan]-3"-yl)phenyl 4-((((9H-fluoren-9-yl)methoxy)carbonyl)amino)piperidine-1-carboxylate (B31)

To a scintillation vial containing a Teflon-coated magnetic stir bar under Ar(g) was added trioxolane B30 (6 mg, 0.006 mmol, 1.0 equiv.) and methanol (1 mL). This stirring solution was cooled to 0° C. at which point acetyl chloride (20 ul, 0.024 mmol, 40.0 equiv.) was added. The reaction was allowed to stir at 0° C. for 4 hours at which point the reaction was determined to be complete by LCMS. Solvent was removed under reduced pressure to give amine B31 (5 mg, 100%). MS (ESI) calculated for $C_{47}H_{56}N_4O_8$ [M+H]$^+$ m/z 805.42, found 805.42.

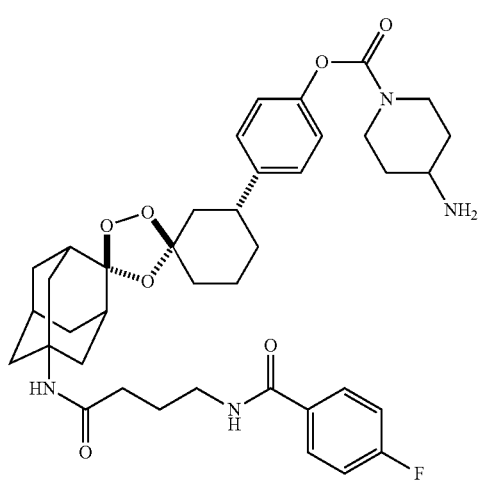

4-((1R,2r,3S,3"R,5S,5'R,7S)-5-(4-(4-fluorobenzamido)butanamido)dispiro[adamantane-2,3'-[1,2,4]trioxolane-5',1"-cyclohexan]-3"-yl)phenyl 4-aminopiperidine-1-carboxylate (B32)

This specifically describes the synthesis of the cold standard. For the synthesis of the hot material, necessary modifications will be made to the purification step for safety and time requirements. To a scintillation vial containing a Teflon-coated magnetic stir bar under Ar(g) was added amine B31 (3 mg, 0.002 mmol, 1.0 equiv.) and SFB (0.65 mg, 0.003 mmol, 1.2 equiv.). To this solid mixture was added N,N-diisopropylethylamine (0.003 ml, 0.017 mmol, 6.0 equiv.) and N,N-dimethylformamide (0.3 mL). Monitoring by LCMS, the reaction appears complete after 30 minutes. To this reaction was added a 40% solution of 4-methylpiperidine in DMF (0.3 mL). Again monitoring by LCMS, the Fmoc deprotection appeared complete after 15 minutes. The crude reaction was purified by silica flash chromatography (0-15% MeOH/DCM+0.7N NH$_3$) to afford the product B32 as a colorless residue (0.6 mg, 33%); MS (ESI) calculated for $C_{39}H_{49}FN_4O_7[M+H]^+$ m/z 705.37, found 705.36.

PROPHETIC EXAMPLES

Example C1: 3-(p-{(1R)-Dispiro[cyclohexane-1,3'-[1,2,4]trioxolane-5',2"-tricyclo[3.3.1.1$^{3,7}$]decan]-3-yl}phenoxy)propylamine

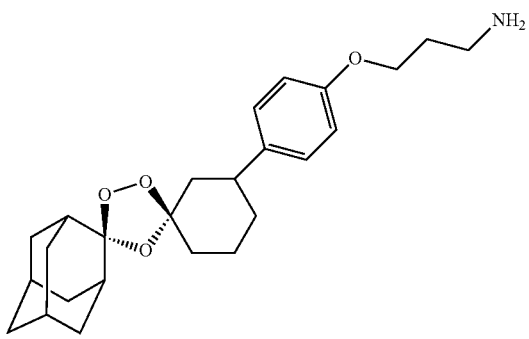

Example C2: 2-(p-{(1R)-Dispiro[cyclohexane-1,3'-[1,2,4]trioxolane-5',2"-tricyclo[3.3.1.1$^{3,7}$]decan]-3-yl}phenoxy)-1,1-dimethylethylamine

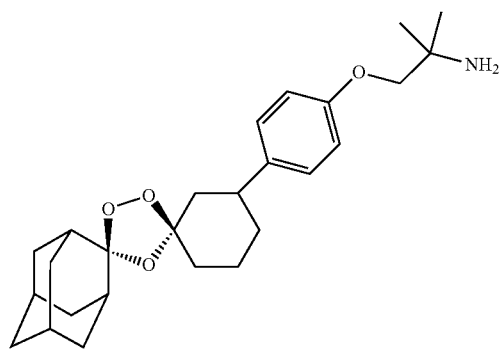

Example C3: (1R)-3-[p-(2-Piperidinoethoxy)phenyl]dispiro[cyclohexane-1,3'-[1,2,4]trioxolane-5',2"-tricyclo[3.3.1.1$^{3,7}$]decane]

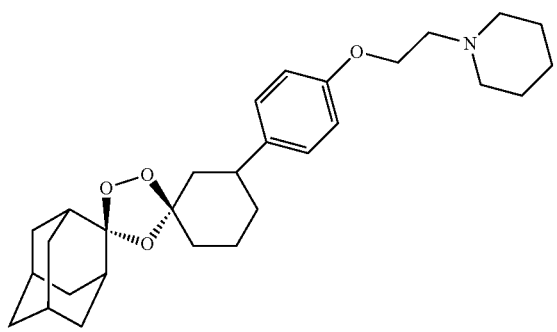

Example C4: (1R)-3-{p-[2-(1,4-Oxazepan-4-yl)ethoxy]phenyl}dispiro[cyclohexane-1,3'-[1,2,4]trioxolane-5',2"-tricyclo[3.3.1.1$^{3,7}$]decane]

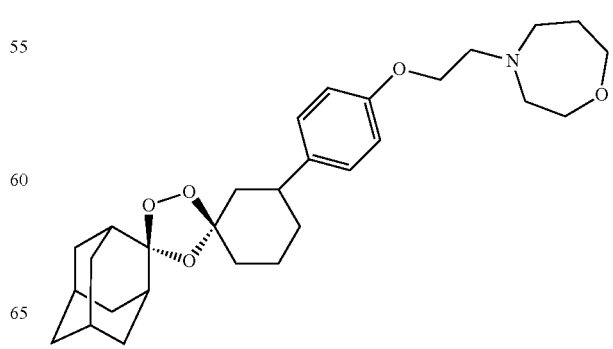

Example C5: 4-[2-(p-{(1R)-Dispiro[cyclohexane-1,3'-[1,2,4]trioxolane-5',2''-tricyclo[3.3.1.1³,⁷]decan]-3-yl}phenoxy)ethyl]-1λ⁴,4-thiazinan-1-one

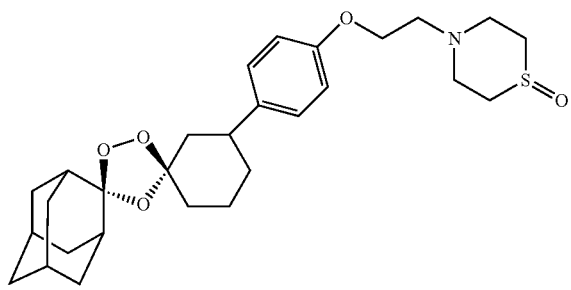

Example C6: (1R)-3-(p-{2-[4-(Methylsulfonyl)-1-piperazinyl]ethoxy}phenyl)dispiro[cyclohexane-1,3'-[1,2,4]trioxolane-5',2''-tricyclo[3.3.1.1³,⁷]decane]

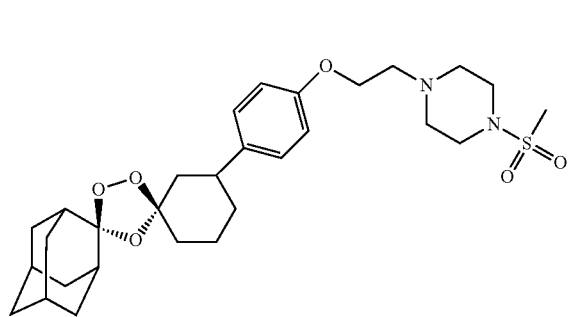

Example C7: 4-(p-{(1R)-Dispiro[cyclohexane-1,3'-[1,2,4]trioxolane-5',2''-tricyclo[3.3.1.1³,⁷]decan]-3-yl}phenoxy)cyclohexylamine

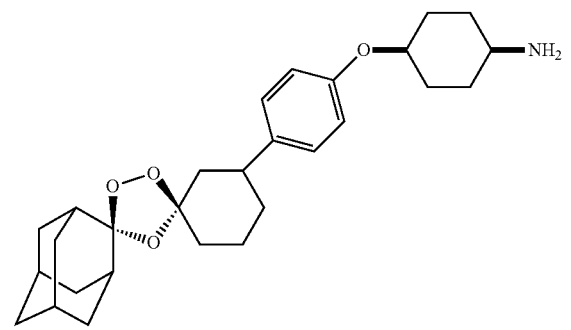

Example C8: 1-[4-(p-{(1R)-Dispiro[cyclohexane-1,3'-[1,2,4]trioxolane-5',2''-tricyclo[3.3.1.1³,⁷]decan]-3-yl}phenoxy)-1-piperidyl]-2-methyl-2-propanol

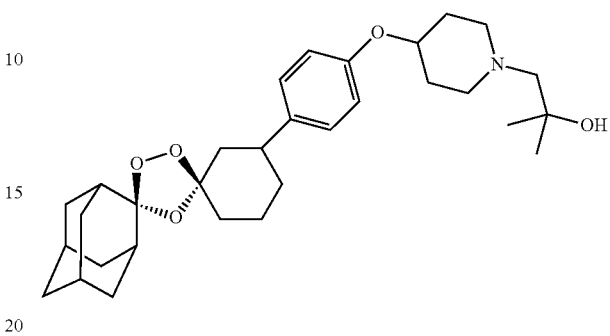

Example C9: [3-(p-{(1R)-Dispiro[cyclohexane-1,3'-[1,2,4]trioxolane-5',2''-tricyclo[3.3.1.1³,⁷]decan]-3-yl}phenoxy)propyl]-tetrahydro-2H-pyran-4-ylamine

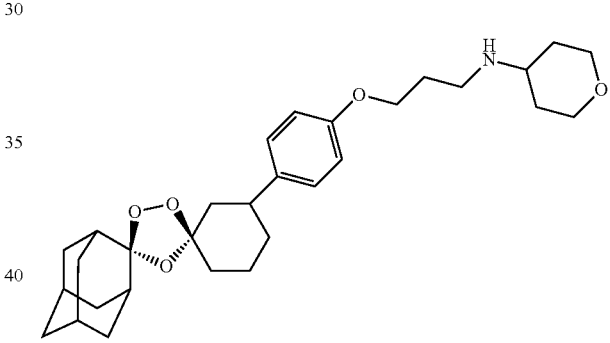

Example C10: 1-[3-(p-{(1R)-Dispiro[cyclohexane-1,3'-[1,2,4]trioxolane-5',2''-tricyclo[3.3.1.1³,⁷]decan]-3-yl}phenoxy)propylamino]-2-methyl-2-propanol

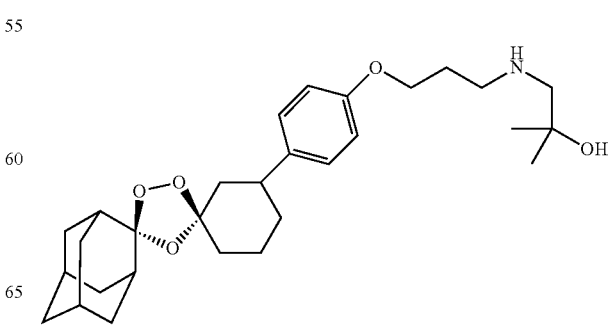

Example C11: 4-[(p-{(1R)-Dispiro[cyclohexane-1,
3'-[1,2,4]trioxolane-5',2"-tricyclo[3.3.1.1³,⁷]decan]-
3-yl}phenoxy)methyl]-4-piperidinol

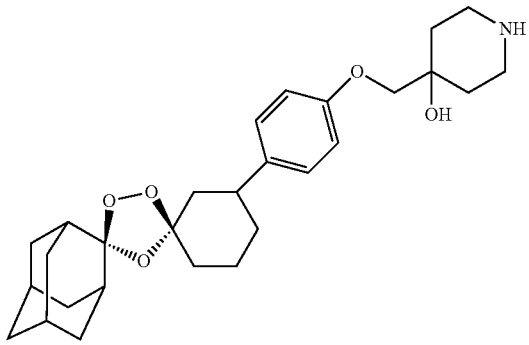

Example C12: p-{(1R)-Dispiro[cyclohexane-1,3'-[1,
2,4]trioxolane-5',2"-tricyclo[3.3.1.1³,⁷]decan]-3-
yl}phenyl 1-piperidinecarboxylate

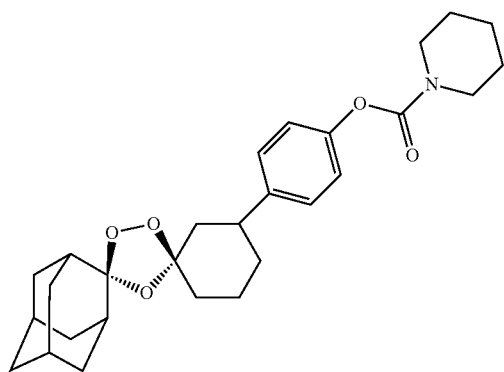

Example C13: 3-(p-{(1R)-Dispiro[cyclohexane-1,3'-
[1,2,4]trioxolane-5',2"-tricyclo[3.3.1.1³,⁷]decan]-3-
yl}phenyl)propionamide

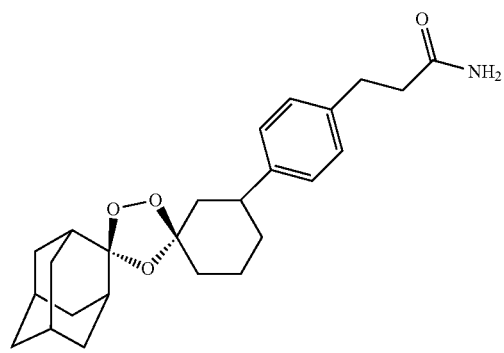

Example C14: (1R)-3-[m-(2-Morpholinoethoxy)
phenyl]dispiro[cyclohexane-1,3'-[1,2,4]trioxolane-5',
2"-tricyclo[3.3.1.1³,⁷]decane]

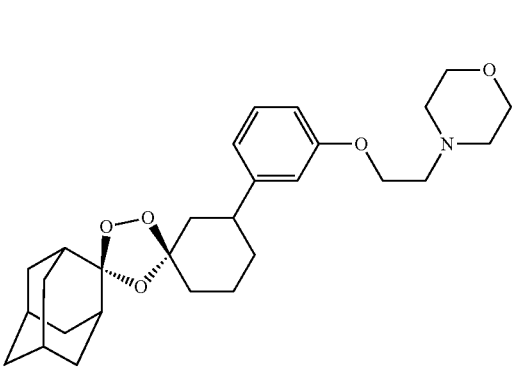

Example C15

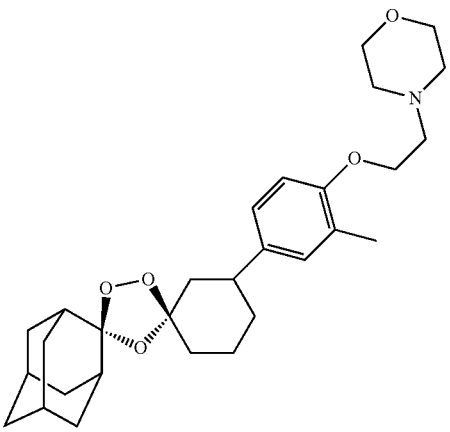

Example C16: (1R)-3-[4-(2-Morpholinoethoxy)
tolyl]dispiro[cyclohexane-1,3'-[1,2,4]trioxolane-5',
2"-tricyclo[3.3.1.1³,⁷]decane]

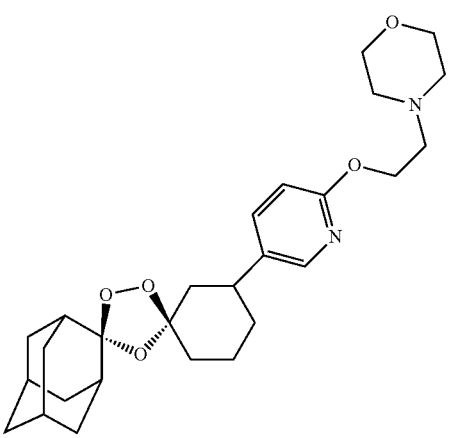

Example C17: 2-(p-{(1R)-Dispiro[cyclohexane-1,3'-[1,2,4]trioxolane-5',2''-tricyclo[3.3.1.1³,⁷]decan]-3-yl}phenyl)ethylamine

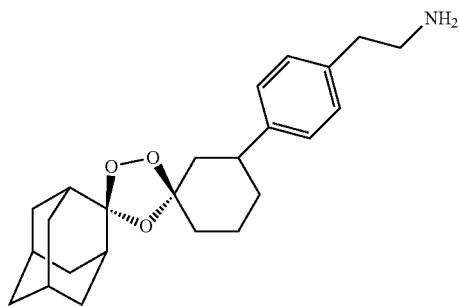

Example C18: (1R)-3-[p-(2-Aminoethylaminocarbonyloxy)phenyl]dispiro[cyclohexane-1,3'-[1,2,4]trioxolane-5',2''-tricyclo[3.3.1.1³,⁷]decane]

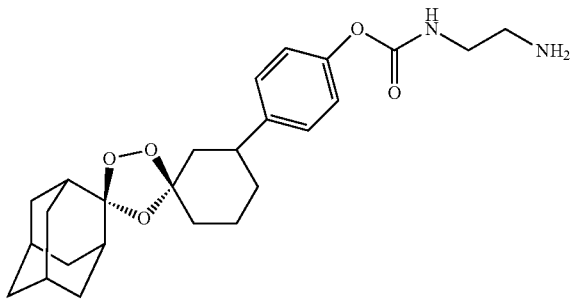

Example C19: (1R)-3-{p-[(Carbamoylmethyl)aminocarbonyloxy]phenyl}dispiro[cyclohexane-1,3'-[,2,4]trioxolane-5',2''-tricyclo[3.3.1.1³,⁷]decane]

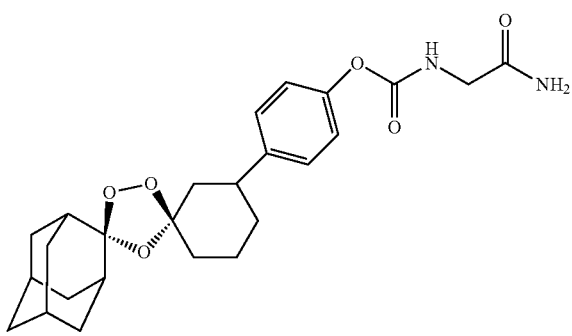

Example C20: (1R)-3-[p-(2-Amino-2-methylpropylaminocarbonyloxy)phenyl]dispiro[cyclohexane-1,3'-[1,2,4]trioxolane-5',2''-tricyclo[3.3.1.1³,⁷]decane]

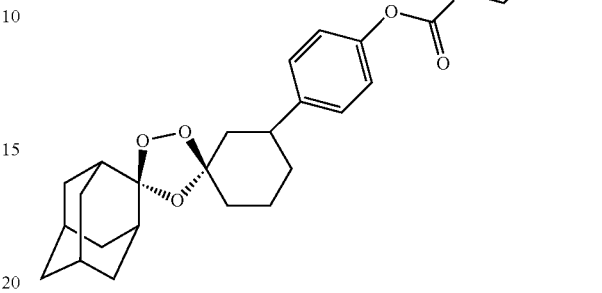

Example C21: 4-(2-(4-((1R,3S,5R,5'R,7R)-dispiro[adamantane-2,3'-[1,2,4]trioxolane-5',1''-cyclohexan]-3''-yl)-3-methylphenoxy)ethyl)morpholine

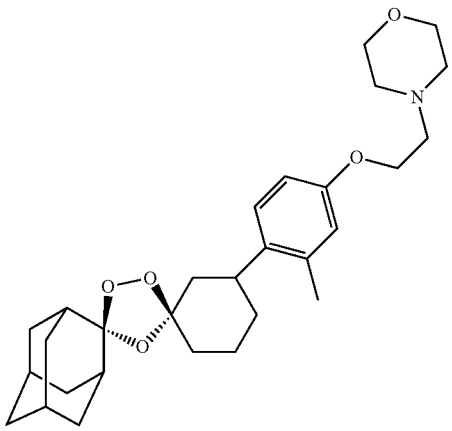

Example C1A

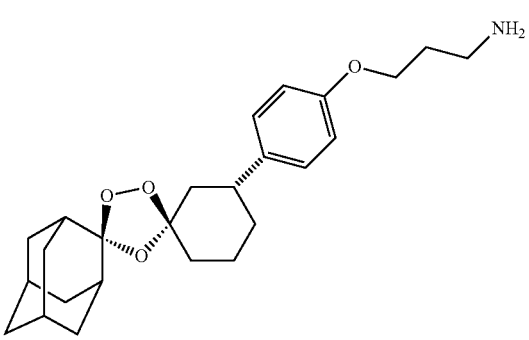

3-(p-{(1R,3R)-Dispiro[cyclohexane-1,3'-[1,2,4]trioxolane-5',2''-tricyclo[3.3.1.1³,⁷]decan]-3-yl}phenoxy)propylamine Example C2A

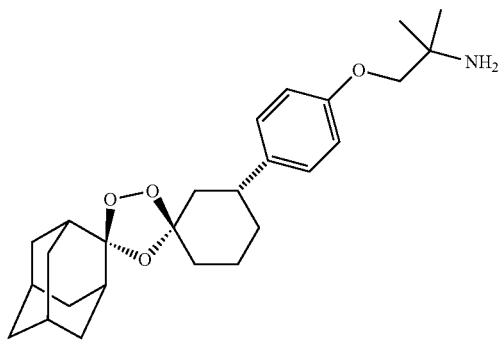

2-(p-{(1R,3R)-Dispiro[cyclohexane-1,3'-[1,2,4]tri-
oxolane-5',2''-tricyclo[3.3.1.1$^{3,7}$]decan]-3-
yl}phenoxy)-1,1-dimethylethylamine Example C4A

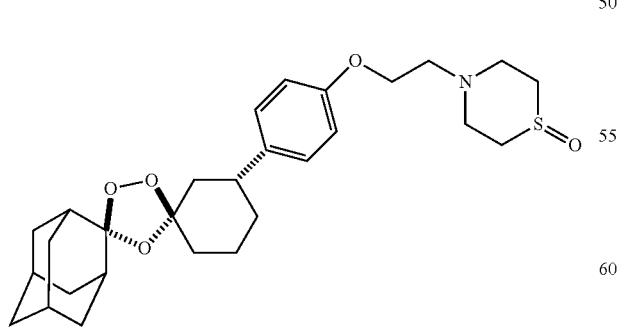

(1R,3R)-3-{p-[2-(1,4-Oxazepan-4-yl)ethoxy]
phenyl}dispiro[cyclohexane-1,3'-[1,2,4]trioxolane-
5',2''-tricyclo[3.3.1.1$^{3,7}$]decane]

Example C5A

4-[2-(p-{(1R,3R)-Dispiro[cyclohexane-1,3'-[1,2,4]
trioxolane-5',2''-tricyclo[3.3.1.1$^{3,7}$]decan]-3-
yl}phenoxy)ethyl]-1λ$^4$,4-thiazinan-1-one Example C6A

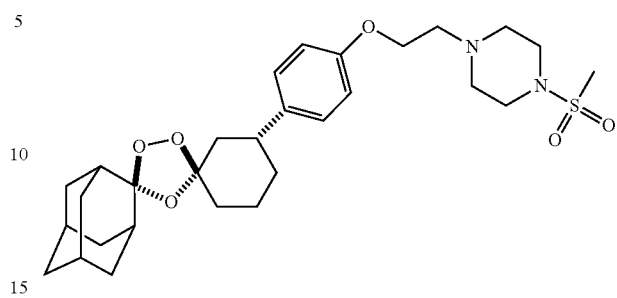

(1R,3R)-3-(p-{2-[4-(Methylsulfonyl)-1-piperazinyl]
ethoxy}phenyl)dispiro[cyclohexane-1,3'-[1,2,4]tri-
oxolane-5',2''-tricyclo[3.3.1.1$^{3,7}$]decane]

Example C7A

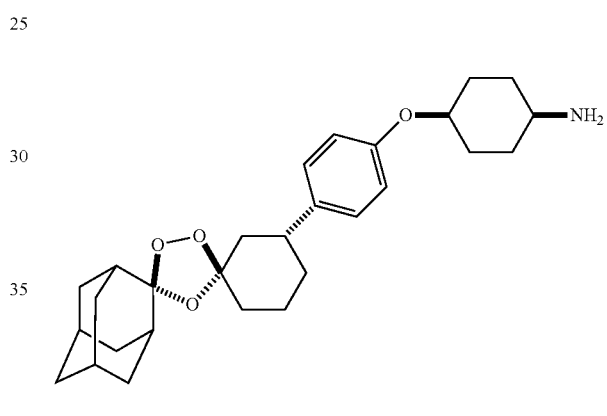

4-(p-{(1R,3R)-Dispiro[cyclohexane-1,3'-[1,2,4]tri-
oxolane-5',2''-tricyclo[3.3.1.1$^{3,7}$]decan]-3-
yl}phenoxy)cyclohexylamine Example C8A

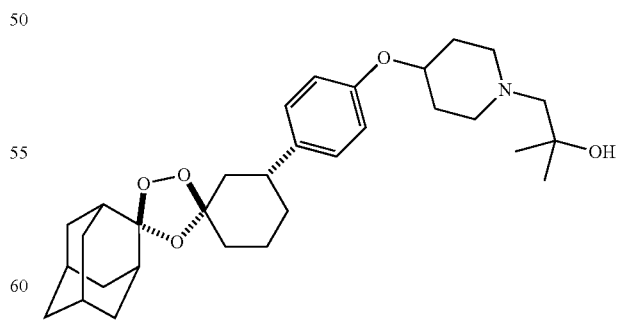

1-[4-(p-{(1R,3R)-Dispiro[cyclohexane-1,3'-[1,2,4]
trioxolane-5',2''-tricyclo[3.3.1.1$^{3,7}$]decan]-3-
yl}phenoxy)-1-piperidyl]-2-methyl-2-propanol

195

Example C9A

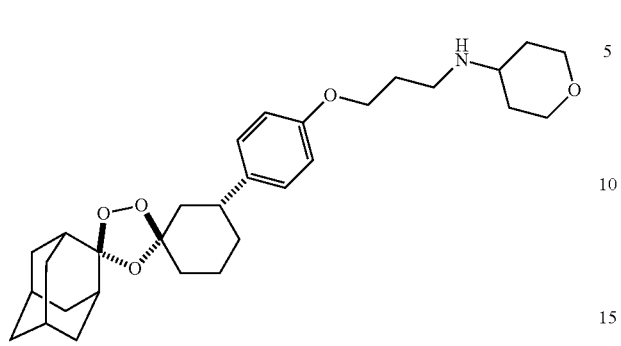

[3-(p-{(1R,3R)-Dispiro[cyclohexane-1,3'-[1,2,4]
trioxolane-5',2"-tricyclo[3.3.1.1$^{3,7}$]decan]-3-
yl}phenoxy)propyl]-tetrahydro-2H-pyran-4-ylamine

Example C10A

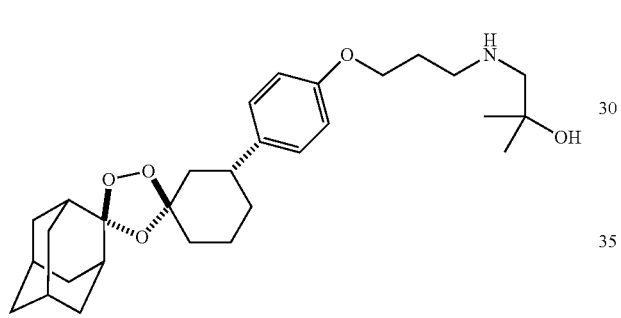

1-[3-(p-{(1R,3R)-Dispiro[cyclohexane-1,3'-[1,2,4]
trioxolane-5',2"-tricyclo[3.3.1.1$^{3,7}$]decan]-3-
yl}phenoxy)propylamino]-2-methyl-2-propanol

Example C11A

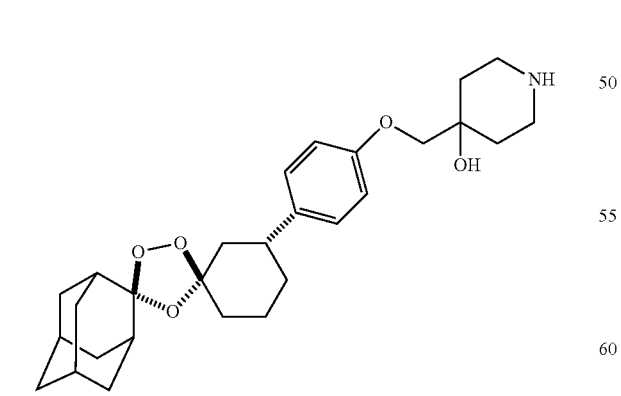

4-[(p-{(1R,3R)-Dispiro[cyclohexane-1,3'-[1,2,4]
trioxolane-5',2"-tricyclo[3.3.1.1$^{3,7}$]decan]-3-
yl}phenoxy)methyl]-4-piperidinol

196

Example C12A

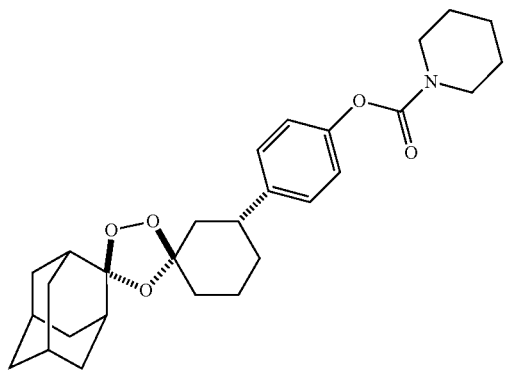

p-{(1R,3R)-Dispiro[cyclohexane-1,3'-[1,2,4]trioxo-
lane-5',2"-tricyclo[3.3.1.1$^{3,7}$]decan]-3-yl}phenyl
1-piperidinecarboxylate

Example C13A

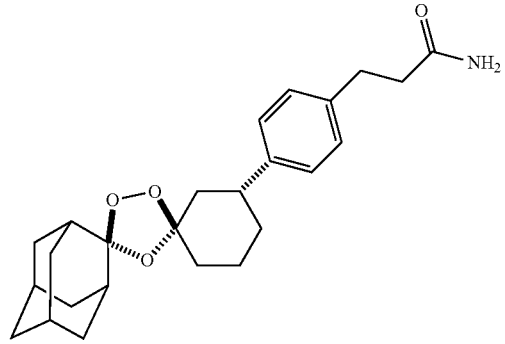

3-(p-{(1R,3R)-Dispiro[cyclohexane-1,3'-[1,2,4]tri-
oxolane-5',2"-tricyclo[3.3.1.1$^{3,7}$]decan]-3-yl}phenyl)
propionamide

Example C15A

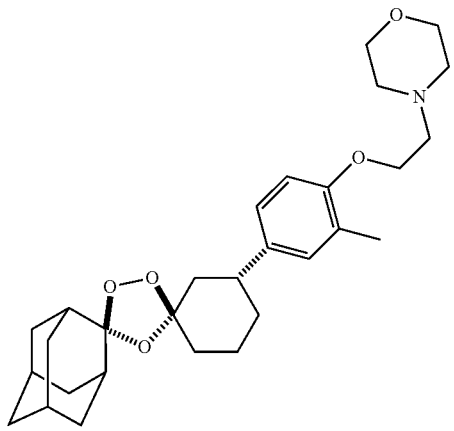

(1R,3R)-3-[4-(2-Morpholinoethoxy)tolyl]dispiro
[cyclohexane-1,3'-[1,2,4]trioxolane-5',2"-tricyclo
[3.3.1.1$^{3,7}$]decane]

Example C16A

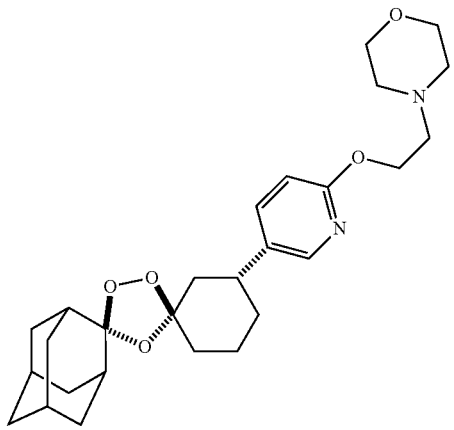

(1R,3R)-3-[6-(2-Morpholinoethoxy)-3-pyridyl]
dispiro[cyclohexane-1,3'-[1,2,4]trioxolane-5',2"-
tricyclo[3.3.1.1$^{3,7}$]decane]

Example C17A

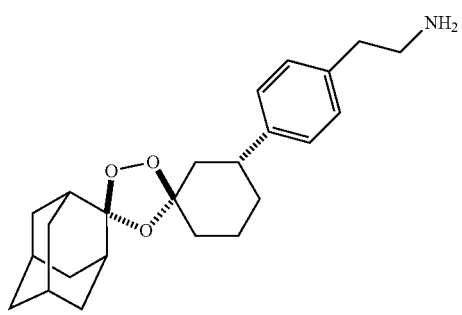

2-(p-{(1R,3R)-Dispiro[cyclohexane-1,3'-[1,2,4]tri-
oxolane-5',2"-tricyclo[3.3.1.1$^{3,7}$]decan]-3-yl}phenyl)
ethylamine

Example C19A

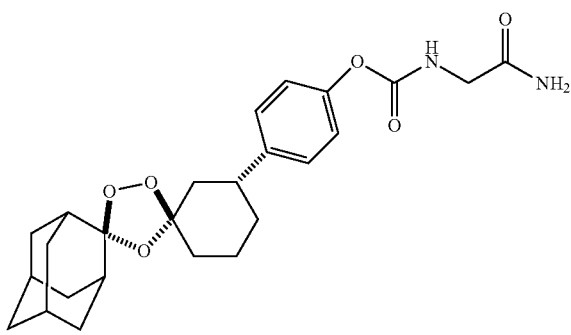

(1R,3R)-3-{p-[(Carbamoylmethyl)aminocarbony-
loxy]phenyl}dispiro[cyclohexane-1,3'-[1,2,4]trioxo-
lane-5',2"-tricyclo[3.3.1.1$^{3,7}$]decane]

Example C21A

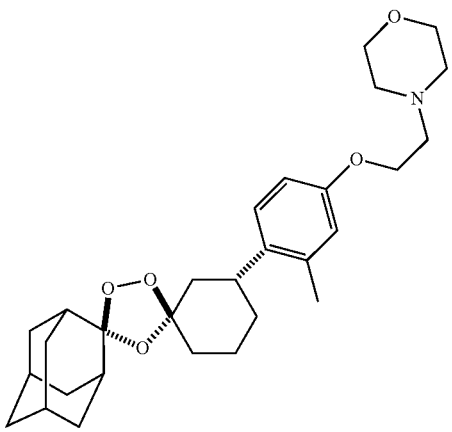

4-(2-(4-((1R,3 S,3"R,5R,5'R,7R)-dispiro[adaman-
tane-2,3'-[1,2,4]trioxolane-5',1"-cyclohexan]-3"-yl)-
3-methylphenoxy)ethyl)morpholine

C. In Vitro Evaluation of Congener Pairs

The effect of $R^A$-substitution ($R^A$ in Scheme 1) on antiplasmodial activity was evaluated by comparing the regioisomeric analogs 2a-j (Scheme 2) and 12a-j (Chart 1 below, Scheme 4). New trans-$R^A$ ($R^A$ in Scheme 1) analogs exhibited potent, low nM activities against the chloroquine-resistant W2 strain of P. falciparum, with activity comparable to that of cis-$R^B$($R^B$ in Scheme 1) comparators. Moreover, structure-activity trends tracked remarkably closely in the regioisomeric scaffolds, consistent with our hypothesis that trans-$R^A$ substitution ($R^A$ in Scheme 1) would confer similar conformational constraints and Fe(II) reactivity as cis-$R^B$ substitution ($R^B$ in Scheme 1). In both scaffolds, piperidine amides (12e/2e) were the least potent, approximately 10 to 20-fold weaker than piperazine analogs 12g/2g. The most significant difference between regioisomer pairs was observed for morpholine amides 12f/2f, where 3" analog 12f was three-fold more potent than 2f. Overall, these findings confirmed that trans-$R^A$ substitution ($R^A$ in Scheme 1) modulates 1,2,4-trioxolane reactivity in a pharmacologically relevant range, producing effects on cultured parasites that are comparable to traditional cis-$R^B$ substitution.

Chart 1$^a$ In vitro activity of trioxolanes 12a-j (Scheme 4) and 2a-j (Scheme 2) against W2 P. falciparum parasites

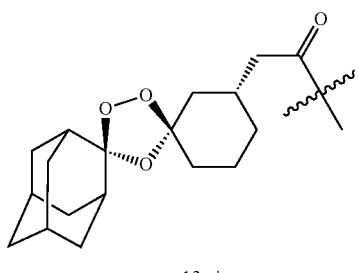

12a-j

-continued

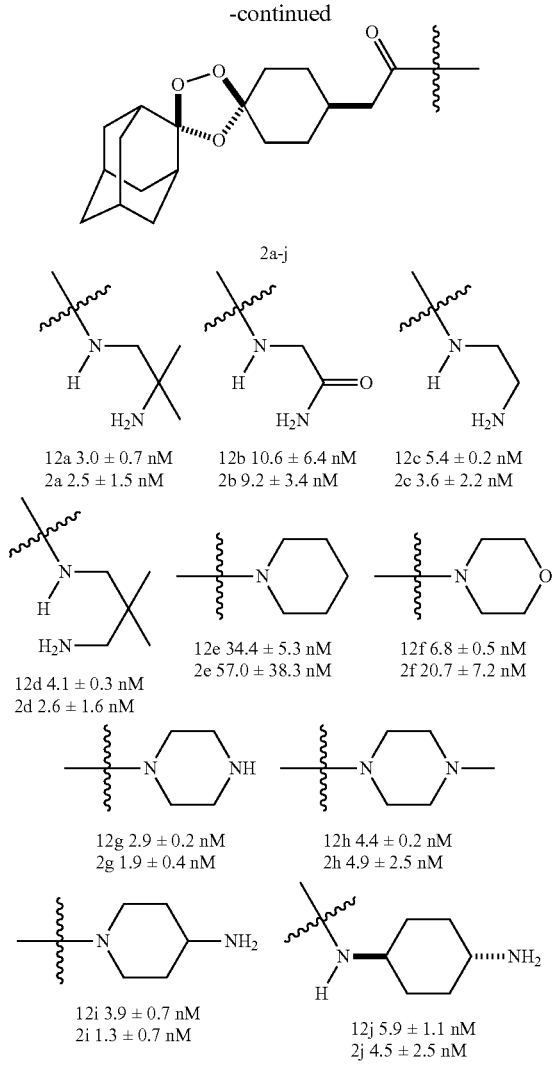

12a 3.0 ± 0.7 nM
2a 2.5 ± 1.5 nM 12b 10.6 ± 6.4 nM
2b 9.2 ± 3.4 nM 12c 5.4 ± 0.2 nM
2c 3.6 ± 2.2 nM 12d 4.1 ± 0.3 nM
2d 2.6 ± 1.6 nM 12e 34.4 ± 5.3 nM
2e 57.0 ± 38.3 nM 12f 6.8 ± 0.5 nM
2f 20.7 ± 7.2 nM 12g 2.9 ± 0.2 nM
2g 1.9 ± 0.4 nM 12h 4.4 ± 0.2 nM
2h 4.9 ± 2.5 nM 12i 3.9 ± 0.7 nM
2i 1.3 ± 0.7 nM 12j 5.9 ± 1.1 nM
2j 4.5 ± 2.5 nM

[a] In vitro activity of 12a-j (Scheme 4) and 2a-j (Scheme 2) against W2 *P. falciparum* parasites ($EC_{50}$ ± SEM). Reported $EC_{50}$ values are the means of three determinations ± SEM.

A second hypothesis regarding trans-$R^A$ substitution ($R^A$ in Scheme 1) was that the resulting de-symmetrized molecular topology would impact the vivo PK/PD properties of these analogs. Specifically, we reasoned that the chiral trans-$R^A$ analogs ($R^A$ in Scheme 1) might interact differently with CYP enzymes and drug transporters (e.g. P-gp). To explore possible metabolic differences, we evaluated selected analogs with mouse liver microsomes and derived intrinsic clearance ($CL_{int}$) values (Table 1). All the analogs evaluated exhibited low or moderate $CL_{int}$ values that would predict for reasonable exposure in vivo. In four of the six analog pairs evaluated it was the trans-$R^A$ analogs ($R^A$ in Scheme 1) that exhibited higher CLint values, with trans-$R^A$ analogs ($R^A$ in Scheme 1) 12a and 12c showed lower intrinsic clearance than their cis-$R^B$ comparators ($R^B$ in Scheme 1). Clearance appeared to be CYP mediated in all cases, with the possible exception of 2c, where chemical instability or non-CYP mediate clearance was implicated. The kinetic solubilities of arterolane (2a) and its regioisomer 12a were evaluated and found to be comparable. Overall, the in vitro ADME data suggested that trans-$R^A$ analogs ($R^A$ in Scheme 1) were suitable for evaluation in animals and that specific analogs might be differentiated from their comparators in vivo.

TABLE 1

In vitro ADME data for for selected trioxolane analogs and controls. 12a-j (Scheme 4) and 2a-j (Scheme 2)

| Compound | $T_{1/2}$ (min)[a] | $CL_{int}$[b] | $T_{1/2}$ (min) No NADPH | Solubility (μM)[c] |
|---|---|---|---|---|
| 2a | 128 | 5.4 | stable | 433 |
| 12a | 169 | 4.1 | stable | 429 |
| 2b | 124 | 5.6 | stable | — |
| 12b | 37.3 | 18.6 | stable | — |
| 2c | 64.2 | 10.8 | 70 | — |
| 12c | 84.5 | 8.2 | 136 | — |
| 2d | 161 | 4.3 | stable | — |
| 12d | 64.2 | 10.8 | stable | — |
| 2g | 48.1 | 14.4 | 88.9 | — |
| 12g | 25.5 | 27.2 | stable | — |
| 2i | 277 | 2.5 | stable | — |
| 12i | 84.5 | 8.2 | stable | — |
| midazolam | 1.65 | 420 | — | — |
| diclofenac | 55.5 | 12.5 | — | — |
| amiodarone | — | — | — | <3 |
| testosterone | — | — | — | 315 |

[a] Half-life when incubated with mouse liver microsomes.
[b] Clearance in units of μL/min/mg of protein; calculated as $CL_{int} = Ln(2)*1000/T_{1/2}$/protein concentration where protein conc is in mg/mL; midazolam and diclofenac served as controls.
[c] Kinetic solubility in PBS (pH = 7.4) at a final DMSO concentraion of 5%, average of three determinations; amiodarone and testosterone served as controls.

The suppressive 4-day "Peters test"[27] involving *P. berghei* infected mice provides a convenient and cost effective means to assess the overall in vivo performance of preclinical antimalarials. Thus, groups of five *P. berghei* infected female Swiss Webster mice were treated via oral gavage with four daily (QD) doses of either 2a (as the tosylate salt), regioisomeric comparator 12a (both tosylate and free base), or chloroquine control (Table 2). Mice were followed for 30 days and judged to have been cured of the infection based on the lack of detectable parasitemia at the end of the study. In this initial study, trans-$R^A$ analog ($R^A$ in Scheme 1) 12a as either tosylate salt or free base exhibited efficacy comparable to arterolane tosylate, producing cures in all five animals.

TABLE 2

In vivo efficacy of trioxolanes 12a and 2a and controls in *P. berghei* infected mice treated for four days. [a]12a-j (Scheme 4) and 2a-j (Scheme 2)

| Treatment | Salt form | Dose (mg/kg/day) | Mice Cured[b] (%) |
|---|---|---|---|
| 2a | tosylate | 13.6 | 100 |
| 12a | tosylate | 13.6 | 100 |
| 12a | free base | 9.5 | 100 |
| Chloroquine | — | 30 | 80 |
| Vehicle treated | — | — | 0 |
| Untreated | — | — | 0 |

[a] Beginning one hour after infection, cohorts of five *P. berghei* infected female Swiss Webster mice were treated once a day for four days by oral gavage.
[b] Mice were considered cured if there was no detectable parasitemia at 30 days postinfection.

This result indicated that 12a was orally absorbed and achieved systemic exposure sufficient to produce a robust pharmacodynamic response. Prior to evaluating additional trans-$R^A$ analogs ($R^A$ in Scheme 1), we sought to determine the 50% curative dose for both 12a and 2a in this model, and use this dose as a benchmark for future studies. Thus, compounds 12a and 2a (both as free bases) were administered to mice over four days at doses of 10, 6, 4, or 1 mg/kg/day, and survival and parasitemia were monitored until 30 days post infection. This study revealed a clear dose-efficacy relationship and allowed us to estimate 50% curative dose values of ~6 mg/kg/day for 12a and ~4 mg/kg/day for 2a (Table 3). With the trans-$R^A$ chemotype ($R^A$ in Scheme 1) validated in vivo and a relatively stringent dose/efficacy benchmark established, we set out to more broadly evaluate the matched pairs of regioisomeric analogs in animals.

TABLE 3

In vivo efficacy of 12a and 2a in *P. berghei* infected mice following four daily doses. [a]12a-j (Scheme 4) and 2a-j (Scheme 2)

| Treatment | Dose[a] (mg/kg/day) | Mice Cured[b] (%) |
|---|---|---|
| 12a | 1 | 0 |
|  | 4 | 0 |
|  | 6 | 60 |
|  | 10 | 100 |
| 2a | 1 | 0 |
|  | 4 | 80 |
|  | 6 | 100 |
|  | 10 | 100 |
| Vehicle | — | 0 |
| Untreated | — | 0 |

[a]Beginning one hour after infection, cohorts of five *P. berghei* infected female Swiss Webster mice were treated once a day for four days by oral gavage at the indicated daily dose.
[b]Mice were considered cured if there was no detectable parasitemia at 30 days postinfection.

As noted previously, the cis-$R^B$ amide comparators ($R^B$ in Scheme 1) were selected in part based on in vivo efficacy data. Therefore, all nine additional analog pairs were judged to have potential for good in vivo efficacy, though whether this could be achieved at the relatively low $PD_{50}$ values exhibited by 12a/2a was unclear. In the next large study, all twenty test compounds (2a-j and 12a-j) were evaluated at both the 4 mg/kg and 6 mg/kg daily dose in groups of five Swiss Webster mice. Controls 12a and 2a again showed good efficacy at these low doses, with analog 12a more effective than 2a in this study (Table 4). Among the other nine analog pairs, four pairs failed to cure any mice at either dosing level. These analogs included the glycinamide (12b/2b), piperidine (12e/2e), morpholine (12f/2f) and N-methyl piperazine (12h/2h) analogs. Interestingly, in comparison to the piperidine and piperazine analogs in these studies, the structurally very similar 4-aminopiperidine derivatives 12i/2i were among the most efficacious analogs examined, curing all animals at the lowest dose of 4 mg/kg/day, and proving superior to 12a/2a.

le;.5qOf greatest interest were those analog pairs for which in vivo efficacy varied between the trans-$R^A$ and cis-$R^B$ comparators ($R^A$ and $R^B$ in Scheme 1). Most strikingly, cis-$R^B$ analogs ($R^B$ in Scheme 1) 2d and 2g were fully effective at 4 mg/kg/day while the analogous trans-$R^A$ comparators ($R^A$ in Scheme 1) 12d and 12g were weakly effective (Table 4). In the case of the analog pair 12c/2c, however, it was the novel trans-$R^A$ analog ($R^A$ in Scheme 1) 12c that produced full cure at either dose while the cis-$R^B$ derivative ($R^B$ in Scheme 1) 2c was essentially ineffective. Thus, regioisomeric trioxolane analogs can exhibit starkly different efficacy in vivo despite having similar intrinsic potency in cultured parasites. This confirmed expectations that trans-$R^A$ substitution ($R^A$ in Scheme 1) might offer new avenues for the optimization of PK/PD properties in preclinical 1,2,4-trioxolanes. In the case of 12c/2c, 12d/2d, and 12g/2g, $CL_{int}$ values from the mouse liver microsome assay correctly predicted the superior analog in each pair (cf. Tables 1 and 4). However, the magnitude of differences in $CL_{int}$ values seems insufficient to fully explain the differences observed, nor do the $CL_{int}$ values alone explain the efficacy of 12b/2b. It appears that additional in vivo PK/PD studies will be required to fully understand the relative merits of 3" and 4" substitution within the context of specific side chain types.

TABLE 4

In vivo efficacy of matched analog pairs in *P. berghei* infected mice. [a]12a-j (Scheme 4) and 2a-j (Scheme 2)

| Compound | Dose (mg/kg/day) | Mice Cured[b] (%) |
|---|---|---|
| 12a | 4 | 60 |
|  | 6 | 100 |
| 2a | 4 | 20 |
|  | 6 | 80 |
| 12b | 4 | 0 |
|  | 6 | 0 |
| 2b | 4 | 0 |
|  | 6 | 0 |
| 12c | 4 | 100 |
|  | 6 | 100 |
| 2c | 4 | 0 |
|  | 6 | 20 |
| 12d | 4 | 0 |
|  | 6 | 0 |
| 2d | 4 | 40 |
|  | 6 | 100 |
| 12e | 4 | 0 |
|  | 6 | 0 |
| 2e | 4 | 0 |
|  | 6 | 0 |
| 12f | 4 | 0 |
|  | 6 | 0 |
| 2f | 4 | 0 |
|  | 6 | 0 |
| 12g | 4 | 0 |
|  | 6 | 20 |
| 2g | 4 | 100 |
|  | 6 | 100 |
| 12h | 4 | 0 |
|  | 6 | 0 |
| 2h | 4 | 0 |
|  | 6 | 0 |
| 12i | 4 | 100 |
|  | 6 | 80 |
| 2i | 4 | 100 |
|  | 6 | 100 |
| 12j | 4 | 60 |
|  | 6 | 100 |
| 2j | 4 | 80 |
|  | 6 | 80 |
| Chloroquine | 30 | 40 |
| Vehicle | — | 0 |

[a]Beginning one hour after infection, cohorts of five *P. berghei* infected female Swiss Webster mice were treated once a day for four days by oral gavage.
[b]Mice were considered cured if there was no detectable parasitemia at 30 days postinfection.

Given that the novel analogs 12c and 12i demonstrated complete cures at 4 mg/kg/day, we next explored whether even lower doses of these agents might be effective in mice. While 12c and 12i again cured all animals at a 4 mg/kg/day dose, both were less effective at reduced doses of 2, 1, or 0.5 mg/kg/day (Table 5). We next asked whether a full four days of treatment at 4 mg/kg/day was necessary to achieve cures with 12c and 12i, cognizant that current antimalarial target product profiles seek agents with shortened dosing regimens. When 12c and 12i were administered at 4 mg/kg for 4, 3, 2, or a single day, a predictable decline in efficacy with the number of doses was observed (Table 6). Thus, both compounds were again fully effective at four daily doses of 4 mg/kg, while 12i was shown to be superior to 12c with three daily doses of 4 mg/kg (60% vs. 20% of animals cured for 12i and 12c, respectively). Neither compound was effective with one or two daily doses of 4 mg/kg, however.

TABLE 5

In vivo efficacy of 12c and 12i in *P. berghei* infected mice at various dosing levels.[a] 12a-j (Scheme 4) and 2a-j (Scheme 2)

| Compound | Dose (mg/kg/day) | Mice Cured[b] (%) |
|---|---|---|
| 12c | 0.5 | 0 |
|  | 1 | 0 |
|  | 2 | 0 |
|  | 4 | 100 |
| 12i | 0.5 | 0 |
|  | 1 | 0 |
|  | 2 | 0 |
|  | 4 | 100 |

[a] Beginning one hour after infection, cohorts of five *P. berghei* infected female Swiss Webster mice were treated once a day for four days by oral gavage.
[b] Mice were considered cured if there was no detectable parasitemia at 30 days postinfection.

TABLE 6

In vivo efficacy of 12c and 12i in *P. berghei* infected mice with less frequent dosing.[a] 12a-j (Scheme 4) and 2a-j (Scheme 2)

| Compound | Dose (mg/kg) | Number of Doses | Mice Cured[b] (%) |
|---|---|---|---|
| 12c | 4 | 4 | 100 |
|  | 4 | 3 | 20 |
|  | 4 | 2 | 0 |
|  | 4 | 1 | 0 |
| 12i | 4 | 4 | 100 |
|  | 4 | 3 | 60 |
|  | 4 | 2 | 0 |
|  | 4 | 1 | 0 |

[a] Beginning one hour after infection, cohorts of five *P. berghei* infected female Swiss Webster mice were treated once a day by oral gavage for either four, three, two, or one day as shown above.
[b] Mice were considered cured if there was no detectable parasitemia at 30 days postinfection.

In a final in vivo study, we evaluated the efficacy of 12c and 12i following a single dose of 40 or 80 mg/kg, and two doses of 40 mg/kg (Table 7). We included as a positive control in this study artefenomel (3Z)[4,28], which is known to be highly effective in these models with a single exposure. Indeed, a single dose of 3Z was remarkably effective, curing all animals at all doses examined. While the new analogs 12c and 12i were completely effective with two doses of 40 mg/kg/day, a single dose of 40 mg/kg was only partially effective for 12i and less effective for 12c. Both compounds were partially effective with a single 80 mg/kg dose and again 12i proved superior to 12c (60% cures vs. 20%). Thus, multiple PD studies consistently revealed analog 12i to be the most promising of the novel trans-3" analogs explored herein, measurably superior to arterolane (2a) but still inferior to artefenomel (3Z).

TABLE 7

Efficacy of 12c, 12i and artefenomel in *P. berghei* infected mice following a single or repeated dose.[a] 12a-j (Scheme 4) and 2a-j (Scheme 2)

| Compound | Dose (mg/kg) | Number of Doses | Mice Cured[b] (%) |
|---|---|---|---|
| 3Z (artefenomel) | 40 | 1 | 100 |
|  | 80 | 1 | 100 |

TABLE 7-continued

Efficacy of 12c, 12i and artefenomel in *P. berghei* infected mice following a single or repeated dose.[a] 12a-j (Scheme 4) and 2a-j (Scheme 2)

| Compound | Dose (mg/kg) | Number of Doses | Mice Cured[b] (%) |
|---|---|---|---|
| 12c | 40 | 2 | 100 |
|  | 40 | 1 | 0 |
|  | 80 | 1 | 20 |
| 12i | 40 | 2 | 100 |
|  | 40 | 1 | 20 |
|  | 80 | 1 | 60 |

[a] Beginning one hour after infection, cohorts of five *P. berghei* infected female Swiss Webster mice were treated by oral gavage for either one or two days at the indicated dose.
[b] Mice were considered cured if there was no detectable parasitemia at 30 days postinfection.

The unusual Fe(II)-dependent pharmacology of antimalarial 1,2,4-trioxolanes necessitates an equally unusual approach to their optimization, namely one that recognizes and exploits the strong connection between conformational dynamics, chemical reactivity, and antiparasitic effects.[15] Clinical experience with 2a and 3Z perfectly illustrates this point. Thus, early clinical studies of 2a revealed inferior drug exposure and half-life in malaria patients when compared to healthy volunteers. This effect was traced to reaction of 2a with endogenous Fe(II) sources in infected individuals. Nevertheless, by modifying the nature of the cis-4" side chain, an improved drug candidate (3Z) with much improved Fe(II) stability and in vivo PK properties was identified.[4] An improved understanding[13] of how K13 mutant parasites escape endoperoxide exposure provides new motivation and rationale for identifying endoperoxides that more rapidly kill *P. falciparum* K13 mutant ring forms, while retaining stability toward endogenous Fe(II) sources in the host.

Here we present the first systematic study comparing the canonical cis-4" substituted pharmacophore of 2a and 3Z with regioisomeric trans-3" substituted analogs. Based on their in vitro and in vivo properties, we conclude that the trans-3" side chain modulates peroxide reactivity in a pharmacologically relevant regime. In this preliminary study, we examined ten side chains employed previously in cis-4" analogs. With this survey two novel analogs were identified that exhibited in vivo properties superior to 2a in the *P. berghei* model, and one that afforded single-dose cures at higher doses.

Figure 3:
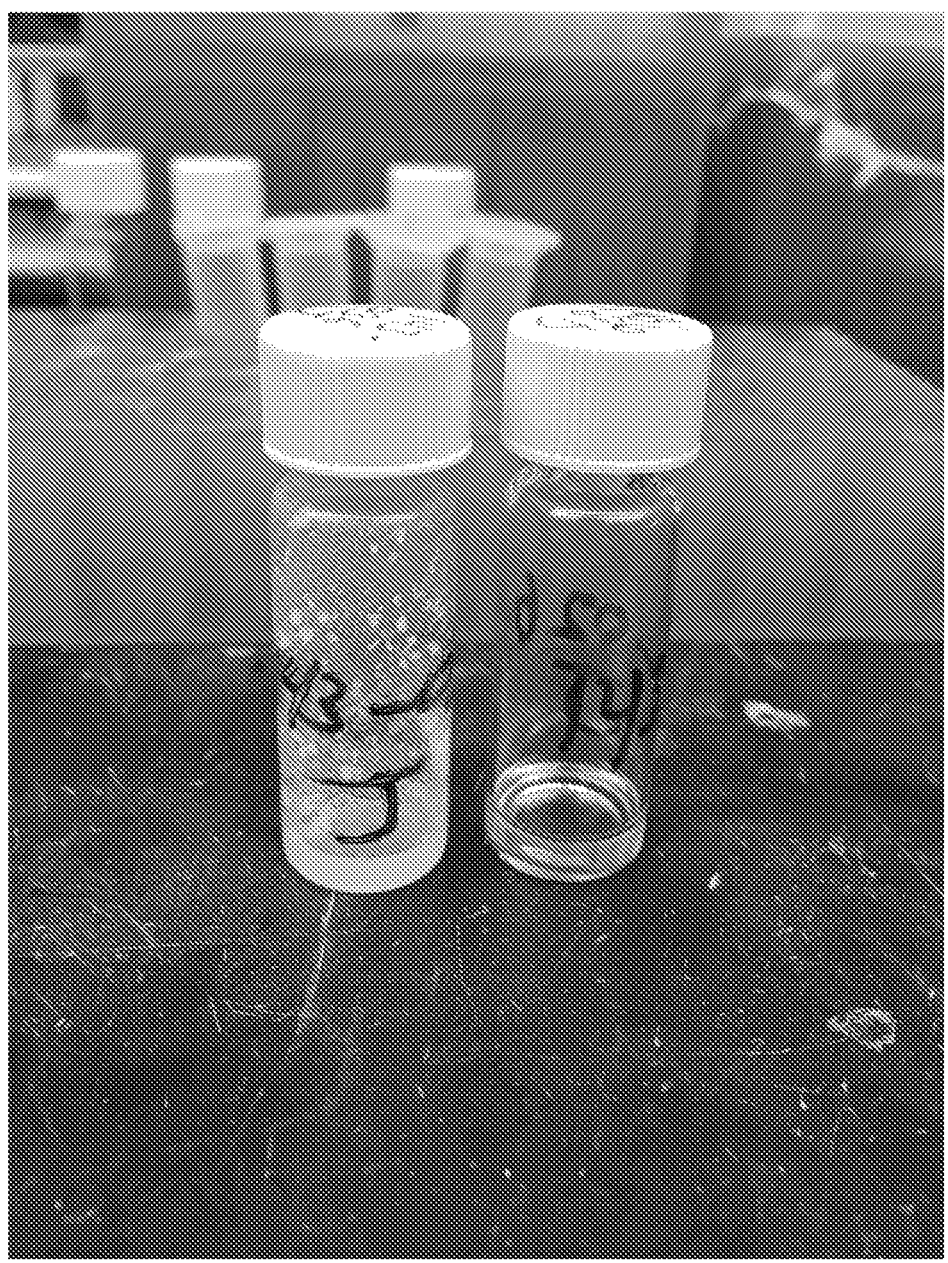
FIG. 3. Vial containing equimolar amounts of OZ439/3Z (vial at left) and A5 (vial at right) mixed with an equal volume of DMSO.

D. In Vitro and In Vivo Activity of Trans-3" Aryl Substituted Trioxolane Analogs Additional analogs substituted at the trans-3" position with an aryl ring were synthesized as described herein, and tested for in vitro antiplasmodial activity as compared to the canonical cis-4" aryl-substituted drug candidate artefenomel (OZ439, 3Z, Chart 2 and FIG. 1) currently in human clinical trials. The novel trans-3" analogs exhibited low-nM potencies that were similar to that of 3Z, thus confirming that trans-3" aryl substitution, like canonical cis-4" aryl substitution affords trioxolane analogs with antiplasmodial activity in a useful potency range. In addition, while preparing samples for in vitro analysis, we observed that trans-3" analog A5, the direct regiosiomer of OZ439, dissolved much more rapidly in DMSO than did OZ439, the latter requiring heating and sonication to dissolve in an equal volume of DMSO (FIG. 3).

E. Pharmacokinetic Analysis of Trans-3" Aryl Analog A11

Figure 4:
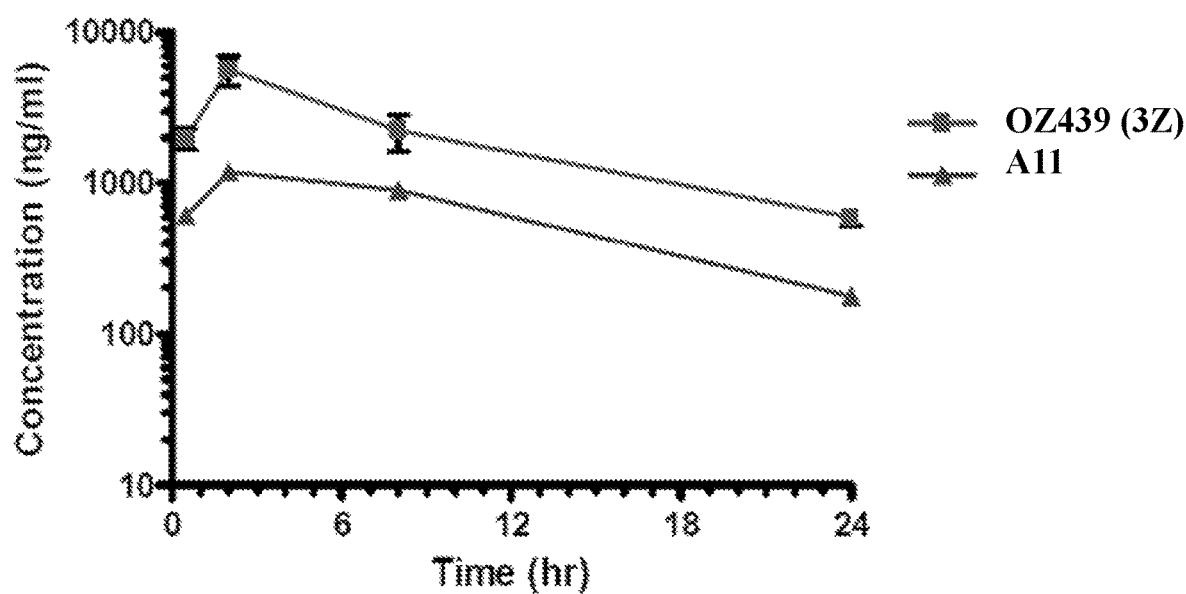
FIG. 4. Plasma concentrations of test article following a single dose of 50 mg/kg in CD-1 mice. Each data point is the mean+standard deviation (SD) for n=3 mice.
Figure 5:
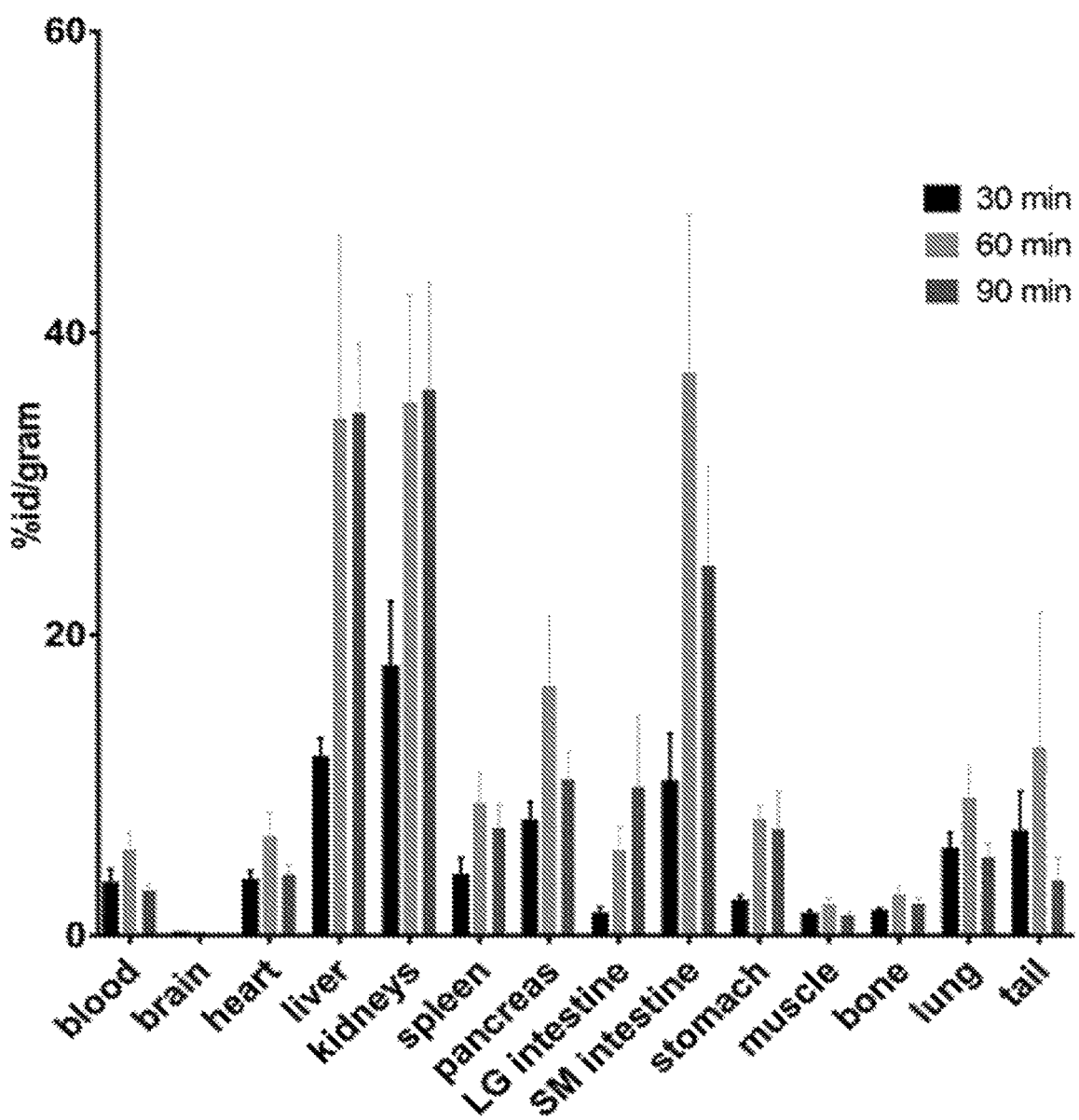
FIG. 5. B9[$^{18}$F] biodistribution in Black6 mice. An intravenous injection of 300 µCi was given at the tail vein of each mouse. At 30, 60 and 90 minutes post-injection, healthy Black6 mice were sacrificed and their organs collected.
Figure 6:
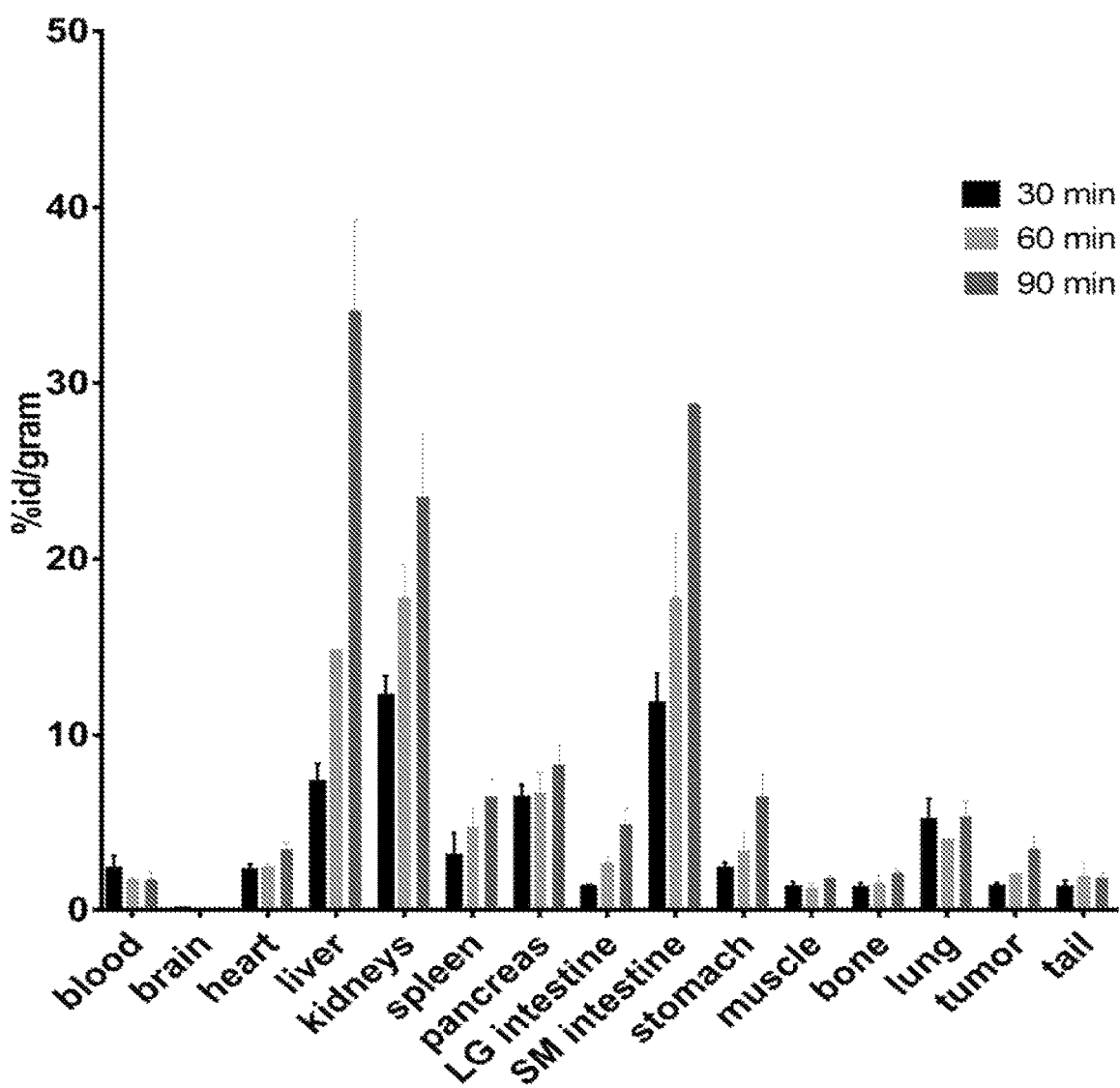
FIG. 6. B9[$^{18}$F] biodistribution in PC3-bearing mice. An intravenous injection of 300 µCi was given at the tail vein of each mouse. At 30, 60 and 90 minutes post-injection, mice were sacrificed and their organs collected. The radioactivity in the tumor can be seen steadily increasing over the 90-minute timeframe reaching up to 4% id/gram.
Figure 7:
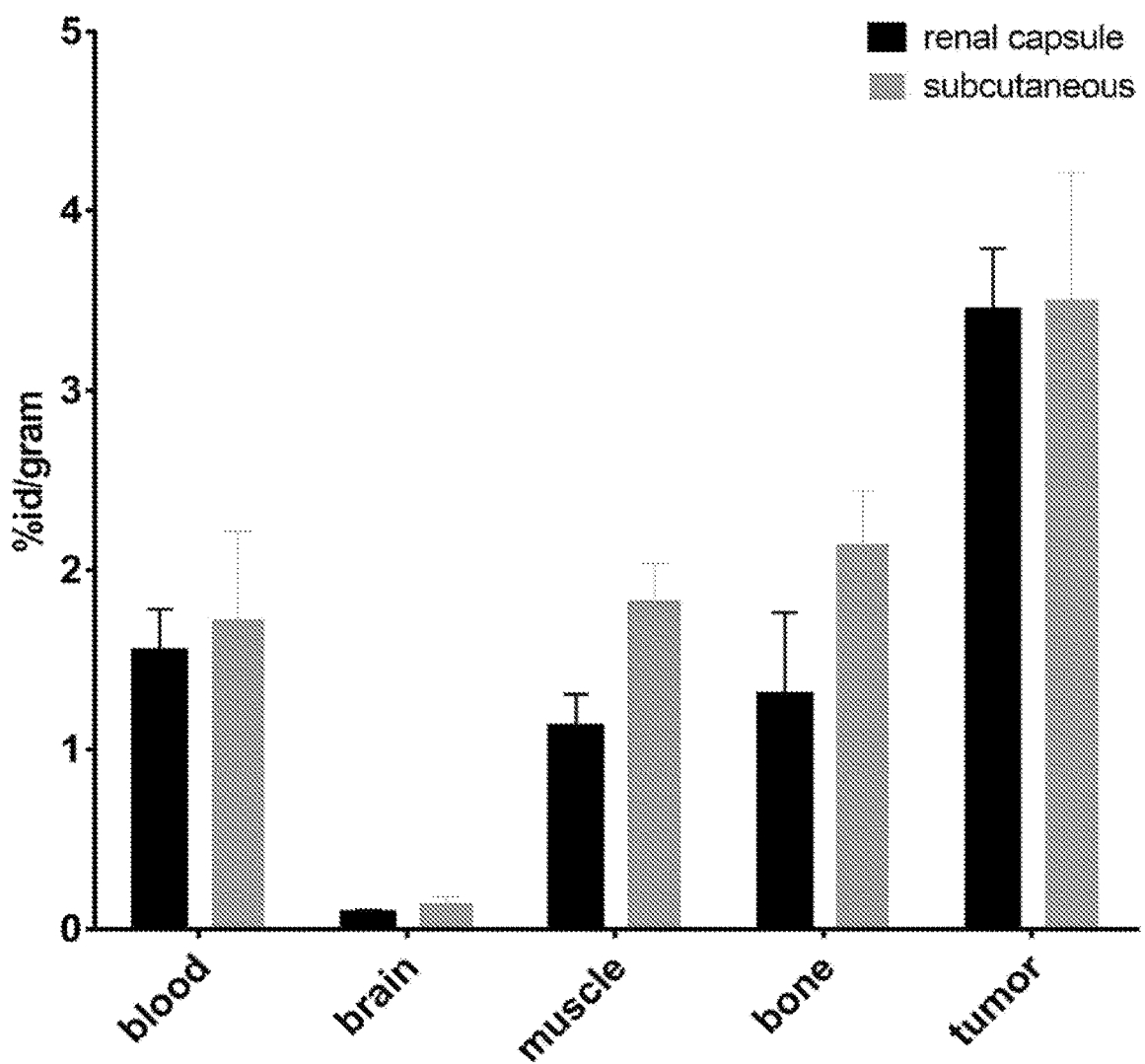
FIG. 7. B9[$^{18}$F] biodistribution in PC3-bearing mice. An intravenous injection of 300 µCi was given at the tail vein of mice containing either a subcutaneous PC3 tumor or a renal capsule PC3 tumor. At 60 minutes post-injection, mice were sacrificed and their organs collected. There was no major differences noticed between the two xenograft models.
Figure 8:
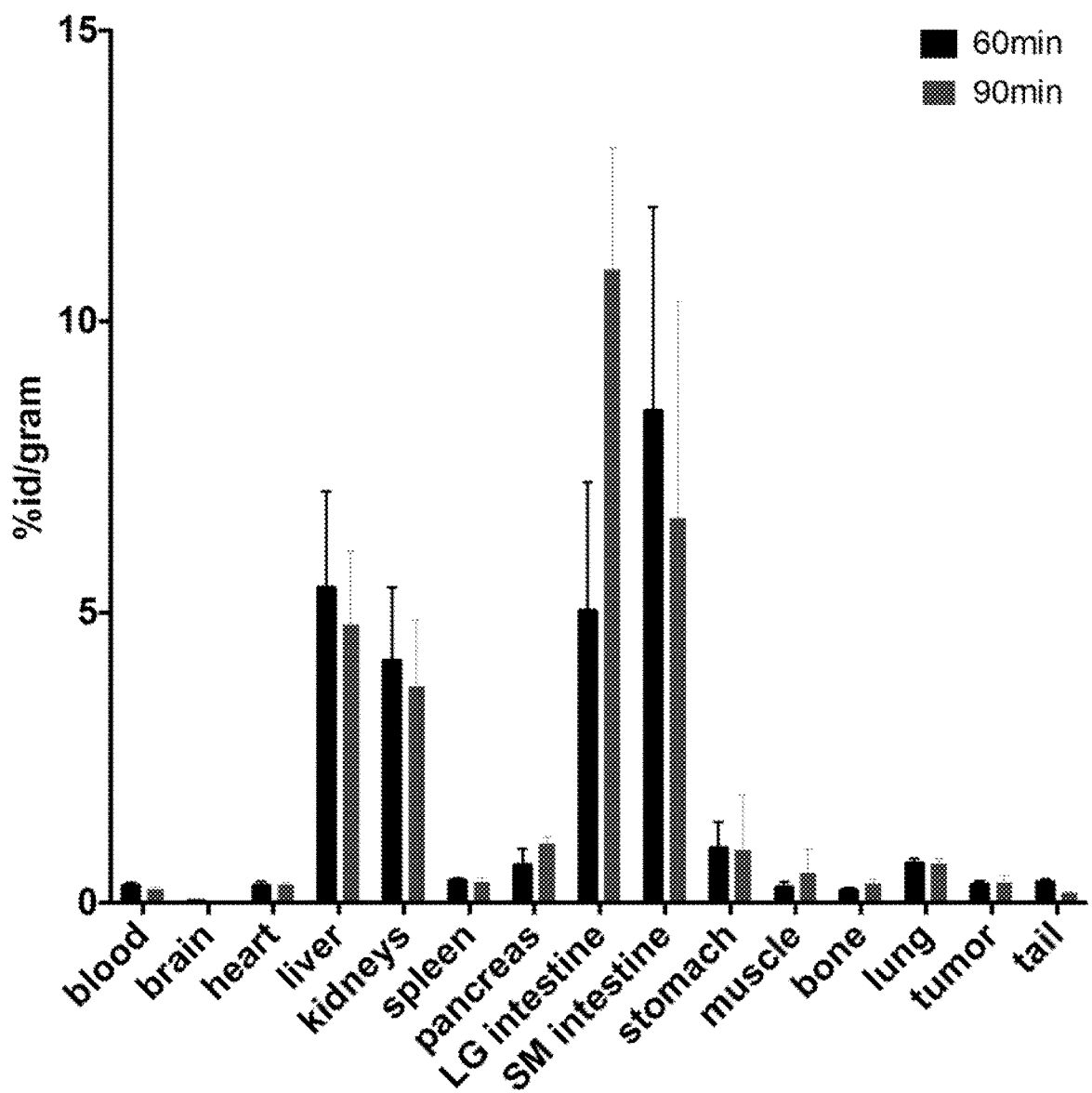
FIG. 8. B20[$^{18}$F] biodistribution in PC3 tumor-bearing nude mice: An intravenous injection of 300 µCi was given at the tail vein of each mouse. At 60 and 90 minutes post-injection, mice were sacrificed and their organs collected. The radioactivity in the tumor appears to be stable at about 0.3% id/gram.

The novel analog A11 was further evaluated in a mouse pharmacokinetic study (50 mg/kg PO, single dose, FIG. 4) where the compound showed a prolonged exposure profile and slow clearance that was very similar overall to OZ439 (3Z). This suggests that trans-3" aryl substituted trioxolane analogs can achieve significant and extended exposure profiles in mammals.

Chart 2. In vitro activity of examples A5-A9, A11-A15, D5-D6, D8-D9, and 3Z (OZ439) against W2 *P. falciparum* parasites.[a]

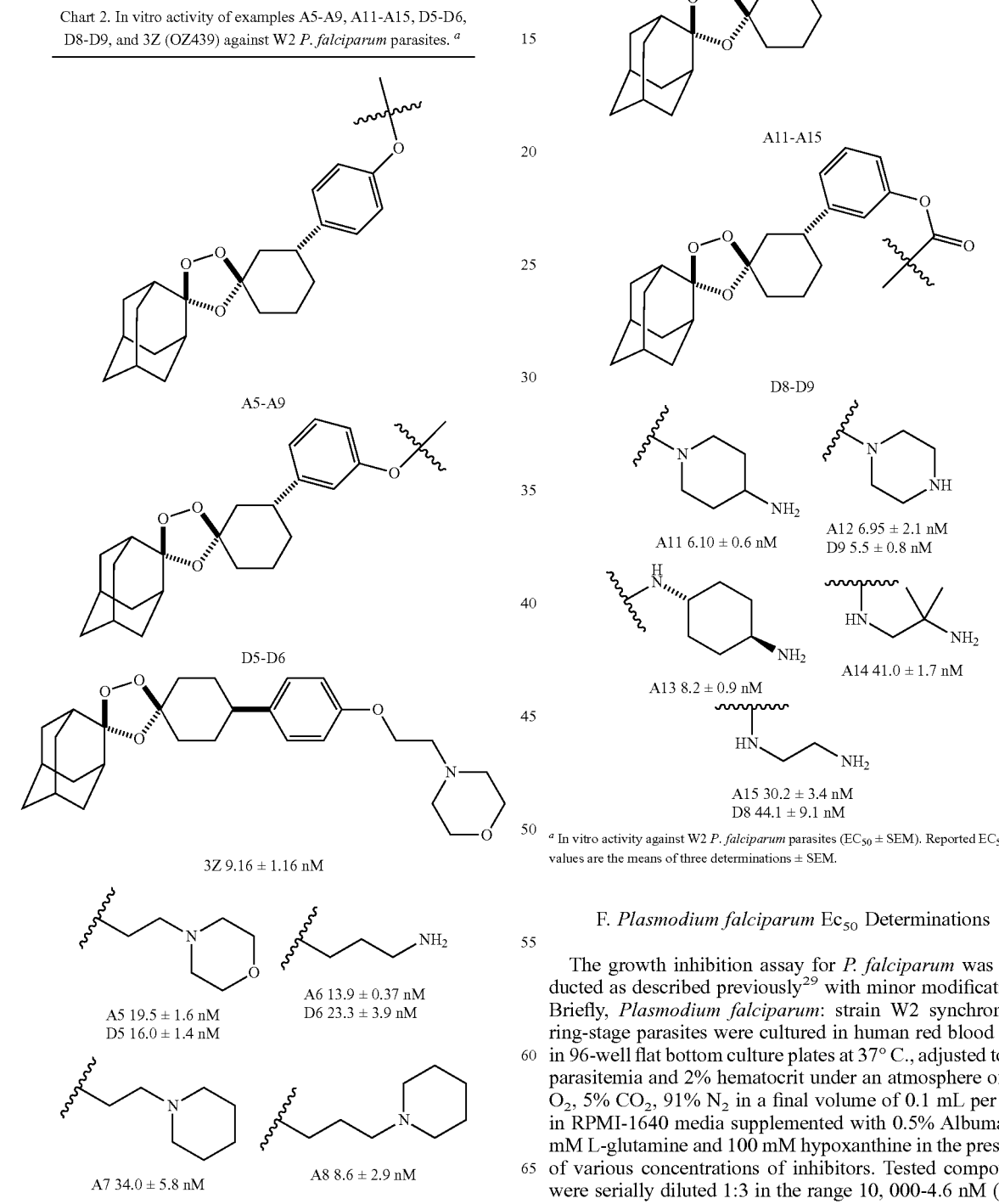

[a] In vitro activity against W2 *P. falciparum* parasites (EC$_{50}$ ± SEM). Reported EC$_{50}$ values are the means of three determinations ± SEM.

F. *Plasmodium falciparum* Ec$_{50}$ Determinations

The growth inhibition assay for *P. falciparum* was conducted as described previously[29] with minor modifications. Briefly, *Plasmodium falciparum*: strain W2 synchronized ring-stage parasites were cultured in human red blood cells in 96-well flat bottom culture plates at 37° C., adjusted to 1% parasitemia and 2% hematocrit under an atmosphere of 3% O$_2$, 5% CO$_2$, 91% N$_2$ in a final volume of 0.1 mL per well in RPMI-1640 media supplemented with 0.5% Albumax, 2 mM L-glutamine and 100 mM hypoxanthine in the presence of various concentrations of inhibitors. Tested compounds were serially diluted 1:3 in the range 10, 000-4.6 nM (or 1, 000-0.006 nM for more potent analogs), with a maximum DMSO concentration of 0.1%. Following 48 hours of incubation, the cells were fixed by adding 0.1 ml of 2% formaldehyde in phosphate buffered saline, pH=7.4 (PBS). Parasite growth was evaluated by flow cytometry on a FACsort (Becton Dickinson) equipped with AMS-1 loader (Cytek Development) after staining with 1 nM of the DNA dye YOYO-1 (Molecular Probes) in 100 mM $NH_4Cl$, 0.1% Triton x-100 in 0.8% NaCl. Parasitemias were determined from dot plots (forward scatter vs. fluorescence) using CELLQUEST software (Becton Dickinson). $EC_{50}$ values for growth inhibition were determined from plots of percentage control parasitemia over inhibitor concentration using GraphPad Prism software.

G. Plasmodium berghei Mouse Malaria Model

Female Swiss Webster Mice (average of 20 g body weight) were infected intraperitoneally with $10^6$ Plasmodium berghei-infected erythrocytes collected from a previously infected mouse. Beginning 1 hour after inoculation the mice were treated once daily by oral gavage for 1-4 days with 100 μL of solution of test compound formulated in 10% DMSO, 50% PEG 400, 8% 2-HP beta-cyclodextrin in water. There were five mice in each test arm. Infections were monitored by daily microscopic evaluation of Giemsa-stained blood smears starting on day seven. Parasitemia were determined by counting the number of infected and uninfected erythrocytes. Body weight was measured over the course of the treatment. Mice were euthanized when parasitemia exceeded 50% or when weight loss of more than 15% occurred. Animal survival and morbidity were closely monitored for up to 30 days post-infection when the experiment was terminated. In some cases survival is expressed as a $PD_{100}$ or $PD_{50}$, the dose that produces respectively 100% or 50% cures in treated animals at 30 days post infection.

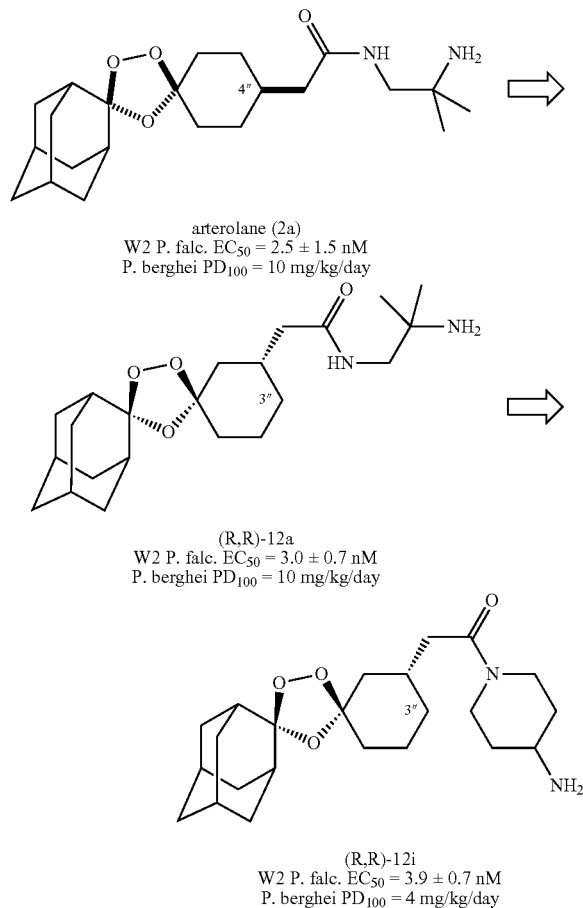

arterolane (2a)
W2 P. falc. $EC_{50}$ = 2.5 ± 1.5 nM
P. berghei $PD_{100}$ = 10 mg/kg/day (R,R)-12a
W2 P. falc. $EC_{50}$ = 3.0 ± 0.7 nM
P. berghei $PD_{100}$ = 10 mg/kg/day (R,R)-12i
W2 P. falc. $EC_{50}$ = 3.9 ± 0.7 nM
P. berghei $PD_{100}$ = 4 mg/kg/day

H. Formulation of OZ439 Regioisomers and Observed Solubility

Based off the strong in vitro data that was obtained for the 3' regioisomer of OZ439, which was found to possess potency comparable to that of the parent 4' analog (19.5±1.6 nM vs. 7.9±0.2 nM against P. falciparum), the new analog was analyzed to determine if it possessed better in vivo efficacy. As such, we chose to screen the two regioisomers in a head-to-head study against P. berghei infected mice. In order to carry out this experiment, both compounds first needed to be formulated in a manner that would allow for treatment of the mice by oral gavage. We chose to employ the same formulation that our group has previously utilized successfully (most recently for the 3' regioisomers of arterolane), which is comprised of 10% DMSO, 40% of a 20% solution of 2-hydroxypropyl-β-cyclodextrin in water, and 50% PEG400.

The way in which the formulations were prepared involved preparing a stock solution of the compound in DMSO, and then performing dilutions from this stock such that the requisite final concentration was obtained after the addition of all the necessary formulation components. Practically speaking, this was accomplished by partitioning a portion of each compound into separate 4 mL vials, and then placing these vials on the lyophilizer to ensure the compounds were completely dry. This led to a vial containing 49.5 mg of the 3' OZ439 regioisomer, while the other held 51.0 mg of OZ439. DMSO was then added to these vials, such that a final concentration of 160 mg/mL (341 mM) was achieved in each. This entailed adding 309.4 μL of DMSO to the vial with the 3' OZ439 regioisomer, whereas 318.8 μL of DMSO was added to the vial containing actual OZ439. In the past, an issue has not arisen when doing this. However, this time, a major problem presented itself. The problem was not with the newly developed 3' regioisomer of OZ439, but with OZ439 itself. After addition of DMSO to the vials, the majority of the 3' regioisomer dissolved, whereas none of the actual OZ439 did. In an attempt to assist with dissolving the material, the two vials were then placed a water bath set to 42° C. Within 3 minutes, the 3' regioisomer had completely dissolved, and the material stayed in solution when allowed to cool back down to room temperature. However, after 30 mins at this temperature, the actual OZ439 did not dissolve. At this point, it was then placed in a 55° C. water bath for 60 minutes, which did not facilitate dissolution of this material. The vial was then placed in a bath sonicator for 60 minutes, ultimately to no avail as this did enable dissolution of the material. Essentially, the vial appeared to possess a heterogeneous solution, where the bright white compound appeared to be suspended in the DMSO (FIG. 3 showing the two compounds in DMSO at a concentration of 160 mg/mL, where only the 3' regioisomer of OZ439 had completely dissolved). At this point, the vial was then placed on the Hi-Vac to remove the DMSO. Once dry, the material was partitioned again in an attempt to get the material to dissolve at a lower concentration.

Returning to the 3' regioisomer, the actual doses were then successfully prepared according to the following instructions. The necessary amount of DMSO solution was removed from the vial and added to a new vial. For the 80 mg/kg dose, no additional DMSO was needed to be added to the vial. For all of the other doses, an additional amount of DMSO was added such that the final concentration of DMSO in the vial would be 10%. After this addition, the remaining 90% of the volume of dose, which is the aqueous portion (a solution of PEG400 and aqueous 2-hydroxypropyl-β-cyclodextrin that had been prepared separately) of the formulation, was added to the DMSO solution. Upon adding the aqueous portion to the 80, 40, and 30 mg/kg doses, a white solution formed (resembled more of an emulsion then a heterogeneous solution). The vials were then placed in a bath sonicator in an attempt to redissolve the material. Within a few minutes, the material in the 40 and 30 mg/kg vials had completely dissolved, but it took nearly 60 minutes to get the material in the 80 mg/kg doses to fully redissolve. However, even after storing the material at −20° C., the compound was not observed to crash out of the formulation again.

For the second attempt at preparing the necessary formulation for the actual OZ439, the material was partitioned such that when the dilutions were performed, the highest concentration that would be prepared from the stock solution would be the 10 mg/kg doses. As such, the 80, 40, and 30 mg/kg doses were all prepared directly by partitioning the requisite amounts into separate vials and then adding the necessary amounts of the formulation to reach the desired concentration. For the vial that was employed in aliquoting from to prepare the other concentrations, it contained 15.5 mg of OZ439. DMSO (775 µL) was then added to this vial, to yield a final concentration of 20 mg/mL (55 mM). Now, even though this solution was 8 times less concentrated than the first attempt, the material still did not readily dissolve. Only after allowing the vial to warm in a 55° C. water bath for 30 minutes did the material finally dissolve. At this point, the material was brought back to the bench to aliquot the material en route to preparing the remaining doses. However, upon being removed from the bath, the compound began to crash out as it cooled to room temperature. For this reason, the vial was heated with a heat gun for about 10-15 seconds to get the material to dissolve fully once again. Once dissolved, the necessary aliquots were all removed as quickly as possible, and placed in separate vials, and subsequently diluted with additional DMSO if necessary to reach the necessary 10% DMSO in the final formulation. Not surprisingly, attempting to dissolve the higher concentration doses in DMSO was unsuccessful. It was then thought that perhaps adding the aqueous solution (the remained of the formulation) would help dissolve the material due to the presence of the cyclodextrin and PEG400 in the solution. As such, the corresponding aqueous portion of the formulation was then added to each vial. However, this did not enable the material to dissolve. Instead, the formulated material appeared to exist completely as heterogeneous solutions, where bright white solid material was dispersed throughout the solution. Attempting to dissolve the material by placing the vials in a bath sonicator for 60 minutes, followed by heating at 55° C. for 60 minutes, and even further heating the material with a heat gun for 25 seconds, all proved unsuccessful in getting the material to dissolve. Thus, the 80, 40, and 30 mg/kg doses were delivered to the mouse as a suspension.

I. References (1) Posner, G. H.; Oh, C. H. *A Regiospecifically Oxygen-18 Labeled 1, 2, 4-Trioxane: A Simple Chemical Model System To Probe the Mechanism(s) for the Antimalarial Activity of Artemisinin (Qinghaosu). J. Am. Chem. Soc.* 1992, 114, 8328-8329.

(2) Posner, G. H.; Oh, C. H.; Wang, D.; Gerena, L.; Milhous, W. K.; Meshnick, S. R.; Asawamahasadka, W. *Mechanism-Based Design, Synthesis and in Vitro Antimalarial Testing of New 4-Methylated Trioxanes Structurally Related to Artemisinin: The Importance of a Carbon-Centered Radical for Antimalarial Activity. J. Med. Chem.* 1994, 37, 1256-1258.

(3) Vennerstrom, J. L.; Arbe-Barnes, S.; Brun, R.; Charman, S. A.; Chiu, F. C. K.; Chollet, J.; Dong, Y.; Dorn, A.; Hunziker, D.; Matile, H.; McIntosh, K.; Padmanilayam, M; Santo Tomas, J.; Scheurer, C.; Scorneaux, B.; Tang, Y.; Urwyler, H.; Wittlin, S.; Charman, W. N. *Identification of an Antimalarial Synthetic Trioxolane Drug Development Candidate. Nature* 2004, 430, 900-904.

(4) Charman, S. A.; Arbe-Barnes, S.; Bathurst, I. C.; Brun, R.; Campbell, M.; Charman, W. N.; Chiu, F. C. K.; Chollet, J.; Craft, J. C.; Creek, D. J.; Dong, Y.; Matile, H.; Maurer, M.; Morizzi, J.; Nguyen, T.; Papastogiannidis, P.; Scheurer, C.; Shackleford, D. M; Sriraghavan, K.; Stingelin, L.; Tang, Y.; Urwyler, H.; Wang, X; White, K. L.; Wittlin, S.; Zhou, L.; Vennerstrom, J. L. *Synthetic Ozonide Drug Candidate OZ439 Offers New Hope for a Single-Dose Cure of Uncomplicated Malaria. Proc. Natl. Acad. Sci. U.S.A* 2011, 108, 4400-4405.

(5) Moehrle, J. J.; Duparc, S.; Siethoff C.; van Giersbergen, P. L. M.; Craft, J. C.; Arbe-Barnes, S.; Charman, S. A.; Gutierrez, M.; Wittlin, S.; Vennerstrom, J. L. *First-in-Man Safety and Pharmacokinetics of Synthetic Ozonide OZ439 Demonstrates an Improved Exposure Profile Relative to Other Peroxide Antimalarials. Br. J. Clin. Pharmacol.* 2013, 75, 524-537.

(6) Phyo, A. P.; Jittamala, P.; Nosten, F. H.; Pukrittayakamee, S.; Imwong, M.; White, N. J.; Duparc, S.; Macintyre, F.; Baker, M.; Möhrle, J. J. *Antimalarial Activity of Artefenomel (OZ439), a Novel Synthetic Antimalarial Endoperoxide, in Patients with Plasmodium Falciparum and Plasmodium Vivax Malaria: An Open-Label Phase 2 Trial. Lancet Infect. Dis.* 2016, 16, 61-69.

(7) Ismail, H. M.; Barton, V. E.; Panchana, M.; Charoensutthivarakul, S.; Biagini, G. A.; Ward, S. A.; O'Neill, P. M. *A Click Chemistry-Based Proteomic Approach Reveals That 1,2,4-Trioxolane and Artemisinin Antimalarials Share a Common Protein Alkylation Profile. Angew. Chem., Int. Ed.* 2016, 128, 6511-6515.

(8) Ismail, H. M; Barton, V.; Phanchana, M; Charoensutthivarakul, S.; Wong, M. H. L.; Hemingway, J.; Biagini, G. A.; O'Neill, P. M; Ward, S. A. *Artemisinin Activity-Based Probes Identify Multiple Molecular Targets within the Asexual Stage of the Malaria Parasites Plasmodium Falciparum 3D7. Proc. Natl. Acad. Sci.* 2016, 113, 2080-2085.

(9) Wang, J.; Zhang, C.-J.; Chia, W. N.; Loh, C. C. Y.; Li, Z.; Lee, Y. M; He, Y.; Yuan, L.-X; Lim, T. K.; Liu, M; Liew, C. X; Lee, Y. Q.; Zhang, J.; Lu, N.; Lim, C. T; Hua, Z.-C.; Liu, B.; Shen, H.-M; Tan, K. S. W.; Lin, Q. *Haem-Activated Promiscuous Targeting of Artemisinin in Plasmodium falciparum. Nat. Commun.* 2015, 6, 10111.

(10) Amaratunga, C.; Lim, P.; Suon, S.; Sreng, S.; Mao, S.; Sopha, C.; Sam, B.; Dek, D.; Try, V.; Amato, R.; Blessborn, D.; Song, L.; Tullo, G. S.; Fay, M. P.; Anderson, J. M; Tarning, J.; Fairhurst, R. M. *Dihydroartemisinin-Piperaquine Resistance in Plasmodium falciparum Malaria in Cambodia: A Multisite Prospective Cohort Study. Lancet Infect. Dis.* 2016, 16, 357-365.

(11) Ariey, F.; Witkowski, B.; Amaratunga, C.; Beghain, J.; Langlois, A.-C.; Khim, N.; Kim, S.; Duru, V.; Bouchier, C.; Ma, L.; Lim, P.; Leang, R.; Duong, S.; Sreng, S.; Suon, S.; Chuor, C. M.; Bout, D. M; Menard, S.; Rogers, W. O.; Genton, B.; Fandeur, T.; Miotto, O.; Ringwald, P.; Le Bras, J.; Berry, A.; Barale, J.-C.; Fairhurst, R. M; Benoit-Vical, F.; Mercereau-Puijalon, O.; Ménard, D. *A Molecu-* lar Marker of Artemisinin-Resistant Plasmodium falciparum Malaria. Nature 2014, 505, 50-55.

(12) Dogovski, C.; Xie, S. C.; Burgio, G.; Bridgford, J.; Mok, S.; McCaw, J. M; Chotivanich, K.; Kenny, S.; Gnädig, N.; Straimer, J.; Bozdech, Z.; Fidock, D. A.; Simpson, J. A.; Dondorp, A. M; Foote, S.; Klonis, N.; Tilley, L. *Targeting the Cell Stress Response of Plasmodium falciparum to Overcome Artemisinin Resistance*. PLoS Biol. 2015, 13, e1002132.

(13) Yang, T.; Xie, S. C.; Cao, P.; Giannangelo, C.; McCaw, J.; Creek, D. J.; Charman, S. A.; Klonis, N.; Tilley, L. *Comparison of the Exposure Time Dependence of the Activities of Synthetic Ozonide Antimalarials and Dihydroartemisinin against K13 Wild-Type and Mutant Plasmodium falciparum Strains*. Antimicrob. Agents Chemother. 2016, 60, 4501-4510.

(14) Straimer, J.; Gnadig, N. F.; Witkowski, B.; Amaratunga, C.; Duru, V.; Ramadani, A. P.; Dacheux, M.; Khim, N.; Zhang, L.; Lamn, S.; Gregory, P. D.; Urnov, F. D.; Mercereau-Puijalon, O.; Benoit-Vical, F.; Fairhurst, R. M.; Ménard, D.; Fidock, D. A. *K13-Propeller Mutations Confer Artemisinin Resistance in Plasmodium falciparum Clinical Isolates*. Science 2015, 347, 428-431.

(15) Creek, D.; Charman, W.; Chiu, F. C. K.; Prankerd, R. J.; McCullough, K. J.; Dong, Y.; Vennerstrom, J. L.; Charman, S. A. *Iron-Mediated Degradation Kinetics of Substituted Dispiro-1,2,4-Trioxolane Antimalarials*. J. Pharm. Sci. 2007, 96, 2945-2956.

(16) Tang, Y.; Dong, Y.; Wang, X; Sriraghavan, K.; Wood, J. K.; Vennerstrom, J. L. *Dispiro-1,2,4-Trioxane Analogues of a Prototype Dispiro-1,2,4-Trioxolane: Mechanistic Comparators for Artemisinin in the Context of Reaction Pathways with Iron(II)*. J. Org. Chem. 2005, 70, 5103-5110.

(17) Zhao, Q.; Vargas, M; Dong, Y.; Zhou, L.; Wang, X; Sriraghavan, K.; Keiser, J.; Vennerstrom, J. L. *Structure-Activity Relationship of an Ozonide Carboxylic Acid (OZ78) Against Fasciola hepatica*. J. Med. Chem. 2010, 53, 4223-4233.

(18) Vennerstrom, J. L.; Dong, Y.; Chollet, J.; Matile, H.; Padmanilayam, M.; Tang, Y.; Charman, W. N. Spiro and dispiro 1,2,4-trioxolane antimalarials. U.S. Patent 2004 0039008 A1, Feb. 26, 2004.

(19) Yadav, G. C.; Dorwal, H. N.; Valavala, S.; Sharma, V. K. A process for the preparation of spiro and dispiro 1,2,4-trioxolane antimalarials. PCT WO 2007 138435 A2, Dec. 6, 2007.

(20) Fontaine, S. D.; Dipasquale, A. G.; Renslo, A. R. *Efficient and Stereocontrolled Synthesis of 1,2,4-Trioxolanes Useful for Ferrous Iron-Dependent Drug Delivery*. Org. Lett. 2014, 16, 5776-5779.

(21) Shibasaki, M; Sasai, H.; Arai, T. *Asymmetric Catalysis with Heterobimetallic Compounds*. Angew. Chem., Int. Ed. 1997, 36, 1236-1256.

(22) Shimizu, S.; Ohori, K.; Arai, T; Sasai, H.; Shibasaki, M. *A Catalytic Asymmetric Synthesis of Tubifolidine*. J. Org. Chem. 1998, 63, 7547-7551.

(23) Xu, Y.; Ohori, K.; Ohshima, T.; Shibasaki, M. A. *A Practical Large-Scale Synthesis of Enantiomerically Pure 3-[Bis(methoxycarbonyl)methyl]cyclohexanone via Catalytic Asymmetric Michael Reaction*. Tetrahedron 2002, 58, 2585-2588.

(24) Tzvetkov, N. T.; Schmoldt, P.; Neumann, B.; Stammler, H.-G.; Mattay, J. *Synthesis of Optically Active (1R, 4S, 6S)-6-hydroxybicyclo[2.2.2]octan-2-One*. Tetrahedron: Asymmetry 2006, 17, 993-998.

(25) Riguet, E. *Novel Guanidinyl Pyrrolidine Salt-Based Bifunctional Organocatalysts: Application in Asymmetric Conjugate Addition of Malonates to Enones*. Tetrahedron Lett. 2009, 50, 4283-4285.

(26) Wascholowski, V.; Knudsen, K. R.; Mitchell, C. E. T.; Ley, S. V. *A General Organocatalytic Enantioselective Malonate Addition to α,β-Unsaturated Enones*. Chem. Eur. J. 2008, 14, 6155-6165.

(27) Peters, W. *In Chemotherapy and Drug Resistance in Malaria*; Academic Press, Inc.: New York, 1987; pp 145-273.

(28) Vennerstrom, J. L.; Dong, Y.; Charman, S. A.; Wittlin, S.; Chollet, J.; Creek, D. J.; Wang, X; Sriraghavan, K.; Zhou, L.; Matile, H.; Charman, W. N. Dispiro 1,2,4-trioxolane antimalarials. PCT WO 2009/058859 A2, May 7, 2009.

(29) Sijwali, P. S.; Rosenthal, P. J. *Gene Disruption Confirms a Critical Role for the Cysteine Protease Falcipain-2 in Hemoglobin Hydrolysis by Plasmodium falciparum*. Proc. Natl. Acad. Sci. 2004, 101, 4384-4389.

J. Embodiments

Embodiment P1

A compound having the formula:

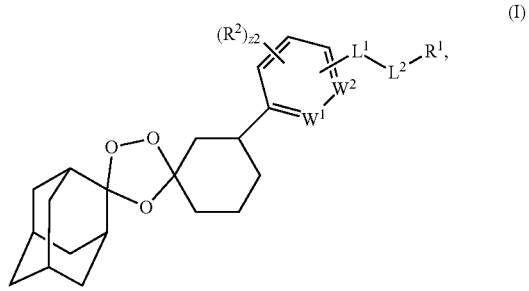

(I)

wherein
$W^1$ and $W^2$ are independently $=N-$, $=C(R^2)-$, or $=CH-$; $L^1$ is a bond, $-O-$, $-NH-$, $-OC(O)-$, $-C(O)O-$, $-NHC(O)-$, $-C(O)NH-$, $-OC(O)O-$, $-OC(O)NH-$, $-NHC(O)O-$, $-NHC(O)NH-$, $-S-$; $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z2 is an integer from 0 to 4; each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; each X, $X^1$, and $X^2$ is independently —F, —Cl, —Br, or —I; n1 is independently an integer from 0 to 4; and m1 and v1 are independently 1 or 2.

Embodiment P2

The compound of embodiment P1, having the formula:

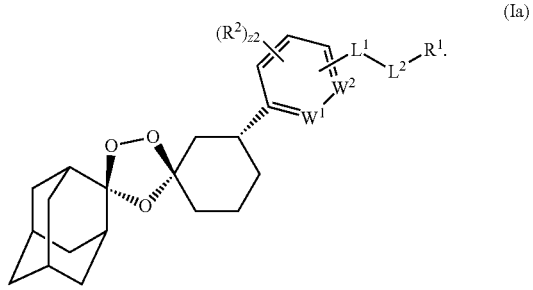

(Ia)

Embodiment P3

The compound of one of embodiments P1 to P2, wherein $W^1$ is =N—.

Embodiment P4

The compound of one of embodiments P1 to P2, wherein $W^1$ is =CH—.

Embodiment P5

The compound of one of embodiments P1 to P4, wherein $W^2$ is =N—.

Embodiment P6

The compound of one of embodiments P1 to P4, wherein $W^2$ is =CH—.

Embodiment P7

The compound of one of embodiments P1 to P6, wherein $R^2$ is independently unsubstituted $C_1$-$C_3$ alkyl.

Embodiment P8

The compound of one of embodiments P1 to P7, wherein z2 is 0.

Embodiment P9

The compound of one of embodiments P1 to P8, wherein $L^1$ is —O—.

Embodiment P10

The compound of one of embodiments P1 to P8, wherein $L^1$ is —OC(O)—.

Embodiment P11

The compound of one of embodiments P1 to P8, wherein $L^1$ is —OC(O)NH—.

Embodiment P12

The compound of one of embodiments P1 to P8, wherein $L^1$ is a bond.

Embodiment P13

The compound of one of embodiments P1 to P12, wherein $L^2$ is a substituted or unsubstituted $C_1$-$C_4$ alkylene.

Embodiment P14

The compound of one of embodiments P1 to P12, wherein $L^2$ is an unsubstituted $C_1$-$C_4$ alkylene.

Embodiment P15

The compound of one of embodiments P1 to P12, wherein $L^2$ is a substituted or unsubstituted $C_4$-$C_6$ cycloalkylene.

Embodiment P16

The compound of one of embodiments P1 to P12, wherein $L^2$ is a bond.

Embodiment P17

The compound of one of embodiments P1 to P16, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, or $R^{20}$-substituted or unsubstituted 5 to 7 membered heterocycloalkyl; $R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

Embodiment P18

The compound of one of embodiments P1 to P16, wherein $R^1$ is —$NR^{1A}R^{1B}$, —$C(O)NR^{1A}R^{1B}$, or $R^{20}$-substituted or unsubstituted 6 to 7 membered heterocycloalkyl; $R^{20}$ is independently oxo, —OH, —S(O)$_2$CH$_3$; and each $R^{1A}$ and $R^{1B}$ is independently hydrogen, OH-substituted C$_1$-C$_4$ alkyl, NH$_2$-substituted C$_1$-C$_4$ alkyl, or unsubstituted 5 to 6 membered heterocycloalkyl.
Embodiment P19
The compound of embodiment P1 having the formula:
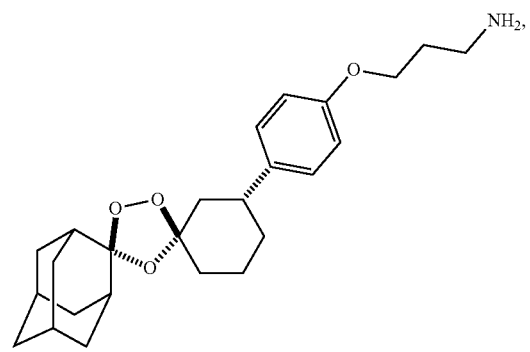
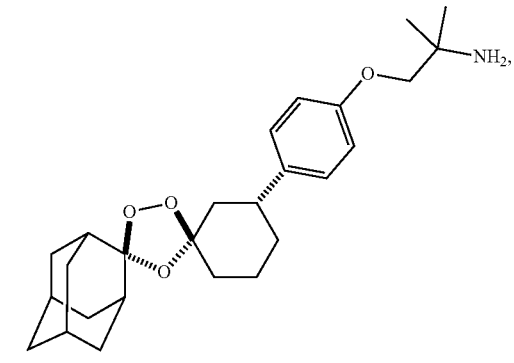
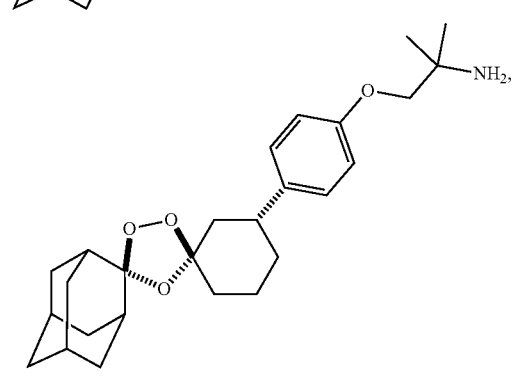
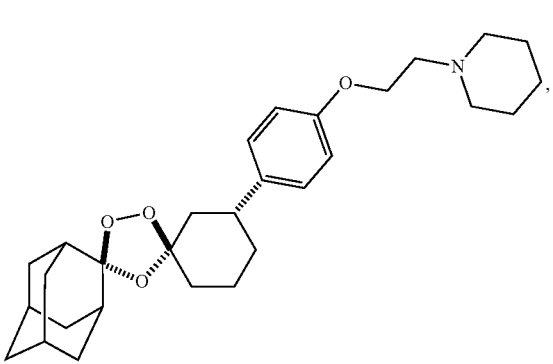
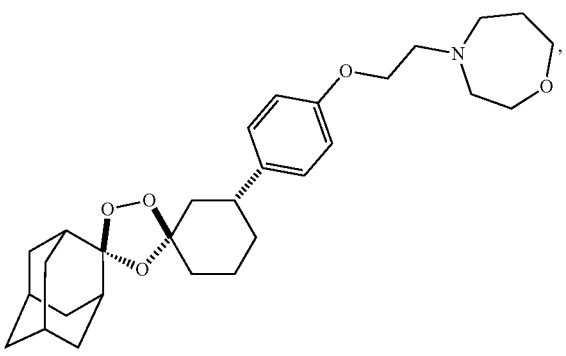
-continued
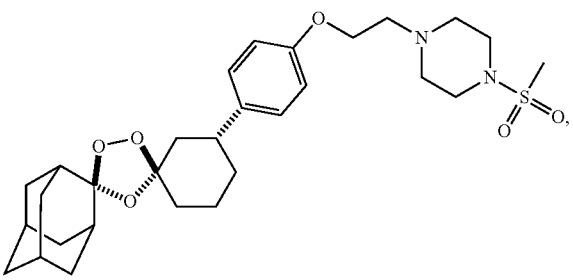
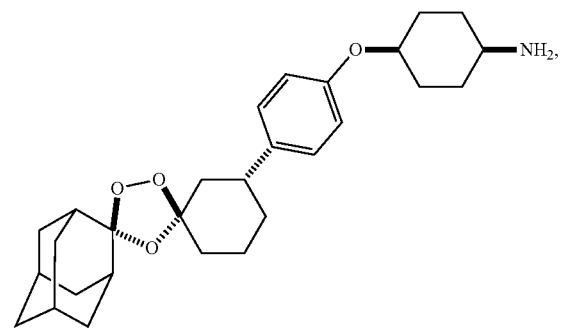
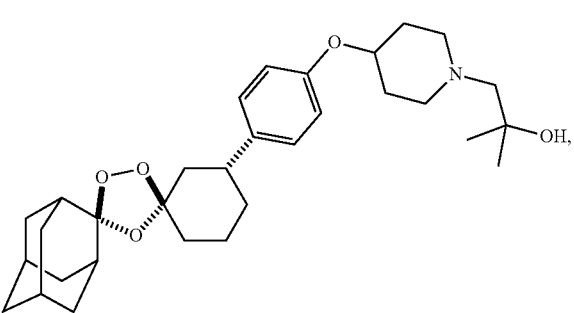
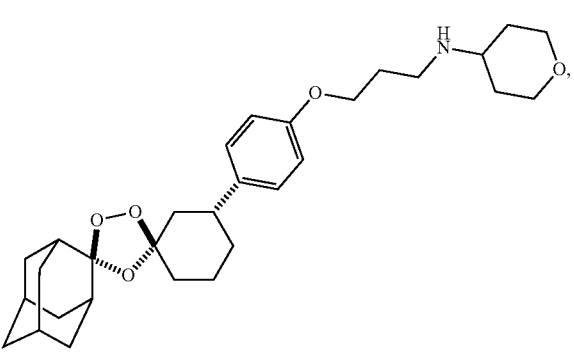

217
-continued
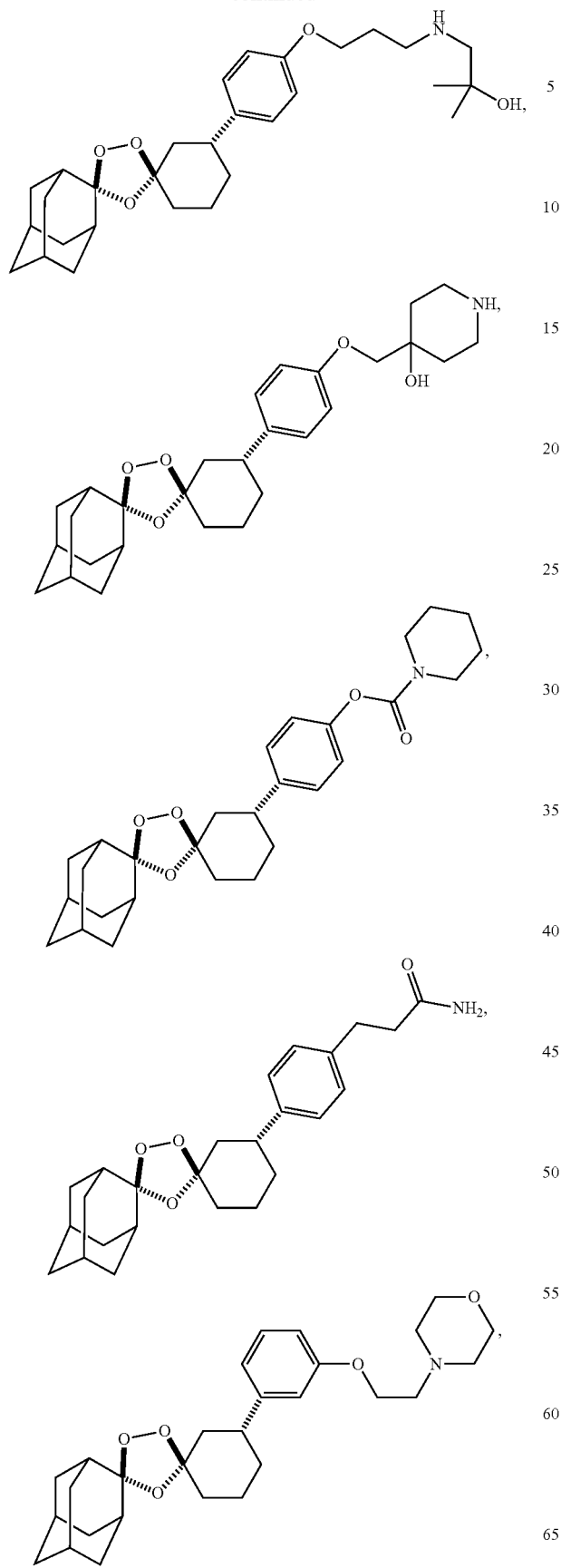
218
-continued
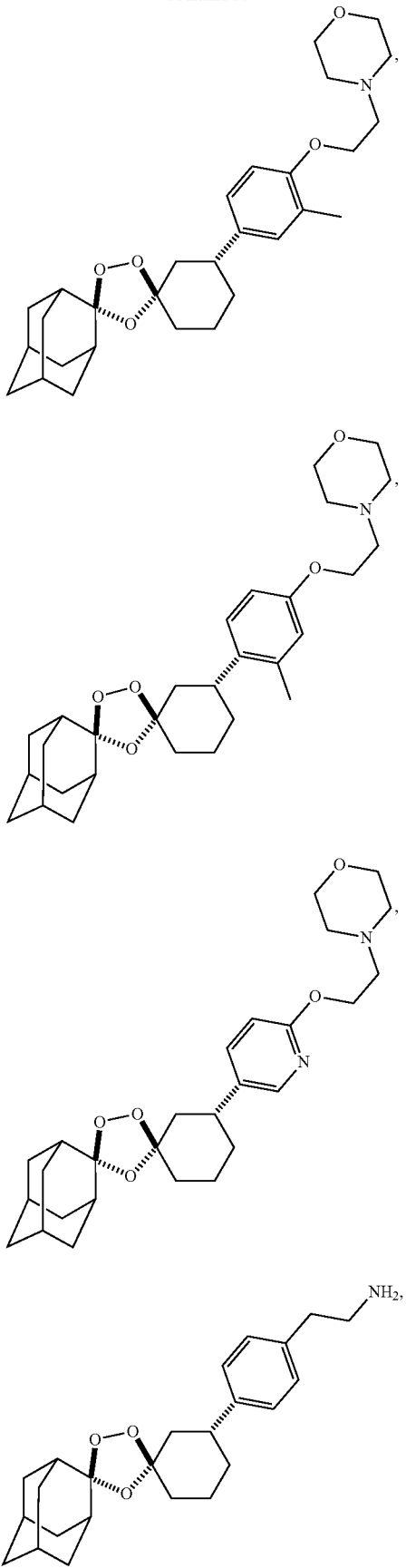

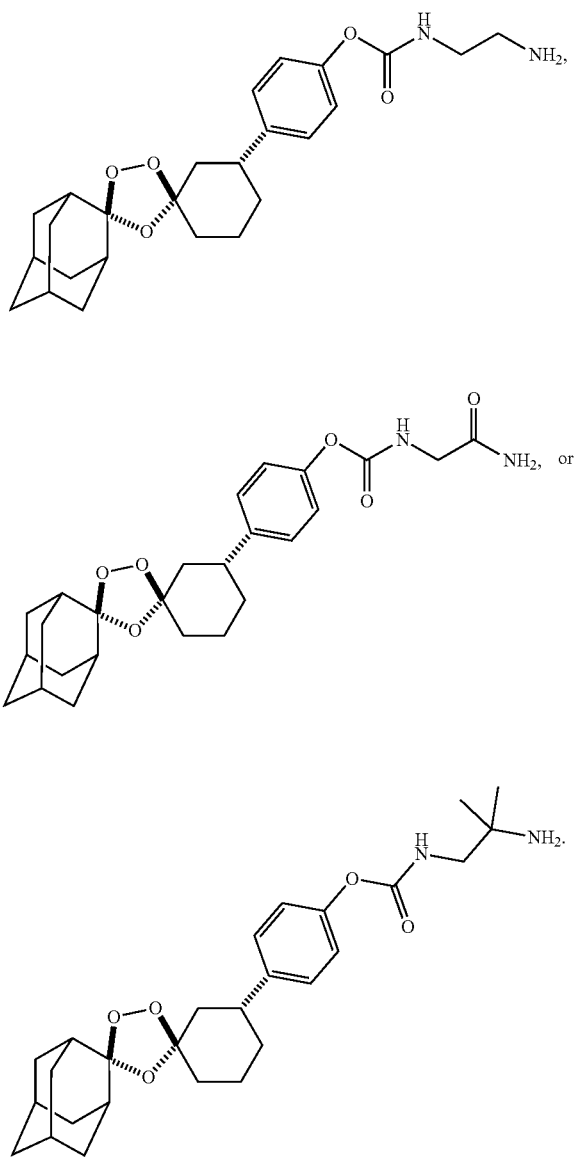

Embodiment P20

The compound of embodiment P1 having the formula:

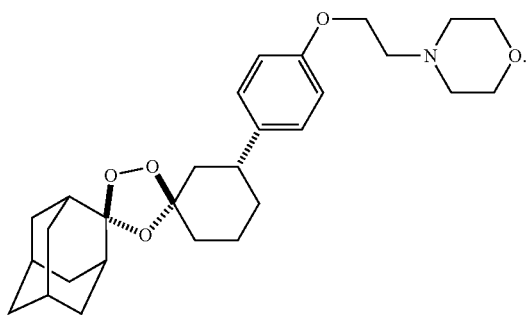

Embodiment P21

A compound having the formula:

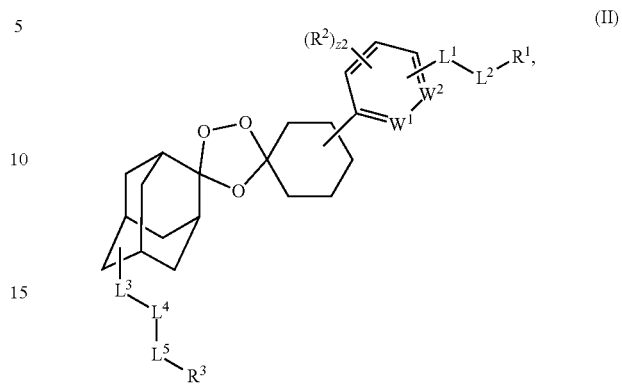

wherein
W$^1$ and W$^2$ are independently =N—, =C(R$^2$)—, or =CH—. L$^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, or —S—. L$^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^1$ is hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O) OR$^{1C}$, —NR$^{1A}$OR$^{1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is independently halogen, —CX$^2_3$, —CHX$^2_2$, —CH$_2$X$^2$, —OCX$^2_3$, —OCH$_2$X$^2$, —OCHX$^2_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z2 is an integer from 0 to 4; each R$^{1A}$, R$^{1B}$, R$^{1C}$, and R$^{1D}$ is independently hydrogen, —CX$_3$, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; each X, X$^1$, and X$^2$ is independently —F, —Cl, —Br, or —I; n1 is independently an integer from 0 to 4; m1 and v1 are independently 1 or 2; L$^3$, L$^4$, and L$^5$ are independently a bond, —O—, —NH—, —OC(O)—, —C(O)O—, —NHC(O)—, —C(O) NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. And R$^3$ is a detectable moiety.

Embodiment P22

The compound of embodiment P21 having the formula:

(IIa)

Embodiment P23

The compound of embodiment P21 having the formula:

(IIb)

Embodiment P24

The compound of embodiment P21 having the formula:

(IIf)

Embodiment P25

The compound of embodiment P21 having the formula:

(IIm)

Embodiment P26

The compound of embodiment P21 having the formula:

(IIi)

Embodiment P27

The compound of embodiment P21 having the formula:

(IIp)

Embodiment P28

The compound of one of embodiments P22 to P27, wherein $W^1$ is =N—.

Embodiment P29

The compound of one of embodiments P22 to P27, wherein $W^1$ is =CH—.

Embodiment P30

The compound of one of embodiments P22 to P29, wherein $W^2$ is =N—.

Embodiment P31

The compound of one of embodiments P22 to P29, wherein $W^2$ is =CH—.

Embodiment P32

The compound of one of embodiments P22 to P31, wherein $R^2$ is independently unsubstituted $C_1$-$C_3$ alkyl.

Embodiment P33

The compound of one of embodiments P22 to P32, wherein z2 is 0.

Embodiment P34

The compound of one of embodiments P22 to P33, wherein $L^1$ is —O—.

Embodiment P35

The compound of one of embodiments P22 to P33, wherein $L^1$ is —OC(O)—.

Embodiment P36

The compound of one of embodiments P22 to P33, wherein $L^1$ is —OC(O)NH—.

Embodiment P37

The compound of one of embodiments P22 to P33, wherein $L^1$ is a bond.

Embodiment P38

The compound of one of embodiments P22 to 3P7, wherein $L^2$ is a substituted or unsubstituted $C_1$-$C_4$ alkylene.

Embodiment P39

The compound of one of embodiments P22 to P37, wherein $L^2$ is an unsubstituted $C_1$-$C_4$ alkylene.

Embodiment P40

The compound of one of embodiments P22 to P37, wherein $L^2$ is a substituted or unsubstituted $C_4$-$C_6$ cycloalkylene.

Embodiment P41

The compound of one of embodiments P22 to 3P7, wherein $L^2$ is a bond.

Embodiment P42

The compound of one of embodiments P22 to P41, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, or $R^{20}$-substituted or unsubstituted 5 to 7 membered heterocycloalkyl; $R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

Embodiment P43

The compound of one of embodiments P22 to P41, wherein $R^1$ is —$NR^{1A}R^{1B}$, —$C(O)NR^{1A}R^{1B}$, or $R^{20}$-substituted or unsubstituted 6 to 7 membered heterocycloalkyl; $R^{20}$ is independently oxo, —OH, —$S(O)_2CH_3$; and each $R^{1A}$ and $R^{1B}$ is independently hydrogen, OH-substituted $C_1$-$C_4$ alkyl, $NH_2$-substituted $C_1$-$C_4$ alkyl, or unsubstituted 5 to 6 membered heterocycloalkyl.

Embodiment P44

The compound of one of embodiments P22 to P43, wherein -$L^3$-$L^4$-$L^5$- is —$C(O)NHCH_2CH_2CH_2NHC(O)Ph$-.

Embodiment P45

The compound of one of embodiments P22 to P44, wherein $R^3$ is a radionuclide.

Embodiment P46

The compound of one of embodiments P22 to P44, wherein $R^3$ is a positron emitting radionuclide.

Embodiment P47

The compound of one of embodiments P22 to P44, wherein $R^3$ is carbon-11, nitrogen-13, oxygen-15, or fluorine-18.

Embodiment P48

The compound of one of embodiments P22 to P44, wherein $R^3$ is fluorine-18 or fluorine-19.

Embodiment P49

The compound of one of embodiments P22 to P44, wherein $R^3$ is fluorine-18.

Embodiment P50

The compound of one of embodiments P22 to P44, wherein $R^3$ is gallium-68, zirconium-89, rubidium-82, or iodine-124.

Embodiment P51

The compound of one of embodiments P45 to P49 having the formula:

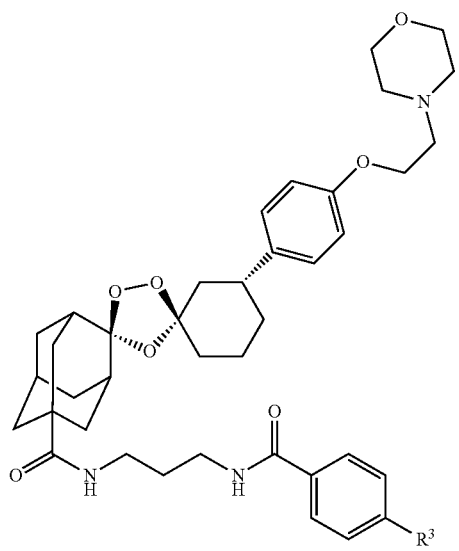

Embodiment P52

The compound of one of embodiments P45 to P49 having the formula:

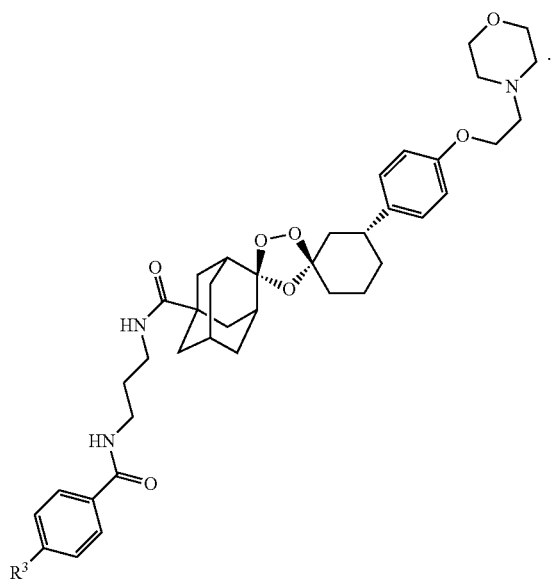

Embodiment P53

The compound of one of embodiments P45 to P49 having the formula:

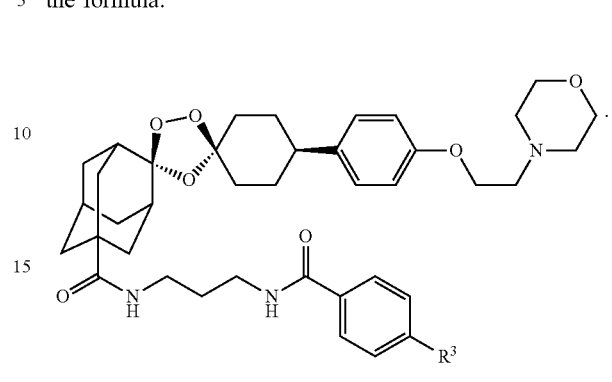

Embodiment P54

The compound of one of embodiments P45 to P49 having the formula:

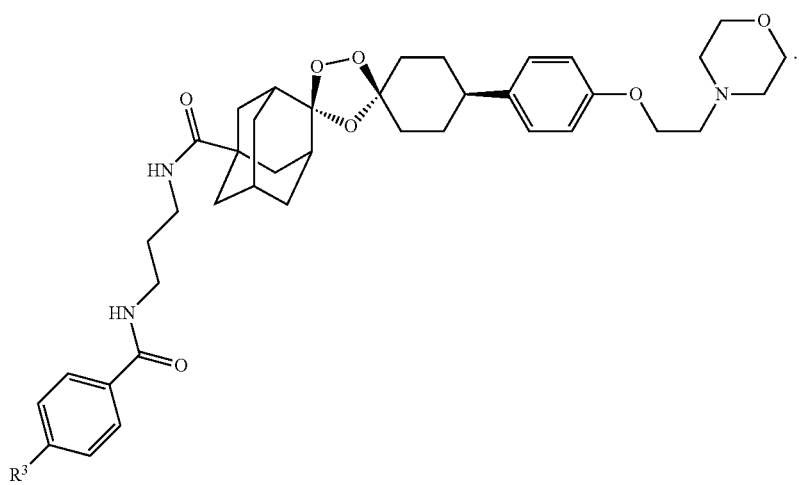

Embodiment P55

A pharmaceutical composition comprising a pharmaceutically acceptable excipient and a compound of one of embodiments P1 to P54.

Embodiment P56

A method of treating a disease in a patient in need of such treatment, said method comprising administering a therapeutically effective amount of a compound of one of claims one of embodiments P1 to P54 to said patient.

Embodiment P57

The method of embodiment P56, wherein the disease is associated with a cell or organism having an increased $Fe^{II}$ level compared to a standard control.

Embodiment P58

The method of embodiment P56, wherein the disease is cancer.

Embodiment P59

The method of embodiment P56, wherein the disease is malaria.

Embodiment P60

The method of embodiment P56, wherein the disease is a parasitic disease.

Embodiment P61

A method of detecting a disease associated with a cell or organism having an increased $Fe^{II}$ level compared to a standard control, in a subject, said method comprising administering an effective amount of a compound of one of embodiments P22 to P54 to the subject and measuring the level of the compound in the subject.

Embodiment P62

The method of embodiment P61, comprising measuring the level of compound in the subject using positron emission tomography.

Embodiment P63

The method of one of embodiments P61 to P62, wherein the disease is cancer, malaria, or an inflammatory disease.

K. Additional Embodiments

Embodiment 1

A compound having the formula:

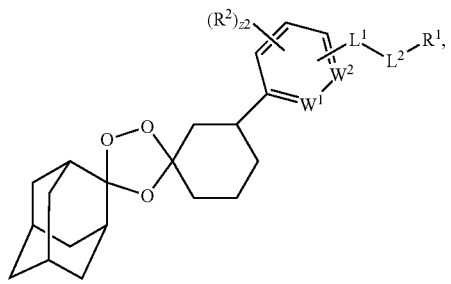

(I)

wherein
$W^1$ and $W^2$ are independently =N—, =C($R^2$)—, or =CH—; $L^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, or —S—; $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}C(O)R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z2 is an integer from 0 to 4; each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; each X, $X^1$, and $X^2$ is independently —F, —Cl, —Br, or —I; n1 is independently an integer from 0 to 4; and m1 and v1 are independently 1 or 2.

Embodiment 2

The compound of embodiment 1, having the formula:

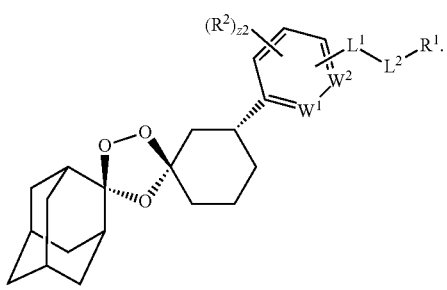

(Ia)

Embodiment 3

The compound of embodiments 1 to 2, wherein $W^1$ is =N—.

Embodiment 4

The compound of embodiments 1 to 2, wherein $W^1$ is =CH—.

Embodiment 5

The compound of embodiments 1 to 4, wherein $W^2$ is =N—.

Embodiment 6

The compound of embodiments 1 to 4, wherein $W^2$ is =CH—.

Embodiment 7

The compound of embodiments 1 to 6 wherein $R^2$ is independently unsubstituted $C_1$-$C_3$ alkyl.

Embodiment 8

The compound of embodiments 1 to 7, wherein z2 is 0.

Embodiment 9

The compound of embodiments 1 to 8, wherein $L^1$ is —O—.

Embodiment 10

The compound of embodiments 1 to 8, wherein $L^1$ is —OC(O)—.

Embodiment 11

The compound of embodiments 1 to 8, wherein $L^1$ is —OC(O)NH—.

Embodiment 12

The compound of embodiments 1 to 8, wherein $L^1$ is —OC(O)O—.

Embodiment 13

The compound of embodiments 1 to 8, wherein $L^1$ is a bond.

Embodiment 14

The compound of embodiments 1 to 13, wherein $L^2$ is a substituted or unsubstituted $C_1$-$C_4$ alkylene.

Embodiment 15

The compound of embodiments 1 to 13, wherein $L^2$ is an unsubstituted $C_1$-$C_4$ alkylene.

Embodiment 16

The compound of embodiments 1 to 13, wherein $L^2$ is a substituted or unsubstituted $C_4$-$C_6$ cycloalkylene.

Embodiment 17

The compound of embodiments 1 to 13, wherein $L^2$ is a substituted or unsubstituted 5 to 7 membered heterocycloalkylene.

Embodiment 18

The compound of embodiments 1 to 13, wherein $L^2$ is a bond.

Embodiment 19

The compound of embodiments 1 to 18, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, $R^{20}$-substituted or unsubstituted phenyl, or $R^{20}$-substituted or unsubstituted 5 to 7 membered heterocycloalkyl; $R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

Embodiment 20

The compound of embodiments 1 to 18, wherein $R^1$ is —$NR^{1A}R^{1B}$, —$C(O)NR^{1A}R^{1B}$, or $R^{20}$-substituted or unsubstituted 6 to 7 membered heterocycloalkyl; $R^{20}$ is independently oxo, —OH, —$S(O)_2CH_3$; and each $R^{1A}$ and $R^{1B}$ is independently hydrogen, OH-substituted $C_1$-$C_4$ alkyl, $NH_2$-substituted $C_1$-$C_4$ alkyl, or unsubstituted 5 to 6 membered heterocycloalkyl.

Embodiment 21

The compound of embodiments 1 to 18, wherein $R^1$ is —$OR^{1D}$ and $R^{1D}$ is hydrogen or unsubstituted $C_1$-$C_3$ alkyl.

Embodiment 22

The compound of embodiment 1 having the formula:

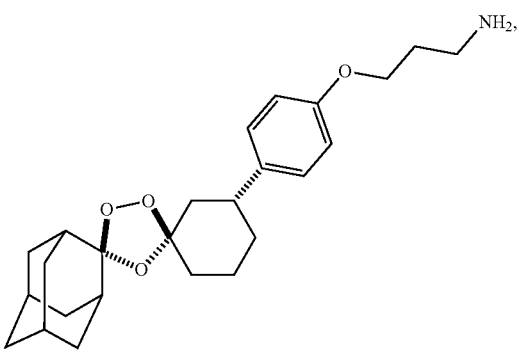

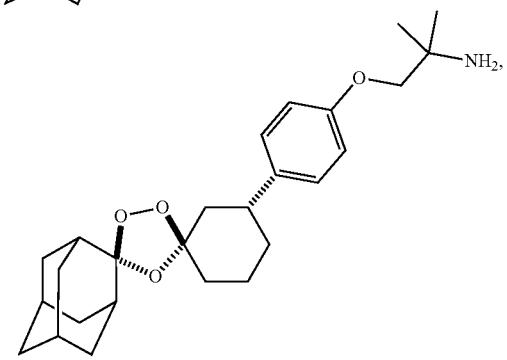

231
-continued
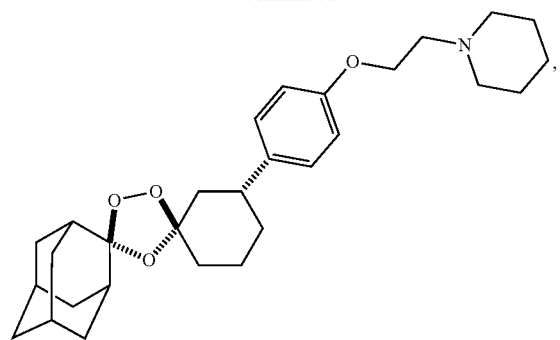
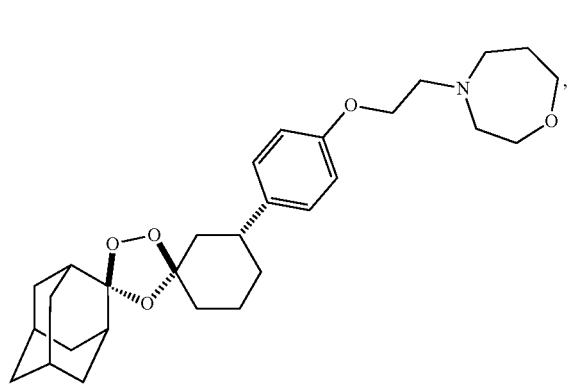
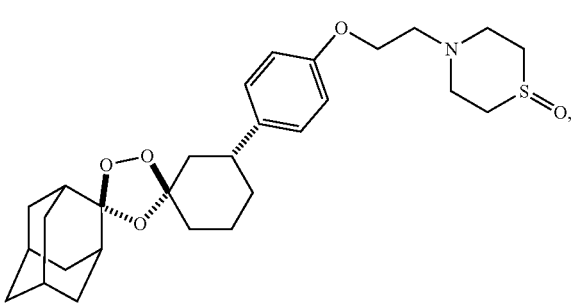
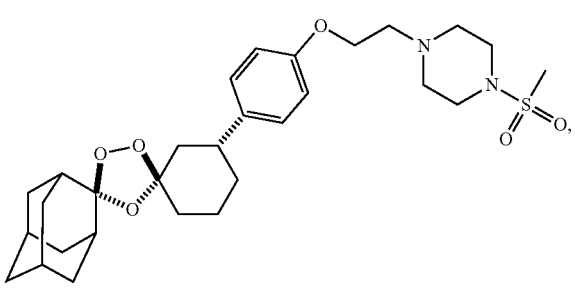
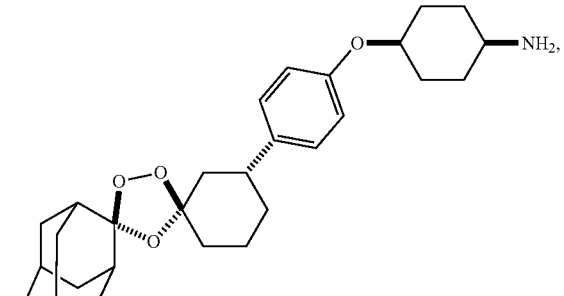
232
-continued
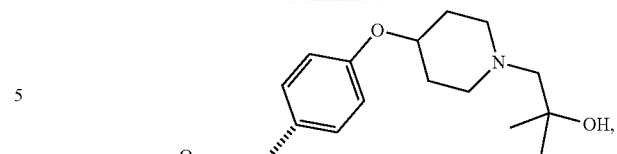
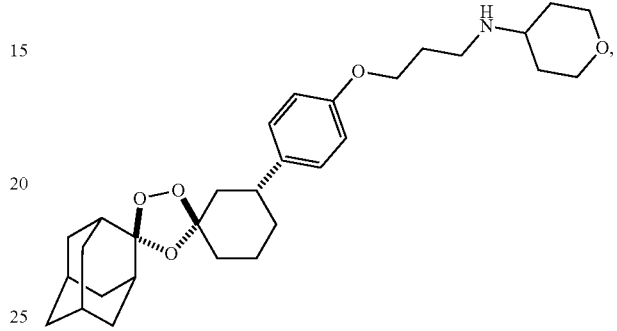
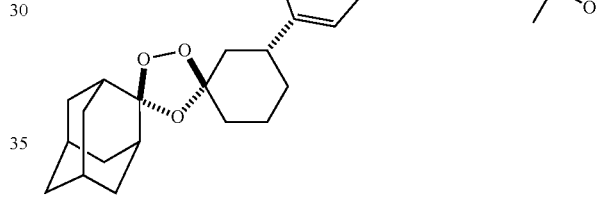
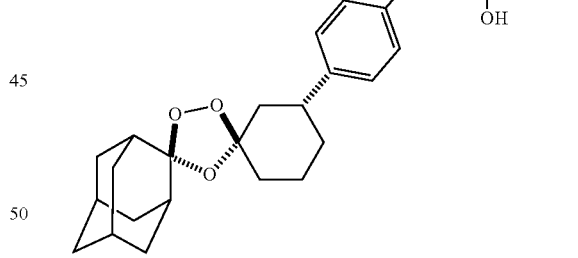
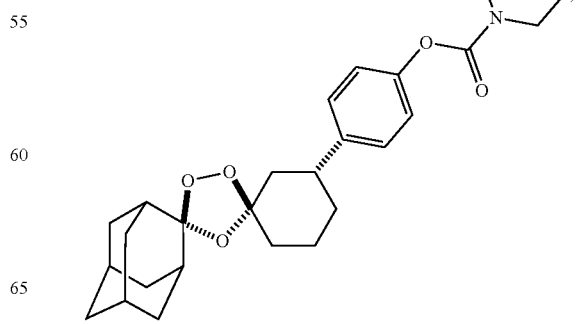

233
-continued
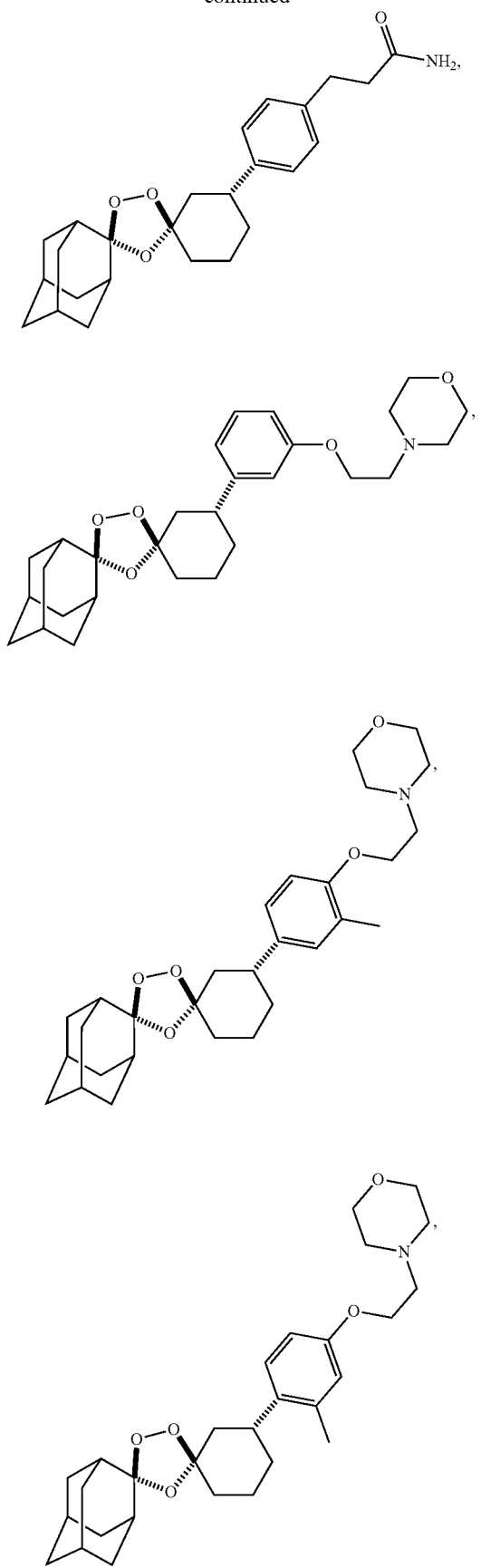
234
-continued
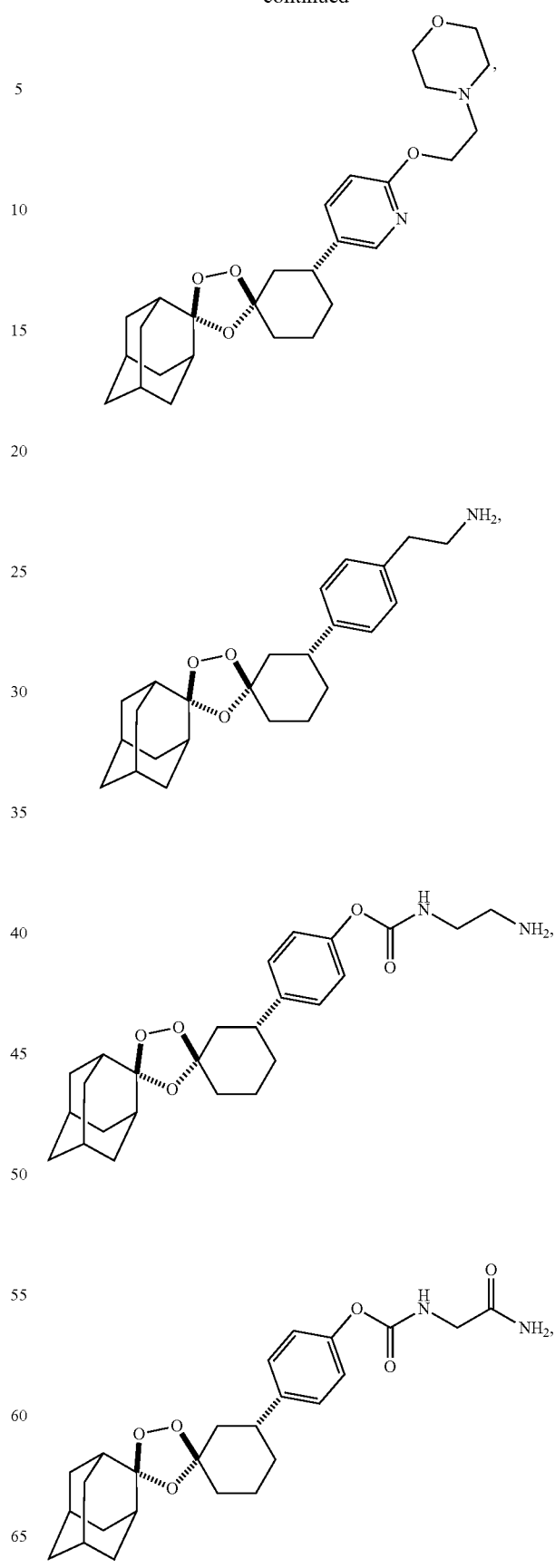

235
-continued
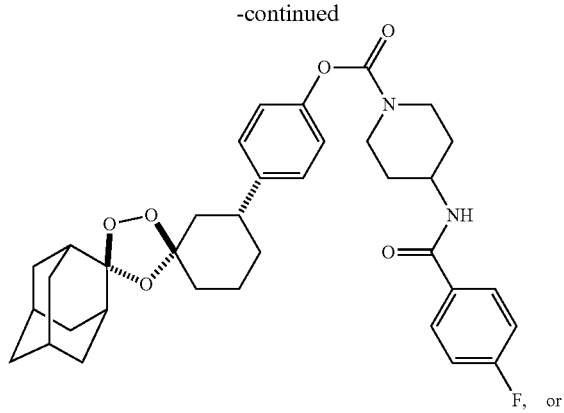
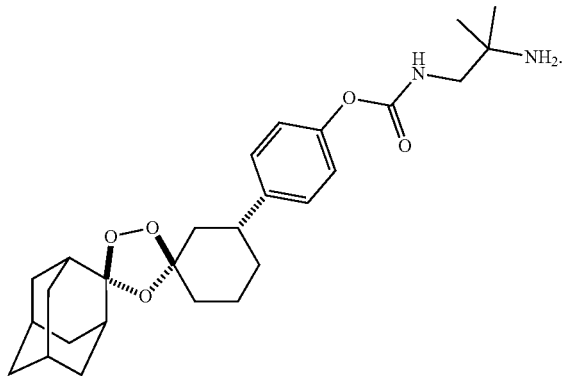
Embodiment 23
The compound of embodiment 1 having the formula:
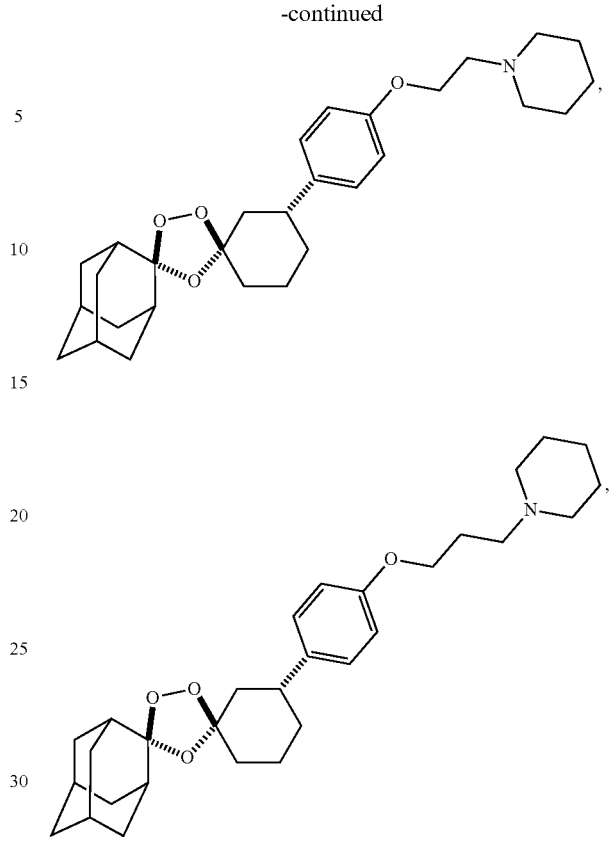
Embodiment 24
The compound of embodiment 1 having the formula:
236
-continued
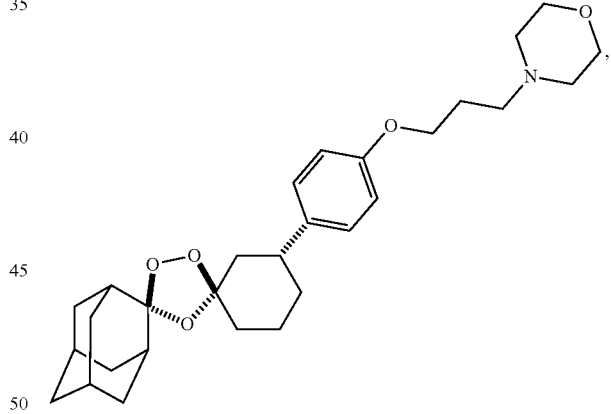
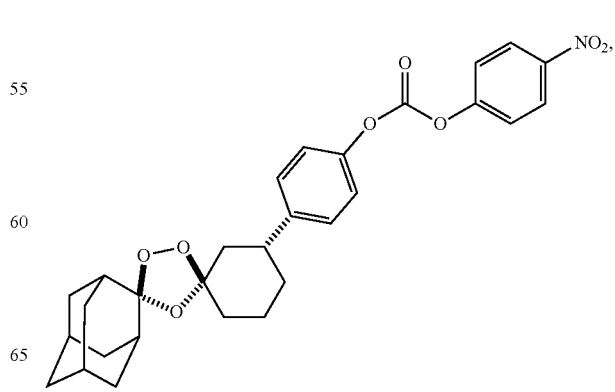

237
-continued
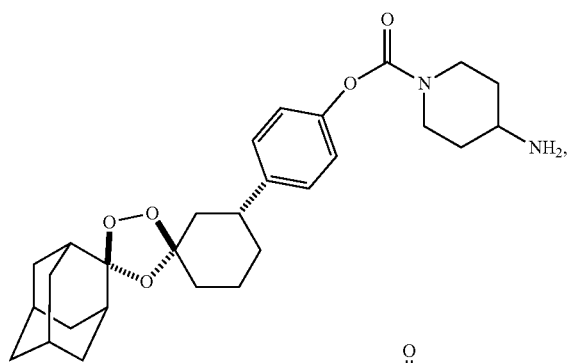
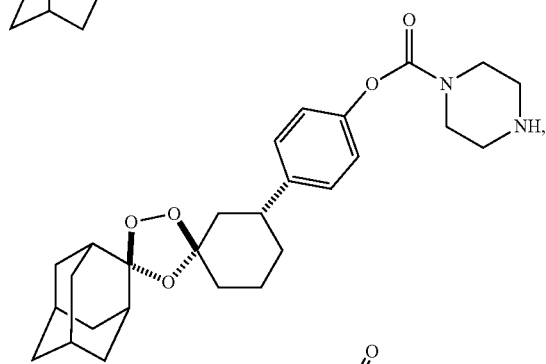
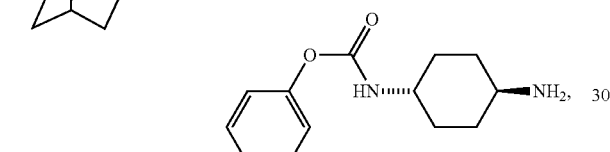, or
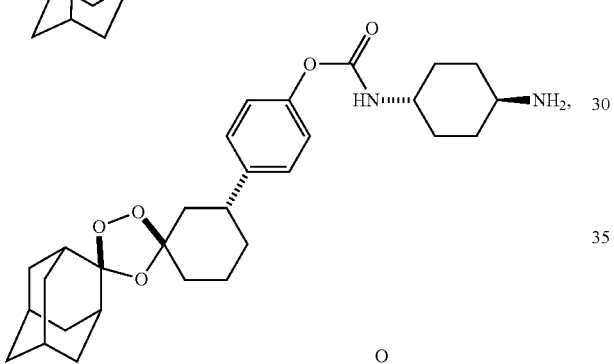
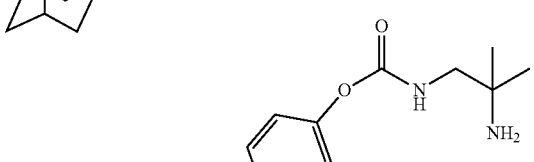.
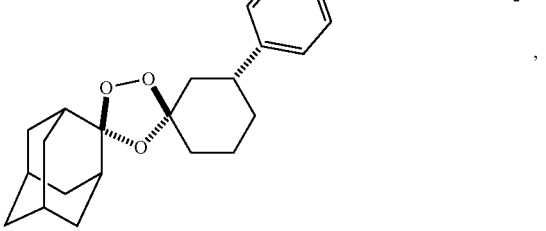
238
Embodiment 25
The compound of embodiment 1 having the formula:
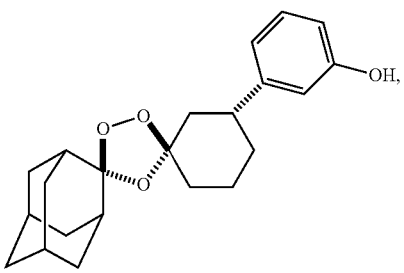
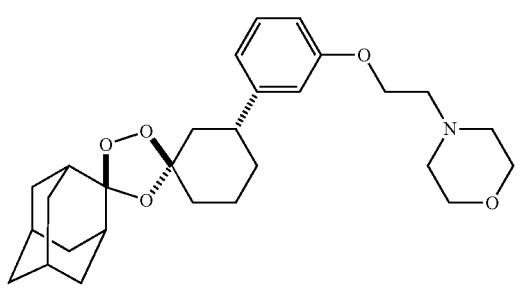,
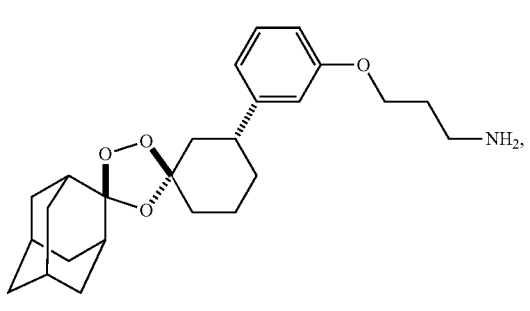,
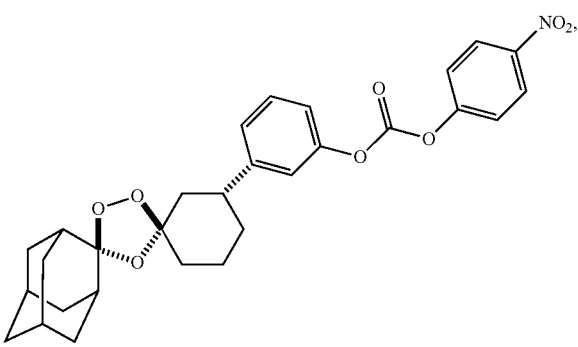,
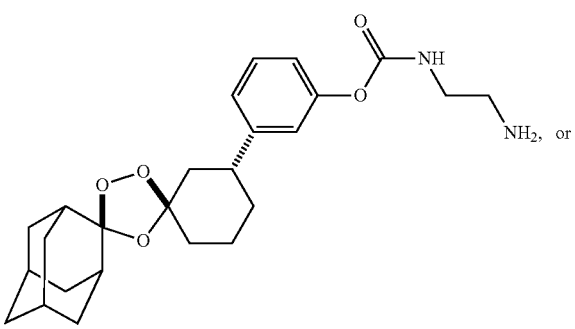, or -continued

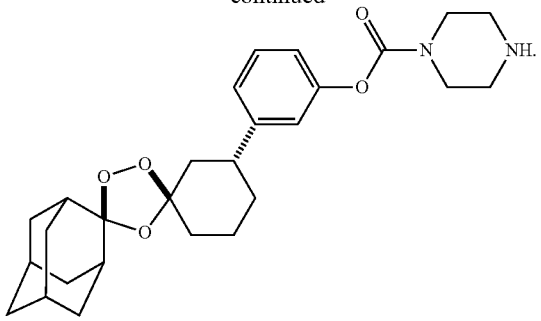

Embodiment 26

The compound of embodiment 1 having the formula:

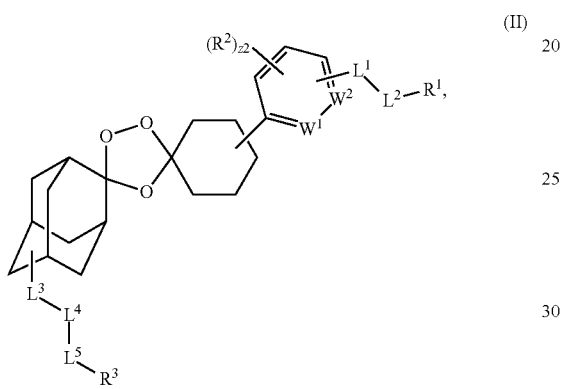

(II)

wherein
$W^1$ and $W^2$ are independently =N—, =C($R^2$)—, or =CH—; $L^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—; $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z2 is an integer from 0 to 4; each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; each X, $X^1$, and $X^2$ is independently —F, —Cl, —Br, or —I; n1 is independently an integer from 0 to 4; m1 and v1 are independently 1 or 2; $L^3$, $L^4$, and $L^5$ are independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^3$ is a detectable moiety.

Embodiment 27

The compound of embodiment 26 having the formula:

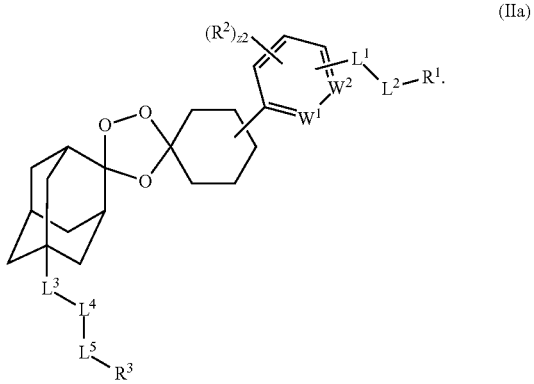

(IIa)

Embodiment 28

The compound of embodiment 26 having the formula:

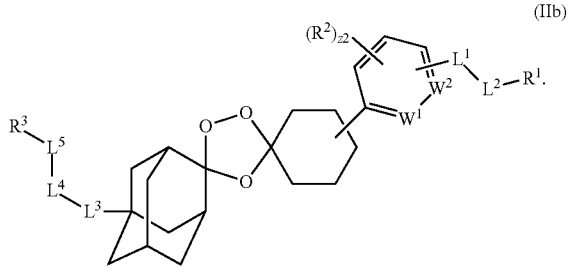

(IIb)

Embodiment 29

The compound of embodiment 26 having the formula:

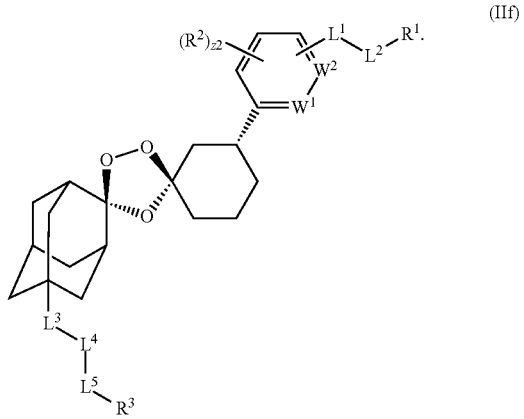

(IIf)

Embodiment 30

The compound of embodiment 26 having the formula:

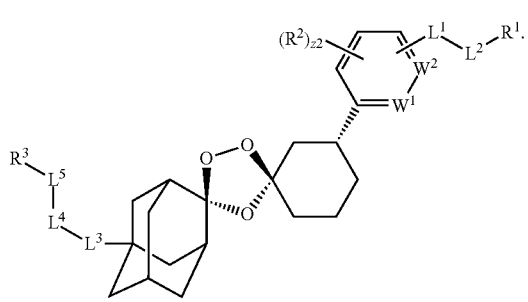

(IIm)

Embodiment 31

The compound of embodiment 26 having the formula:

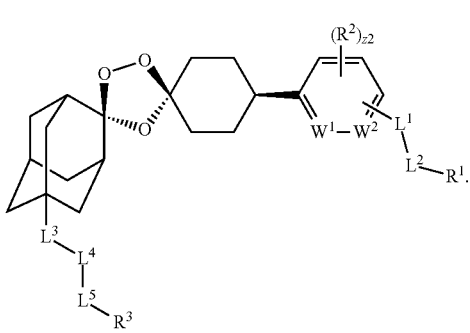

(IIi)

Embodiment 32

The compound of embodiment 26 having the formula:

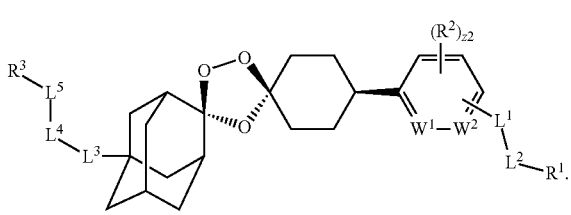

(IIp)

Embodiment 33

The compound of embodiments 26 to 32, wherein $W^1$ is =N—.

Embodiment 34

The compound of embodiments 26 to 32, wherein $W^1$ is =CH—.

Embodiment 35

The compound of embodiments 26 to 34, wherein $W^2$ is =N—.

Embodiment 36

The compound of embodiments 26 to 34, wherein $W^2$ is =CH—.

Embodiment 37

The compound of embodiments 26 to 36, wherein $R^2$ is independently unsubstituted $C_1$-$C_3$ alkyl.

Embodiment 38

The compound of embodiments 26 to 37, wherein z2 is 0.

Embodiment 39

The compound of embodiments 26 to 38, wherein $L^1$ is —O—.

Embodiment 40

The compound of embodiments 26 to 38, wherein $L^1$ is —OC(O)—.

Embodiment 41

The compound of embodiment 26 to 38, wherein $L^1$ is —OC(O)NH—.

Embodiment 42

The compound of embodiments 26 to 38, wherein $L^1$ is a bond.

Embodiment 43

The compound of embodiments 26 to 42, wherein $L^2$ is a substituted or unsubstituted $C_1$-$C_4$ alkylene.

Embodiment 44

The compound of embodiments 26 to 42, wherein $L^2$ is an unsubstituted $C_1$-$C_4$ alkylene.

Embodiment 45

The compound of embodiments 26 to 42, wherein $L^2$ is a substituted or unsubstituted $C_4$-$C_6$ cycloalkylene.

Embodiment 46

The compound of embodiments 26 to 42, wherein $L^2$ is a bond.

Embodiment 47

The compound of embodiments 26 to 46, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, or $R^{20}$-substituted or unsubstituted 5 to 7 membered heterocycloalkyl; $R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

Embodiment 48

The compound of embodiments 26 to 46, wherein $R^1$ is —$NR^{1A}R^{1B}$, —$C(O)NR^{1A}R^{1B}$, or $R^{20}$-substituted or unsubstituted 6 to 7 membered heterocycloalkyl; $R^{20}$ is independently oxo, —OH, —$S(O)_2CH_3$; and each $R^{1A}$ and $R^{1B}$ is independently hydrogen, OH-substituted $C_1$-$C_4$ alkyl, $NH_2$-substituted $C_1$-$C_4$ alkyl, or unsubstituted 5 to 6 membered heterocycloalkyl.

Embodiment 49

The compound of embodiments 26 to 48, wherein -$L^3$-$L^4$-$L^5$- is —$C(O)NHCH_2CH_2CH_2NHC(O)Ph$-.

Embodiment 50

The compound of embodiments 26 to 49, wherein $R^3$ is a radionuclide.

Embodiment 51

The compound of embodiments 26 to 49, wherein $R^3$ is a positron emitting radionuclide.

Embodiment 52

The compound of embodiments 26 to 497, wherein $R^3$ is carbon-11, nitrogen-13, oxygen-15, or fluorine-18.

Embodiment 53

The compound of embodiments 26 to 49, wherein $R^3$ is fluorine-18 or fluorine-19.

Embodiment 54

The compound of embodiments 26 to 49, wherein $R^3$ is fluorine-18.

Embodiment 55

The compound of embodiments 26 to 49, wherein $R^3$ is gallium-68, zirconium-89, rubidium-82, or iodine-124.

Embodiment 56

The compound of embodiments 50 to 54 having the formula:

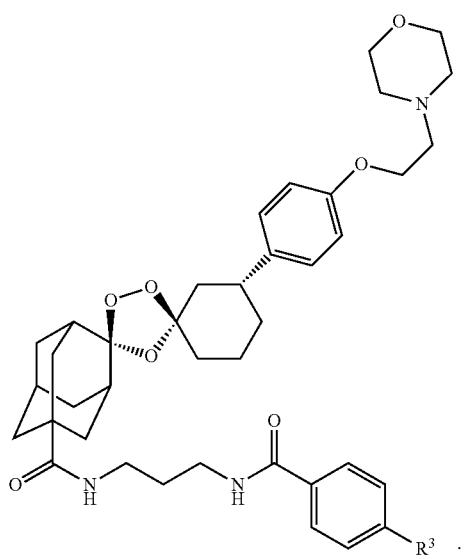

Embodiment 57

The compound of embodiments 50 to 54 having the formula:

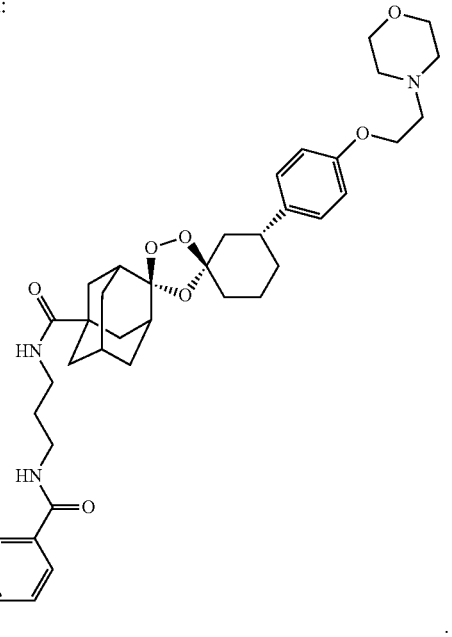

Embodiment 58

The compound of embodiments 50 to 54 having the formula:

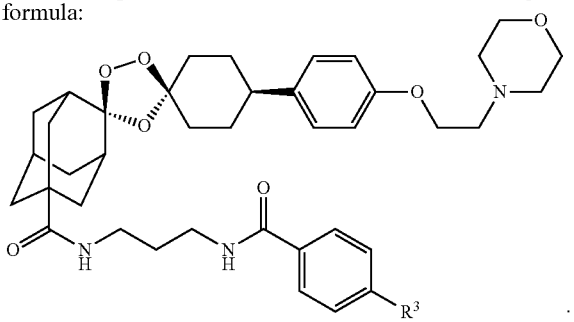

Embodiment 59

The compound of embodiments 50 to 54 having the formula:

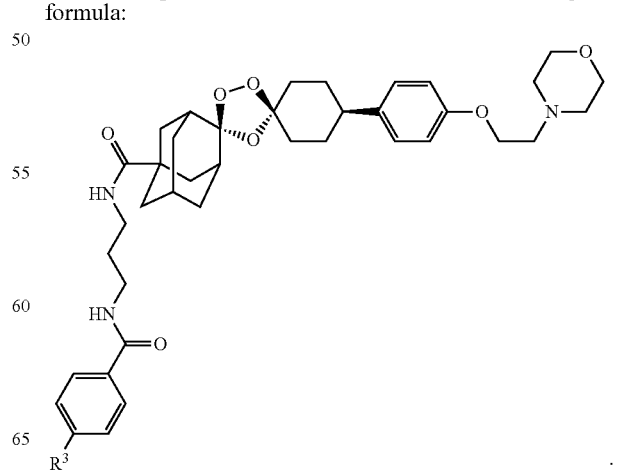

Embodiment 60

A pharmaceutical composition comprising a pharmaceutically acceptable excipient and a compound of one of embodiments 1 to 59.

Embodiment 61

A method of treating a disease in a patient in need of such treatment, said method comprising administering a therapeutically effective amount of a compound of one of claims one of embodiments 1 to 59 to said patient.

Embodiment 62

The method of embodiment 61, wherein the disease is associated with a cell or organism having an increased $Fe^{II}$ level compared to a standard control.

Embodiment 63

The method of embodiment 61, wherein the disease is cancer.

Embodiment 64

The method of embodiment 61, wherein the disease is malaria.

Embodiment 65

The method of embodiment 61, wherein the disease is a parasitic disease.

Embodiment 66

A method of detecting a disease associated with a cell or organism having an increased $Fe^{II}$ level compared to a standard control, in a subject, said method comprising administering an effective amount of a compound of one of embodiments 26 to 59 to said subject and measuring the level of the compound in the subject.

Embodiment 67

The method of embodiment 66, comprising measuring the level of compound in the subject using positron emission tomography.

Embodiment 68

The method of embodiments 66 to 67, wherein the disease is cancer, malaria, or an inflammatory disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

wherein
  $W^1$ and $W^2$ are independently =N—, =C($R^2$)—, or =CH—;
  $L^1$ is a bond, —O—, —NH—, —OC(O)—, —C(O)O—, —NHC(O)—, —C(O)NH—, —OC(O)O—, —OC(O)NH—, —NHC(O)O—, —NHC(O)NH—, or —S—;
  $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
  $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
  $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
  z2 is an integer from 0 to 4;
  each $R^{1A}$, $R^{1B}$, $R^{1C}$, and $R^{1D}$ is independently hydrogen, —$CX_3$, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl;
  each X, $X^1$, and $X^2$ is independently —F, —Cl, —Br, or —I;
  n1 is independently an integer from 0 to 4;
  m1 and v1 are independently 1 or 2.

2. The compound of claim 1, having the formula:

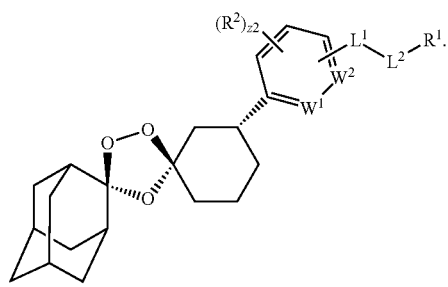

(Ia)

3. The compound of claim 1, wherein $L^1$ is —O—, —OC(O)—, —OC(O)NH—, —OC(O)O—, or a bond.

4. The compound of claim 1, wherein $L^2$ is a substituted or unsubstituted $C_1$-$C_4$ alkylene, a substituted or unsubstituted $C_4$-$C_6$ cycloalkylene, a substituted or unsubstituted 5 to 7 membered heterocycloalkylene, or a bond.

5. The compound of claim 1, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, $R^{20}$-substituted or unsubstituted phenyl, or $R^{20}$-substituted or unsubstituted 5 to 7 membered heterocycloalkyl;

$R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

6. The compound of claim 1 having the formula:

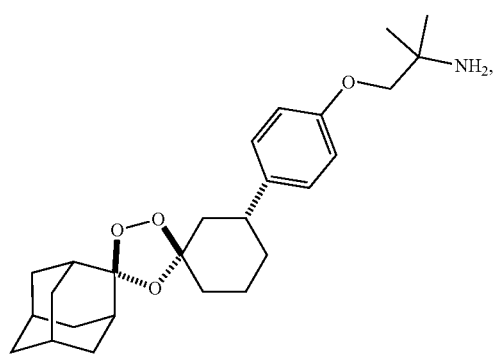

-continued

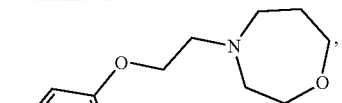

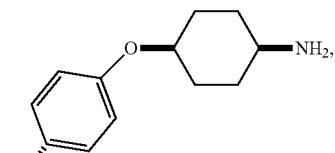

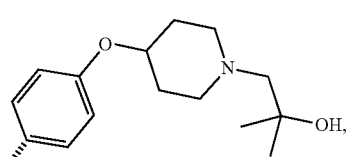

249
-continued
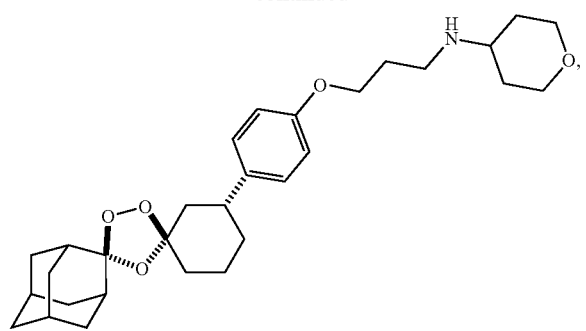
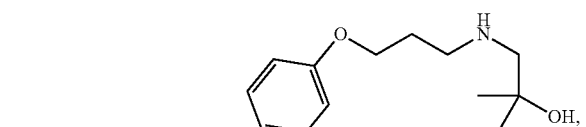
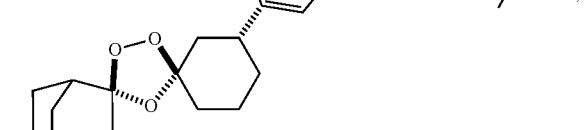
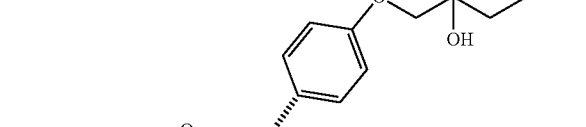
250
-continued
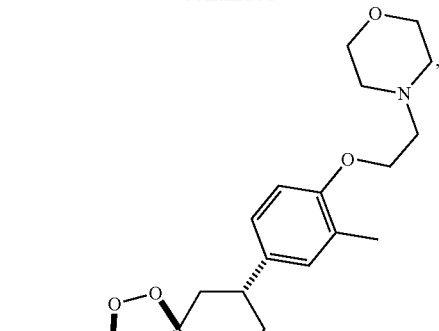
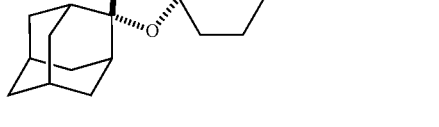
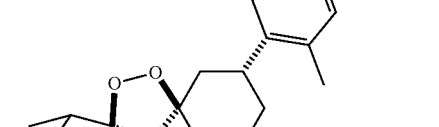

251
-continued
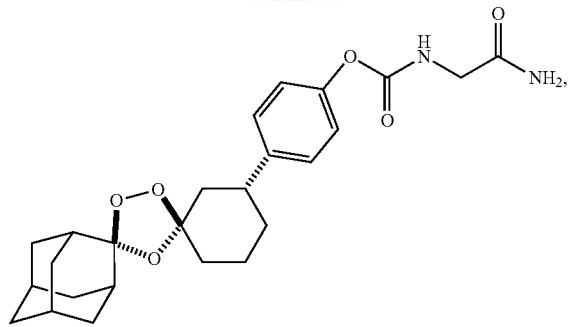
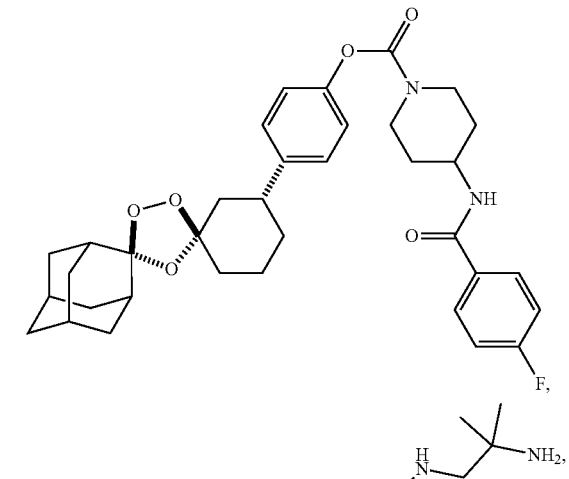
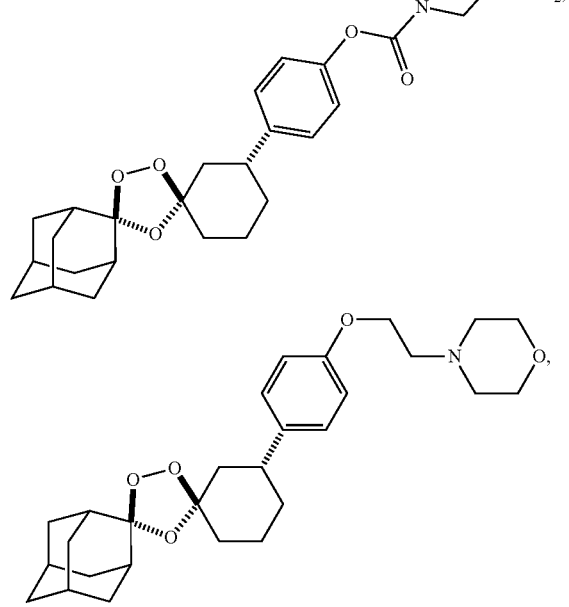
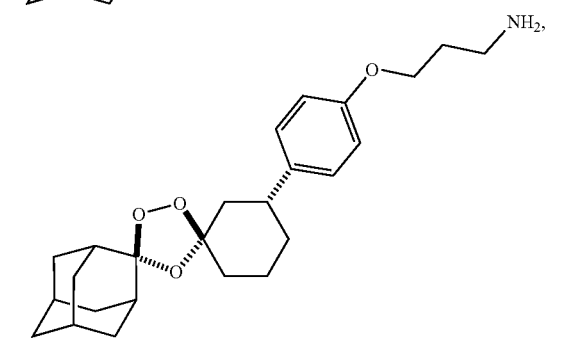
252
-continued
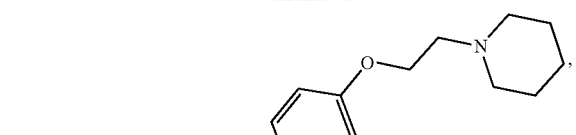
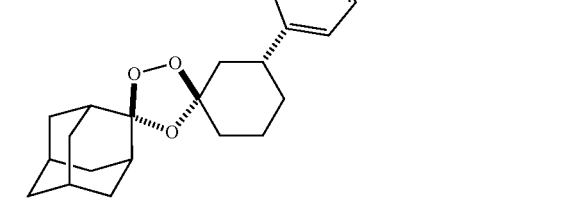
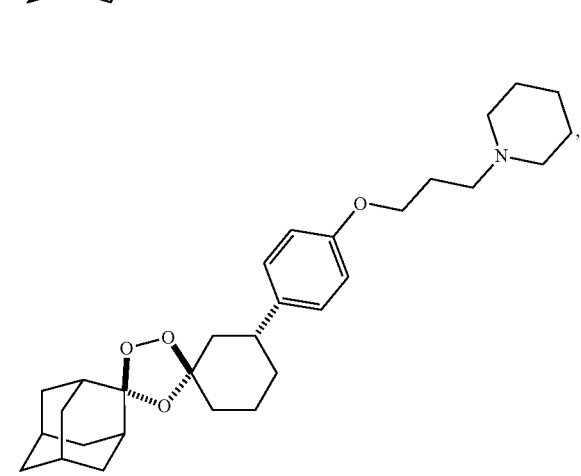
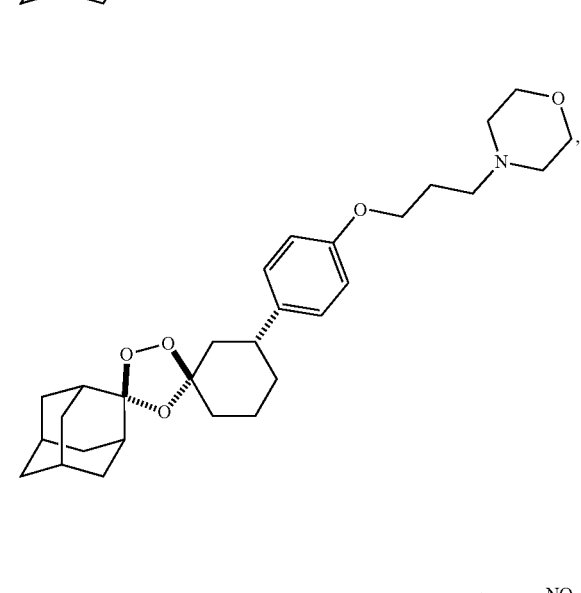
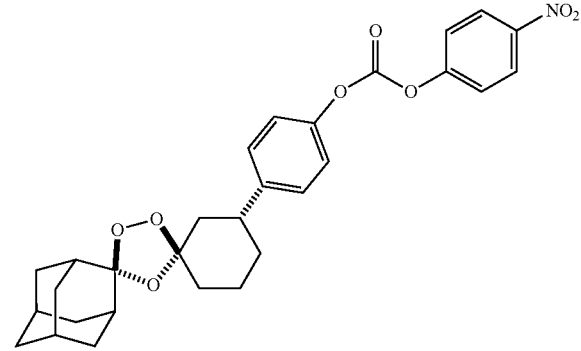

253
-continued
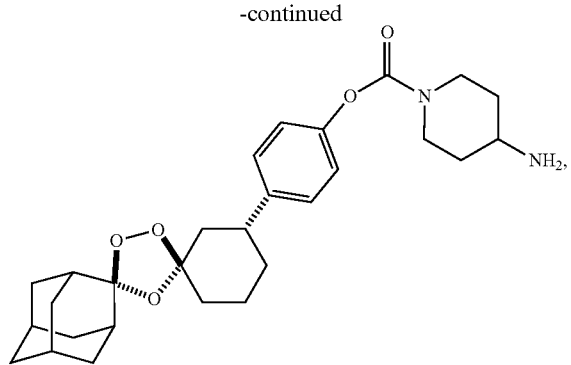
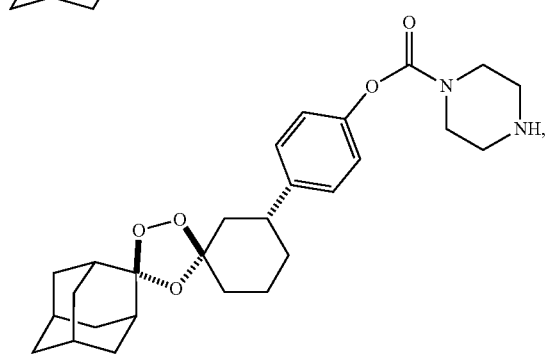
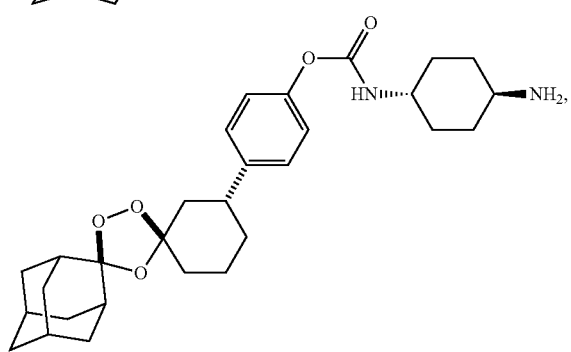
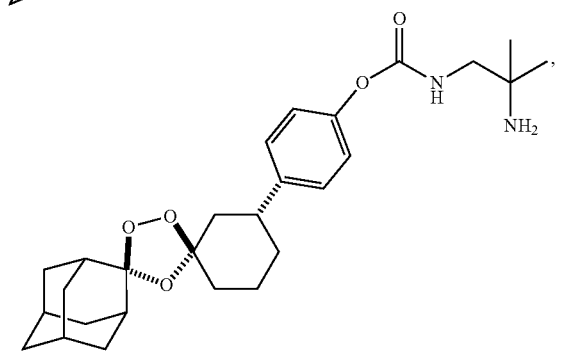
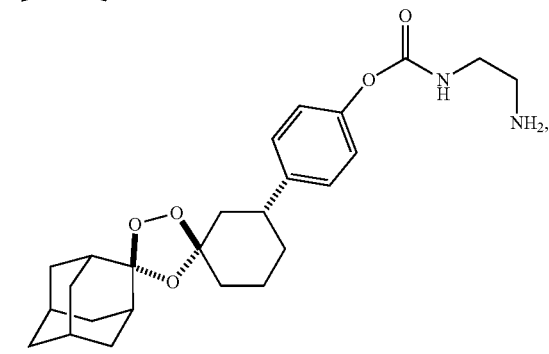
254
-continued
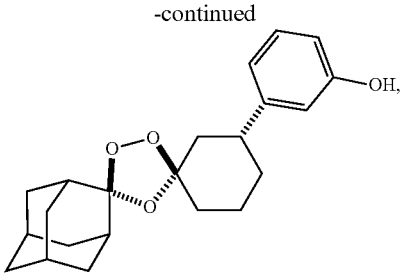
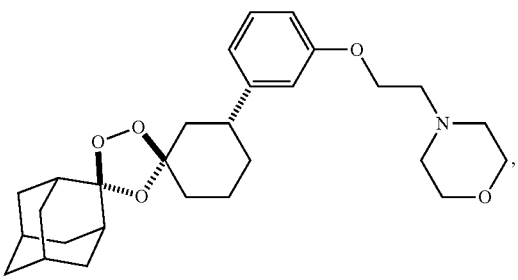
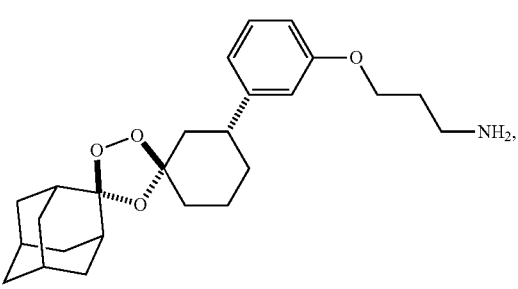
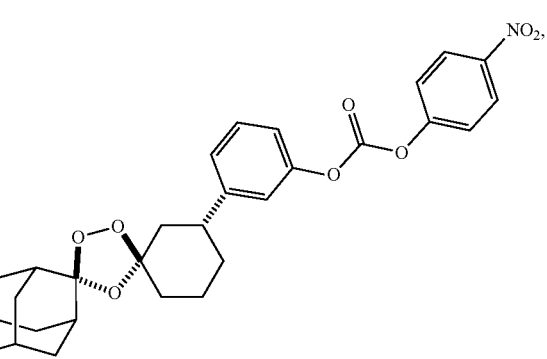
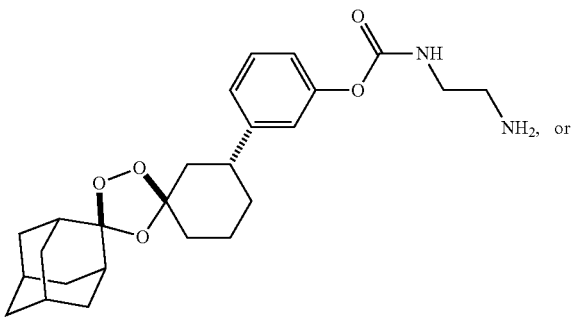

-continued

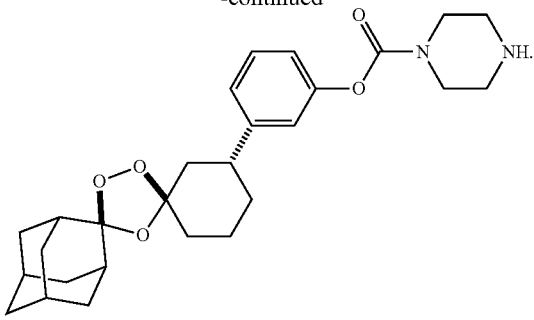

7. A compound having the formula:

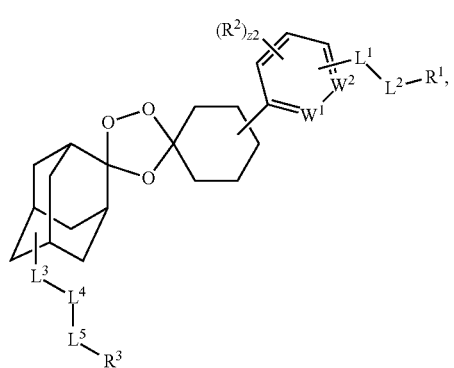

wherein

W¹ and W² are independently =N—, =C(R²)—, or =CH—;

L¹ is a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—;

L² is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R¹ is hydrogen, halogen, —CX¹₃, —CHX¹₂, —CH₂X¹, —OCX¹₃, —OCH₂X¹, —OCHX¹₂, —CN, —SO$_{n1}$R¹$^D$, —SO$_{v1}$NR¹$^A$R¹$^B$, —NHC(O)NR¹$^A$R¹$^B$, —N(O)$_{m1}$, —NR¹$^A$R¹$^B$, —C(O)R¹$^C$, —C(O)—OR¹$^C$, —C(O)NR¹$^A$R¹$^B$, —OR¹$^D$, —NR¹$^A$SO₂R¹$^D$, —NR¹$^A$C(O)R¹$^C$, —NR¹$^A$C(O)OR¹$^C$, —NR¹$^A$OR¹$^C$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is independently halogen, —CX²₃, —CHX²₂, —CH₂X², —OCX²₃, —OCH₂X², —OCHX²₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z2 is an integer from 0 to 4;

each R¹$^A$, R¹$^B$, R¹$^C$, and R¹$^D$ is independently hydrogen, —CX₃, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹$^A$ and R¹$^B$ substituents bonded to the same nitrogen atom may optionally be joined to form a substituted or unsubstituted heterocycloalkyl or substituted or unsubstituted heteroaryl;

each X, X¹, and X² is independently —F, —Cl, —Br, or —I;

n1 is independently an integer from 0 to 4;

m1 and v1 are independently 1 or 2;

L³ L⁴ and L⁵ are independently a bond, —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R³ is a radionuclide.

8. The compound of claim 7 having the formula:

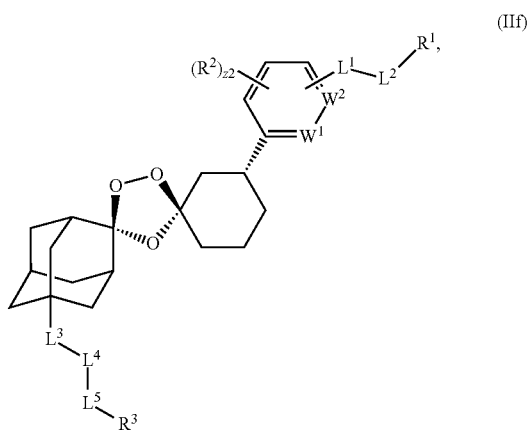

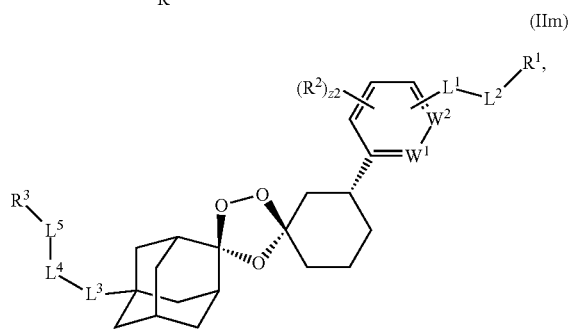

-continued

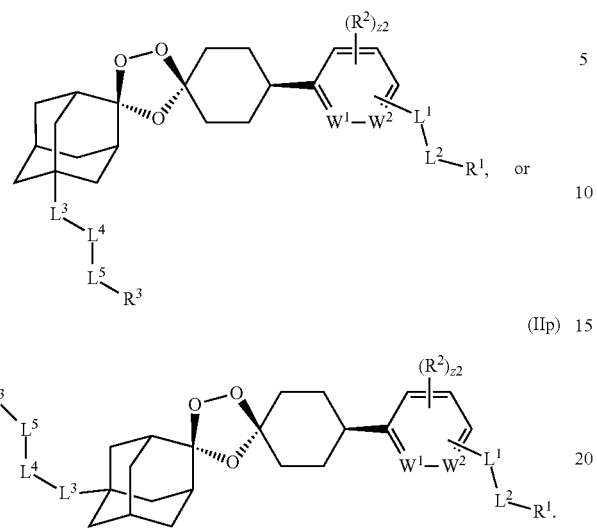

9. The compound of claim 7, wherein $W^1$ is =N— or =CH— and $W^2$ is =N— or =CH—.

10. The compound of claim 7, wherein z2 is 0.

11. The compound of claim 7, wherein $L^1$ is —O—, —OC(O)—, —OC(O)NH—, or a bond.

12. The compound of claim 7, wherein $L^2$ is a substituted or unsubstituted $C_1$-$C_4$ alkylene, a substituted or unsubstituted $C_4$-$C_6$ cycloalkylene, or a bond.

13. The compound of claim 7, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, or $R^{20}$-substituted or unsubstituted 5 to 7 membered heterocycloalkyl;

$R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

14. The compound of claim 7, wherein $R^1$ is —$NR^{1A}R^{1B}$, —$C(O)NR^{1A}R^{1B}$, or $R^{20}$-substituted or unsubstituted 6 to 7 membered heterocycloalkyl;

$R^{20}$ is independently oxo, —OH, —$S(O)_2CH_3$; and each $R^{1A}$ and $R^{1B}$ is independently hydrogen, OH-substituted $C_1$-$C_4$ alkyl, $NH_2$-substituted $C_1$-$C_4$ alkyl, or unsubstituted 5 to 6 membered heterocycloalkyl.

15. The compound of claim 7, wherein $R^3$ is carbon-11, nitrogen-13, oxygen-15, fluorine-18, fluorine-19, gallium-68, zirconium-89, rubidium-82, or iodine-124.

16. The compound of claim 7 having the formula:

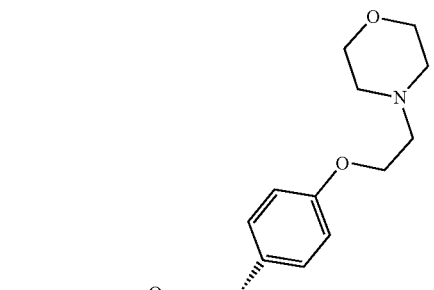

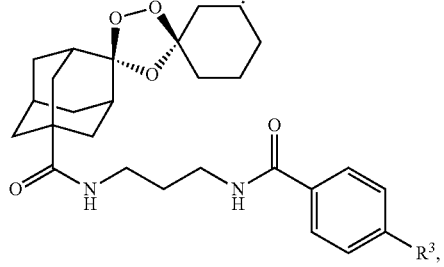

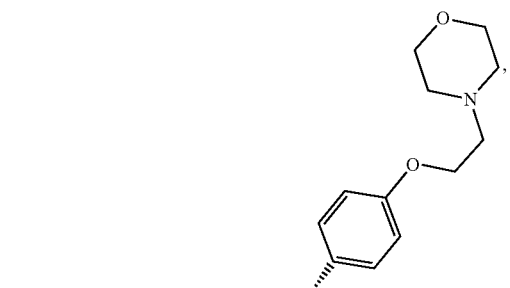

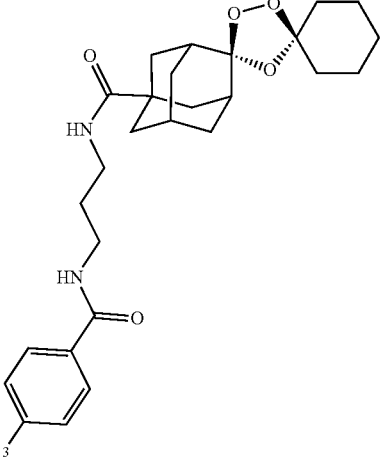

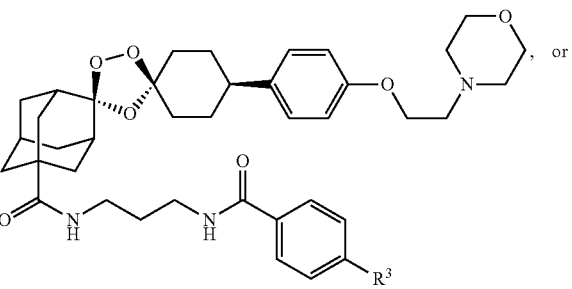

-continued

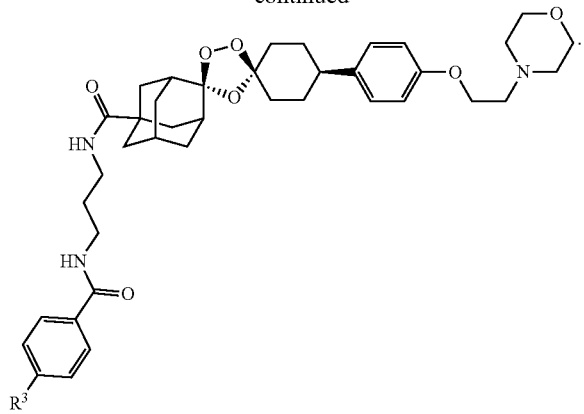

17. A pharmaceutical composition comprising a pharmaceutically acceptable excipient and a compound of claim 1.

18. A method of treating malaria in a patient in need of such treatment, said method comprising administering a therapeutically effective amount of a compound of claim 1 to said patient.

19. A pharmaceutical composition comprising a pharmaceutically acceptable excipient and a compound of claim 7.

20. A method of treating malaria in a patient in need of such treatment, said method comprising administering a therapeutically effective amount of a compound of claim 7 to said patient.

21. The compound of claim 7, wherein $R^1$ is —$NR^{1A}R^{1B}$, —$C(O)NR^{1A}R^{1B}$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_5$-$C_7$ cycloalkyl, $R^{20}$-substituted or unsubstituted phenyl, or $R^{20}$-substituted 5 to 7 membered heterocycloalkyl;

$R^{20}$ is independently oxo, halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —$NO_2$, —SH, —$S(O)_2CH_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and each $R^{1A}$ and $R^{1B}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{1A}$ and $R^{1B}$ substituents bonded to the same nitrogen atom may optionally be joined to form a substituted or unsubstituted 5 to 6 membered heterocycloalkyl.

22. The compound of claim 7, wherein $L^3$ is independently —O—, —NH—, —OC(O)—, —C(O)O—, —NHC(O)—, —C(O)NH—, —OC(O)O—, —OC(O)NH—, —NHC(O)O—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

23. The compound of claim 7, wherein $R^3$ is fluorine-18.

* * * * *